US009486499B2

(12) United States Patent
Akil et al.

(10) Patent No.: US 9,486,499 B2
(45) Date of Patent: *Nov. 8, 2016

(54) ADMINISTRATION OF FGF9 FOR TREATMENT OF ANXIETY

(71) Applicant: BOARD OF TRUSTEES OF THE LELAND STANFORD JUNIOR UNIVERSITY, Palo Alto, CA (US)

(72) Inventors: Huda Akil, Ann Arbor, MI (US); Stanley J. Watson, Ann Arbor, MI (US); Cortney Turner, Ann Arbor, MI (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 13/776,647

(22) Filed: Feb. 25, 2013

(65) Prior Publication Data
US 2014/0073568 A1 Mar. 13, 2014

Related U.S. Application Data

(63) Continuation of application No. 11/158,530, filed on Jun. 21, 2005, now Pat. No. 8,415,298.

(60) Provisional application No. 60/581,998, filed on Jun. 21, 2004, provisional application No. 60/621,252, filed on Oct. 22, 2004, provisional application No. 60/667,296, filed on Mar. 31, 2005.

(51) Int. Cl.
*A61K 38/18* (2006.01)
*C12Q 1/68* (2006.01)
*G01N 33/68* (2006.01)
*G01N 33/74* (2006.01)

(52) U.S. Cl.
CPC ......... *A61K 38/1825* (2013.01); *C12Q 1/6883* (2013.01); *G01N 33/6896* (2013.01); *G01N 33/74* (2013.01); *C12Q 2600/136* (2013.01); *C12Q 2600/156* (2013.01); *C12Q 2600/158* (2013.01); *C12Q 2600/172* (2013.01); *G01N 2333/726* (2013.01); *G01N 2800/304* (2013.01)

(58) Field of Classification Search
None
See application file for complete search history.

(56) References Cited

U.S. PATENT DOCUMENTS

| | | | |
|---|---|---|---|
| 6,024,734 A | 2/2000 | Brewitt | |
| 6,342,478 B1 | 1/2002 | Frey, II | |
| 6,685,934 B1 | 2/2004 | Mallet et al. | |
| 7,309,687 B1 | 12/2007 | Brines et al. | |
| 2002/0169102 A1 | 11/2002 | Frey, II | |
| 2002/0192817 A1 | 12/2002 | Weiss et al. | |
| 2003/0072793 A1* | 4/2003 | Frey et al. | 424/449 |
| 2003/0096264 A1 | 5/2003 | Altar et al. | |
| 2003/0152972 A1 | 8/2003 | Sklar et al. | |
| 2003/0166555 A1 | 9/2003 | Alberini et al. | |
| 2003/0175253 A1 | 9/2003 | Akil et al. | |
| 2003/0191061 A1 | 10/2003 | Brewitt | |
| 2004/0152107 A1 | 8/2004 | Altar et al. | |
| 2004/0152111 A1 | 8/2004 | Akil et al. | |
| 2006/0051786 A1 | 3/2006 | Akil et al. | |
| 2007/0213401 A1 | 9/2007 | Dooley et al. | |

FOREIGN PATENT DOCUMENTS

| | | |
|---|---|---|
| EP | 1233075 A2 | 8/2002 |
| EP | 1586657 A1 | 10/2005 |
| EP | 1766077 B1 | 3/2012 |
| JP | 2005-503120 A | 2/2005 |
| WO | 94/12201 A1 | 6/1994 |
| WO | 95/26409 A1 | 10/1995 |
| WO | 97/34618 A1 | 9/1997 |
| WO | 99/15697 A1 | 4/1999 |
| WO | 99/62522 A1 | 12/1999 |
| WO | 00/42173 A1 | 7/2000 |
| WO | 00/58510 A | 10/2000 |
| WO | 02/057790 A2 | 7/2002 |
| WO | 02/077199 A2 | 10/2002 |
| WO | 2004/043395 A2 | 5/2004 |
| WO | 2004/047727 A2 | 6/2004 |
| WO | 2005/014623 A2 | 2/2005 |
| WO | 2005/046434 A2 | 5/2005 |
| WO | 2007/059064 A2 | 5/2007 |

OTHER PUBLICATIONS

Martin. The epidemiology of anxiety disorders: a review. Dialogues Clin Neurosci. Sep. 2003;5(3):281-98.*
Belluardo et al., "Central nicotinic receptors, neurotrophic factors and neuroprotection," Behav. Brain Res. Aug. 2000; 113(1-2):21-34.
Bezchlibnyk et al., "Gene expression differences in bipolar disorder revealed by cDNA array analysis of post-mortem frontal cortex," Journal of Neurochemistry, 2001, vol. 79, pp. 826-834.
Bunney et al., "Microarray Technology: A Review of New Strategies to Discover Candidate Vulnerability Genes in Psychiatric Disorders"; Am J Psychiatry; 2003; vol. 160, pp. 657-666.
Chen et al., "Discordant Protein and mRNA Expression in Lung Adenocarcinomas," 2002, Molecular & Cellular Proteomics, vol. 1, pp. 304-313.

(Continued)

*Primary Examiner* — Gregory S Emch
(74) *Attorney, Agent, or Firm* — Kilpatrick Townsend & Stockton LLP

(57) ABSTRACT

The present invention provides methods for diagnosing mental disorders. The invention also provides methods of identifying modulators of mental disorders as well as methods of using these modulators to treat patients suffering from mental disorders.

7 Claims, 67 Drawing Sheets

(56) References Cited

OTHER PUBLICATIONS

DataBase: NCBI, GenBank Accession No. AB030073, Version No. AB030073.1, GI: 6691444, "*Homo sapiens* mRNA," Jul. 2, 2007, 3 pages.
DataBase: NCBI, GenBank Accession No. AB030074, Version No. AB030074.1, GI: 6691446, "*Homo sapiens* mRNA," Jul. 2, 2007, 3 pages.
DataBase: NCBI, GenBank Accession No. AB030075, Version No. AB030075.1, GI: 6691448, "*Homo sapiens* mRNA," Jul. 2, 2007, 3 pages.
DataBase: NCBI, GeneID: 2263, "FGFR2," Jul. 2, 2007, 14 pages.
El-Husseini, et al., "Basic Fibroblast Growth Factor (BFGF) and Two of its Receptors, FGFR1 and FGFR2: Gene Expression in the Rat Brain During Postnatal Development as Determined by Quantitative RT-PCR," Molecular and Cellular Endocrinology, 1994, vol. 104: pp. 191-200.
Evans, S.J. et al. "Dysregulation of the fibroblast growth factor system in major depression," PNAS, 2004, vol. 43, No. 101, pp. 15506-15511.
Fatemi et al.; Altered levels of Reelin and its isoforms in schizophrenia and mood disorders; NeuroReport; Oct. 29, 2001; vol. 12, No. 15: pp. 3209-3215.
Gaughran et al.; Hippocampal FGF-2 and FGFR1 mRNA expression in major depression, schizophrenia and bipoloar disorder; Elsevier Brain Research Bulletin; 2006; 70: pp. 221-227.
Gomez-Pinilla et al., "Basic FGF in Adult Rat Brain: Cellular Distribution and Response to Entorhinal Lesion and Fimbria-fornix Transection," J. Neurosci. Jan. 1992; 12(1):344-355.
Gomez-Pinilla, Fernando et al. "Diazepam induces FGF-2 mRNA in the hippocampus and striatum," Brain Research Bulletin, 2000, vol. 53, No. 3, pp. 283-289.
Grimes et al., "Cholinergic Stimulation of Early Growth Response-1 DNA Binding Activity Requires Protein Kinase C and Mitogen-Activated Protein Kinase Kinase Activation and Is Inhibited by Sodium Valproate in SH-SY5Y Cells," J. Neurochem., 1999, vol. 73(4), pp. 1384-1392, Lippincott Williams & Wilkins, Inc., Phila.
Haynes et al., "Protein Analysis: Biological Assay or Data Archive?" Electrophoresis, 1998, vol. 19, pp. 1862-1871.
Heiskanen et al., "CGH, cDNA and Tissue Microarray Analyses Implicate FGFR2 Amplification in a Small Subset of Breast Tumors," Analytical Cellular Pathology, 2001, vol. 22(4): pp. 229-234.
Herdegen at al., "JUN, FOS, KROX, and CREB Transcription Factor Proteins in the Rat Cortex: Basal Expression and Induction by Spreading Depression and Epileptic Seizures," J. Comparative Neurology, 1993, vol. 333(2), pp. 271-288.
Knable et al.; Multivariate analysis of prefrontal cortical data from the Stanley Foundation Neuropathology Consortium; Elsevier Brain Research Bulletin; 2001; vol. 55, No. 5: pp. 651-659.
Knuuttila, Juha E. A. et al., "Effects of antidepressant drug imipramine on gene expression in rat prefrontal cortex," Neurochemical Research, Jun. 1, 2004, vol. 29, No. 6, pp. 1235-1244.
Kuromitsu et al., Reduced Neuropeptide Y mRNA Levels in the Frontal Cortex of People with Schizophrenia and Bipolar Disorder, Gene Expression Patterns, 2001, pp. 17-21.
Landgrebe, J. et al., "Molecular characterization of antidepressant effects in the mouse brain using gene expression profiling," Journal of Psychiatric Research, May 1, 2002, vol. 36, No. 3, pp. 119-129.
Mallei, Alessandra et al., "Antidepressant Treatments Induce the Expression of Basic Fibroblast Growth Factor in Cortical and Hippocampal Neurons," Molecular Pharmacology, 2002, vol. 61, pp. 1017-1024.
Mickle et al., "Genotype-phenotype relationships in cystic fibrosis," Med. clin. North Am. May 2000; 84(3):597-607.
Miki, T. et al., "Determination of ligand-binding specificity by alternative splicing: two distinct growth factor receptors encoded by a single gene," PNAS, 89:246-250, 1992.
Mills et al., "DMA Microarrays and Beyond: Completing the Journey from Tissue to Cell," 2001, Nature Cell Biology, vol. 3: pp. E175-E178.
Nechifor, M., "Magnesium in Psychoses", New Perspectives in Magnesium Research, 2007, Chapter 30, pp. 369-377.
Newton, S. et al., "Regulation of neurogenesis and angiogenesis in depression," Current Neurovascular Res., 1:261-267, 2004.
Ovalle, Sergio et al. "Fibroblast growth factor-2 is selectively modulated in the rat brain by E-5842, a preferential sigma-1 receptor ligand and putative atypical antipsychotic," European Journal of Neuroscience, 2001, vol. 13, pp. 909-915.
Pekonen, F. et al., "Differential expression of keratinocyte growth factor and its receptor an the human uterus," Mol. Cell. Endocrin., 95(1-2):43-49, 1993.
Sabban et al., "Differential Effects of Stress on Gene Transcription Factors in Catecholaminergic Systems," Ann. N.Y. Acad. Sci., 2004, vol. 1032, pp. 130-140.
Turner et al., "Antidepressant-like Effects of Intracerebroventricular FGF2 in Rats," Brain Research, 2008, V. 1224, pp. 63-68.
Vawter et al., "Microarray Screening of Lymphocyte Gene Expression Differences in a Multiplex Schizophrenia Pedigree," Schizophrenia Research, 2004, vol. 67, pp. 41-52.
Voet et al., Biochemistry. 1990. John Wiley & Sons, Inc. 126-129 and 228-234.
Wagner et al., "Stimulation of Neonatal and Adult Brain Neurogenesis by Subcutaneous Injection of Basic Fibroblast Growth Factor," J. Neurosci, 1999; vol. 19(14), pp. 6006-6016.
Yamada, S. et al., "Histological and genetic diagnosis of gliomatosis cerebri: case report," J. Neuro-oncology, 52(3):237-240, 2001.
Yan et al., "Two-amino acid molecular switch in an epithelial morphogen that regulates binding to two distinct receptors," Science 2000; 290:523-527.
Zhu et al., "Glu-96 of Basic Fibroblast Growth Factor is Essential for High Affinity Receptor Binding," J Biol. Chem., 1995; vol. 270(37), pp. 21869-21874.

\* cited by examiner

Differential Expression of FGF System Transcripts in MDD Cortex

| | | | | |
|---|---|---|---|---|
| Hs.278954 | FGF1 | <0.01+ | Decreased | 0.01 | Decreased |
| Hs.284244 | FGF2 | NS | | <0.01* | Decreased |
| Hs.433252 | FGF7 | NS | | NS | |
| Hs.111 | FGF9 | <0.01 | Increased | <0.01* | Increased |
| Hs.343809 | FGF12 | NS | | <0.01* | Increased |
| Hs.6540 | FGF13 | NS | | NS | |
| Hs.223851 | FGF14 | 0.05 | Increased | NS | |
| Hs.748 | FGFR1 | NS | | <0.01* | Decreased |
| Hs.404081 | FGFR2 | <0.01+ | Decreased | <0.01 | Decreased |
| Hs.1420 | FGFR3 | <0.01+ | Decreased | | |

*Observation was confirmed in an independent cohort of MDD and control subjects.
+Observation was confirmed by real-time PCR analysis with p<0.05.
NS = not significant.

*FIG. 2*

Environmental Complexity:
FGF2 and Anxiety-Like Behavior

- Young Adult Rats: 21 Days of Environmental Complexity (EC) vs. Controls
- Look at Neurogenesis, FGF2 Gene Expression, Spatial Learning, Anxiety-Like Behavior
- EC Leads to Increase in FGF2 Expression
- EC Leads to Improved Performance in MWM
- EC Leads to Decreased Anxiety-Like Behavior
- Positive Correlation Between FGF2 Expression in Time Spent in Anxiety-Provoking Task

FIG. 5

Conclusions: FGF and Negative Affect

- Several FGF system transcripts are differentially expressed in frontal cortical regions of MDD subjects. This effict is specific to MDD and not seen in BPD.

- Confirmation by qRT-PCR for FGF1, FGFR2 & FGFR3.

- Confirmation by microarray in an independent cohort for FGF1, FGF13, FGFR2 and FGFR3.

- Effect Not Due to Antidepressant Treatment
    - In Human Samples: Greater Effect in Untreated Subjects
    - In Rat: FGFR2 is increased by fluoxetine in hippocampal and frontal conrtical regions, a change opposite to that seen in MDD.

- Rodent Studies are Beginning to Implicate FGF System in Emotional Reactivity: Early Exposure to FGF2 Increases Exploration, and Environmental Enrichment Increases FGF2 and Decreases Anxiety

*FIG. 7*

FIG. 8 qRT-PCR Validation of Microarray Data

Anterior cingulate cortex

| Symbol | UniGene | Gene name | Fold change BPD | | Fold change MDD | |
|---|---|---|---|---|---|---|
| | | | U95Av2 | qRT-PCR | U95Av2 | qRT-PCR |
| Ligand | | | | | | |
| NPY | Hs.1832 | neuropeptide Y | 1.33* | 1.46** | | |
| SST | Hs.12409 | somatostatin | 1.48* | 1.38 | | |
| GPCR | | | | | | |
| CCKBR | Hs.203 | cholecystokinin B receptor | 1.24* | 1.44** | | |
| GPR37 | Hs.406094 | G protein-coupled receptor 37 | 1.52* | 1.87** | | |
| GPRC5B | Hs.448805 | G protein-coupled receptor C-5-B | 1.27* | 1.34 | -1.43* | -1.55** |
| G protein | | | | | | |
| GNAQ | Hs.469951 | G protein, q polypeptide | 1.3* | 1.29** | | |
| GNAZ | Hs.437081 | G protein, alpha z polypeptide | 1.34* | 1.20** | | -1.36 |

Dorsolateral prefrontal cortex

| Symbol | UniGene | Gene name | Fold change BPD | | Fold change MDD | |
|---|---|---|---|---|---|---|
| | | | U95Av2 | qRT-PCR | U95Av2 | qRT-PCR |
| GPCR | | | | | | |
| EDNRB | Hs.82002 | endothelin receptor type B | | | -1.22* | -1.31 |
| GPR37 | Hs.406094 | G protein-coupled receptor 37 | 1.45* | 1.97** | -1.44* | -1.01 |
| GPRC5B | Hs.448805 | G protein-coupled receptor C-5-B | 1.34* | 1.59** | -1.33* | -1.18 |
| G protein | | | | | | |
| GNAQ | Hs.469951 | G protein, q polypeptide | | | 1.26* | 1.08 |
| GNB5 | Hs.155090 | G protein, beta 5 polypeptide | 1.24* | 1.98** | 1.31* | 1.61** |

Criteria of significance
*Microarray U95Av2 PLMfit analysis, top 5% T
**qRT-PCR, one tailed Student's t-test, p<0.05

Up regulation
Down regulation

H. Tomita et. al. 2004

FIG. 10

Gene Category Over-Representation Analysis of the 3 Downstream Signaling Pathways
(p value)

| | BPD | | MDD | |
|---|---|---|---|---|
| | AnCg | DLPFC | AnCg | DLPFC |
| cAMP signaling | N.S. | N.S. | N.S. | N.S. |
| Phosphatidylinositol signaling | 0.018 | N.S. | N.S. | 0.005 |
| MAPK signaling | 0.008 | N.S. | N.S. | 0.01 |

N.S.; not significant

H. Tomita et. al. 2004

Phosphatidylinositol Metabolism in Bipolar Disorder cAMP Signaling Pathway in Bipolar Disorder

FIG. 17 – SHEET 1

1. Where each exon begins and ends on mRNA sequence of PSPHL-A and PSPHL-B

PSPHL-A (BC065228) 841 bp  cDNA clone IMAGE:5552627

Exon 1

```
  1 ccgaaggctt ctgcctggcc gccgccgcct ataagctacc aggaggagct ttacgacttc
 61 ccgtcctgcg ggaagtggcg ggcacgatcg caaggtagcg cagaagcttc tcaatggcca
121 gcgccagctg cagccccggc ggcgcactcg cctcacctga gcctgg
```

Exon 2

```
                                                          gagg aaaattcttc
181 caaggatgat ctcccactca gagctgagga agctttttcta ctcagcagat gctgtgtgtt
241 ttgatgttga cagcacggtc atcagtgaag aaggaatcg
```

Exon 3

```
                                                       g acggagtctc gctctgtcac
301 caggctggag tgcaatggtg caatctcggc tcactgcaac ctccgcctcc tgggttcagg
361 cagttctcct gcctccacct cctgagtagc tgaaactaca g
```

Exon 4

```
                                         gatgctttc attggctttg
421 gaggaaatgt gatcaggcaa caagtcaagg ataacgccaa atgtatatc actgattttg
481 tagagctgct gggagaaccg gaagaataac atccattgtc atacagctcc aaacaacttc
541 agatgaattt ttacaagtta cacagattga tactgtttgc ttacaattgc ctattacaac
601 ttgctataga aagttggtac agatgatctg taaactacag ctactgtcaag ttaggaatcc
651 tcaaagattg gtttgttttgt tttttaactgt agttccagta ttatatgatc actattgatt
721 tcctggagag ttttgtaatc tgaattcttt atgtatattc ctagctatat ttcatacaaa
781 gtgttttaag agtggagagt caattaaaca cctttactct taggaaaaaa aaaaaaaaaa
841 a
```

PSPHL-B (AJ001612) 839 bp

Exon 1

```
  1 aagccacagg ctccctggct ggcgtcagct aaagtggctg ttgggtgtcc gcaggcttct
```

FIG. 17 – SHEET 2

```
 61 gcctgccgc cgccgcctat aagctaccag gaggagcttt acgacttccc gtcctgcggg
121 aagtgcggg cacgatcgca agtagcgca gaagcttctc aatggccagc gccagctgca
181 gcccggcgg cgcactcgcc tcacctgagc ctgg
```

Exon 2

```
                                        gaggaa aattcttcca aggatgatct
241 cccactcaga gctgaggaag cttttctact cagcagatgc tgtgtgtttt gatgtttgaca
301 gcacggtcat cagtgaagaa ggaatcg
```

Exon 4

```
                                gat gctttcattg gatttggagg aaatgtgatc
361 aggcaacaag tcaaggataa cgccaaatgg tatatcactg attttgtaga gctgctggga
421 gaaccggaag aataacatcc attgtcatac agctccaaac aacttcagat gaatttttac
481 aagttacaca gattgatact gtttgcttac aattgcctat tacaacttgc tataaaaagt
541 tggtacagat gatctgcact gtcaagtaaa ctacagttag gaatcctcaa agattggttt
601 gtttgttttt aactgtagtt ccagtattat atgatcacta tcgatttcct ggagagtttt
661 gtaatctgaa ttctttatgt atattcctag ctatatttca tacaaagtgt tttaagagtg
721 gagagtcaat taaacactt tactcttagg aatatagatt cggcagcctt cagtgaatat
781 tggttttttt cccttggta tgtcaataaa agtttatcca tgtgtcagaa aaaaaaaa
```

2. Primers to detect insertion/deletion polymorphism of PSPHL locus

Primer sequence to detect insertion allele

| PSPHL-F1 | aggctcctgcctgc      |
|----------|---------------------|
| PSPHL-R1 | caggtcaggtgaggcg    |

Primer sequence to detect deletion allele

| PSPHL-G-F2 | aagccagtgcgtctacaggtg      |
|------------|----------------------------|
| PSPHL-G-R2 | gtgccagaagaaccacacagtc     |

3. Representative Gel Image for PSPHL Insertion/Deletion Alleles

Mitogen Activated Protein Kinase Signaling Pathway in Limbic System of Major Depressive Disorder

Effects of Environmental Complexity on Individual Differences in Anxiety Behavior and FGF-2 Gene Expression
J. Perez[1], C.A. Turner[1], C. Isgor[2], S.J. Watson[1] and H. Akil[1]
[1]Mental Health Research Institute, University of Michigan, Ann Arbor, MI 48109.
[2]Biomed. Sci. Center, Florida Atlantic Univ. Boca Raton FL.

INTRODUCTION

While evidence has linked growth factors such as BDNF to environmental complexity (EC), responsiveness to stress, and antidepressant action[1,2], few studies focused on the role of the Fibriblast Growth Factor (FGF) system in emotional reactivity. Recent data from our laboratory suggest that a single postnatal injection of FGF-2 significantly alters locomotor activity in response to a novel environment (Turner et al., SFN abstracts 2004). Since increased responsiveness to novelty is associated with decreased anxiety-like behavior [3], we propose that FGF-2 may be correlated with other indices of emotionality. Using rats selectively bred for showing differences in locomotor activity in response to a novel environment; high responders (HR) and low responders (LR), we examined the effects of Environmental Complexity (E.C.) on anxiety-like behavior and FGF-2 gene expression in HR and LR. We tested the hypothesis that changes in emotionality associated with EC may be related to FGF-2 gene expression in the hippocampus.

MATERIALS and METHODS

*Animals:* Sixty male Sprague-Dawley rats from a selective in-house breeding colony from the $F_5$ generation weighing 385-450g were housed in pairs or on a Complex Environment and kept on a 12 hr light/dark cycle (lights on 7 A.M.). Food and water were available *ad libitum*.

*Locomotor testing:* Locomotor activity was assessed at six weeks of age between the hours of 0900 and 1100. . During the 60 min testing period, animals were placed in clear acrylic 43 x 21.5 x 25.5 cm (high) cages equipped with infrared photocell emitters mounted 2.3 cm and 6.5 cm above the grid floor to monitor horizontal and rearing movements, respectively. Locomotor activity was monitored in 5 min intervals for 60 min and counted by a microcomputer. Total locomotion scores for each rat were calculated by adding the total number of horizontal and rearing movements. The rats that exhibited locomotor scores in the highest third of the sample population and were classified as high responders (HR), whereas animals with scores in the lowest third of the population were classified as low responders (LR). Animals whose scores fell in the middle third of the population were classified as intermediate responders (IR).

*Environmental Complexity: (see photo below):* Two weeks after locomotion testing animals were housed on standard cages or in a Complex Environment for 21 day (n=6 per group). E.C cages were made up of wire-mesh with 3ft x3ft x 3ft dimensions. At the beginning of training cages were empty. The complexity of the environment increased each day so that toys were added every 24hrs, thus by the end of 21 days the E.C reached maximum complexity. Each day animals were placed in an open field with various new toys for 45 minutes to allow the experimenter to sanitize and increase the complexity of the E.C cages. During the first week latency to explore the new set up of toys in the open filed was measured.

*Elevated Plus-maze:* The apparatus is constructed of black Plexiglass with four elevated open arms (70cm from the floor, 45cm long, and 12cm wide). The illumination was provided by 40-watt desk lamp facing the wall and placed behind one of the closed arms. (n=9 per group).

FIG. 22A

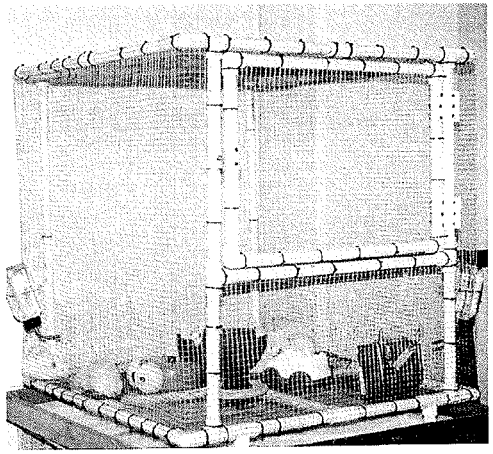
E.C. at week 1

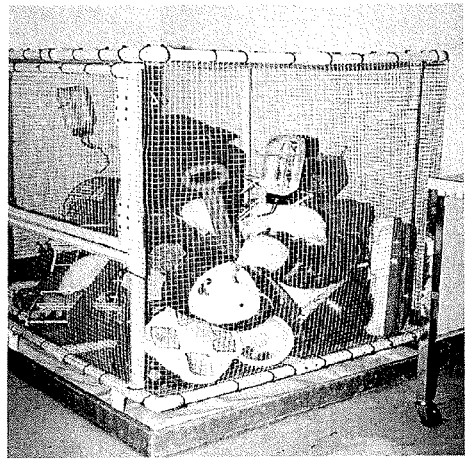
E.C. at week 3

*In-situ Hybridization:* At the end of the 21 day period animals were sacrificed and brains were removed and flashed frozen with isopentane. Brains were sectioned at the level of the hippocamapus with a thickness of 20μm and at 200 μm intervals. After following standard procedures FGF-2 mRNA was labelled using a $S^{35}$ C-RNA probe from a 278bp fragment at a location of 716-994 of the coding sequence (NM_019305), (n=6 per group).

RESULTS

*HRs exhibit less anxiety-like behavior than LRs, as illustrated by their increased time spent in the open arms. Similar to previous reports[4], E.C. animals showed decreased anxiety when compared to standard control animals.*

Total Time in the Open Arm

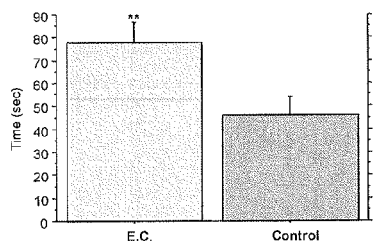

Figure 1. The mean ± SEM for the Total Time Spent in the Open Arm. Two-ANOVA revealed an effect of E.C. vs Control Group; E.C. animals had an increase in the Total Time spent in the Open Arms relative to control animals(**P=0.006).

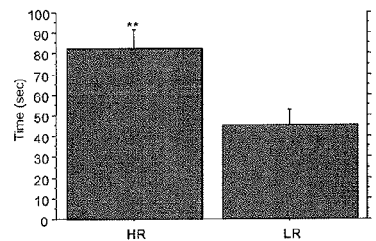

Figure 2. The mean ± SEM for time spent in the open arm. Two-way ANOVA revealed an effect of Loco Group; HR animals spent more time in the open arms when compared to LR animals (**P=0.002).

*E.C. animals show enhanced FGF-2 Gene expression in the Hippocamapus. Interestingly, this effects seems are more robust in the LRs than in HRs.*

FIG. 22B

FGF-2 Gene Expression in the Hippocampus
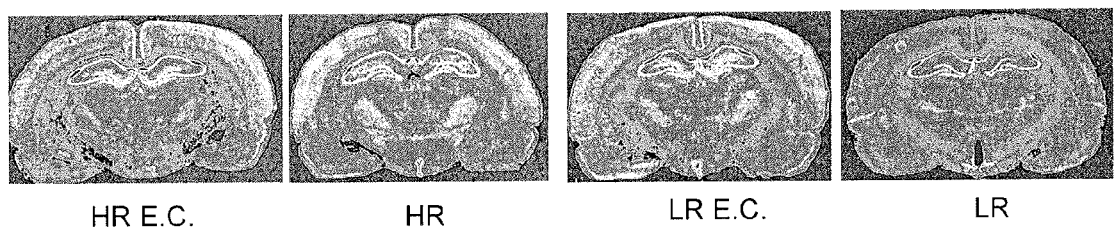
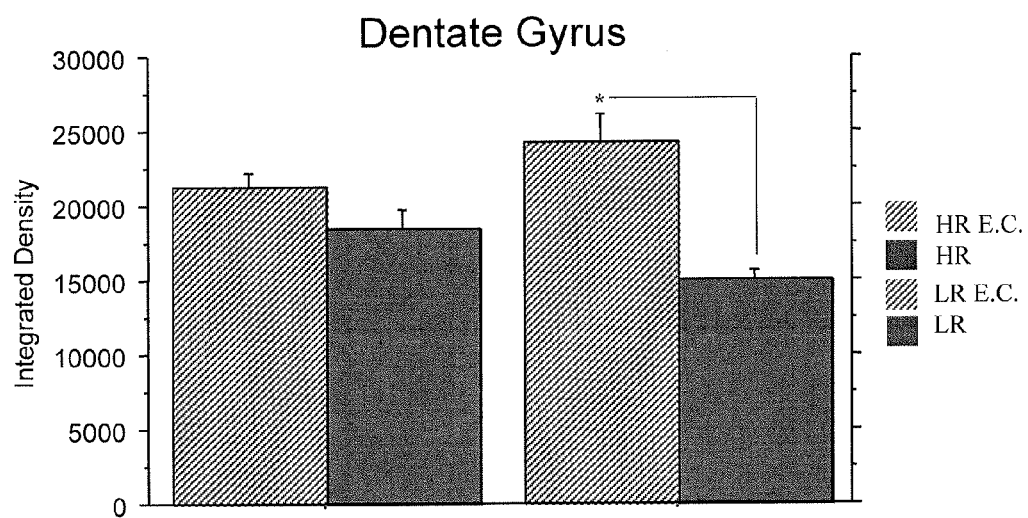
Figure 3. The mean ± SEM for the Integrated density of FGF-2 mRNA expression. Two way -ANOVA revealed an effect of E.C. vs Control Group and an interaction effect; E.C. animals had an increase in the mRNA expression of FGF-2 ( ***P=.0001) The effect of E.C was more Robust in the LR than in the HR (* P=.02).
FIG. 22C

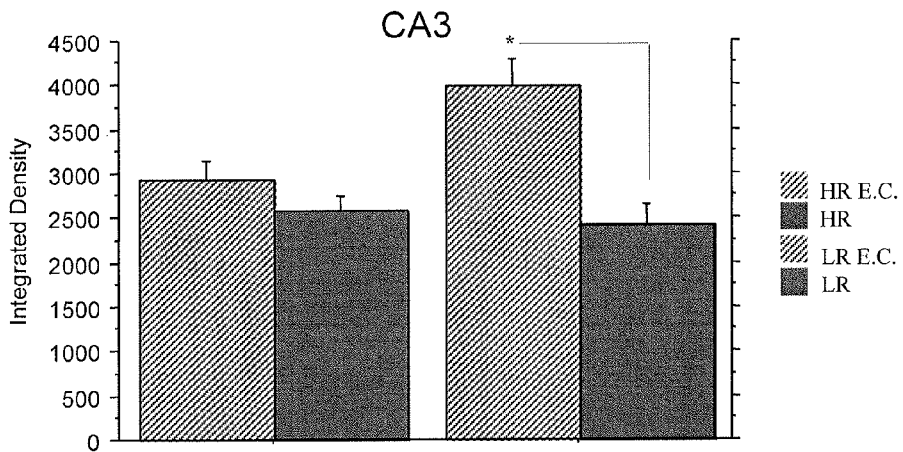

Figure 4. The mean ± SEM for the Integrated density of FGF-2 mRNA expression.
Two way -ANOVA revealed an effect of E.C. vs Control Group and an interaction effect;
E.C. animals had an increase in the mRNA expression of FGF-2 ( ***P=.0006)
A greater effect of E.C was seen in the LR than in the HR (* P=.02).

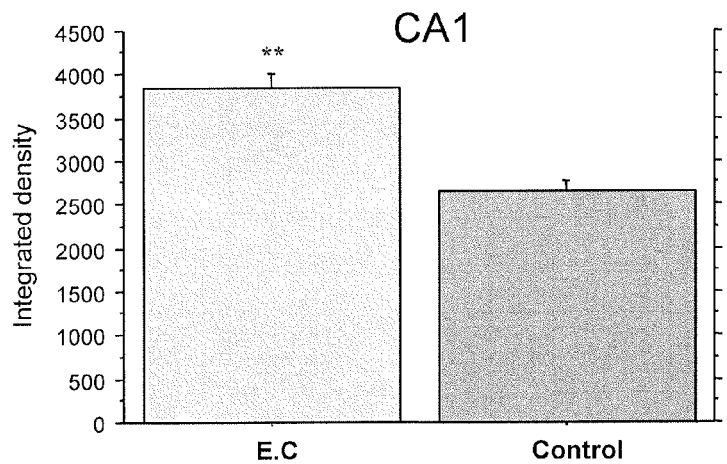

Figure 5. The mean ± SEM for the Integrated density of FGF-2 mRNA expression.
Two way -ANOVA revealed an effect of E.C. vs Control Group;
E.C. animals had an increase in the mRNA expression of FGF-2 ( ***P<.0001)

*E.C. animals had a significant increase in the Dentate Granule cell Layer Volume compared to standard controls. Correlational analyses revealed interesting interaction patterns between FGF-2 expression and Dentate Granule Cell layer Volume, suggesting that the FGF-2 may mediate neuronal plasticity in the hippocampus.*

*FIG. 22D*

DISCUSSION

The present study examined the effects of Environmental Complexity on individual differences in anxiety behavior and FGF-2 gene expression. Environmental Complexity is one of the most common models of neurobehavioral plasticity that provides reliable effects on different behaviors such as anxiety and learning. Using an animal model of individual differences in anxiety behavior, sensation seeking, we expected to see differences in the effects of E.C on typical behaviors of HR and LR animals. As expected HRs exhibited decreased anxiety behavior compared to LRs. On the other hand while E.C. reduced anxiety in the LR it also enhanced the risk taking behavior of HRs. This results were also accompanied by an increase in FGF-2 gene expression in the Dentate Gyrus, CA3 and CA1 regions of the Hippocamapus. The effects on FGF-2 gene expression seemed to favor mostly the LRs and to a lesser extent the HRs. These results suggest that FGF-2 may in part play role in the in reducing anxiety-like behavior in the LR animals, while a saturation effect may have explained the small gene expression changes seen in the HR. On the other hand animals that were exposed to E.C. also had an increase in the Volume of the Dentate granule Cell layer. Correlational analyses further revealed that FGF-2 gene expression may benefit E.C. animals via an enhancement in granule cell layer plasticity. Animals that had a greater FGF-2 gene expression had greater volume in the granule cell layer. The following results suggest that the FGF-2 may be factor in reducing anxiety like behavior and that its mechanism of action may involve effects on neuronal plasticity.

CONCLUSIONS

- HRs exhibit decreased anxiety compared to LRs.
- E.C reduces anxiety in both in HR and LR, yet individual differences are still well maintained.
- E.C increases FGF-2 gene expression in the Dentate Gyrus and CA3 in the LRs, while FGF-2 is increased in the CA1 region of both HR and LR animals.
- E.C. increases Dentate granule cell layer volume, an effect that positively correlates with FGF-2 gene expression.

REFERENCES

1,

2,

3, Kabbaj M, Devine D, Savage V and Akil H. *Journal of Neuroscience* 20(18): 6983-6988, 2000.

Effects of Postnatal FGF-2 Administration on Neurogenesis, Emotionality and Gene Expression in Adult Rats

Cortney A. Turner, Ceylan Isgor, Simon J. Evans, Charles R. Neal, Jr., Huda Akil & Stanley J. Watson
Mental Health Research Institute, Department of Psychiatry
University of Michigan, Ann Arbor, MI, 48109

353.12

ABSTRACT

Recent microarray findings in human postmortem tissue have pointed to significant changes in the FGF system in severe depression (Evans et al., under review). These results have suggested a potential role of the FGF system in the control of mood and emotions. We tested the hypothesis that neonatal administration of FGF-2 may alter emotionality, as well as neurogenesis and gene expression in the hippocampus. Sprague-Dawley rats were injected with either vehicle or FGF-2 (20ng/g, s.c.) on postnatal day 2. Three weeks after injection we evaluated dentate gyrus volume and cell counts by Nissl staining. We also assessed neurogenesis by BrdU and Ki-67 immunohistochemistry. As adults, we tested locomotor activity, anxiety behavior and learning and memory. Animals were sacrificed, and the brains collected for *in situ* hybridization. Results to date have shown the following: FGF-2 injected rats exhibited a 10.5% increase in dentate gyrus volume. When tested as adults, a single neonatal exposure of FGF-2 significantly increased locomotor activity over controls in a novel environment. Increased activity in response to novelty has been associated with a host of other measures including decreased anxiety-like behavior. Adult rats that received FGF-2 as neonates also performed significantly better than controls in the Morris water maze. These results indicate long-term alterations in hippocampal volume, emotional reactivity and learning and memory after a postnatal FGF-2 injection. Whether or not these changes also correlate with alterations in neurogenesis and/or gene expression is currently being determined. These findings provide evidence supporting the hypothesis that the FGF system may play a role in mood disorders. *Supported By: The Pritzker Neuropsychiatric Disorder Research Consortium Fund and NIMH Program Project Grant #MH42251-01.*

"Several of the authors (including the senior authors) are members of the Pritzker Neuropsychiatric Disorders Research Consortium which is supported by the Pritzker Family Philanthropic Fund. A shared intellectual property agreement exists between the Pritzker Family Philanthropic Fund and all the universities involved in the Pritzker Consortium, in order to encourage the development of appropriate findings for research and clinical applications".

*FIG. 23A*

INTRODUCTION

Previous studies in our lab have found several members of the FGF system (FGF1, FGF2, FGFR2, FGFR3) to be downregulated in individuals with major depressive disorder in several brain regions.

Furthermore, anti-depressants have been shown to increase FGF2 mRNA levels.

The FGF system has been shown to promote cell proliferation, differentiation and survival and improve learning and memory in rodents.

Previously, early postnatal FGF2 administration has been shown to increase dentate gyrus volume, total cell counts and cell survival three weeks post-injection, however not much is known about long-lasting changes in the adult animal.

We sought to assess differences in behavior, neurogenesis, morphology, and gene expression in the adult rat after neonatal injection of FGF2.

METHODS

Sprague-Dawley rats were injected with either vehicle or rhFGF2 (20ng/g, s.c.) at PD2 and allowed to grow to adulthood.

Adult rats were then assessed for locomotor behavior, anxiety-like behavior (EPM, LD), depression (FST, SD), and learning and memory (MWM).

Adult rats were also assessed for differences in volume, total number of cells, cell proliferation, numbers of glia and numbers of neurons in the dentate gyrus.

Finally, adult rats were sacrificed one week after locomotor testing and assessed for differences in FGF2, FGF9, FGFR1, MR and GR mRNA levels in the hippocampus by in situ hybridization.

FIG. 23B

RESULTS
Locomotion
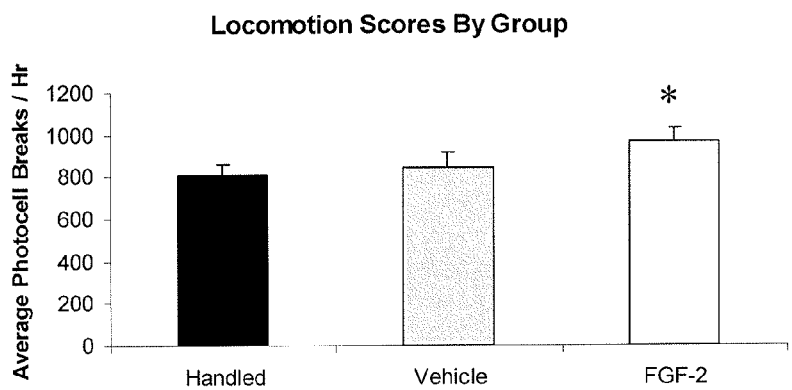
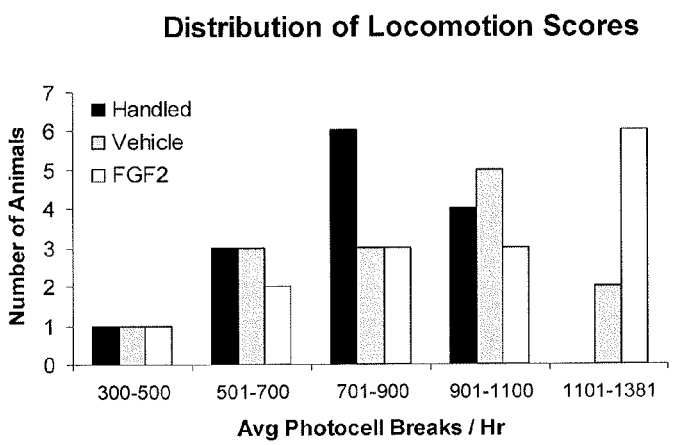
*FGF2 animals exhibited significantly higher levels of locomotor activity in a novel environment, an index of lower anxiety.*
FIG. 23C

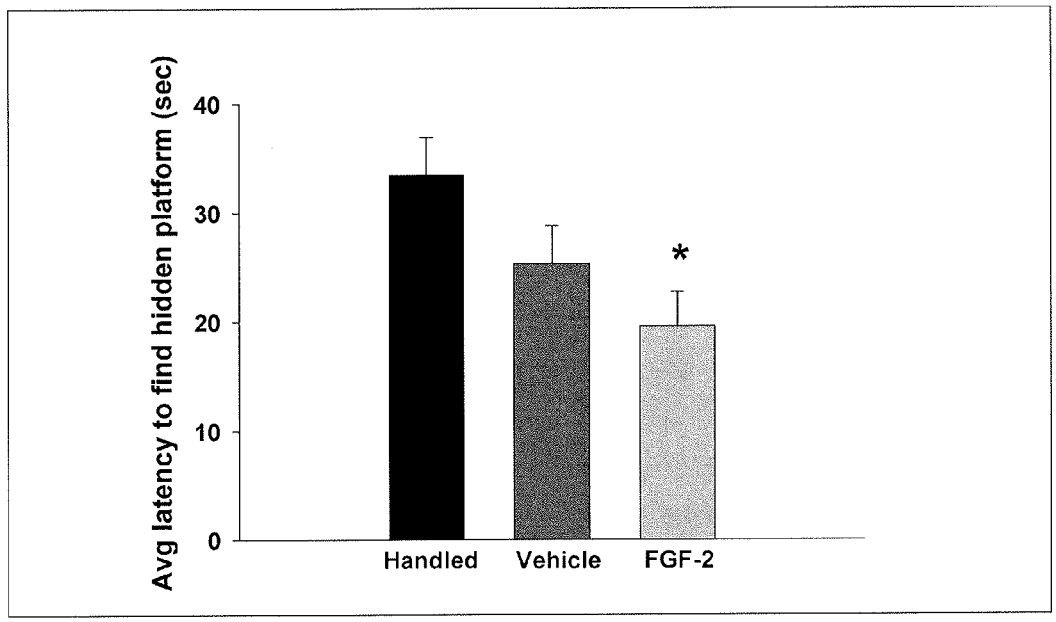
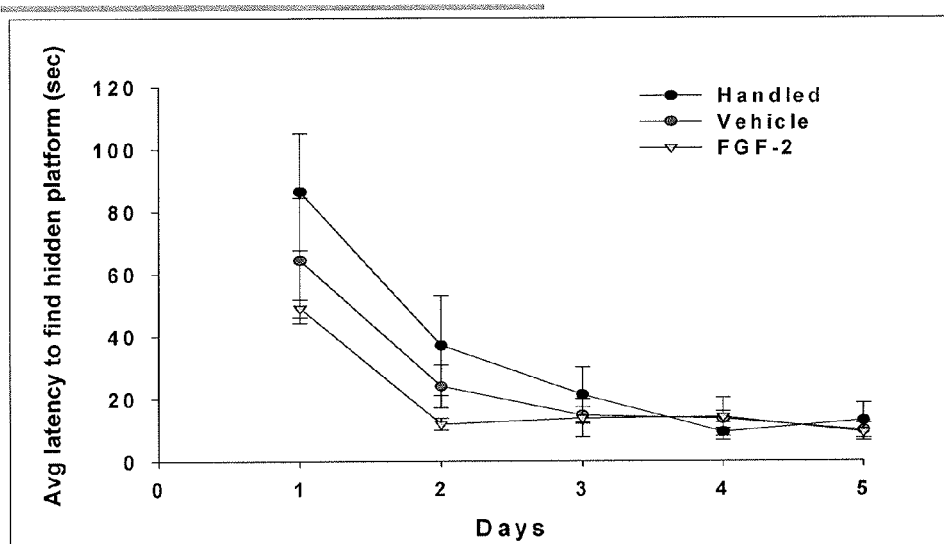
*FGF2 animals performed significantly better on a learning and memory task, an effect evident from the second trial.*
FIG. 23D

CELL PROLIFERATION
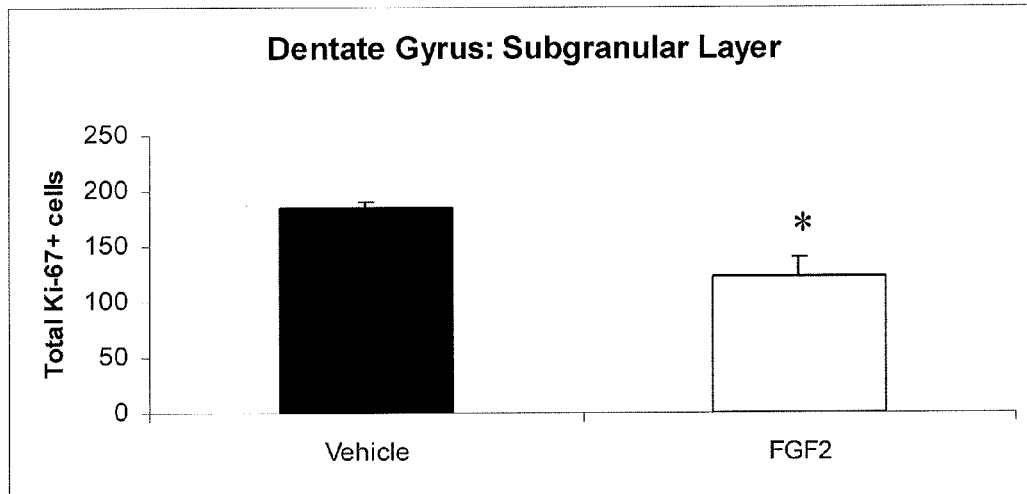
*FGF2 animals had significantly less cell proliferation than controls in the dentate gyrus.*
Cell Density
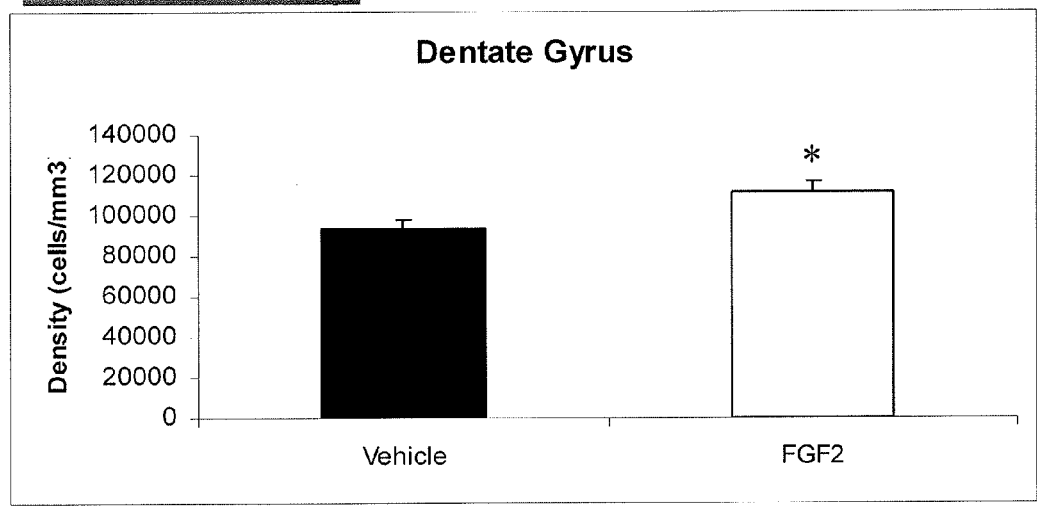
*FGF2 animals had a significantly higher cell density in the dentate gyrus than controls.*
FIG. 23E

*FGF2 animals had significantly more neurons in the dentate gyrus than controls.*

DISCUSSION

Behavior: As adults, FGF2 animals exhibited significantly higher levels of locomotor activity in a novel environment than controls, an index of lower anxiety levels. The FGF2 group also performed significantly better on a learning and memory task than controls. There were no differences, however, on tests of anxiety or depression.

Morphology: As adults, FGF2 animals showed significantly increased cell density in the dentate gyrus than controls. The FGF2 group also showed significantly more neurons in the dentate gyrus, and significantly less cell prolieration than controls. (Higher locomotion animals have previously been shown to exhibit lower levels of cell prolieration.) There were no significant differences in numbers of glial cells, total cells or volume of the dentate gyrus.

Gene expression: There were no differences between FGF2 animals and controls in the levels of either FGF2, FGF9, FGFR1, MR or GR in any areas of the hippocampus.

In conclusion, the effects of early FGF2 administration results in hyperactivity in a novel environment, better learning and memory, less cell proliferation, more neurons and a higher cell density in the dentate gyrus in the adult animal.

These results may suggest a leftward shift in the timing of neurogenesis and dentate gyrus development after neonatal FGF2 administration.

*FIG. 23H*

 *GABA/Glutamate Signaling Pathways in Bipolar and Major Depressive Disorders* 

P.V. Choudary[1,*]; J.Z. Li[4]; H. Tomita[4]; M. Molnar[1]; S.J. Evans[4]; M.P. Vawter[3]; J.F. Lopez[4]; C.R. Neal[4]; J.D. Stead[4]; R.C. Thompson[4]; R.M. Myers[2]; W.E. Bunney, Jr[3]; H. Akil[4]; S.J. Watson[4]; E.G. Jones[1].
1. Ctr. Neurosci., Univ. California, Davis, CA; 2. Human Genome Ctr., Stanford Univ., Stanford, CA; 3. Psychiatry, Univ. California, Irvine, CA; 4. Mental Hlth. Res. Inst., Univ. Michigan, Ann Arbor, MI.

799.13

ABSTRACT:

To understand the pathophysiology of the mood disorders, bipolar affective disorder (BPD) and major depressive disorder (MDD), we have compared gene expression profiles of patients and healthy subjects. Total RNA samples from four different regions, i.e., the anterior cingulate cortex (AnCg), dorsolateral prefrontal cortex (DLPFC), amygdala (Amy) and hippocampus (HC), of postmortem brains were each probed with Affymetrix high-density oligonucleotide microarrays. Analysis of duplicate datasets using the probe level model (PLM) and GCRMA showed signal transmission as a prominent biological process with a distinctly altered gene expression pattern. BPD and MDD both showed a trend of upregulation of genes encoding various subunits of GABA receptors and glutamate receptors. Some members of the solute carrier superfamily of genes also showed altered expression levels, indicating impaired small molecule transport and selective neurotransmitter reuptake. The results, together with altered energy metabolism, cell cycle and growth, stress, and apoptosis functions, suggest a possible impairment of GABA and glutamate signaling pathways in mood disorders. Validation of a subset of candidate genes is underway using quantitative real time PCR (qRT-PCR) and in situ hybridization histochemistry (ISHH) analyses. Confirmation of our findings will lend support to the brain-based models of depression, provide insights into the involvement of various regions in mood disorders, and define novel pharmacological targets.

INTRODUCTION:

The mood disorders, BPD and MDD, are highly prevalent and heterogeneous group of neuropsychiatric illnesses, affecting an estimated 121 million people worldwide. By comparing region-wise gene expression profiles of the postmortem brains of depressed individuals and unaffected individuals, we have identified several candidate genes. Gene Ontology (GO) annotation, followed by validation by other techniques, e.g., qRT-PCR and ISHH or by results of published studies using other approaches, e.g., imaging or whole genome scan analysis, allowed identification of biological processes corresponding to specific subsets of these candidate genes. The fibroblast growth factor (FGF) system is an example of the biological processes we thus found to be impaired in MDD (see 114.10; Evans et al, 2004). The other affected pathways include: G-protein signaling (799.16); mitochondrial function (799.20); and GABA/ glutamate signaling pathways, which is the subject of this poster.

*FIG. 24A*

METHODS:

- The brain tissue was obtained from depressed subjects (diagnosed according to DSM-IV criteria) and unaffected control individuals, matched by sex, age and agonal state. Patient data on the cause(s) of death, smoking history, medication history, agonal state, and postmortem interval were recorded (see Walsh et al, 799.17). Brains were collected at autopsy, stored, and dissected as previously described (Jones et al, 1992).
- pH of the phosphate-buffered saline extracts of 1-inch (diameter) tissue blocks punched out from randomly selected brain slices of postmortem brains was monitored. Total RNA was extracted from snap-frozen postmortem brain slices using Trizol reagent according to vendor's instructions (see Atz et al, 799.6; Vawter et al, 799.20).
- Ten-microlitre aliquots of each total RNA sample were simultaneously interrogated at two or three different laboratories (of the Consortium) with Affymetrix GeneChips, HG_U133 set or U133 plus 2.0, and scanned using GeneChip scanner 2500, following manufacturer's protocols. This step provided us with chip replicates.
- Data from chip replicates were inspected (see Atz et al, 799.6) and those passing the QC criteria (Li et al, 2004; Tomita et al, 2004), were analyzed as described below (see Evans et al, 144.10).

DATA ANALYSIS:

CEL files created from the DAT files were normalized and condensed to signal intensity values using the GCRMA algorithm (Wu and Irizarry, 2004) and a custom-designed CDF mapping file, available at (http://brainarray.mhri.med.umich.edu/brainarray). The custom CDF file was designed to assign all probes to Unigene clusters based on the latest UniGene Build, thus removing probe set redundancy. Output from GCRMA was imported into Partek software for statistical analysis, which used a multi-variate mixed model ANOVA, using processing site, batch (cohort) and diagnosis as factors. Post-hoc tests were run simultaneously to evaluate expression differences between MDD and controls or BPD and controls. Genes from each of the target regions showing a p-value of <0.05 and a fold change of => 1.2 were selected as up-regulated candidates and those with a fold change of <= 0.83 as down-regulated candidates, respectively. The candidate genes were annotated using Gene Ontology (GO) terms for biological processes, molecular functions and cellular components (www.geneontology.org). Individual genes of the biological process were cataloged and analyzed for their involvement in each of the regions for region-specific role(s) and for concordance or discordance in expression patterns.

CANDIDATE GENE VALIDATION:

Candidate genes were validated using qRT-PCR as described (Li et al, 2004) and *in situ* hybridization histochemistry (Molnar et al, 2003).

*FIG. 24B*

- All three limbic structures examined in MDD were consistent in their pattern of decreased expression of EAAT1 (glutamate transporter-1/SLC1A3).
- Decreased glutamate reuptake activity can result in rapid buildup of extracellular glutamate levels.
- Extracellular accumulation of glutamate can impair the termination of glutamatergic transmission.

2. Decreased glutamate transporter-1 and glutamine synthetase expression in MDD converge in AnCg and Amy

| Gene | Symbol | MDD Fold Change | |
|---|---|---|---|
| | | AnCg | Amy |
| Glu transporter-1 | EAAT1 | 0.71 | 0.81 |
| Glu transporter-2 | EAAT2 | 0.65 | |
| Gln synthetase | GLUL | 0.72 | 0.86 |

- ❖ Both AnCg and Amy in MDD showed a concurrent decrease of EAAT1 and GLUL, while AnCg additionally showed decreased levels of EAAT2.
- ❖ These results indicate impairment of the glutamate reuptake system as well as a glutamate detoxification mechanism.
- ❖ HC involvement was limited to EAAT1 decrease.
- ❖ Collectively, these results predict the limbic system, especially AnCg and Amy, as a seat of glutamate transport dysfunction in MDD.

*FIG. 24D*

4. Increase of 3 different GABA-A receptor subunits in DLPFC may enhance inhibitory signaling in MDD

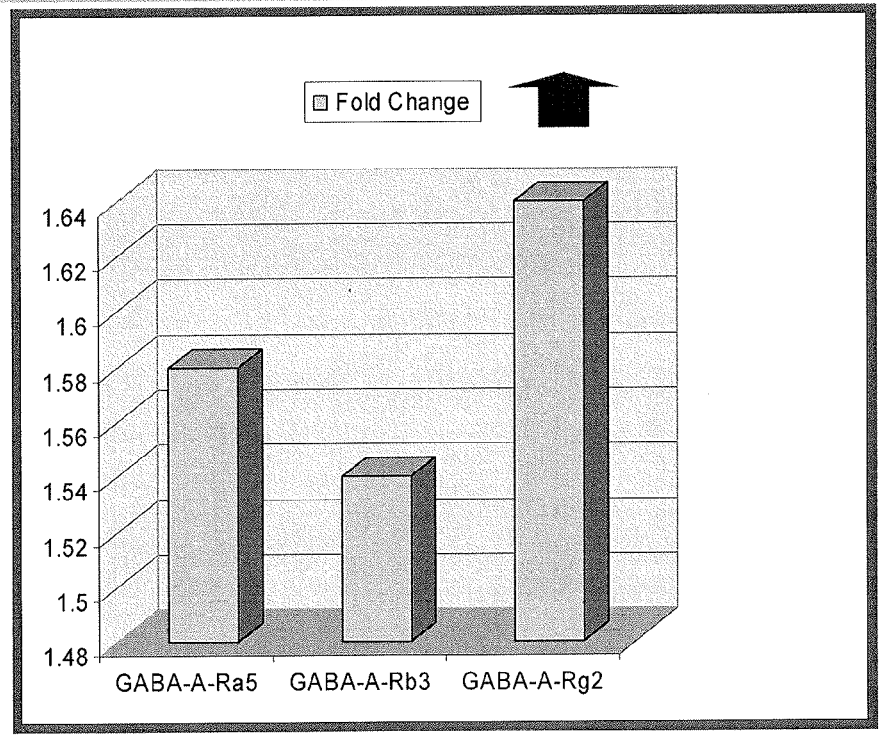

- Concurrent upregulation of 3 of the 5 subunits of GABA-A receptor, i.e., α5 (a5), (β3) (b3) and γ2 (g2) suggests likely involvement of the GABA signaling pathway in MDD.
- Both GABA-A-Rα5 and GABA-A-Rβ3 map to the same locus, 15q11.2.
- This supports previous implication of GABA-A-Rα5 in MDD.
- Note the relatively higher levels of expression of GABA-A-Rγ2 than the rest.

*FIG. 24F*

5. *In situ* hybridization: GABA-A-Rα5 expression is increased in both AnCg as well as DLPFC in BPD and in DLPFC in MDD

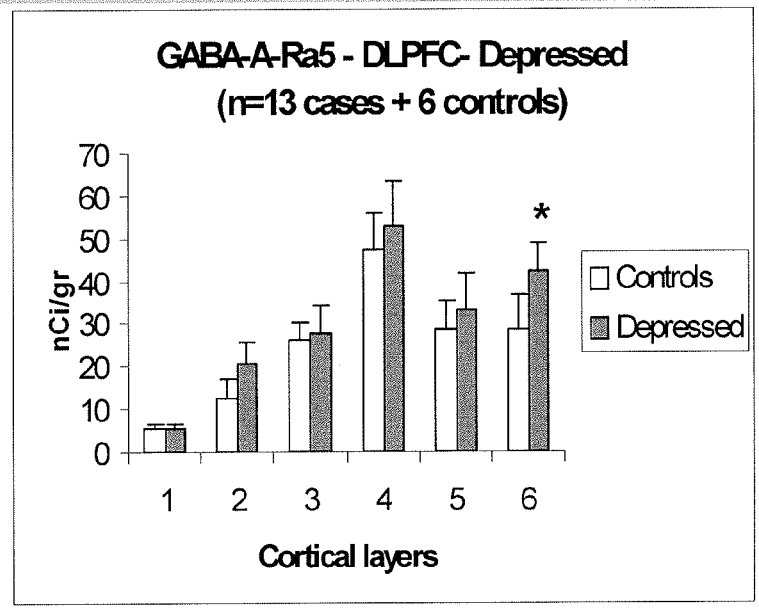

- ❖ Note the trend toward an increase of the GABA-A-Rα5 mRNA levels in all cortical layers, except layer 1. The increase was statistically significant in layer 6, as determined by the two-tailed paired t-test analysis ($p \leq 0.02$).
- ❖ The direction and magnitude of change were confirmed by qRT-PCR (results not shown).

*FIG. 24G*

6. Differentially expressed GABA/ glu signaling genes were relatively larger in number and wider in regional distribution in MDD than in BPD (a) GABA/ Glu genes: number and distrubution patterns

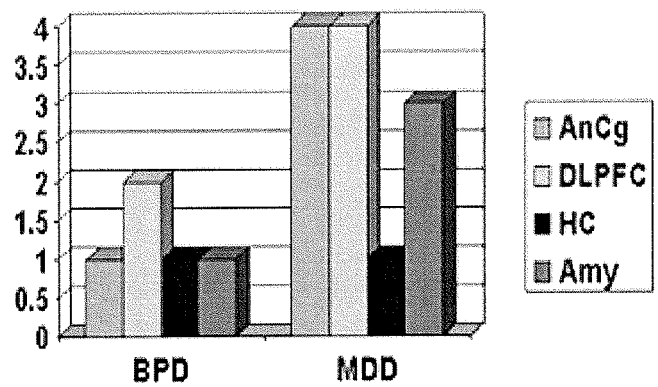

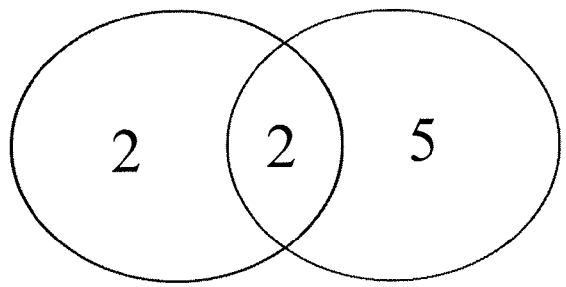

(b)

- In both disorders, GABAergic genes were upregulated and glutamate transporter genes were downregulated (with the exception of mGluR3).
- Overall, GABA/ glutamate signaling system impairment was pronounced in MDD (Fig. 6a).
- Out of the nine GABA/glutamate genes that were affected in depressed individuals, only two (1 GABAergic and 1 glutamatergic) genes were common between BPD and MDD (Fig. 6b).

*FIG. 24H*

SUMMARY OF RESULTS:

1. GABA/glutamate signaling system displayed differential expression of a large number of genes, encoding three GABA-A receptor subunits ($\alpha 5$, $\beta 3$, and $\gamma 2$) and two glial glutamate transporters (EAAT1 and EAAT2), in MDD.

2. By comparison to MDD, the involvement of BPD was limited to a select few of the genes of the GABA/ glutamate system, i.e., GABA-A-R$\alpha$5, mGluR3 and EAAT1.

3. The impairment of GABA/ glutamate signaling pathways in MDD spanned across most of the limbic areas examined, i.e., AnCg, HC and Amy.

4. In contrast, the differential expression in BPD was sparse, with EAAT1 restricted to HC, mGluR3 to DLPFC, and GABA-A-R$\alpha$5 to DLPFC and AnCg, but none spanning the limbic system.

5. The meagre overlap of BPD with MDD was in the up-regulated genes, encoding the subunits of GABA and glutamate receptors, which comprise the major segment of its differential expression.

6. Out of a total of 9 GABA/glutamate system genes that were differentially expressed, only two were shared between BPD and MDD.

CONCLUSIONS:

* Signal transmission is likely significantly altered in mood disorders - MDD and BPD - due to impaired small molecule transport and selective neurotransmitter reuptake mechanisms.
* Concerted down-regulation of glutamate reuptake function and glutamate detoxification - spread across the limbic system, with concomitant increase in GABAergic inhibitory action, has "excitotoxic" implications for the pathophysiology of MDD, and a comparatively milder effect on BPD.
* Mood disorders share select combinations of various elements of the GABA/glutamate signaling impairment with disparate diseases, including schizophrenia, Lou Gehrig's disease, Alzheimer's disease, Huntington's disease, and Parkinson's disease (Maragakis and Rothstein, 2004).
* Our study provides new insights into the pathophysiology of mood disorders and the involvement of various brain areas in the disease process.
* Further studies validating our findings could provide new therapeutic targets in the form of specific molecules/pathways identified in this study or their functional relatives.

*FIG. 24I*

REFERENCES:

1. Evans SJ et al. Dysregulation of the fibroblast growth factor system in major depression. Proc Natl Acad Sci USA 101: 15506–15511.
2. Jones EG et al. A method for fixation of previously fresh-frozen human adult and fetal brains that preserves histological quality and immunoreactivity. J Neurosci Methods 44: 133-44, 1992.
3. Li J et al. Systematic changes in gene expression in postmortem human brains associated with tissue pH and terminal medical conditions. Human Molecular Genetics 13: 609-616.
4. Maragakis NJ, Rothstein JD. Glutamate transporters: animal models to neurologic disease. Neurobiol Dis. 15: 461-73, 2004.
5. Molnar M et al. mRNA expression patterns and distribution of white matter neurons in dorsolateral prefrontal cortex of depressed patients differ from those in schizophrenia patients. Biol Psychiatry 53: 39-47, 2003.
6. Tomita H et al. Effect of agonal and postmortem factors on gene expression profile: quality control in microarray analyses of postmortem human brain. Biological Psychiatry 55: 346-352.
7. Wu Z, Irizarry. Preprocessing of oligonucleotide array data. Nature Bio/Technology 22: 656-658, 2004.

ACKNOWLEDGEMENTS:

We gratefully acknowledge the valuable contributions of Xiaohong Fan, Phong Nguyen and Malalai Yusufzai of UCD; Sharon Burke, Mary Hoversten, Fan Meng, and Manhong Dai of UMICH; David Walsh, Mary Atz, Kevin Overman, and Preston Cartenaga of UCI; the Orange County (CA) Coroner's office; Terrence Speed, Ben Bolstad and Julia Brettschneider of UCB; and all the other members of the Pritzker Neuropsychiatric Disorders Research Consortium. Funding for this work was provided by the Pritzker Family Philanthropic Fund\*, NIH Conte Center grant #L99MH60398, WM Keck Foundation and Penzner Foundation.

*CONFLICT OF INTEREST STATEMENT:

All the authors of this work are members of the Pritzker Neuropsychiatric Disorders Research Consortium, supported by the Pritzker Family Philanthropic Fund. To encourage development of further research and clinical applications of the present findings, patent applications have been filed jointly by the academic and philanthropic entities involved, under a shared intellectual property agreement.

\*Correspondence to: <pvchoudary@ucdavis.edu>; <egjones@ucdavis.edu>

*FIG. 24J*

NCAM1 Genetic Polymorphisms And Association With Bipolar Disorder
M. Vawter[1#]; M. Atz[1]; B. Galke-Rollins[1]; K. Cooper[1]; K. Overman[1]; H. Tomita[1]; W. Byerley[2]
[1] Psychiatry, University of California, Irvine, CA, USA. [2]Psychiatry, University of California, San Francisco, CA, USA. # And *Other Pritzker Consortium Members.

Abstract

NCAM1 is involved in multiple neural functions such as synaptic plasticity, neurodevelopment, memory, long-term potentiation, and neurogenesis. The brain expressions of NCAM1 isoforms are differentially altered in bipolar disorder and in schizophrenia [reviewed in Vawter, M., Eur J Pharmacol. 2000 Sep 29;405(1-3):385-95]. Recently, several single nucleotide polymorphisms were significantly associated with bipolar disorder in the Japanese population [Arai, M. et al., Biol Psychiatry. 2004 Apr 15;55(8):804-10.]. We are conducting a case-control study of bipolar disorder from samples of northern European descent using the same SNPs reported to be associated with bipolar disorder. A second question is whether any alternative splicing mechanisms might be associated with bipolar disorder risk within the NCAM1 gene. We report results of the SNP association study and alternative splicing in bipolar disorder.

*FIG. 25A*

Methods

- Brain collection, RNA extraction and cDNA synthesis.
    - Human postmortem brain tissue was acquired with consent from the decedents' next-of-kin.
    - Total RNA was extracted from human post-mortem dorsalateral prefrontal cortex (DLPFC) brain tissue using Trizol (Invitrogen)
    - cDNA was synthesized using Taqman Reverse Transcription Reagents (Applied Biosystems).

- Primer design, PCR, band purification and sequencing
    - Primers were designed for each DNA segment and possible combination of splice variants (a, b, c, and SEC) exons using Applied Biosystems Primer Express software (ABI).
    - PCR was analyzed on an Aglient 2100 Bioanalyzer using the DNA 500 LabChip Kit to confirm the correct base pair size.
    - The product was also visualized by agarose gel electrophoresis and the band of correct size was purified using a GFX PCR DNA and Gel Band Purification Kit (Amersham Biosciences) and then sequenced to confirm the correct exon was amplified.
    - Primers where then used in various combinations to amplify each possible splice varian and using the Bioanalyzer to quantitate peak height and areas, 13 controls, 8 bipolar, and 10 major depressive cases were analysed.

- DNA extraction and SNP analysis (sequencing and TaqMan)
    - Genomic DNA was extracted from human postmortem cerebellum tissue following a Trizol (Invitrogen) extraction and ethanol precipitation protocol.
    - Primers were designed for SNP9 and the cerebellum gDNA of 40 patients (20 controls, 9 BPDs and 11 MDDs) were sequenced with both the forward and reverse primers.
    - A Taqman Genotyping Assay (ABI) was also used for SNP9 (Assay ID: c_2998872_20) allele calls with the Allelic Determination program (ABI 7000 sequence detection system). The remaining 3 SNPs (SNP6: c_613361_20, SNP b: c_2998870_1 and SNP c: c_2998868_10) were genotyped on the ABI 7000 Taqman machine using pre-designed kits from ABI.
    - The genotypes were collected on an additional 30 bipolar genomic DNA samples from lymphocytes for all 4 SNPs.

- Quantitative RT-PCR Using SybrGreen
    - The total amounts of secreted exon (SEC), NCAM1, and VASE were determined by real time quantitative PCR (Q-PCR) reactions.

*FIG. 25B*

Demographics for Splicing Study

DLPFC

| Diagnosis | Gender (M/F) | Age AVG (STDev) | PMI AVG (STDev) |
|---|---|---|---|
| Control n=13 | 11/2 | 48.2 (17.6) | 21.3 (6.3) |
| BPD n=8 | 5/3 | 52.0 (17.9) | 16.6 (8.9) |
| MDD n=10 | 7/3 | 48.5 (13.51) | 23.98 (4.5) |
| Total n=31 | 23/8 | 49.2 (17.7) | 19.1 (7.4) |

CB

| Diagnosis | Gender (M/F) | Age AVG (STDev) | PMI AVG (STDev) |
|---|---|---|---|
| Control n=20 | 13/7 | 52.6 (16.5) | 22.3 (7.0) |
| BPD n=9 | 6/3 | 53.9 (17.7) | 16.8 (8.3) |
| MDD n=11 | 7/4 | 50.7 (14.8) | 23.9 (4.3) |
| Total n=40 | 26/24 | 52.6 (16.5) | 22.3 (7.0) |

*FIG. 25C*

Genetic Structure of Human NCAM1

SEC NCAM Splice Variants

|     | a–b | a–c | a–b–c | a–sec | b–c | b–sec | a–c–sec | b–c–sec | c–sec |
|-----|-----|-----|-------|-------|-----|-------|---------|---------|-------|
| C1* | X | X | X | X | X | X | 0 | X | X |
| C2  | X | X | 0 | X | X | X | 0 | X | X |
| C3  | X | X | X | 0 | X | X | 0 | X | X |
| C4  | X | X | 0 | 0 | X | X | 0 | 0 | X |
| C5  | 0 | 0 | 0 | X | X | X | 0 | 0 | X |
| C6  | X | X | X | X | X | X | 0 | 0 | X |
| C7  | X | X | 0 | 0 | X | X | 0 | X | X |
| C8  | X | X | 0 | 0 | X | X | 0 | 0 | X |
| C9  | X | X | 0 | X | X | X | 0 | 0 | X |
| C10 | X | X | 0 | X | X | X | 0 | X | X |
| C11 | X | X | 0 | X | X | X | 0 | X | X |
| C12 | X | X | X | X | X | X | 0 | X | X |
| C13 | X | X | 0 | X | X | X | 0 | X | X |
| BP1 | X | X | X | 0 | X | X | 0 | 0 | X |
| BP2 | X | X | 0 | 0 | X | X | 0 | X | X |
| BP3 | X | X | 0 | X | X | X | 0 | X | X |
| BP4 | X | X | 0 | X | X | X | 0 | X | X |
| BP5 | 0 | 0 | 0 | X | X | X | 0 | 0 | X |
| BP6 | X | X | 0 | 0 | X | X | 0 | X | X |
| BP7 | X | X | 0 | X | X | X | 0 | X | X |
| BP8 | X | X | 0 | 0 | X | X | 0 | X | X |
| MDD1 | X | X | 0 | X | X | X | 0 | X | X |
| MDD2 | X | X | 0 | X | X | X | 0 | X | X |
| MDD3 | X | X | X | X | X | X | 0 | 0 | X |
| MDD4 | X | X | X | 0 | X | X | 0 | X | X |
| MDD5 | X | X | 0 | X | X | X | X | X | X |
| MDD6 | X | X | 0 | 0 | X | X | 0 | X | X |
| MDD7 | X | X | 0 | 0 | X | X | 0 | X | X |
| MDD8 | X | X | 0 | X | X | X | 0 | X | X |
| MDD9 | X | X | 0 | 0 | X | X | 0 | X | X |
| MD10 | X | X | 0 | 0 | X | X | 0 | X | X |

* C=Control, BP=Bipolar disorder and MDD=Major depressive disorder

*FIG. 25F*

SEC exon and mini-exons a, b, c Splice Variant Algorithm in DLPFC

The NCAM SEC exon is spliced in 100% of the time with mini-exon b.
The NCAM SEC exon is spliced in 100% of the time with mini-exon c.
The NCAM SEC exon is spliced out 90-100% with introduction of mini-exon a to either mini-exon b or mini-exon c.
Mini-exons b or c result in a truncated NCAM1 protein that can be secreted.
Mini-exon 'a' turns out to be pivotal for intact versus truncated NCAM1.

- If a, then 50% chance of SEC exon+ or SEC exon-.
- If a with b or c, then 92-96% chance NCAM SEC exon is spliced out.
- If a with b and c, then 92% chance of SEC exon is spliced out.

*FIG. 25G*

NCAM SNP Genotype Bipolar And Controls

| SNP 9 | Control | All BP |
|---|---|---|
| C/C | 14 | 17 |
| C/A | 6 | 12 |
| A/A | 0 | 0 |

| SNP 6 | Control | All BP |
|---|---|---|
| G/G | 2 | 7 |
| G/C | 11 | 5 |
| C/C | 7 | 17 |

| SNP Exon b | Control | All BP |
|---|---|---|
| T/T | 5 | 8 |
| T/C | 10 | 18 |
| C/C | 5 | 3 |

| SNP Exon c | Control | All BP |
|---|---|---|
| G/G | 4 | 5 |
| G/A | 16 | 24 |
| A/A | 0 | 0 |

*FIG. 25H*

LD (r²) from Ensembl.org

Genotype and Splice Variant
(significant p-values shown)

| SNP | Genotype | Splice Variant | BP vs C | M vs C | BP&MDD vs C |
|---|---|---|---|---|---|
| SNP9 | C/A | a-b-c | 0.028 ↓ | | |
| SNP9 | C/A | c-sec | 0.017 ↑ | | |
| SNP9 | C/A | c-sec | | | 0.026 ↑ |
| SNP9 | C/A | b-c | | | 0.019 ↑ |
| SNP6 | C/C | a-sec | | 0.035 ↓ | |
| Exon c | G/A | c-sec | | 0.043 ↑ | |

Normalized Q-PCR Results

| | BP vs C | MDD vs C | BP vs MDD |
|---|---|---|---|
| NCAM | | 0.005 ↓ | |
| SEC | | | 0.032 ↑ |
| VASE | 0.033 ↓ | | |

*FIG. 25J*

Conclusions

- The SEC exon which can lead to truncation and secretion of NCAM in the brain was clearly regulated by certain combinations of mini-exons.

- The difference in splice variants relative amounts is related to certain genotypes.

- The mini-exons are not in strong LD even though <1000 bp apart.

- Genotype frequency in bipolar disorder for SNP 9 shows a trend for over transmission of the C allele in bipolar disorder similar to the association study of bipolar disorder in Japan (Arai et al., 2004).

- Subjects of northern European extraction do not show LD among SNPs 6 and 9 as published by Arai et al., 2004.

- Taken together, the simplified splicing rules and associations with genotypes promote a rich variation in the amount of secreted NCAM available in the brain.

- Variations in secreted NCAM could function similar to cleaved NCAM (Vawter et al., 2000) in that non-tethered NCAM can easily interact with other extracellular molecules tenascin and L1 and receptors such as the FGF and AMPA receptors. These molecules can form assemblies within the membrane for long term potentiation and synaptic plasticity, or assemblies between different cells to guide cellular migration and neurogenesis. These functional differences may be important mediators in the synaptic deficits found in neuropsychiatric illness.

FIG. 25K

References

Arai M, Itokawa M, Yamada K, Toyota T, Arai M, Haga S, Ujike H, Sora I, Ikeda K, Yoshikawa T (2004) Biol Psychiatry 55(8):804-10.

Hamshere M, Dickson G, Eperon I (1991) Nucleic Acid Research 19(17):4709-4716.

Holst BD, Vanderklish PW, Krushel LA, Zhou W, Langdon RB, McWhirter JR, Edelman GM, Crossin KL. (1998) Proc Natl Acad Sci U S A. 95(5):2597-602.

Neiiendam JL, Kohler LB, Christensen C, Li S, Pedersen MV, Ditlevsen DK, Kornum MK, Kiselyov VV, Berezin V, Bock E. (2004) J Neurochem. 91(4):920-35.

Vawter MP, Howard AL, Hyde TM, Kleinman JE, Freed WJ (1999) Mol Psychiatry 4(5):467-75.

Vawter MP (2000) Eur J Pharmacol 405(1-3):385-95.

Acknowledgements

* We wish to acknowledge the following members of the Pritzker Neuropsychiatric Disorders Research Consortium for providing postmortem brain samples and RNA for this study: David Walsh, Psy.D.[1], Preston Cartagena, Psy.D.[1], Richard A. Stein, Ph.D.[1], Steven G. Potkin, M.D.[1], Jun Li, Ph.D.[2], Rick Myers, Ph.D.[2], Edward G. Jones, M.D., Ph.D.[3], Stanley J. Watson, M.D., Ph.D.[4], Huda Akil, Ph.D.[4], Simon Evans, Ph.D.[4], Prabha Choudary, Ph.D.[3] and William E. Bunney, Jr., M.D.[1]

[1] Department of Psychiatry and Human Behavior, College of Medicine, University of California, Irvine, California, USA. [2] Stanford Human Genome Center and Department of Genetics, Stanford University School of Medicine, Stanford, California, USA. [3] Center for Neurosciences, University of California, Davis, Davis, California, USA. [4] Mental Health Research Institute, University of Michigan, Ann Arbor, Michigan, USA.

All of the authors are members of the Pritzker Neuropsychiatric Disorders Research Consortium, which is supported by the Pritzker Neuropsychiatric Disorders Research Fund L.L.C. A shared intellectual property agreement exists between this philanthropic fund and the University of Michigan, the University of California, and Stanford University to encourage the development of appropriate findings for research and clinical applications. The research was funded by The National Institute of Mental Health (NIMH) Conte Center Grant P50 MH60398, and the William Lion Penzner Foundation. We appreciate the assistance of Chief Deputy Coroner Jacque Berndt and staff of the Orange County Sheriff-Coroner's Office; as well as Kathleen Burke, Claudia Cervantes, and Karen Lopez. F. Warren Lovell, M.D, performed a neuropathological evaluation of the postmortem brains. Tissue specimens obtained from the Human Brain and Spinal Fluid Resource Center, VA West Los Angeles Healthcare Center, Los Angeles, CA 90073, which is sponsored by NINDS/NIMH, National Multiple Sclerosis Society, and Department of Veterans Affairs under the direction of Wallace W. Tourtellotte, M.D., Ph.D.

*FIG. 25L*

ADMINISTRATION OF FGF9 FOR TREATMENT OF ANXIETY

CROSS-REFERENCES TO RELATED APPLICATIONS

The present application is a continuation of U.S. application Ser. No. 11/158,530, filed Jun. 21, 2005, which claims priority to U.S. Application No. 60/581,998, filed Jun. 21, 2004, U.S. Application No. 60/621,252, filed Oct. 22, 2004, and U.S. Application No. 60/667,296, filed Mar. 31, 2005 each of which is incorporated herein in its entirety by reference.

STATEMENT AS TO RIGHTS TO INVENTIONS MADE UNDER FEDERALLY SPONSORED RESEARCH AND DEVELOPMENT

Not applicable.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-13-4. TXT, created on Oct. 25, 2013, 8, 192bytes, machine format IBM-PC, MS-Windows operating system, is hereby incorporated by reference in its entirety for all purposes.

BACKGROUND OF THE INVENTION

Clinical depression, including both bipolar disorders and major depression disorders, is a major public health problem, affecting an estimated 9.5% of the adult population of the United States each year. While it has been hypothesized that mental illness, including mood disorders such as major depression ("MDD") and bipolar disorder ("BP") as well as psychotic disorders such as schizophrenia, may have genetic roots, little progress has been made in identifying gene sequences and gene products that play a role in causing these disorders, as is true for many diseases with a complex genetic origin (see, e.g., Burmeister, *Biol. Psychiatry* 45:522-532 (1999)).

The current lack of biomarkers and the ineffectiveness and reliability of the diagnosis and rates are important issues for the treatment of mental disorders. For example, around 15% of the population suffers from MDD while approximately 1% suffers from BP disorders. Diagnosing bipolar disorder is difficult when, as sometimes occurs, the patient presents only symptoms of depression to the clinician. At least 10-15% of BP patients are reported to be misdiagnosed as MDD. The consequences of such misdiagnosis include a delay in being introduced to efficacious treatment with mood stabilizers and a delay in seeking or obtaining counseling specific to bipolar disorder. Also treatment with antidepressants alone induces rapid cycling, switching to manic or mixed state, and consequently increases suicide risk. Furthermore, in addition to a lack of efficacy, long onset of action and side effects (sexual, sleep, weight gain, etc.), there are recent concerns relating to the undesirable effects of ADs on metabolic syndromes, such as diabetes and hypercholesteremia.

BRIEF SUMMARY OF THE INVENTION

Relying on the discovery that certain genes expressed in particular brain pathways and regions are likely involved in the development of mental illness, the present invention provides methods for diagnosis and treatment of mental illness, as well as methods for identifying compounds effective in treating mental illness.

In order to further understand the neurobiology of mood disorders such as bipolar disorders (BP) and major depression disorders (MDD), the inventors of the present application have used DNA microarrays to study expression profiles of human post-mortem brains from patients diagnosed with BP or MDD. In one aspect, the present invention relates to differential gene expression in the Anterior Cingulate (AnCg), Dorsolateral Prefrontal (DLPFC), and Cerebellar (CB) cortices, Hippocampus, Nucleus Accumbens and Amygdala regions of the brain, wherein the differential gene expression is associated with Bipolar Disorder (BPD) and Major Depressive Disorder (MDD). Certain genes in these regions are considered "unique" to a given disorder such as BP or MDD when differentially expressed in a particular mood disorder and not another (see, e.g., Tables 3, 4, 14-20). In other cases, where the genes are differentially expressed in both BP and MDD relative to healthy controls, the genes are considered to be involved in both disorders. Expression of the differentially expressed genes may be detected using any suitable methods of detection, e.g., microarrays, PCR or in situ hybridization. Gene expression may be detected in brain tissue, brain tissue samples, or other tissue samples (e.g., blood samples in the case of NCAM1).

In one aspect, the present invention relates to differential gene expression associated with G protein-coupled receptors (GPCR)s and downstream signaling pathways, mediated by cyclic adenosine monophosphate (cAMP) and phosphatidylinositol (PI), wherein the gene expression differentially occurs in the Anterior Cingulate (AnCg), Dorsolateral Prefrontal (DLPFC), and Cerebellar (CB) cortices, Hippocampus, Nucleus Accumbens and Amygdala regions of the brains of patients with Bipolar Disorder (BPD) and/or Major Depressive Disorder (MDD), relative to healthy controls (see, e.g., Tables 14-20).

In another aspect, the present invention relates to differential gene expression associated with G protein-coupled receptors (GPCR)s and downstream signaling pathways, mediated by cyclic adenosine monophosphate (cAMP) and phosphatidylinositol (PI), wherein the gene expression differentially occurs in the Hippocampus, Nucleus Accumbens and Amygdala regions of the brains of patients with Bipolar Disorder (BPD) and/or Major Depressive Disorder (MDD), relative to healthy controls (see, e.g., Tables 18-20).

The present invention also demonstrates differential expression of the FGF pathway in the frontal cortex of MDD subjects. Particular FGF-related genes, such as FGF2, are dysregulated by antidepressant therapy, environmental complexity, and the correlation to anxiety-like behavior (see, e.g., Tables 1a, 1b, and 2, and FIGS. 1-7 and 22). The FGF pathway is also related to neurogenesis, e.g., neural stem cell proliferation and differentiation, and the genes disclosed herein can be used for diagnosis and therapeutics related to neurogenesis. Furthermore, FIG. 23 shows the effects of postnatal FGF-2 administration on neurogenesis, emotionality and gene expression in adult rats. The FGF injected animals exhibit significantly increased cell survival and proliferation in the dentate gyrus of the hippocampus. As adults, the animals show higher locomotor activity in a novel environment, an index of lower anxiety, and have better learning and memory.

The present invention also demonstrates that the genes of the glutamate/GABA signaling pathways are involved in MDD and BP (see FIG. 24 and Table 8).

The present invention also demonstrates that mitochondrial genes are involved in MDD and BP (see Table 10).

The present invention also demonstrates that 40 genes encoding growth factor family members and growth factor receptors are significantly differentially expressed in BP or MDD in the DLPFC or AnCg (see Tables 5, 6 and 7).

The present invention demonstrates that genes involved in G protein coupled receptors and their downstream signaling pathways, including cyclic AMP, phosphatidylinositol, and mitogen-activated protein kinase signaling pathways are dysregulated in BP and/or MDD (see Tables 6 and 9 and FIGS. 8-13 and 17-19).

Finally the present invention provides for the first time a novel insertion/deletion polymporphism in the phosphoserine phosphatase-like gene (PSPHL) and demonstrates that a novel deletion polymorphism of PSPHL is related to susceptibility to bipolar disorder. Therefore, detection of this polymorphism is useful for diagnosis of BP, as well as for drug discovery assays for BP therapeutics. In addition, the serine amino acid metabolic pathway, of which PSPHL is a member, is a target for drug discovery for BP therapeutics. The PSPHL gene was first cloned by Planitzer et al., *Gene* 210 297-306 (1998). The accession number for a representative nucleic acid sequence is AJ0016112 and the accession number for a representative protein sequence is CAA04865.1. See FIGS. 14-16.

The present invention demonstrates, for the first time, unique expression of the 24 nucleic acids listed in Table 3 in the brains of bipolar disorder subjects but not major depression subjects; the unique expression of the 24 nucleic acids listed in Table 4 in the brains of major depression subjects but not bipolar subjects, and the differential and/or unique expression of the nucleic acids listed in Tables 5-10 in the brains of patients suffering from bipolar disorder and major depression disorder, in comparison with normal control subjects. In addition, the present invention identifies biochemical pathways involved in uniquely or differentially in mood disorders, where the proteins encoded by the nucleic acids listed in Table 3-10 are components of the biochemical pathways (e.g., the growth factor, e.g., FGF, signal transduction pathway, GPCR signal transduction pathways, mitochondrial pathways, and glutamate/GABA signaling pathways). Furthermore, the invention demonstrates the unique expression of a PSPHL deletion polymorphism and it's associate with BP.

Genes and pathways that are uniquely or differentially expressed in MDD or BP are useful in diagnosing mood disorders and in assaying for therapeutics that can specifically treat MDD or BP, or can be used to treat both MDD and BP. Differential expression by brain region similarly is a useful diagnostic and therapeutic tool, as certain mood disorders primarily affect certain brain regions. Each brain region plays a unique and critical role in the overall phenotype of any particular mood disorder. Furthermore, because of the relationship between BP and psychotic disorders such as schizo affective disorders, the gene described herein unique to BP can also be uniquely expressed in schizophrenia, and so can be used for differential diagnosis with MDD.

This invention thus provides methods for determining whether a subject has or is predisposed for a mental disorder such as bipolar disorder or major depression disorder. The invention also provides methods of providing a prognosis and for monitoring disease progression and treatment. Furthermore, the present invention provides nucleic acid and protein targets for assays for drugs for the treatment of mental disorders such as bipolar disorder and major depression disorder.

In some embodiments, the methods comprise the steps of: (i) obtaining a biological sample from a subject; (ii) contacting the sample with a reagent that selectively associates with a polynucleotide or polypeptide encoded by a nucleic acid that hybridizes under stringent conditions to a nucleotide sequence listed in Tables 3-10 and FIG. 14; and (iii) detecting the level of reagent that selectively associates with the sample, thereby determining whether the subject has or is predisposed for a mental disorder.

In some embodiments, the reagent is an antibody. In some embodiments, the reagent is a nucleic acid. In some embodiments, the reagent associates with a polynucleotide. In some embodiments, the reagent associates with a polypeptide. In some embodiments, the polynucleotide comprises a nucleotide sequence listed in Table 3-6. In some embodiment, the polypeptide comprises an amino acid sequence of a gene listed in Table 3-6. In some embodiments, the level of reagent that associates with the sample is different (i.e., higher or lower) from a level associated with humans without a mental disorder. In some embodiments, the biological sample is obtained from amniotic fluid. In some embodiments, the mental disorder is a mood disorder. In some embodiments, the mood disorder is selected from the group consisting of bipolar disorder and major depression disorder.

The invention also provides methods of identifying a compound for treatment of a mental disorder. In some embodiments, the methods comprises the steps of: (i) contacting the compound with a polypeptide, which is encoded by a polynucleotide that hybridizes under stringent conditions to a nucleic acid comprising a nucleotide sequence of Table 2, 3, or 4; and (ii) determining the functional effect of the compound upon the polypeptide, thereby identifying a compound for treatment of a mental disorder.

In some embodiments, the contacting step is performed in vitro. In some embodiment, the polypeptide comprises an amino acid sequence of a gene listed in Table 3-6. In some embodiments, the polypeptide is expressed in a cell or biological sample, and the cell or biological sample is contacted with the compound. In some embodiments, the mental disorder is a mood disorder or psychotic disorder. In some embodiments, the mood disorder is selected from the group consisting of bipolar disorder and major depression. In some embodiments, the psychotic disorder is schizophrenia. In some embodiments, the methods further comprise administering the compound to an animal and determining the effect on the animal, e.g., an invertebrate, a vertebrate, or a mammal. In some embodiments, the determining step comprises testing the animal's mental function.

In some embodiments, the methods comprise the steps of (i) contacting the compound to a cell, the cell comprising a polynucleotide that hybridizes under stringent conditions to a nucleotide sequence of Table 3-6; and (ii) selecting a compound that modulates expression of the polynucleotide, thereby identifying a compound for treatment of a mental disorder. In some embodiments, the polynucleotide comprises a nucleotide sequence listed in Table 3-6. In some embodiment, the expression of the polynucleotide is enhanced. In some embodiments, the expression of the polynucleotide is decreased. In some embodiments, the methods further comprise administering the compound to an animal and determining the effect on the animal. In some embodiments, the determining step comprises testing the animal's mental function. In some embodiments, the mental disorder is a mood disorder or a psychotic disorder. In some embodiments, the mood disorder is selected from the group consisting of bipolar disorder and major depression. In some embodiments, the psychotic disorder is schizophrenia.

The invention also provides methods of treating a mental disorder in a subject. In some embodiments, the methods comprise the step of administering to the subject a therapeutically effective amount of a compound identified using the methods described above. In some embodiments, the mental disorder is a mood disorder or a psychotic disorder. In some embodiments, the mood disorder is selected from the group consisting of bipolar disorder and major depression. In some embodiments, the psychotic disorder is schizophrenia. In some embodiments, the compound is a small organic molecule, an antibody, an antisense molecule, or a peptide.

The invention also provides methods of treating mental illness in a subject, comprising the step of administering to the subject a therapeutically effective amount of a polypeptide, which is encoded by a polypeptide that hybridizes under stringent conditions to a nucleic acid of Table 3-6. In some embodiments, the polypeptide comprises an amino acid sequence encoded by a gene listed in Table 3-6. In some embodiments, the mental illness is a mood disorder or a psychotic disorder. In some embodiments, the psychotic disorder is schizophrenia. In some embodiments, the mood disorder is a bipolar disorder or major depression.

The invention also provides methods of treating mental illness in a subject, comprising the step of administering to the subject a therapeutically effective amount of a polypeptide, wherein the polypeptide hybridizes under stringent conditions to a nucleic acid of Table 3-6. In some embodiments, the mental illness is a mood disorder or a psychotic disorder. In some embodiments, the psychotic disorder is schizophrenia. In some embodiments, the mood disorder is a bipolar disorder or major depression.

BRIEF DESCRIPTION OF THE DRAWINGS

FIG. 2: summarizes differential expression of FGF system transcripts in MDD cortex.

FIG. 5: shows environmental complexity: FGF2 and anxiety-like behavior.

FIG. 7: shows summarizes FGF and negative affect.

FIG. 8: shows qRT-PCR validation of microarray data.

FIG. 10: shows gene category over-representation analysis of the three downstream GPCR signaling pathways.

FIG. 17: shows where each exon begins and ends in the PSPHL mRNA (SEQ ID NOS:14-20) and provides primers to detect insertion/deletion polymorphisms in the PSPHL locus (SEQ ID NOS:21-24).

FIGS. 22A-F: show the effects of environmental complexity on differences in anxiety behavior and FGF2 gene expression.

FIGS. 23A-H: show the effects of postnatal FGF2 administration on neurogenesis, emotionality and gene expression in adult rats.

FIGS. 24A-J: show GABA/glutamate signaling pathways in BP and MDD.

FIGS. 25A-L: show NCAM SNPs and splice variants involved in mood disorders such as bipolar disorder.

TABLE LEGENDS

Figure 1:
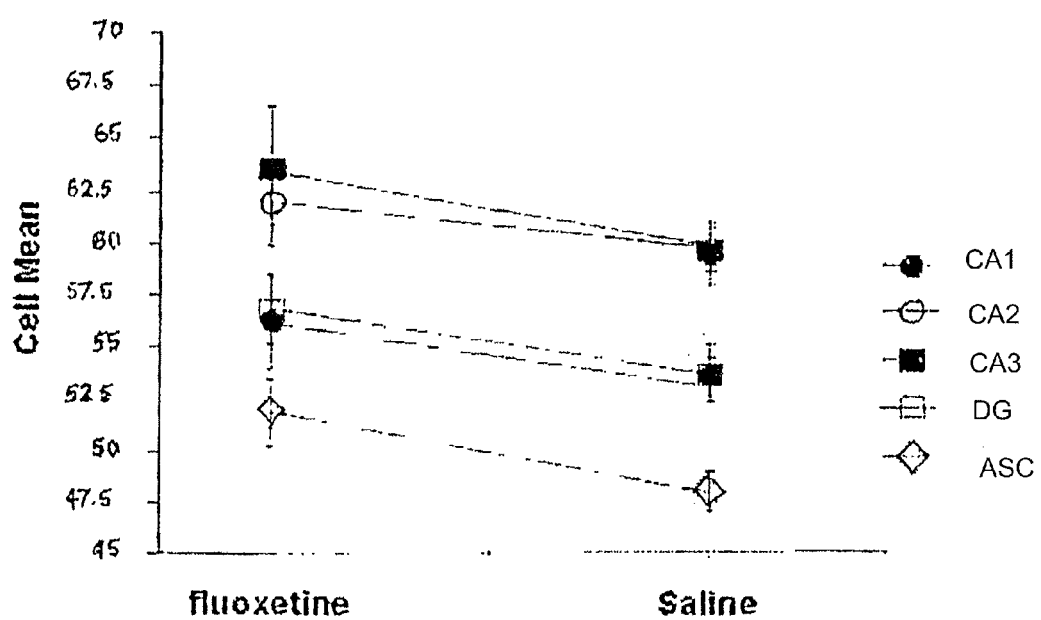
FIG. 1: Rodent FGFR2 ISH. Graph shows mean grayscale (n=6 per group) intensity and standard error bars for 35 S signal for regions indicated for both fluoxetine treated and saline treated rats. The increase in signal in the fluoxetine treated group is significant as determined boy a tow-way ANOVA (treatment, brain region) with p=0.0049, Fisher's PLSD.
Figure 3:
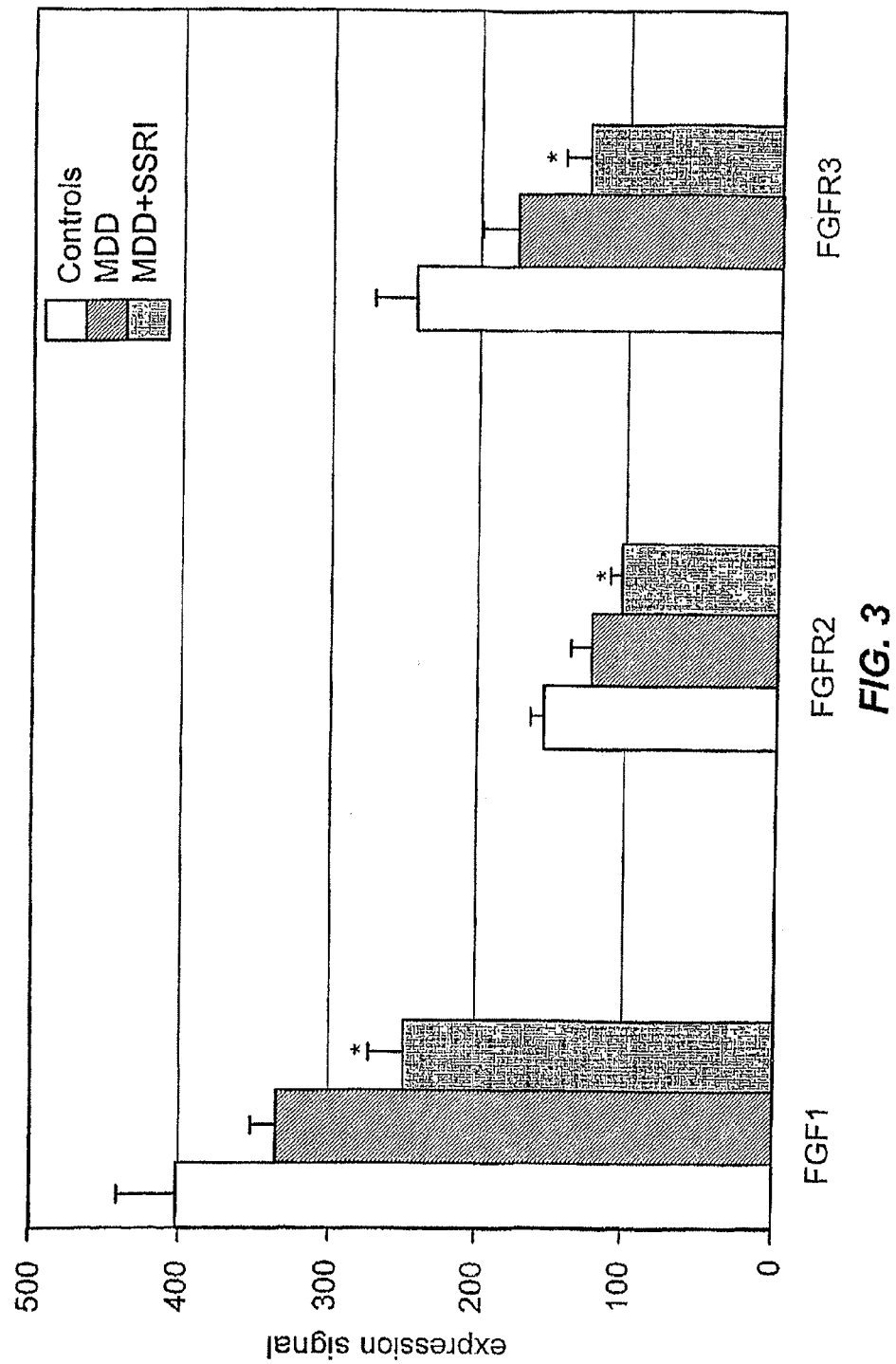
FIG. 3: shows FGF dysregulation is attenuated by antidepressant therapy.
Figure 4:
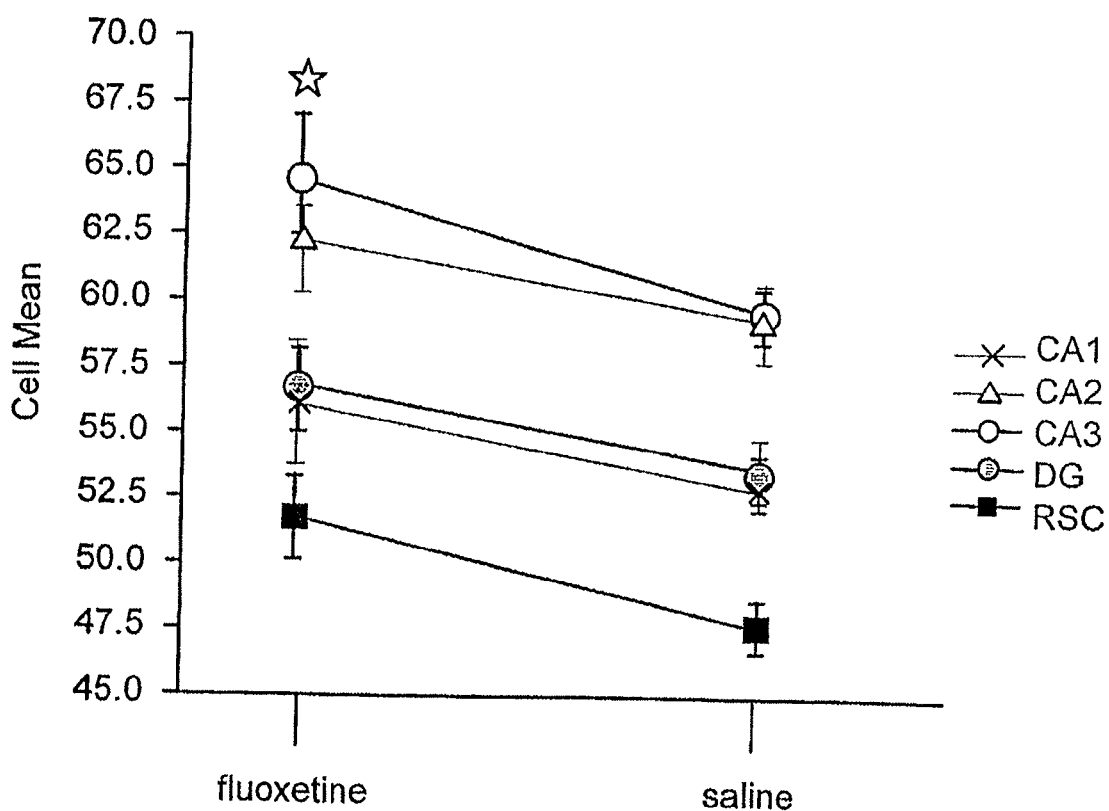
FIG. 4: shows that chronic fluoxetine treatment increases FGFR2 expression in rat forebrain.
Figure 6:
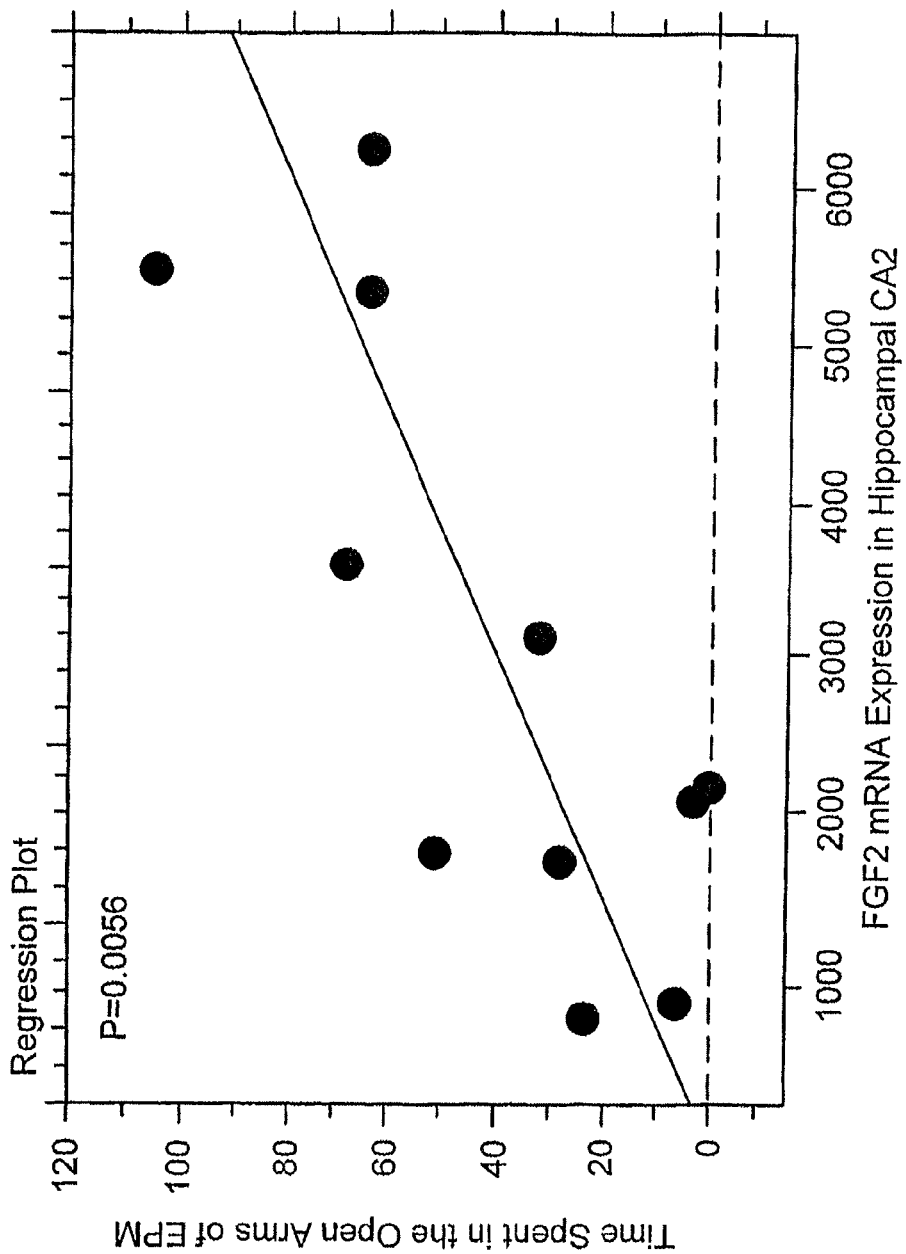
FIG. 6: shows FGF expression negatively correlates with anxiety-like behavior.
Figure 9:
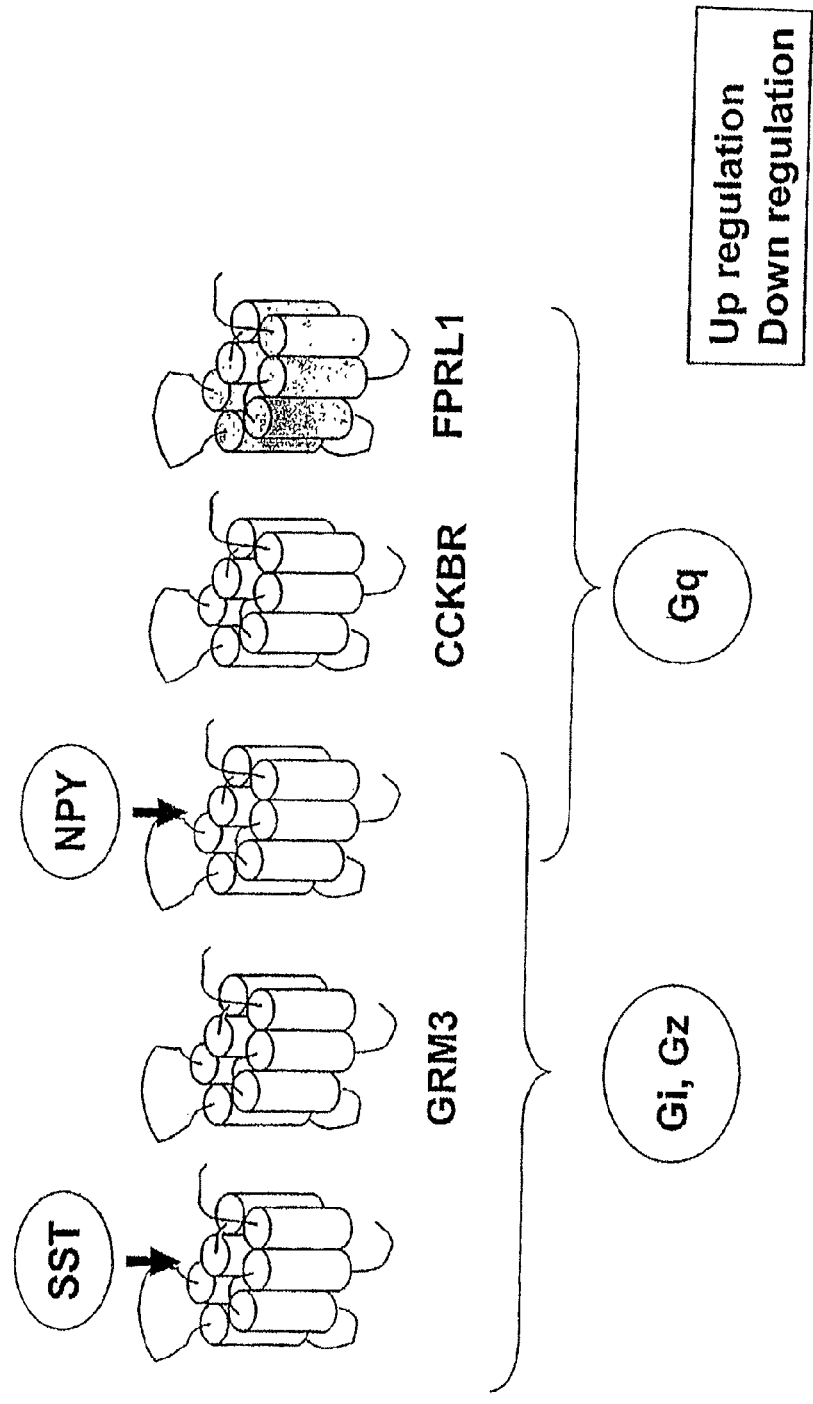
FIG. 9: shows G-protein coupled receptor (GPCR) and ligands dysregulated in anterior cingulated cortex of BP subjects.
Figure 11:
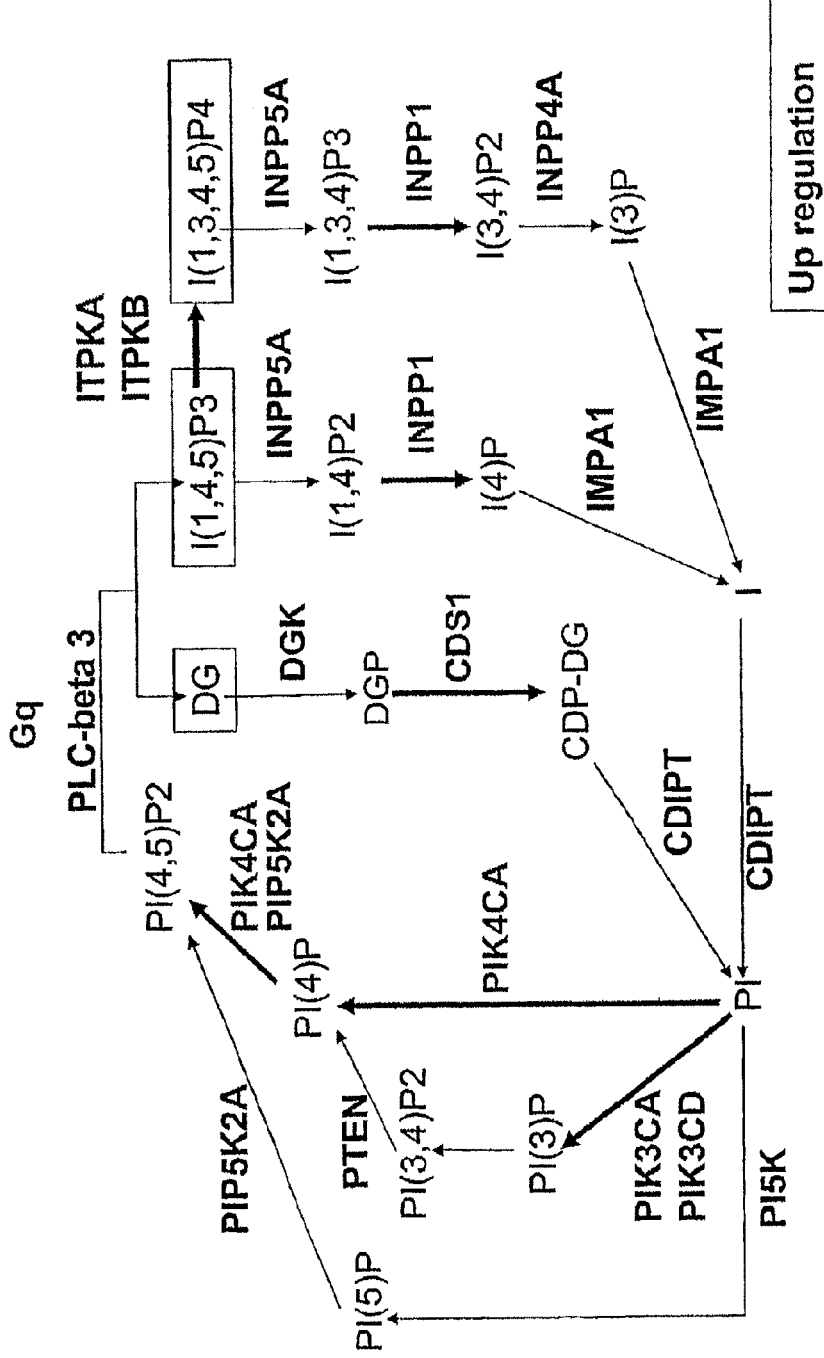
FIG. 11: shows phosphatidylinositol metabolism in BP disorder.
Figure 12:
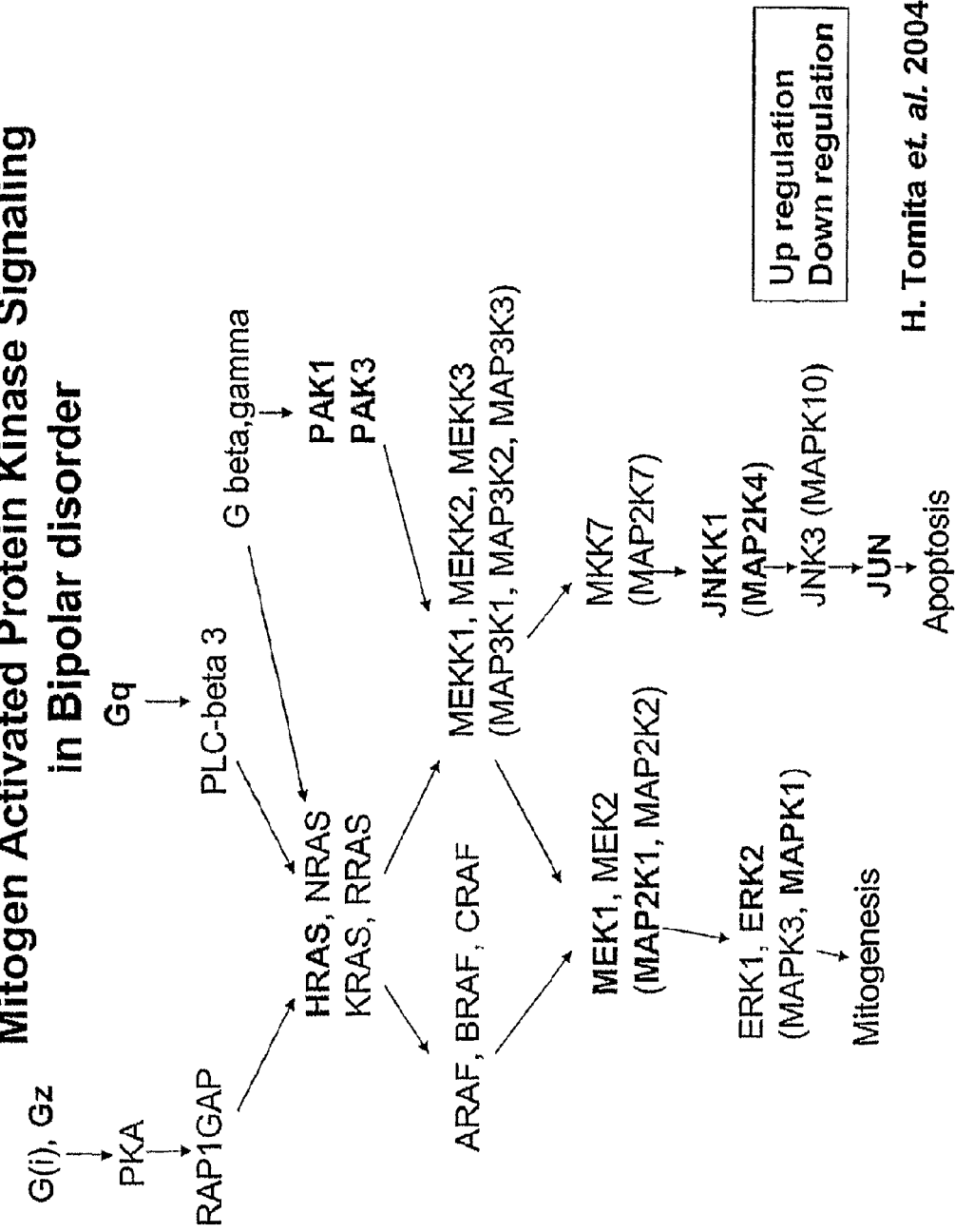
FIG. 12: shows mitogen activated protein kinase signaling in BP disorder.
Figure 13:
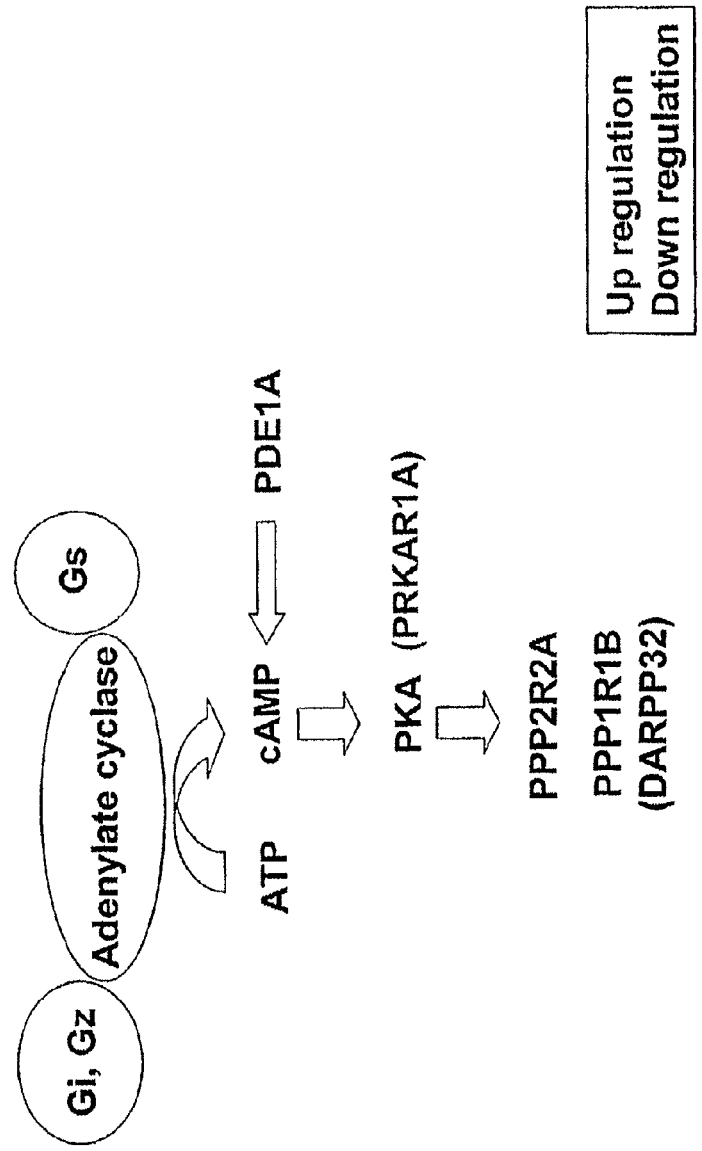
FIG. 13: shows cAMP signaling pathway in BP subjects

Table 1a: Table 1a lists subject data for cohort A.

Table 1b: Table 1b lists subject data for cohort B.

Table 2: Table 2 shows microarray data for all FGF transcripts detected in either DLPFC or AnCg and summary data for confirmation studies.

Table 3: Table 3 lists genes uniquely expressed in BP subjects.

Table 4: Table 4 lists genes uniquely expressed in MDD subjects.

Table 5: Table 5 lists growth factor pathway genes expressed in MDD and BP subjects.

Table 6: Table 6 lists GPCR pathway genes expressed in MDD and BP subjects.

Table 7: Table 7 lists growth factor pathway genes expressed in MDD and BP subjects.

Table 8: Table 8 lists GABA and glutamate signaling pathway genes expressed in MDD and BP subjects.

Table 9: Table 9 lists GPCR pathway genes expressed in MDD and BP subjects.

Table 10: Table 10 lists mitochondrial genes expressed in MDD and BP subjects.

Table 11: Table 11 lists genes expressed in MDD, BP, and schizophrenia subjects.

Table 12: Table 12 lists genes expressed in MDD, BP, and schizophrenia subjects.

Table 13: Table 13 lists GPCR pathway genes expressed in MDD and BP.

Table 14: GPCRs and related signaling genes dysregulated in anterior cingulate cortex.

Table 15: GPCRs and related signaling genes dysregulated in dorsolateral prefrontal cortex.

Table 16: GPCRs and related signaling genes dysregulated in cerebellar cortex.

Table 17: Quantitative RT-PCR data. Fold changes in microarray and qRT-PCR analyses for representative ligand peptides, GPCRs, G protein regulator (NPY, SST, GPR37, GPRC5B, RGS20), which were dysregulated in BPD/MDD compared to the control group. N.S., No significant change; *. $p<0.05$; **, $p<0.01$.

Table 18: GPCRs and related signaling genes dysregulated in amygdala, hippocampus, nucleus accumbens of BPD.

Table 19: GPCRs and related signaling genes dysregulated in amygdala, hippocampus, nucleus accumbens of MDD.

Table 20: Table 20 shows the genes that were differentially expressed in BPD or MDD by >1.2 fold change and were down-regulated in agonal factor control comparisons by <1.0. The opposite genes are also shown, where there was a decrease in mood disorder by <−1.2 fold change, and the agonal factor control comparison showed an increase >1.0 fold change. These genes were found in 4 major classifications listed: mitochondria, chaperone, apoptosis, and proteasome.

Table 21: Real time Q-PCR validation results for selected mitochondrial related candidate genes for mood disorders in two cortical regions. These genes are nuclear-encoded. Significant by Q-PCR $p<0.05$ one-tailed t-test. The Q-PCR t-test MDD, BPD, and control groups used subjects with no agonal factors and pH>6.8 similar to microarray analysis #3 groups MDD-High, BPD-High, and Control-High.

Table 22: Mitochondrial DNA (mtDNA) encoded genes were analyzed by real time Q-PCR for differential expression in BPD and MDD compared to controls. Nuclear encoded genes in BPD and MDD subjects appeared to generally be increased while several mtDNA genes showed a significant decrease by Q-PCR in mood disorders.

Table 23: Primers for each DNA segment and possible combination of splice variants (a, b, c, SEC and VASE) (SEQ ID NOS:1-11), as well as, for SNP 9 (SEQ ID NOS:12-13) and an exon outside of the splice sites for measuring total NCAM1. The numbering is shown in FIG. 26 according to accession M22094. *1—Only the forward primer could be designed because exon a is 14 bps. 2—Exon 3 is before the variable exons and only the forward primer was needed to PCR outside the exons. 3—Exon 8 is after the variable exons and only the reverse primer was needed to PCR outside the exons.

Table 24: Genotypic Association Results. The odds ratio, chi-square (chi2) and p-values where all calculated using the DeFinetti program Tests for Deviation from HWE and Tests for Association (C.I.: 95% confidence interval).

Table 25: SNP 9 and SNP b haplotype frequency, odds ratio and p-values. P-values were calculated from the Chi-squared values derived from the EHplus program.

Table 26: Genotypic and Allelic Distributions for Controls, Bipolar Disorder and Schizophrenia. Fisher's exact p-values are shown for allelic distribution between case-controls.

Table 27: Genotype×Splice Variant Differences×Diagnosis (p-values). For each SNP genotype and splice variant the splice variant amounts were evaluated by t-test based on diagnosis and the significant p-values were reported.

Tables 28: Genes upregulated (28.1) and downregulated (28.2) by Lithium in monkey brains.

Table 29: Values of V-ATPase Subunits differential expression in Non-human primate model of depression.

Table 30: Genes differentially expressed in the frontal cortex of rats subjected to chronic unpredictable stress (CUS) and antidepressant administration (All=fluoxetine, desipramine, and bupropion). Controls were administered water (H2O treated).

DEFINITIONS

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"A psychotic disorder" refers to a condition that affects the mind, resulting in at least some loss of contact with reality. Symptoms of a psychotic disorder include, e.g., hallucinations, changed behavior that is not based on reality, delusions and the like. See, e.g., DSM IV. Schizophrenia, schizoaffective disorder, schizophreniform disorder, delusional disorder, brief psychotic disorder, substance-induced psychotic disorder, and shared psychotic disorder are examples of psychotic disorders.

"Schizophrenia" refers to a psychotic disorder involving a withdrawal from reality by an individual. Symptoms comprise for at least a part of a month two or more of the following symptoms: delusions (only one symptom is required if a delusion is bizarre, such as being abducted in a space ship from the sun); hallucinations (only one symptom is required if hallucinations are of at least two voices talking to one another or of a voice that keeps up a running commentary on the patient's thoughts or actions); disorganized speech (e.g., frequent derailment or incoherence); grossly disorganized or catatonic behavior; or negative symptoms, i.e., affective flattening, alogia, or avolition. Schizophrenia encompasses disorders such as, e.g., schizoaffective disorders. Diagnosis of schizophrenia is described in, e.g., DSM IV. Types of schizophrenia include, e.g., paranoid, disorganized, catatonic, undifferentiated, and residual.

An "antidepressant" refers to an agents typically used to treat clinical depression. Antidepressants includes compounds of different classes including, for example, specific serotonin reuptake inhibitors (e.g., fluoxetine), tricyclic antidepressants (e.g., desipramine), and dopamine reuptake inhibitors (e.g, bupropion). Typically, antidepressants of different classes exert their therapeutic effects via different biochemical pathways. Often these biochemical pathways overlap or intersect. Additional diseases or disorders often treated with antidepressants include, chronic pain, anxiety disorders, and hot flashes.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

"Determining the functional effect" refers to assaying for a compound that increases or decreases a parameter that is indirectly or directly under the influence of a polynucleotide or polypeptide of the invention (such as a polynucleotide of Table 3-6 or a polypeptide encoded by a gene of Table 3-6), e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the polynucleotides, polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *Adv. Drug Res.* 15:29 (1986); Veber and Freidinger *TINS* p. 392 (1985); and Evans et al., *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a CCX CKR, but have one or more peptide linkages optionally replaced by a linkage selected from the group consisting of, e.g., —$CH_2NH$—, —$CH_2S$—, —$CH_2$—$CH_2$—, —CH=CH— (cis and trans), —$COCH_2$—, —CH(OH) $CH_2$—, and —$CH_2SO$—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of a polypeptide or polynucleotide of the invention or inhibiting or increasing the enzymatic activity or expression of a polypeptide or polynucleotide of the invention.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)). The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

Figure 14:
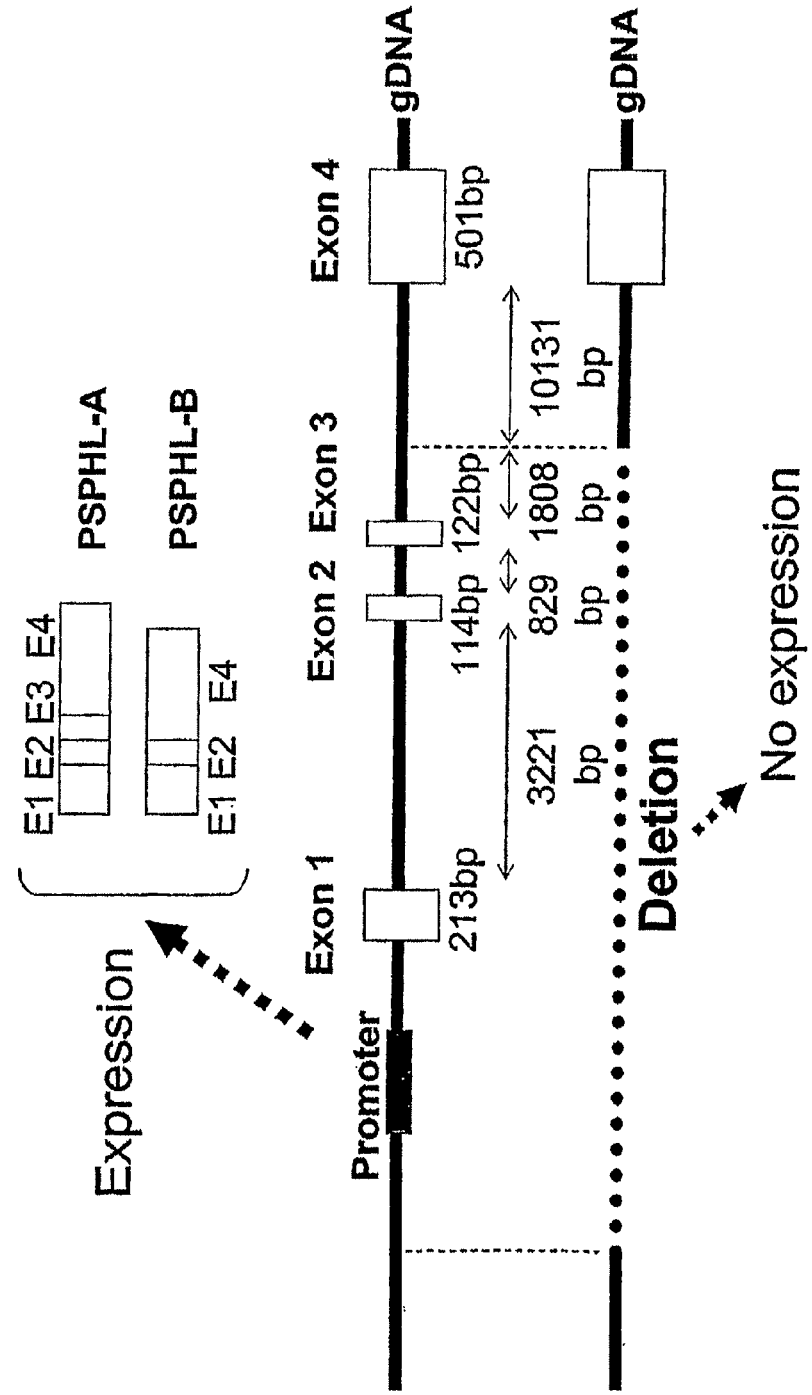
FIG. 14: shows genomic structure of the PSPHL gene and the deletion polymorphism of PSPHL that is related to BP susceptibility.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, 0.1% SDS at 65° C. Such washes can be performed for 5, 15, 30, 60, 120, or more minutes. Nucleic acids that hybridize to the genes listed in Tables 3-10 and FIG. 14 are encompassed by the invention.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (1990).

The phrase "a nucleic acid sequence encoding" refers to a nucleic acid that contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

One who is "predisposed for a mental disorder" as used herein means a person who has an inclination or a higher likelihood of developing a mental disorder when compared to an average person in the general population.

DETAILED DESCRIPTION OF THE INVENTION

I. Introduction

To understand the genetic basis of mental disorders, studies have been conducted to investigate the expression patterns of genes that are differentially expressed specifically in central nervous system of subjects with mood disorders. Differential and unique expression of known and novel genes was determined by way of interrogating total RNA samples purified from postmortem brains of BP and MDD patients with Affymetrix Gene Chips® (containing high-density oligonucleotide probe set arrays). The fundamental principles is that by identifying genes and pathways that are differentially expressed in BP and/or MDD (relative to healthy control subjects), via global expression profiling of the transcriptomes as above, one can identify genes that cause, effect, or are associated with the disease, or that interact with drugs used to treat the disease, for use in diagnostic and therapeutic applications.

The present invention therefore demonstrates the altered expression (either higher or lower expression as indicated herein) and in some cases unique differential expression of the genes of Tables 3-10 at the mRNA level in selected brain regions of patients diagnosed with mood disorders, as well as the PSPHL gene (see, e.g., FIG. 14) (e.g., bipolar disorder and major depression disorder) in comparison with normal individuals. This invention thus provides methods for diagnosis of mental disorders such as mood disorders (e.g., bipolar disorder, major depression, and the like) and other mental disorders having a genetic component by detecting the level of a transcript or translation product of the genes listed in Tables 3-10 and FIG. 14 as well as their corresponding biochemical pathways.

In one embodiment, the present invention relates to a novel insertion-deletion polymorphism of phosphoserine phosphatase-like gene, and the association between deletion allele of PSPHL and susceptibility to bipolar disorder (BPD). The fact that PSPHL shows dichotomous present/absent pattern of expression among individuals with brain-wide consistency suggests genetic variation in its regulation (see Example 2). Most intriguingly, we have identified an insertion/deletion polymorphism at the PSPHL locus. The deleted genomic region spans more than 30 kb, including the promoter region and the exons 1, 2 and 3 of PSPHL gene. This genetic variance explains the present/absent pattern of the PSPHL expression. An over-representation of the deletion allele resulting in the absence of PSPHL expression increases susceptibility to BPD. The invention therefore provides the first evidence linking a genetic variant of the PSPHL gene to bipolar disorder. The finding will facilitate characterization of the physiological and pathological function of the gene relevant to bipolar disorder, and provides novel and significant use of this gene and its variants for diagnosis, treatment and prevention of bipolar disorder.

The invention further provides methods of identifying a compound useful for the treatment of such disorders by selecting compounds that modulates the functional effect of the translation products or the expression of the transcripts described herein. The invention also provides for methods of treating patients with such mental disorders, e.g., by administering the compounds of the invention or by gene therapy.

The genes and the polypeptides that they encode, which are associated with mood disorders such as bipolar disease and major depression, are useful for facilitating the design and development of various molecular diagnostic tools such as GeneChips™ containing probe sets specific for all or selected mental disorders, including but not limited to mood disorders, and as an ante-and/or post-natal diagnostic tool for screening newborns in concert with genetic counseling. Other diagnostic applications include evaluation of disease susceptibility, prognosis, and monitoring of disease or treatment process, as well as providing individualized medicine via predictive drug profiling systems, e.g., by correlating specific genomic motifs with the clinical response of a patient to individual drugs. In addition, the present invention is useful for multiplex SNP and haplotype profiling, including but not limited to the identification of therapeutic, diagnostic, and pharmacogenetic targets at the gene, mRNA, protein, and pathway level. Profiling of splice variants and deletions is also useful for diagnostic and therapeutic applications.

The genes and the polypeptides that they encode, described herein, are also useful as drug targets for the development of therapeutic drugs for the treatment or prevention of mental disorders, including but not limited to mood disorders.

Antidepressants belong to different classes, e.g., desipramine, bupropion, and fluoxetine are in general equally effective for the treatment of clinical depression, but act by different mechanisms. The similar effectiveness of the drugs for treatment of mood disorders suggests that they act through a presently unidentified common pathway. Animal models of depression, including treatment of animals with known therapeutics such as SSRIs, can be used to examine the mode of action of the genes of the invention. Lithium is drug of choice for treating BP.

The genes and the polypeptides that they encode, described herein, as also useful as drug targets for the development of therapeutic drugs for the treatment or prevention of mental disorders, including but not limited to mood disorders. Mental disorders have a high co-morbidity with other neurological disorders, such as Parkinson's disease or Alzheimer's. Therefore, the present invention can be used for diagnosis and treatment of patients with multiple disease states that include a mental disorder such as a mood disorder. These mood disorders include BP, MDD, and other disorders such as psychotic-depression, depression and anxiety features, melancholic depression, chronic depression, BPI and BPII.

II. General Recombinant Nucleic Acid Methods for Use with the Invention

In numerous embodiments of the present invention, polynucleotides of the invention will be isolated and cloned using recombinant methods. Such polynucleotides include, e.g., those listed in Tables 3-10 and FIG. 14, which can be used for, e.g., protein expression or during the generation of variants, derivatives, expression cassettes, to monitor gene expression, for the isolation or detection of sequences of the invention in different species, for diagnostic purposes in a patient, e.g., to detect mutations or to detect expression levels of nucleic acids or polypeptides of the invention. In some embodiments, the sequences of the invention are operably linked to a heterologous promoter. In one embodiment, the nucleic acids of the invention are from any mammal, including, in particular, e.g., a human, a mouse, a rat, a primate, etc.

A. General Recombinant Nucleic Acids Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of the genes listed in Tables 3-10 and FIG. 14, which provide a reference for PCR primers and defines suitable regions for isolating specific probes. Alternatively, where the sequence is cloned into an expression library, the expressed recombinant protein can be detected immunologically with antisera or purified antibodies made against a polypeptide comprising an amino acid sequence encoded by a gene listed in Table 1-8.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Brain cells are an example of suitable cells to isolate RNA and cDNA sequences of the invention.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific sequences of the invention. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying polynucleotides of the invention from mammalian tissues can be derived from the sequences provided herein. For a general overview of PCR, see, Innis et al. *PCR Protocols: A Guide to Methods and Applications*, Academic Press, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding a polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant polypeptides of the invention can be purified for use in functional assays. Naturally occurring polypeptides, e.g., polypeptides encoded by genes listed in Tables 3-10 and FIG. 14, can be purified, for example, from mouse or human tissue such as brain or any other source of an ortholog. Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification Principles and Practice* (1982); U.S. Pat. No. 4,673,641; Ausubel et al., supra; and Sambrook et al., supra).

A number of procedures can be employed when recombinant polypeptides are purified. For example, proteins having established molecular adhesion properties can be reversible fused to polypeptides of the invention. With the appropriate ligand, the polypeptides can be selectively adsorbed to a purification column and then freed from the column in a relatively pure form. The fused protein is then removed by enzymatic activity. Finally the polypeptide can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

IV. Detection of Gene Expression

Those of skill in the art will recognize that detection of expression of polynucleotides of the invention has many uses. For example, as discussed herein, detection of the level of polypeptides or polynucleotides of the invention in a patient is useful for diagnosing mood disorders or psychotic disorders or a predisposition for a mood disorder or psychotic disorders. Moreover, detection of gene expression is useful to identify modulators of expression of the polypeptides or polynucleotides of the invention.

A variety of methods of specific DNA and RNA measurement using nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays,*" *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science,* 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1988); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

V. Immunological Detection of the Polypeptides of the Invention

In addition to the detection of polynucleotide expression using nucleic acid hybridization technology, one can also use immunoassays to detect polypeptides of the invention. Immunoassays can be used to qualitatively or quantitatively analyze polypeptides. A general overview of the applicable technology can be found in Harlow & Lane, *Antibodies: A Laboratory Manual* (1988).

A. Antibodies to Target Polypeptides or Other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature*, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their cross-reactivity against unrelated proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein, such as one comprising an amino acid sequence encoded by a gene listed in Table 1-8 may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein specific antibodies are available, the protein can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the protein (e.g., one has an amino acid sequence encoded by a gene listed in Table 1-8) or a fragment thereof. This antiserum is selected to have low cross-reactivity against different proteins and any such cross-reactivity is removed by immunoabsorption prior to use in the immunoassay.

B. Immunological Binding Assays

In a preferred embodiment, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume* 37: *Antibodies in Cell Biology*, Academic Press, Inc. NY (1993); Stites, supra. Immunological binding assays (or immunoassays) typically utilize a "capture agent" to specifically bind to and often immobilize the analyte (in this case a polypeptide of the present invention or antigenic subsequences thereof). The capture agent is a moiety that specifically binds to the analyte. In a preferred embodiment, the capture agent is an antibody that specifically binds, for example, a polypeptide of the invention. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (in this case the protein) is directly measured. In one preferred "sandwich" assay, for example, the capture agent (e.g., antibodies specific for a polypeptide encoded by a gene listed in Table 1-8) can be bound directly to a solid substrate where it is immobilized. These immobilized antibodies then capture the polypeptide present in the test sample. The polypeptide thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of analyte (such as a polypeptide encoded by a gene listed in Table 1-8) present in the sample is measured indirectly by measuring the amount of an added (exogenous) analyte displaced (or competed away) from a capture agent (e.g., an antibody specific for the analyte) by the analyte present in the sample. In one competitive assay, a known amount of, in this case, the protein of interest is added to the sample and the sample is then contacted with a capture agent, in this case an antibody that specifically binds to a polypeptide of the invention. The amount of immunogen bound to the antibody is inversely proportional to the concentration of immunogen present in the sample. In a particularly preferred embodiment, the antibody is immobilized on a solid substrate. For example, the amount of the polypeptide bound to the antibody may be determined either by measuring the amount of subject protein present in a protein/antibody complex or, alternatively, by measuring the amount of remaining uncomplexed protein. The amount of protein may be detected by providing a labeled protein molecule.

Immunoassays in the competitive binding format can be used for cross-reactivity determinations. For example, a protein of interest can be immobilized on a solid support. Proteins are added to the assay which compete with the binding of the antisera to the immobilized antigen. The ability of the above proteins to compete with the binding of the antisera to the immobilized protein is compared to that of the protein of interest. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of a polypeptide of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the antibodies specifically bind to a polypeptide of interest on the solid support. These antibodies may be directly labeled or alternatively may be subsequently detected using labeled antibodies (e.g., labeled sheep antimouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

In some embodiments, BP or MDD in a patient may be diagnosed or otherwise evaluated by visualizing expression in situ of one or more of the appropriately dysregulated gene sequences identified herein. Those skilled in the art of visualizing the presence or expression of molecules including nucleic acids, polypeptides and other biochemicals in the brains of living patients will appreciate that the gene expression information described herein may be utilized in the context of a variety of visualization methods. Such methods include, but are not limited to, single-photon emission-computed tomography (SPECT) and positron-emitting tomography (PET) methods. See, e.g., Vassaux and Grootwassink, "In Vivo Noninvasive Imaging for Gene Therapy," J. Biomedicine and Biotechnology, 2: 92-101 (2003).

PET and SPECT imaging shows the chemical functioning of organs and tissues, while other imaging techniques—such as X-ray, CT and MRI—show structure. The use of PET and SPECT imaging is useful for qualifying and monitoring the development of brain diseases, including schizophrenia and related disorders. In some instances, the use of PET or SPECT imaging allows diseases to be detected years earlier than the onset of symptoms. The use of small molecules for labelling and visualizing the presence or expression of polypeptides and nucleotides has had success, for example, in visualizing proteins in the brains of Alzheimer's patients, as described by, e.g., Herholz K et al., Mol Imaging Biol., 6(4):239-69 (2004); Nordberg A, Lancet Neurol., 3(9):519-27 (2004); Neuropsychol Rev., Zakzanis K K et al., 13(1): 1-18 (2003); Kung M P et al, Brain Res., 1025(1-2):98-105 (2004); and Herholz K, Ann Nucl Med., 17(2):79-89 (2003).

The dysregulated genes disclosed in Tables 1-30, or their encoded peptides (if any), or fragments thereof, can be used in the context of PET and SPECT imaging applications. After modification with appropriate tracer residues for PET or SPECT applications, molecules which interact or bind with the transcripts in Tables 1-30 or with any polypeptides encoded by those transcripts may be used to visualize the patterns of gene expression and facilitate diagnosis of schizophrenia MDD or BP, as described herein. Similarly, if the encoded polypeptides encode enzymes, labeled molecules which interact with the products of catalysis by the enzyme may be used for the in vivo imaging and diagnostic application described herein.

Antisense technology is particularly suitable for detecting the transcripts identified in Tables 1-30 herein. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10:1766-1775 (2004). Suzuki et al. utilize a delivery system comprising monoclonal antibodies that target transferring receptors at the blood-brain barrier and facilitate transport of the PNA across that barrier. Modified embodiments of this technique may be used to target upregulated genes associated with schizophrenia, BP or MDD, such as the upregulated genes which appear in Tables 1-30, in methods of treating schizophrenic, BP or MDD patients.

In other embodiments, the dysregulated genes listed in Tables 1-30 may be used in the context of prenatal and neonatal diagnostic methods. For example, fetal or neonatal samples can be obtained and the expression levels of appropriate transcripts (e.g., the transcripts in Table 19) may be measured and correlated with the presence or increased likelihood of a mental disorder, e.g., MDD. Similarly, the presence of one or more of the SNPs identified in the Tables, e.g., Table 27 may be used to infer or corroborate dysregulated expression of a gene and the likelihood of a mood disorder in prenatal, neonatal, children and adult patients.

In other embodiments, the brain labeling and imaging techniques described herein or variants thereof may be used in conjunction with any of the dysregulated gene sequences in Tables 1-30 in a forensic analysis, i.e., to determine whether a deceased individual suffered from schizophrenia, BP, or MDD.

VI. Screening for Modulators of Polypeptides and Polynucleotides of the Invention Modulators of polypeptides or polynucleotides of the invention, i.e. agonists or antagonists of their activity or modulators of polypeptide or polynucleotide expression, are useful for treating a number of human diseases, including mood disorders or psychotic disorders. Administration of agonists, antagonists or other agents that modulate expression of the polynucleotides or polypeptides of the invention can be used to treat patients with mood disorders or psychotic disorders.

A. Screening Methods

A number of different screening protocols can be utilized to identify agents that modulate the level of expression or activity of polypeptides and polynucleotides of the invention in cells, particularly mammalian cells, and especially human cells. In general terms, the screening methods involve screening a plurality of agents to identify an agent that modulates the polypeptide activity by binding to a polypeptide of the invention, modulating inhibitor binding to the polypeptide or activating expression of the polypeptide or polynucleotide, for example.

1. Binding Assays

Preliminary screens can be conducted by screening for agents capable of binding to a polypeptide of the invention, as at least some of the agents so identified are likely modulators of polypeptide activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, (1985) "Neurotransmitter, Hormone or Drug Receptor Binding Methods," in *Neurotransmitter Receptor* Binding (Yamamura, H. I., et al., eds.), pp. 61-89. The protein utilized in such assays can be naturally expressed, cloned or synthesized.

Binding assays are also useful, e.g., for identifying endogenous proteins that interact with a polypeptide of the invention. For example, antibodies, receptors or other molecules that bind a polypeptide of the invention can be identified in binding assays.

2. Expression Assays

Certain screening methods involve screening for a compound that up or down-regulates the expression of a polypeptide or polynucleotide of the invention. Such methods generally involve conducting cell-based assays in which test compounds are contacted with one or more cells expressing a polypeptide or polynucleotide of the invention and then detecting an increase or decrease in expression (either transcript, translation product, or catalytic product). Some assays are performed with peripheral cells, or other cells, that express an endogenous polypeptide or polynucleotide of the invention.

Polypeptide or polynucleotide expression can be detected in a number of different ways. As described infra, the expression level of a polynucleotide of the invention in a cell can be determined by probing the mRNA expressed in a cell with a probe that specifically hybridizes with a transcript (or complementary nucleic acid derived therefrom) of a polynucleotide of the invention. Probing can be conducted by lysing the cells and conducting Northern blots or without lysing the cells using in situ-hybridization techniques. Alternatively, a polypeptide of the invention can be detected using immunological methods in which a cell lysate is probed with antibodies that specifically bind to a polypeptide of the invention.

Other cell-based assays are reporter assays conducted with cells that do not express a polypeptide or polynucleotide of the invention. Certain of these assays are conducted with a heterologous nucleic acid construct that includes a promoter of a polynucleotide of the invention that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, chloramphenicol acetyl transferase (CAT); Alton and Vapnek (1979) *Nature* 282:864-869), luciferase, β-galactosidase, green fluorescent protein (GFP) and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of a polynucleotide of the invention and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of expression levels for a control population (e.g., healthy individuals not having or at risk for mood disorders or psychotic disorders). Expression levels can also be determined for cells that do not express a polynucleotide of the invention as a negative control. Such cells generally are otherwise substantially genetically the same as the test cells.

A variety of different types of cells can be utilized in the reporter assays. Cells that express an endogenous polypeptide or polynucleotide of the invention include, e.g., brain cells, including cells from the cerebellum, anterior cingulate cortex, dorsolateral prefrontal cortex, amygdala, hippocampus, or nucleus accumbens. Cells that do not endogenously express polynucleotides of the invention can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

3. Catalytic Activity

Catalytic activity of polypeptides of the invention can be determined by measuring the production of enzymatic products or by measuring the consumption of substrates. Activity refers to either the rate of catalysis or the ability to the polypeptide to bind ($K_m$) the substrate or release the catalytic product ($K_d$).

Analysis of the activity of polypeptides of the invention are performed according to general biochemical analyses. Such assays include cell-based assays as well as in vitro assays involving purified or partially purified polypeptides or crude cell lysates. The assays generally involve providing a known quantity of substrate and quantifying product as a function of time.

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats. As described herein, models using administration of known therapeutics can be useful.

5. Animal Models

Animal models of mental disorders also find use in screening for modulators.

In one embodiment, invertebrate models such as *Drosophila* models can be used, screening for modulators of *Drosophila* orthologs of the human genes disclosed herein. In another embodiment, transgenic animal technology including gene knockout technology, for example as a result of homologous recombination with an appropriate gene targeting vector, or gene overexpression, will result in the absence, decreased or increased expression of a polynucleotide or polypeptide of the invention. The same technology can also be applied to make knockout cells. When desired, tissue-specific expression or knockout of a polynucleotide or polypeptide of the invention may be necessary. Transgenic animals generated by such methods find use as animal models of mental illness and are useful in screening for modulators of mental illness.

Knockout cells and transgenic mice can be made by insertion of a marker gene or other heterologous gene into an endogenous gene site in the mouse genome via homologous recombination. Such mice can also be made by substituting an endogenous polynucleotide of the invention with a mutated version of the polynucleotide, or by mutating an endogenous polynucleotide, e.g., by exposure to carcinogens.

For development of appropriate stem cells, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators of Polypeptides or Polynucleotides of the Invention

The agents tested as modulators of the polypeptides or polynucleotides of the invention can be any small chemical compound, or a biological entity, such as a protein, sugar, nucleic acid or lipid. Alternatively, modulators can be genetically altered versions of a polypeptide or polynucleotide of the invention. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

C. Solid State and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids. Such flexible linkers are known to those of skill in the art. For example, poly(ethelyne glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of the polynucleotides or polypeptides of the invention. In a preferred embodiment, the methods of the invention include such a control reaction. For each of the assay formats described, "no modulator" control reactions that do not include a modulator provide a background level of binding activity.

In some assays it will be desirable to have positive controls to ensure that the components of the assays are working properly. At least two types of positive controls are appropriate. First, a known activator of a polynucleotide or polypeptide of the invention can be incubated with one sample of the assay, and the resulting increase in signal resulting from an increased expression level or activity of polynucleotide or polypeptide determined according to the methods herein. Second, a known inhibitor of a polynucleotide or polypeptide of the invention can be added, and the resulting decrease in signal for the expression or activity can be similarly detected.

D. Computer-Based Assays

Yet another assay for compounds that modulate the activity of a polypeptide or polynucleotide of the invention involves computer assisted drug design, in which a computer system is used to generate a three-dimensional structure of the polypeptide or polynucleotide based on the structural information encoded by its amino acid or nucleotide sequence. The input sequence interacts directly and actively with a pre-established algorithm in a computer program to yield secondary, tertiary, and quaternary structural models of the molecule. Similar analyses can be performed on potential receptors or binding partners of the polypeptides or polynucleotides of the invention. The models of the protein or nucleotide structure are then examined to identify regions of the structure that have the ability to bind, e.g., a polypeptide or polynucleotide of the invention. These regions are then used to identify polypeptides that bind to a polypeptide or polynucleotide of the invention.

The three-dimensional structural model of a protein is generated by entering protein amino acid sequences of at least 10 amino acid residues or corresponding nucleic acid sequences encoding a potential receptor into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary, and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of a polypeptide or polynucleotide of the invention to identify binding sites of the polypeptide or polynucleotide of the invention. Binding affinity between the protein and ligands is determined using energy terms to determine which ligands have an enhanced probability of binding to the protein.

Computer systems are also used to screen for mutations, polymorphic variants, alleles and interspecies homologs of genes encoding a polypeptide or polynucleotide of the invention. Such mutations can be associated with disease states or genetic traits and can be used for diagnosis. As described above, GeneChip™ and related technology can also be used to screen for mutations, polymorphic variants, alleles and interspecies homologs. Once the variants are identified, diagnostic assays can be used to identify patients having such mutated genes. Identification of the mutated a polypeptide or polynucleotide of the invention involves receiving input of a first amino acid sequence of a polypeptide of the invention (or of a first nucleic acid sequence encoding a polypeptide of the invention), e.g., any amino acid sequence having at least 60%, optionally at least 70% or 85%, identity with the amino acid sequence of interest, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various polynucleotides of the invention, and mutations associated with disease states and genetic traits.

VII. Compositions, Kits and Integrated Systems

The invention provides compositions, kits and integrated systems for practicing the assays described herein using polypeptides or polynucleotides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the therapeutic and diagnostic assays of the invention. The kits typically include a probe that comprises an antibody that specifically binds to polypeptides or polynucleotides of the invention, and a label for detecting the presence of the probe. The kits may include several polynucleotide sequences encoding polypeptides of the invention. Kits can include any of the compositions noted above, and optionally further include additional components such as instructions to practice a high-throughput method of assaying for an effect on expression of the genes encoding the polypeptides of the invention, or on activity of the polypeptides of the invention, one or more containers or compartments (e.g., to hold the probe, labels, or the like), a control modulator of the expression or activity of polypeptides of the invention, a robotic armature for mixing kit components or the like.

The invention also provides integrated systems for high-throughput screening of potential modulators for an effect on the expression or activity of the polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Administration and Pharmaceutical Compositions

Modulators of the polynucleotides or polypeptides of the invention (e.g., antagonists or agonists) can be administered directly to a mammalian subject for modulation of activity of those molecules in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

Diseases that can be treated include the following, which include the corresponding reference number from Morrison, *DSM-IV Made Easy,* 1995: Schizophrenia, Catatonic, Subchronic, (295.21); Schizophrenia, Catatonic, Chronic (295.22); Schizophrenia, Catatonic, Subchronic with Acute Exacerbation (295.23); Schizophrenia, Catatonic, Chronic with Acute Exacerbation (295.24); Schizophrenia, Catatonic, in Remission (295.55); Schizophrenia, Catatonic, Unspecified (295.20); Schizophrenia, Disorganized, Subchronic (295.11); Schizophrenia, Disorganized, Chronic (295.12); Schizophrenia, Disorganized, Subchronic with Acute Exacerbation (295.13); Schizophrenia, Disorganized, Chronic with Acute Exacerbation (295.14); Schizophrenia, Disorganized, in Remission (295.15); Schizophrenia, Disorganized, Unspecified (295.10); Schizophrenia, Paranoid, Subchronic (295.31); Schizophrenia, Paranoid, Chronic (295.32); Schizophrenia, Paranoid, Subchronic with Acute Exacerbation (295.33); Schizophrenia, Paranoid, Chronic with Acute Exacerbation (295.34); Schizophrenia, Paranoid, in Remission (295.35); Schizophrenia, Paranoid, Unspecified (295.30); Schizophrenia, Undifferentiated, Subchronic (295.91); Schizophrenia, Undifferentiated, Chronic (295.92); Schizophrenia, Undifferentiated, Subchronic with Acute Exacerbation (295.93); Schizophrenia, Undifferentiated, Chronic with Acute Exacerbation (295.94); Schizophrenia, Undifferentiated, in Remission (295.95); Schizophrenia, Undifferentiated, Unspecified (295.90); Schizophrenia, Residual, Subchronic (295.61); Schizophrenia, Residual, Chronic (295.62); Schizophrenia, Residual, Subchronic with Acute Exacerbation (295.63); Schizophrenia, Residual, Chronic with Acute Exacerbation (295.94); Schizophrenia, Residual, in Remission (295.65); Schizophrenia, Residual, Unspecified (295.60); Delusional (Paranoid) Disorder (297.10); Brief Reactive Psychosis (298.80); Schizophreniform Disorder (295.40); Schizoaffective Disorder (295.70); Induced Psychotic Disorder (297.30); Psychotic Disorder NOS (Atypical Psychosis) (298.90); Personality Disorders, Paranoid (301.00); Personality Disorders, Schizoid (301.20); Personality Disorders, Schizotypal (301.22); Personality Disorders, Antisocial (301.70); Personality Disorders, Borderline (301.83) and bipolar disorders, maniac, hypomaniac, dysthymic or cyclothymic disorders, substance-induced mood disorders, major depression, psychosis, including paranoid psychosis, catatonic psychosis, delusional psychosis, having schizoaffective disorder, and substance-induced psychotic disorder.

In some embodiments, modulators of polynucleotides or polypeptides of the invention can be combined with other drugs useful for treating mental disorders including useful for treating mood disorders, e.g., schizophrenia, bipolar disorders, or major depression. In some preferred embodiments, pharmaceutical compositions of the invention comprise a modulator of a polypeptide of polynucleotide of the invention combined with at least one of the compounds useful for treating schizophrenia, bipolar disorder, or major depression, e.g., such as those described in U.S. Pat. Nos. 6,297,262; 6,284,760; 6,284,771; 6,232,326; 6,187,752; 6,117,890; 6,239,162 or 6,166,008.

The pharmaceutical compositions of the invention may comprise a pharmaceutically acceptable carrier. Pharmaceutically acceptable carriers are determined in part by the particular composition being administered, as well as by the particular method used to administer the composition.

Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the a polypeptide or polynucleotide of the invention, alone or in combination with other suitable components, can be made into aerosol formulations (i.e., they can be "nebulized") to be administered via inhalation or in compositions useful for injection. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the mental disorder. The size of the dose also will be determined by the existence, nature, and extent of any adverse side effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side effects of the modulator at various concentrations, as applied to the mass and overall health of the subject. Administration can be accomplished via single or divided doses.

IX. Gene Therapy Applications

A variety of human diseases can be treated by therapeutic approaches that involve stably introducing a gene into a human cell such that the gene is transcribed and the gene product is produced in the cell. Diseases amenable to treatment by this approach include inherited diseases, including those in which the defect is in a single or multiple genes. Gene therapy is also useful for treatment of acquired diseases and other conditions. For discussions on the application of gene therapy towards the treatment of genetic as well as acquired diseases, see, Miller, *Nature* 357:455-460 (1992); and Mulligan, *Science* 260:926-932 (1993).

In the context of the present invention, gene therapy can be used for treating a variety of disorders and/or diseases in which the polynucleotides and polypeptides of the invention has been implicated. For example, compounds, including polynucleotides, can be identified by the methods of the present invention as effective in treating a mental disorder. Introduction by gene therapy of these polynucleotides can then be used to treat, e.g., mental disorders including mood disorders and psychotic disorders.

A. Vectors for Gene Delivery

For delivery to a cell or organism, the polynucleotides of the invention can be incorporated into a vector. Examples of vectors used for such purposes include expression plasmids capable of directing the expression of the nucleic acids in the target cell. In other instances, the vector is a viral vector system wherein the nucleic acids are incorporated into a viral genome that is capable of transfecting the target cell. In a preferred embodiment, the polynucleotides can be operably linked to expression and control sequences that can direct expression of the gene in the desired target host cells. Thus, one can achieve expression of the nucleic acid under appropriate conditions in the target cell.

B. Gene Delivery Systems

Viral vector systems useful in the expression of the nucleic acids include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors are also useful for introducing the nucleic acids of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

In some embodiments of the invention, an antisense polynucleotide is administered which hybridizes to a gene encoding a polypeptide of the invention. The antisense polypeptide can be provided as an antisense oligonucleotide (see, e.g., Murayama et al., *Antisense Nucleic Acid Drug Dev.* 7:109-114 (1997)). Genes encoding an antisense nucleic acid can also be provided; such genes can be introduced into cells by methods known to those of skill in the art. For example, one can introduce an antisense nucleotide sequence in a viral vector, such as, for example, in hepatitis B virus (see, e.g., Ji et al., *J. Viral Hepat.* 4:167-173 (1997)), in adeno-associated virus (see, e.g., Xiao et al., *Brain Res.* 756:76-83 (1997)), or in other systems including, but not limited, to an HVJ (Sendai virus)-liposome gene delivery system (see, e.g., Kaneda et al., *Ann. NY Acad. Sci.* 811:299-308 (1997)), a "peptide vector" (see, e.g., Vidal et al., *CR Acad. Sci. III* 32:279-287 (1997)), as a gene in an episomal or plasmid vector (see, e.g., Cooper et al., *Proc. Natl. Acad. Sci. U.S.A.* 94:6450-6455 (1997), Yew et al. *Hum Gene Ther.* 8:575-584 (1997)), as a gene in a peptide-DNA aggregate (see, e.g., Niidome et al., *J. Biol. Chem.* 272:15307-15312 (1997)), as "naked DNA" (see, e.g., U.S. Pat. Nos. 5,580,859 and 5,589,466), in lipidic vector systems (see, e.g., Lee et al., *Crit. Rev Ther Drug Carrier Syst.* 14:173-206 (1997)), polymer coated liposomes (U.S. Pat. Nos. 5,213,804 and 5,013,556), cationic liposomes (Epand et al., U.S. Pat. Nos. 5,283,185; 5,578,475; 5,279,833; and 5,334,761), gas filled microspheres (U.S. Pat. No. 5,542, 935), ligand-targeted encapsulated macromolecules (U.S. Pat. Nos. 5,108,921; 5,521,291; 5,554,386; and 5,166,320).

Upregulated transcripts listed in the biomarker tables herein which are correlated with mental disorders may be targeted with one or more short interfering RNA (siRNA) sequences that hybridize to specific sequences in the target, as described above. Targeting of certain brain transcripts with siRNA in vivo has been reported, for example, by Zhang et al., *J. Gene. Med.,* 12:1039-45 (2003), who utilized monoclonal antibodies against the transferrin receptor to facilitate passage of liposome-encapsulated siRNA molecules through the blood brain barrier. Targeted siRNAs represent useful therapeutic compounds for attenuating the over-expressed transcripts that are associated with disease states, e.g., MDD, BP, and other mental disorders.

In another embodiment, conditional expression systems, such as those typified by the tet-regulated systems and the RU-486 system, can be used (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These systems impart small molecule control on the expression of the target gene(s) of interest.

In another embodiment, stem cells engineered to express a transcript of interest can implanted into the brain.

C. Pharmaceutical Formulations

When used for pharmaceutical purposes, the vectors used for gene therapy are formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's *Pharmaceutical Sciences*, Mack Publishing Company, Philadelphia, Pa., 17th ed. (1985).

D. Administration of Formulations

The formulations of the invention can be delivered to any tissue or organ using any delivery method known to the ordinarily skilled artisan. In some embodiments of the invention, the nucleic acids of the invention are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

E. Methods of Treatment

The gene therapy formulations of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2):116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

X. Diagnosis of Mood Disorders and Psychotic Disorders

The present invention also provides methods of diagnosing mood disorders (such as major depression or bipolar disorder), psychotic disorders (such as schizophrenia), or a predisposition of at least some of the pathologies of such disorders. Diagnosis involves determining the level of a polypeptide or polynucleotide of the invention in a patient and then comparing the level to a baseline or range. Typically, the baseline value is representative of a polypeptide or polynucleotide of the invention in a healthy person not suffering from a mood disorder or a psychotic disorder or under the effects of medication or other drugs. Variation of levels of a polypeptide or polynucleotide of the invention from the baseline range (either up or down) indicates that the patient has a mood disorder or a psychotic disorder or at risk of developing at least some aspects of a mood disorder or a psychotic disorder. In some embodiments, the level of a polypeptide or polynucleotide of the invention are measured by taking a blood, urine or tissue sample from a patient and measuring the amount of a polypeptide or polynucleotide of the invention in the sample using any number of detection methods, such as those discussed herein.

Antibodies can be used in assays to detect differential protein expression in patient samples, e.g., ELISA assays, immunoprecipitation assays, and immunohistochemical assays. PCR assays can be used to detect expression levels of nucleic acids, as well as to discriminate between variants in genomic structure, such as insertion/deletion mutations (e.g., PSPHL).

In the case where absence of gene expression is associated with a disorder, the genomic structure of a gene such as PSPHL can be evaluated with known methods such as PCR to detect deletion or insertion mutations associated with disease suspectibility. Conversely, the presence of mRNA or protein corresponding to the PSPHL gene would indicate that an individual does not have the PSPHL deletion associated with susceptibility to BP. Thus, diagnosis can be made by detecting the presence or absence of mRNA or protein, or by examining the genomic structure of the gene. Any combination of exons or non-transcribed regions can be used to detect the deletion allele. For example, the presence of exon 4 but not exons 1, 2, and/or 3 would indicate the presence of the deletion allele. Similarly, deletion of the promoter region would indicate the deletion allele. Any significant mRNA detection, especially detection of an mRNA comprising exons 1, 2, and/or 3, would indicate the absence of the deletion allele, which is not transcribed due to the promoter deletion.

Single nucleotide polymorphism (SNP) analysis is also useful for detecting differences between alleles of the polynucleotides (e.g., genes) of the invention. SNPs linked to genes encoding polypeptides of the invention are useful, for instance, for diagnosis of diseases (e.g., mood disorders such as bipolar disease, major depression, and schizophrenia disorders) whose occurrence is linked to the gene sequences of the invention. For example, if an individual carries at least one SNP linked to a disease-associated allele of the gene sequences of the invention, the individual is likely predisposed for one or more of those diseases. If the individual is homozygous for a disease-linked SNP, the individual is particularly predisposed for occurrence of that disease. In some embodiments, the SNP associated with the gene sequences of the invention is located within 300,000; 200,000; 100,000; 75,000; 50,000; or 10,000 base pairs from the gene sequence.

Various real-time PCR methods can be used to detect SNPs, including, e.g., Taqman or molecular beacon-based assays (e.g., U.S. Pat. Nos. 5,210,015; 5,487,972; Tyagi et al., *Nature Biotechnology* 14:303 (1996); and PCT WO 95/13399 are useful to monitor for the presence of absence of a SNP. Additional SNP detection methods include, e.g., DNA sequencing, sequencing by hybridization, dot blotting, oligonucleotide array (DNA Chip) hybridization analysis, or are described in, e.g., U.S. Pat. No. 6,177,249; Landegren et al., *Genome Research*, 8:769-776 (1998); Botstein et al., *Am*

*J Human Genetics* 32:314-331 (1980); Meyers et al., Methods in Enzymology 155:501-527 (1987); Keen et al., *Trends in Genetics* 7:5 (1991); Myers et al., *Science* 230:1242-1246 (1985); and Kwok et al., *Genomics* 23:138-144 (1994). PCR methods can also be used to detect deletion/insertion polymorphisms, such as the deletion polymorphism of the PSPHL gene associated with suspectibility to BP.

In some embodiments, the level of the enzymatic product of a polypeptide or polynucleotide of the invention is measured and compared to a baseline value of a healthy person or persons. Modulated levels of the product compared to the baseline indicates that the patient has a mood disorder or a psychotic disorder or is at risk of developing at least some aspects of a mood disorder or a psychotic disorder. Patient samples, for example, can be blood, urine or tissue samples.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Identification of FGF Pathway Genes Dysregulated in MDD

Major depressive disorder (MDD) and bipolar disorder (BP) are affective diseases that strike a significant proportion of the population. These complex genetic disorders arise from the interplay of vulnerability genes and environmental stressors, impacting neural circuits that control mood. Beyond the role of limbic structures, mood disorders are hypothesized to involve aberrant activity of the cerebral cortex. Thus, imaging techniques have implicated the dorsolateral prefrontal (DLPFC) and anterior cingulate (AnCg) cortices in mood disorders since affected subjects display changes in volumetric measurements (Harrison, P. J. Brain 125, 1428-49 (2002).) and altered activity in response to a cognitive challenge. (Kruger, S., Seminowicz, D., Goldapple, K., Kennedy, S. H. & Mayberg, H. S. Biol Psychiatry 54, 1274-83 (2003)) Using a candidate approach, studies have demonstrated altered cortical expression of specific neurotransmitter- and stress-related genes in affective illness. However, the full extent of the alteration in cortical activity had not been described, nor had an unbiased "discovery" approach been applied to characterize it.

We have applied microarray technology to the study of DLPFC and AnCg in post-mortem samples from MDD, BP and non-psychiatric controls. This represents the first transcriptional profiling study demonstrating significant alterations of gene expression in major depression, and the first one contrasting the two major mood disorders (MDD and BP) with the same group of controls. Here we report the dysregulation of fibroblast growth factor (FGF) system transcripts specifically in MDD.

Human Studies

The studies were carried out in a carefully selected cohort of postmortem human brains, and replicated in a separate cohort (see Table 1a and 1b). The Affymetrix HG-133A array contains probe sets for 21 FGF system transcripts, including all 4 receptors (FGFR1, 2, 3, 4) and 12 FGF peptide ligands (FGF1, 2, 3, 5, 6, 7, 8, 9, 12, 13, 14, 17, 18, 20, 21, 22, 23). Of these only 10 were reliably detected in the regions assayed and include three of the FGF receptors (FGFR1, 2, and 3) and seven FGF ligands (FGF1, 2, 7, 9, 12, 13, 14). Of the ten FGF transcripts reliably detected, seven were significantly altered in one of the two regions studied—four were significantly differentially expressed in the DLPFC of MDD subjects, including 2 FGF receptors (FGFR2 and 3) and 2 FGF ligands (FGF1 and 9); and six were significantly differentially expressed in the AnCg including two receptors (FGFR2 and 3) and four ligands (FGF1, 2, 9 and 12). The probability that this family of molecules would have emerged by chance, based on a hypergeometric distribution, is $p<0.001$. These data are summarized in Table 2, which also reports on the transcripts confirmed by real-time PCR analysis and/or those replicated in a second independent cohort of MDD and control subjects. Importantly, none of the above transcripts were observed to be differentially expressed in BP by microarray in either cohort or by real-time PCR analysis, demonstrating the specificity of this dysregulation for MDD.

Given this selective dysregulation of FGF system transcripts in MDD we asked whether these changes might be secondary to antidepressant therapy since a subset of the subjects was on antidepressants, and the majority of those were on specific serotonin reuptake inhibitors (SSRI's). Thus, we separated our microarray data into MDD subjects prescribed SSRI's (n=5) and those not prescribed SSRI's (n=4) for statistical comparisons. This analysis showed that FGFR3 and FGF2 had a tendency toward up-regulation ($p=0.15$ and 0.07, respectively) and that FGF 9 showed a tendency toward down-regulation ($p=0.12$) by SSRI treatment, all opposing the directionality of dysregulation we see in MDD subjects relative to controls. No other FGF system transcripts approached significant differences in this analysis. These data strongly suggest that our observations are not secondary to SSRI treatment. Furthermore, the observed attenuation of FGF transcript dysregulation in the SSRI prescribed group suggests that the normalization of FGF system might be one mechanism of action of this class of drugs since several FGF transcripts appear to be altered in severe depression and are partially reversed by SSRI therapy.

Rodent Anatomical Studies; Effect of Fluoxetine.

We studied the anatomical expression of FGFR2 in rats subjected to chronic fluoxetine treatment relative to controls (FIG. 1). FGFR2 mRNA expression was quantified in the retrosplenial cortex and in the hippocampus since this area has recently been implicated in the mode of action of antidepressants (Santarelli, L. et al. Science 301, 805-9 (2003)). Results show that FGFR2 message is significantly increased by fluoxetine in all hippocampal subfields (CA1, CA2, CA3, and dentate gyrus) and the retrosplenial cortex (Fisher's PLSD, $p=0.0049$).

The implication of the FGF system in MDD has emerged from our studies utilizing microarray technology to study human psychiatric illness. Other growth factors have been hypothesized to contribute to the etiology and maintenance of such illnesses and can offer a framework in which to place our own findings. Most notably, brain derived neurotrophic factor (BDNF) has been repeatedly implicated in MDD, BP and in SZ. BDNF mRNA levels are reportedly decreased in the DLPFC (Weickert, C. S., et al., Mol Psychiatry 8, 592-610 (2003)) of schizophrenics and BDNF protein levels are decreased in serum of MDD (Shimizu, E. et al. Biol Psychiatry 54, 70-5 (2003)) patients. Furthermore, BDNF expression is regulated by antipsychotic (Chlan-Fourney, J. et al., Brain Res 954, 11-20 (2002)) and antidepressant drugs (Shimizu, E. et al. Biol Psychiatry 54, 70-5 (2003)), (Dias, B. G., et al., Neuropharmacology 45, 553-63 (2003)). A smaller volume of literature implicates other growth factors, including nerve growth factor (Parikh, V., Evans, D. R., Khan, M. M. & Mahadik, S. P. Schizophr Res 60, 117-23 (2003)), epidermal growth factor (Futamura, T. et al. Mol Psychiatry 7, 673-82 (2002)) and neurotrophin-3 (Hock, C. et al. Mol Psychiatry 5, 510-3 (2000)) in psychiatric illness.

Growth factors play significant roles in development and maintenance of the central nervous system. In the developing brain, they are involved in specific neuronal terminal differentiation and migration to appropriate subfields. In the adult brain they are critical in neuronal survival, axonal branching and synaptic plasticity. Specifically, FGF2 (Viti, J., Gulacsi, A. & Lillien, L. J Neurosci 23, 5919-27 (2003)) and FGF8 (Gunhaga, L. et al. Nat Neurosci 6, 701-7 (2003)) have been shown to interact with Wnt in the development of the cortex in mouse and chick embryos, respectively. In the adult brain, FGF2 promotes neuronal survival and axonal branching (Abe, K. & Saito, H. Pharmacol Res 43, 307-12 (2001)) and its expression is modulated by stress (Molteni, R. et al., Brain Res Rev 37, 249-58 (2001)).

Together, these results lead to the novel hypothesis that dysregulation of the FGF system contributes to either the vulnerability to MDD or the expression of the illness, and that antidepressants might attenuate this dysregulation. Animal models will be crucial for defining the involvement of the FGF system in emotionality and elucidating its role in neural plasticity and antidepressant action.

Example 2

Identification of Novel Insertion/Deletion Polymorphism in PSPHL Gene and Association of Deletion Mutation with BP Susceptibility Evaluation of PSPHL expression in anterior cingulated cortex by quantitative RT-PCR reveals that PSPHL shows a dichotomous (present or absent) pattern of expression among individuals. In our first cohort, none of the 9 BPD patients (0%) shows PSPHL expression, while 7 out of 11 MDD patients (64%) and 8 out of 20 controls (40%) show sufficient expression of PSPHL. The probability of distribution of the present/absent expression pattern between BPD and controls is 0.018, and between MDD and controls is 0.105 based on the Fisher exact test. To assure this significant contrast between BPD and controls, we measured PSPHL expression in an additional 9 BPD and 20 control individuals (for a total of 18 BPD and 40 controls) using quantitative RT-PCR. In this larger sample set, none of the 18 BPD patients (0%) shows any expression of PSPHL, while 16 out of 40 controls (40%) show sufficient expression of the transcript (p value=0.0008).

The fact that PSPHL shows dichotomous present/absent pattern of expression among individuals with brain-wide consistency suggests genetic variation in its regulation. Since genomic organization of PSPHL has not been characterized (Planitzer, supra (1998)), we have identified genomic organization of PSPHL as shown in FIG. 14. The PSPHL gene consists of 4 exons. Exons 1, 2, 3 and 4 are 213 bp, 114 bp, 122 bp and 501 bp, in length, respectively, and span introns 1, 2 and 3 (3221 bp, 829 bp and 11939 bp, in length, respectively). Further, the PSPHL gene has two alternative transcripts, one of which utilizes the exons 1-4 (PSPHL-A in FIG. 14), while another utilizes the exons 1, 2 and 4 (PSPHL-B). We have also identified an insertion/deletion polymorphism at the PSPHL locus. The deleted genomic region spans more than 30 kb, including the promoter region and the exons 1, 2 and 3 of PSPHL gene. This genetic variance explains the present/absent pattern of the PSPHL expression. An over-representation of the deletion allele resulting in the absence of PSPHL expression increases susceptibility to BPD.

Figure 15:
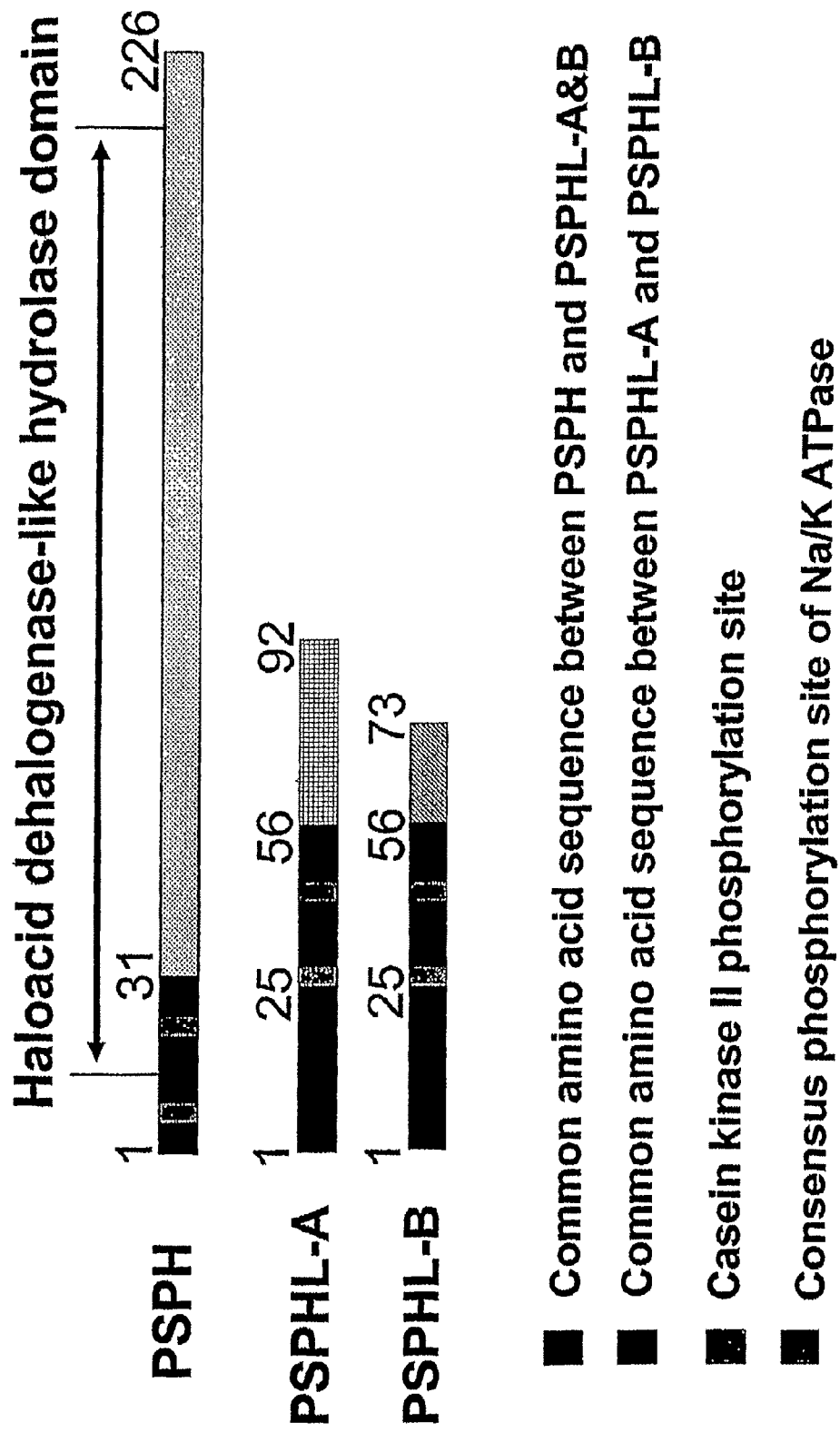
FIG. 15: shows the predicted amino acid sequences for PSPH, PSPHL-A, and PSPHL-B.

PSPHL and PSPH are highly homologous, but appear to be different genes, which are about 200 kb apart from each other on chromosome 7p11.2 region. Especially, exons 2-4 of PSPHL are highly homologous to exons 4 and 8 of PSPH gene. Predicted amino acid sequences of PSPH, PSPHL-A and PSPHL-B are shown in FIG. 15. PSPHL-A and PSPHL-B share N-terminal 57 common amino acids, transcribed from exons 1 and 2. PSPHL-A has unique C-terminal 36 amino acids, transcribed from exon3, while PSPHL-B has unique C-terminal 17 amino acids, transcribed from exon 4. PSPH and PSPHL-A&B have 31 amino acids in common. The common amino acids locates at the N-terminal end of PSPH and middle region (25th-56th amino acids) of PSPHL-A and B. The common region contains consensus phosphorylation site of Na/K ATPase and casein kinase II phospholyration site. Based on the similarity in the structure, PSPHL shares some function with PSPH gene.

Figure 16:
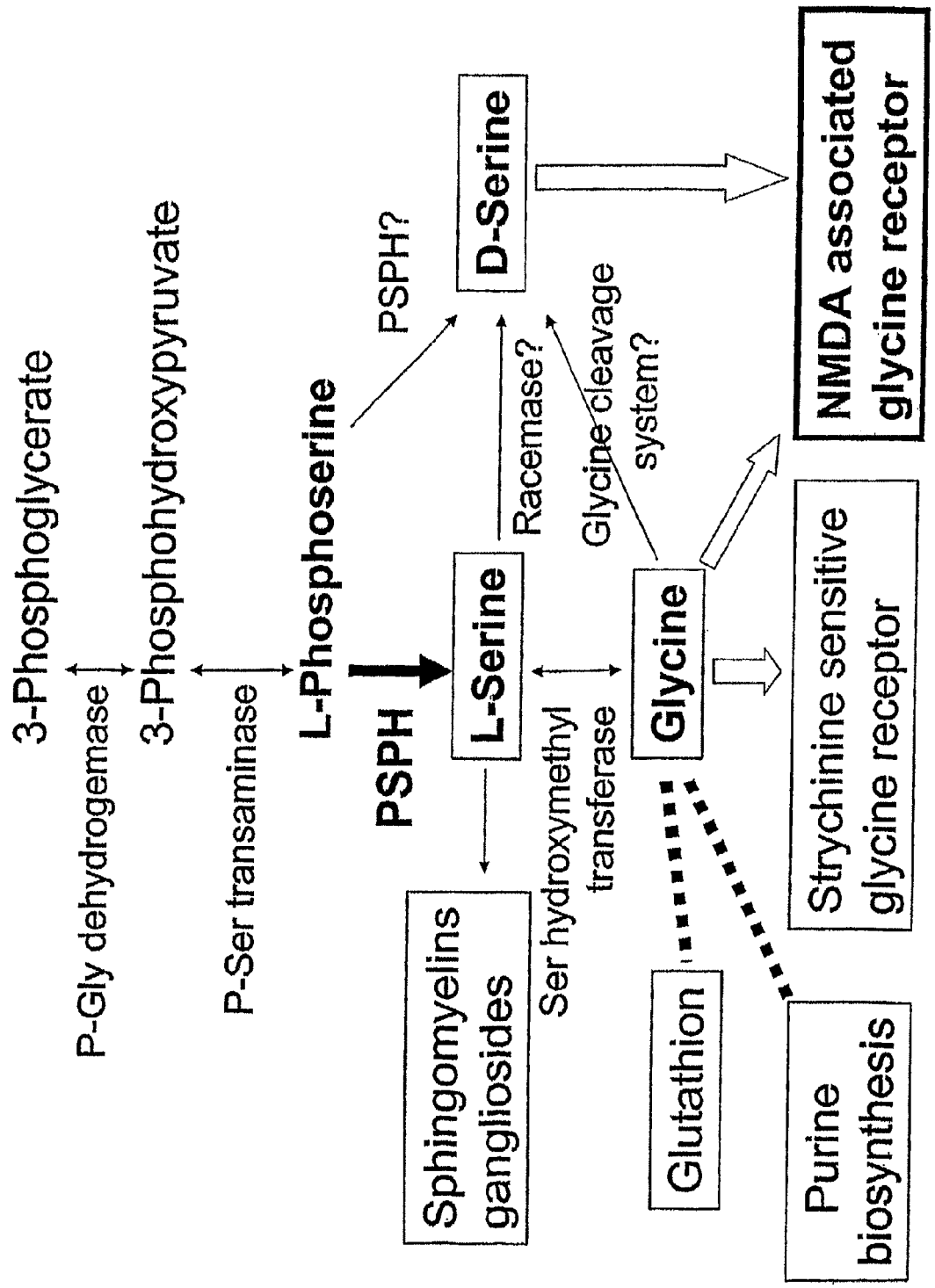
FIG. 16: shows the serine amino acid metabolic pathway.
Figure 18:
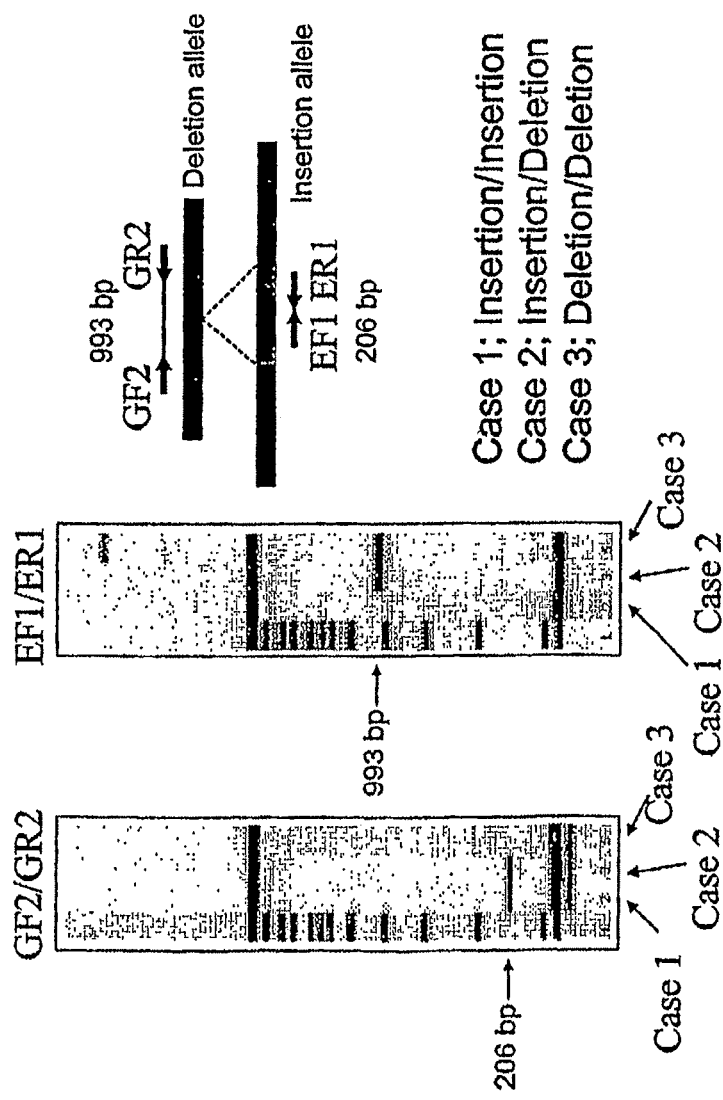
FIG. 18: shows a gel image for PSPHL insertion/deletion alleles.
Figure 19:
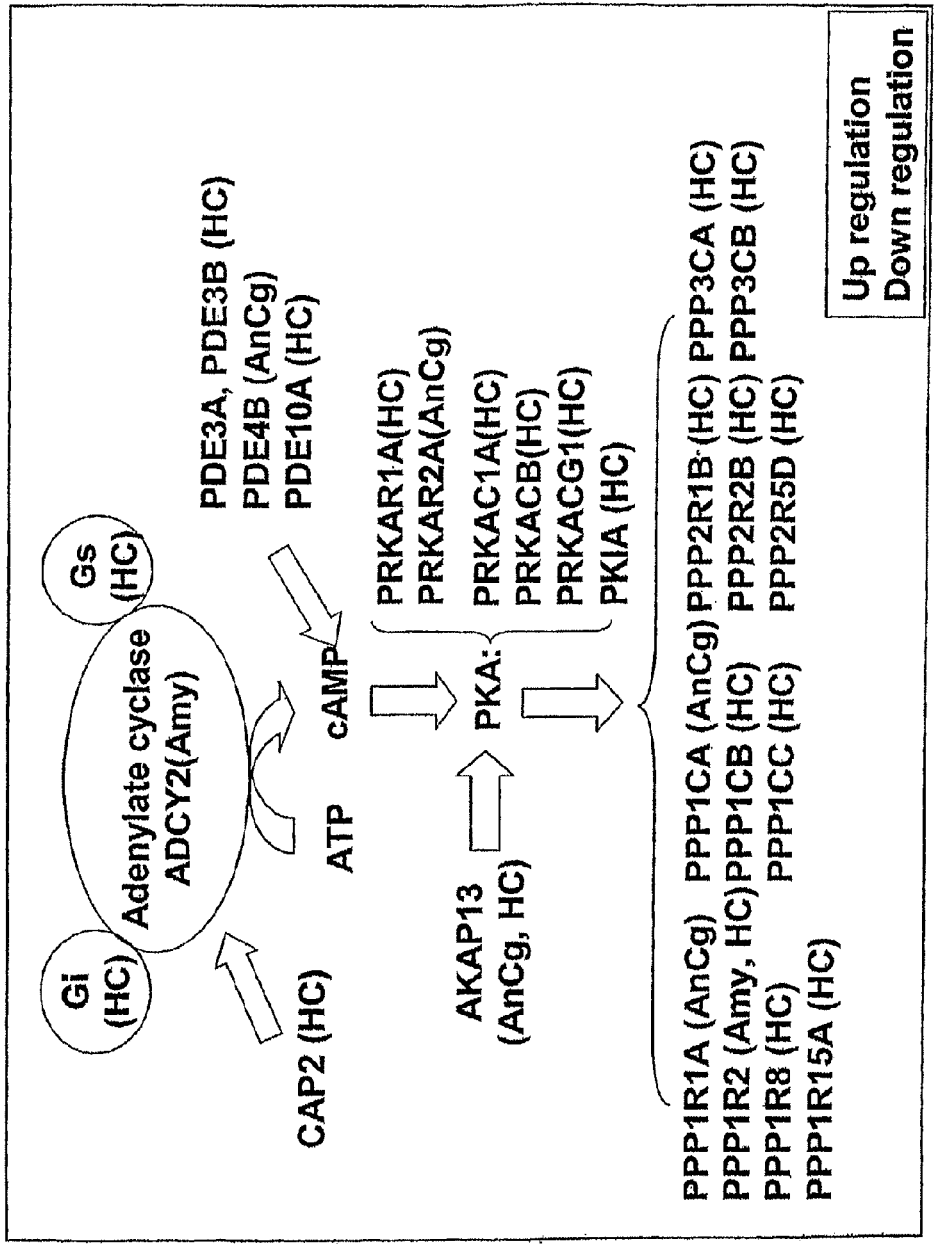
FIG. 19: shows the cAMP signaling pathway in the limbic system for BP.
Figure 20:
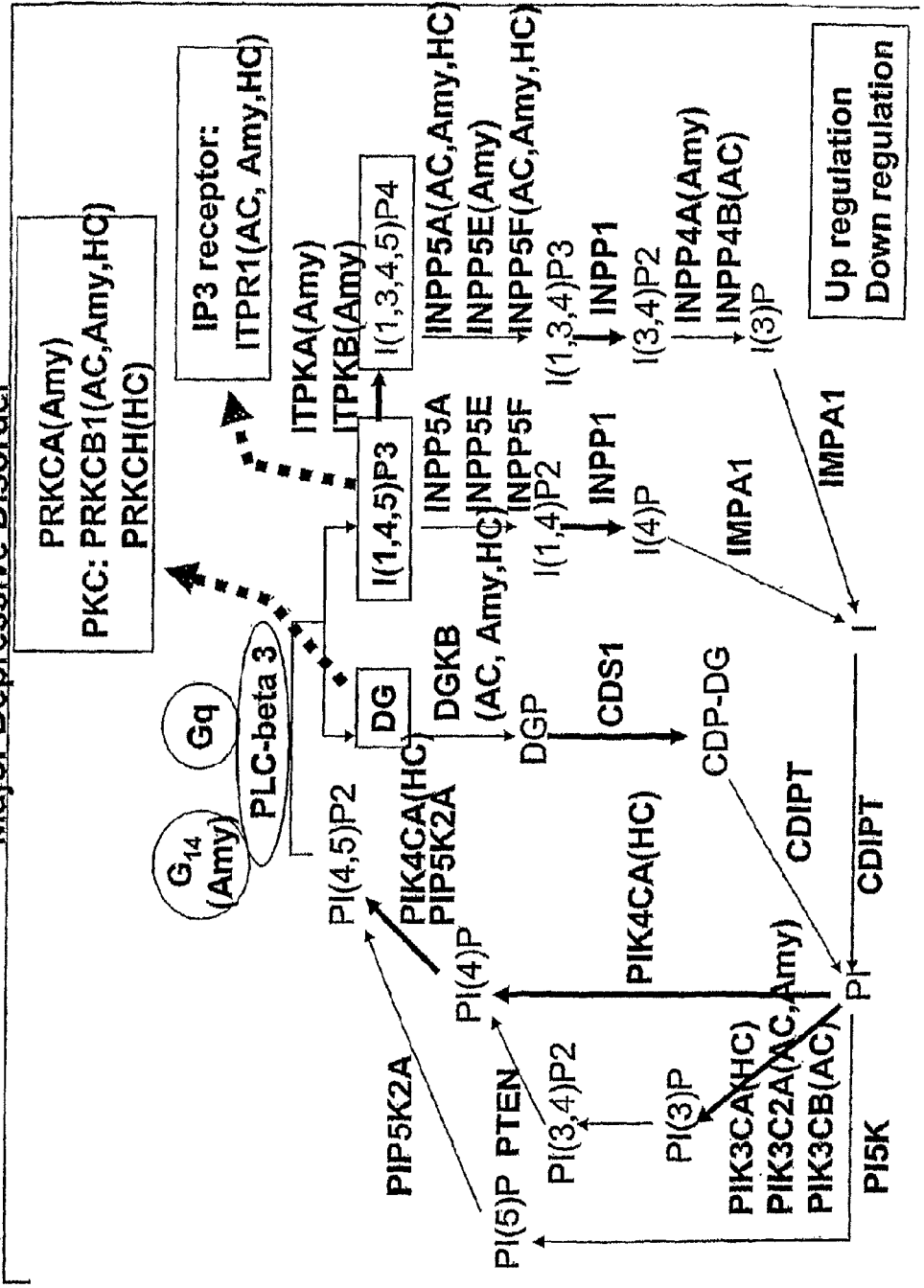
FIG. 20: shows the PI signaling pathway in the limbic system for MDD.
Figure 21:
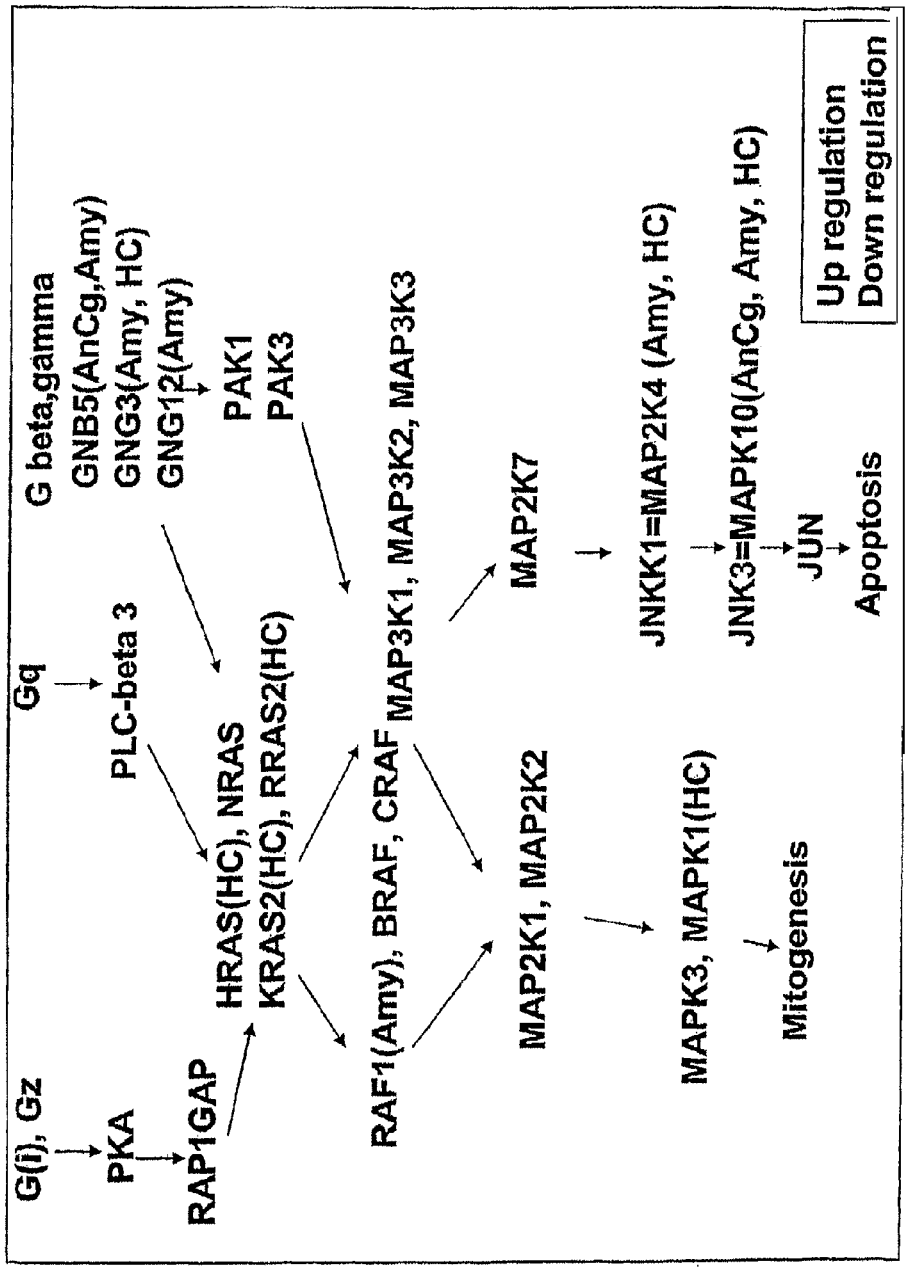
FIG. 21: shows MAPK signaling pathway in the limbic system for MDD.
Figure 22E:
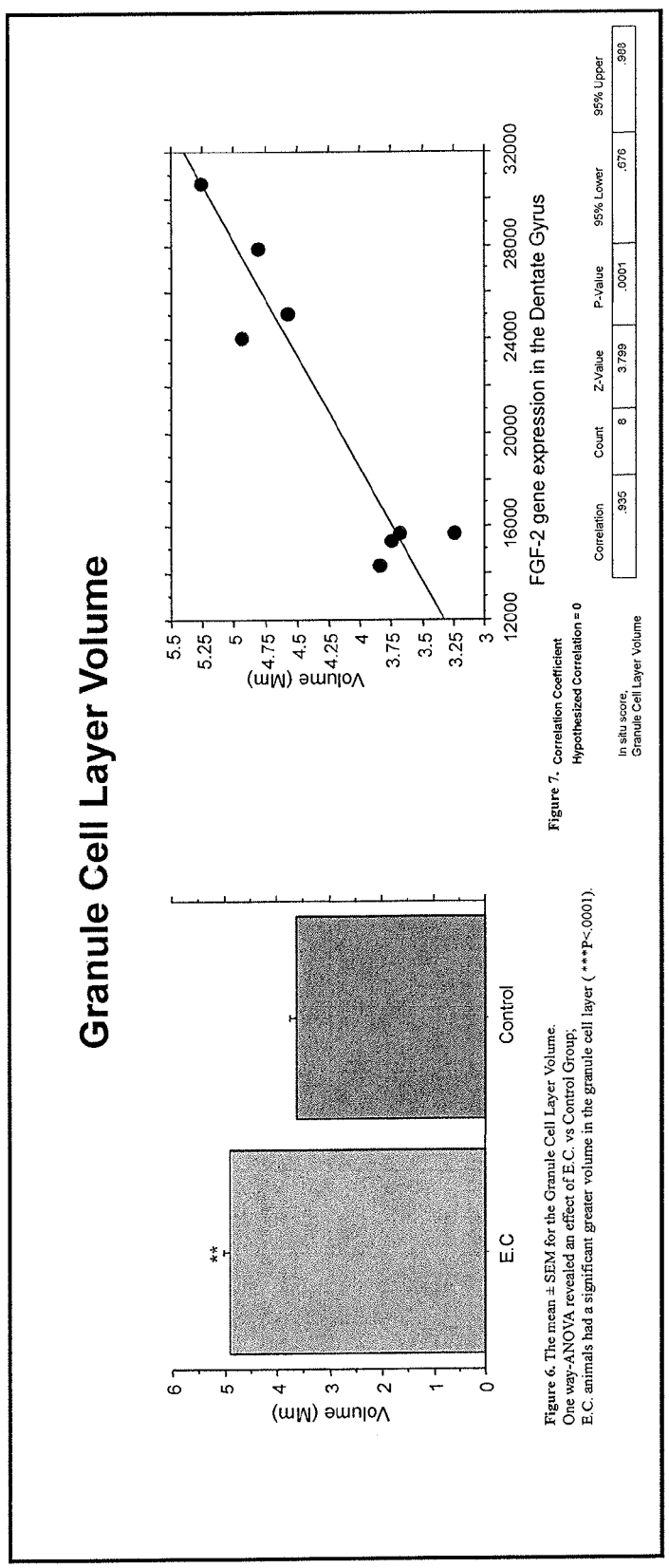
Figure 23F:
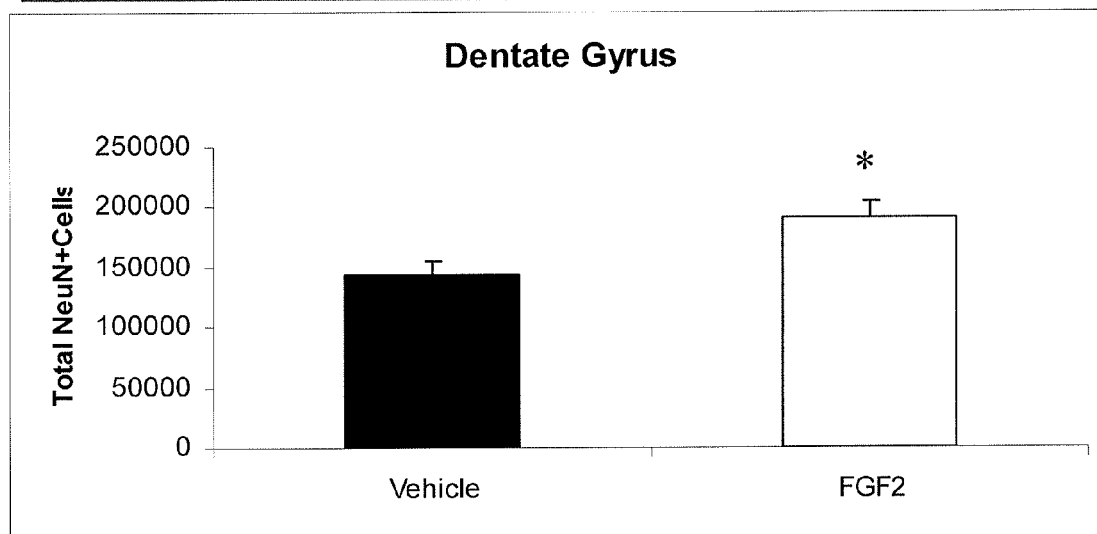
Figure 23G:
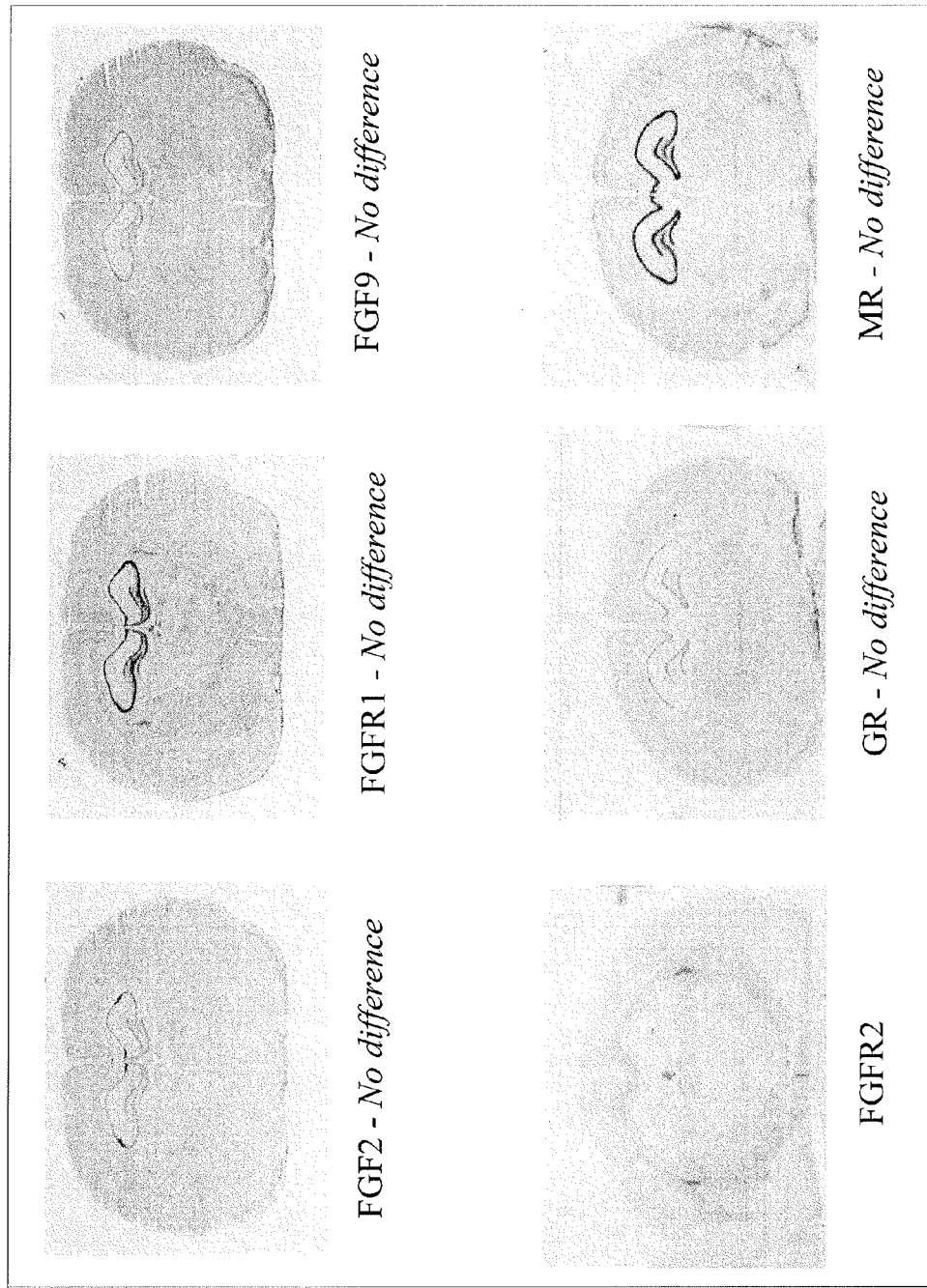
Figure 24C:
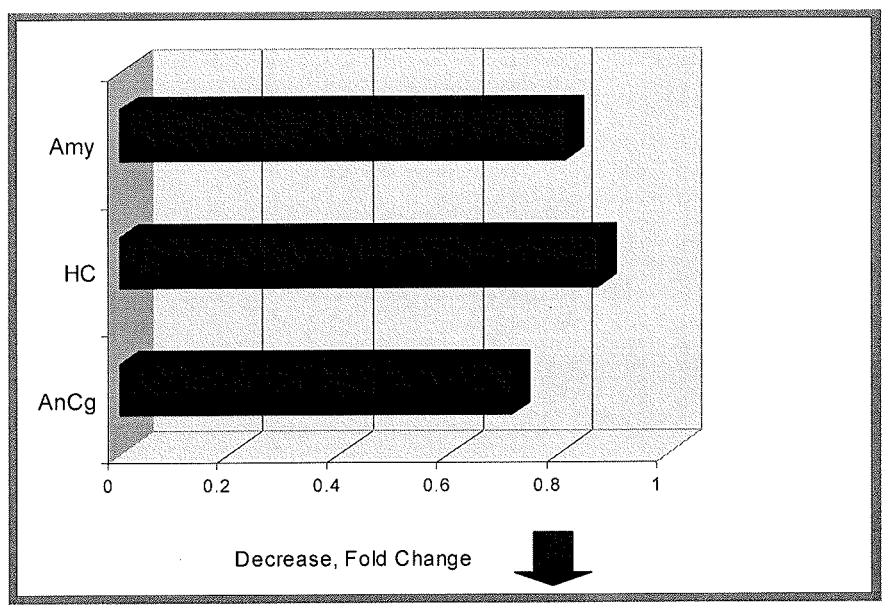
Figure 24E:
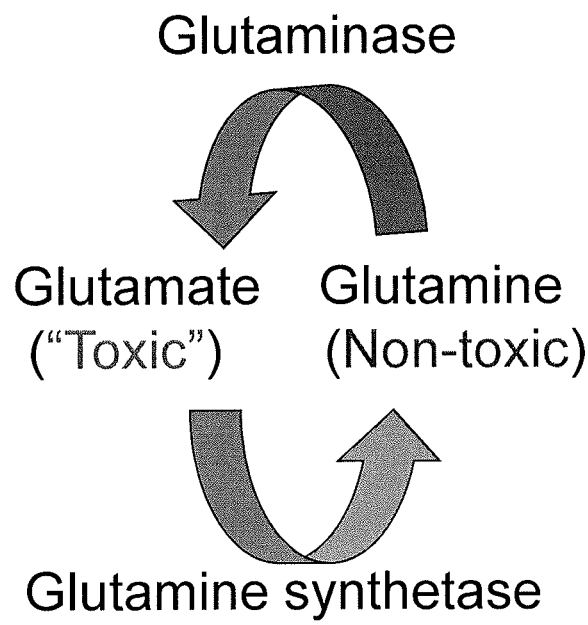
Figure 25D:
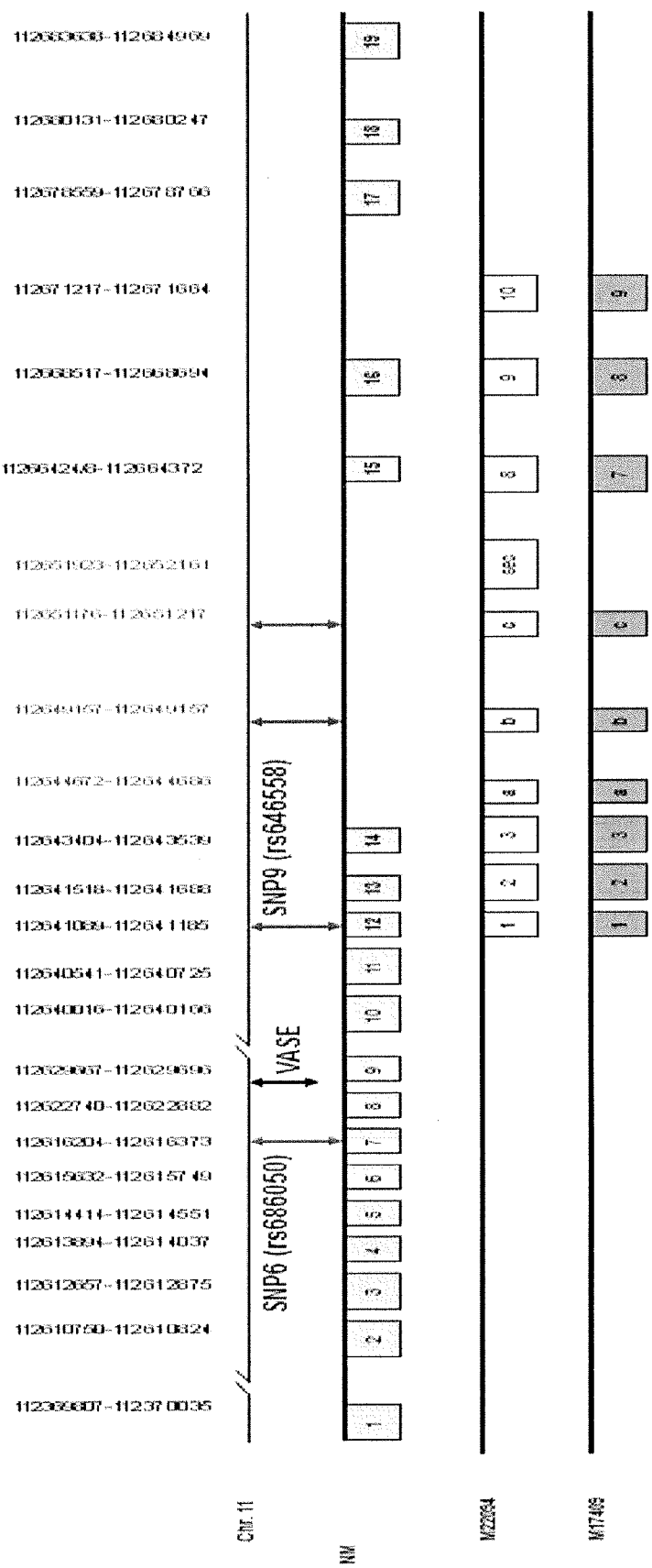
Figure 25E:
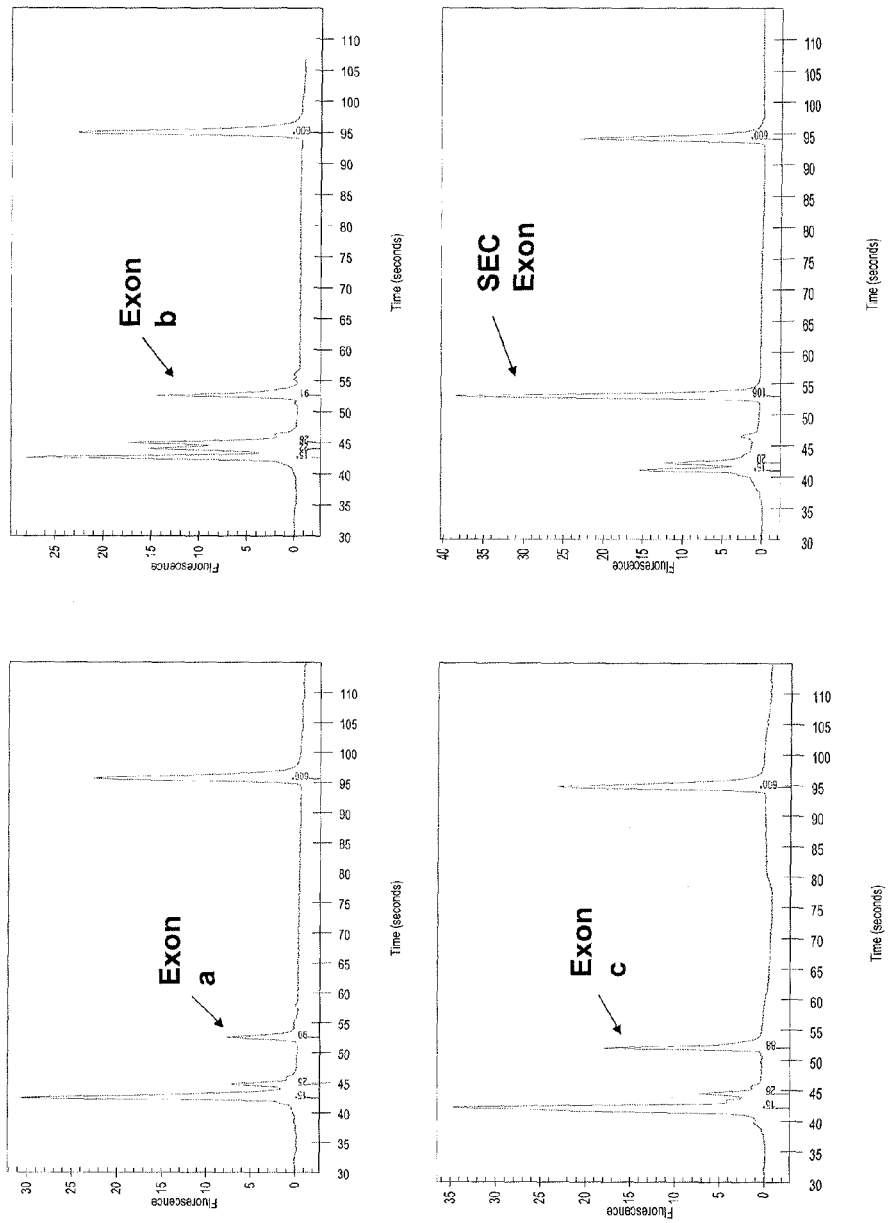
Figure 25I:
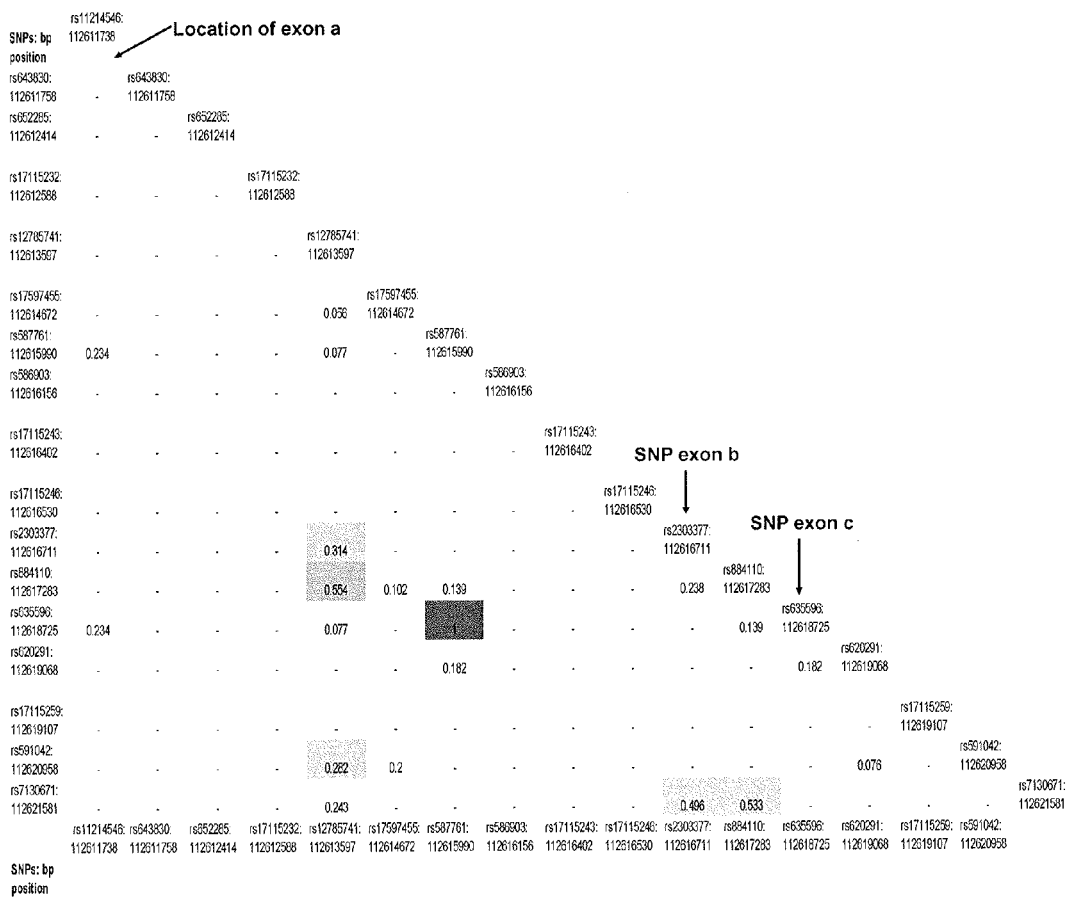

PSPH is the rate limiting enzyme for serine synthesis. PSPH has haloacid dehalogenase-like hydrolase domain, which is responsible for the activity. Greater than 90% of L-serine in brain is formed via the phosphorylated pathway. PSPH may be dimeric from of the enzyme with a monomeric molecular weight of 26 kDa. L-serine is converted to sphingomyelins and gangliosides, as well as L-glycine and D-serine, both of which act as coagonist for NMDA receptor associated glycine binding site. L-glycine is also an agonist for strychnine-sensitive glycine receptor (FIG. 16). PSPHL is involved in serine amino acid metabolic pathway, and may involved in other pathways as well.

Example 3

Post-Natal Injection of FGF2

This Example shows that neonatal administration of FGF-2 affects long-term alterations in hippocampal volume, emotional reactivity and learning and memory. Sprague-Dawley rats were injected with either vehicle or FGF-2 (20 ng/g, s.c.) on postnatal day 2 (PD2). Three weeks after injection we evaluated dentate gyrus volume and cell counts by Nissl staining. We also assessed neurogenesis by BrdU and Ki-67 immunohistochemistry at the 23 day time point. In adult rats, we tested locomotor activity, anxiety behavior and learning and memory. The animals were sacrificed, and the brains collected for in situ hybridization (FGF markers, stress markers). Results to date have shown the following: FGF-2 injected rats exhibited a 10.5% increase in dentate gyrus volume. The results show that FGF-2 significantly increased locomotor activity over controls in a novel environment. Increased activity in response to novelty has been associated with a host of other measures including decreased anxiety-like behavior. Furthermore, adult rats that received FGF-2 as neonates also performed significantly better than controls in the Morris water maze.

Example 4

FGF2 Expression

While evidence has linked growth factors such as BDNF to environmental complexity (EC), responsiveness to stress, and antidepressant action, few studies focused on the role of the FGF system in emotional reactivity. Recent data from our laboratory suggest that a single postnatal injection of FGF-2 significantly alters locomotor activity in response to a novel environment (Turner et al., SFN abstracts 2004). Since increased responsiveness to novelty is associated with decreased anxiety-like behavior, we propose that FGF-2 may be correlated with other indices of emotionality. We tested the hypothesis that changes in emotionality associated with EC may be related to FGF-2 gene expression in the hippocampus. Young adult male Sprague-Dawley rats were either exposed to a complex environment for 21 days or to standard cages. Following this treatment, rats were returned to standard cages for two weeks. Brains were then processed for neurogenesis by BrdU and Ki-67 immunohistochemistry. Another group of rats was tested in the elevated plus-maze (EPM) and then sacrificed for in situ hybridization. Compared to controls, EC rats showed significantly less anxiety-like behavior in the EPM and exhibited a 23% increase in FGF-2 expression in the hippocampus. There was a significant positive correlation between FGF-2 mRNA levels in hippocampal CA2 and time spent in the open arms of the EPM. Whether these results relate to levels of neurogenesis in the hippocampus is currently being determined. These findings are consistent with our observations in human postmortem brains (Evans et al, SIN Abstracts 2004) showing that expression of several members of the FGF family is decreased in major depression. Together, these findings implicate the FGF system in emotionality and mood disorders.

Example 5

Cyclic Amp Signaling Pathway Genes Differentially Expressed in BPD and/or MDD Patients Two independent cohorts A and B were analyzed separately in this study. Cohort A consisted of 22 subjects including 7 healthy control subjects, 6 patients with BPD and 9 patients with MDD. Cohort B consisted of 12 subjects including 5 MDD and 7 controls. All subjects in this study did not have specific agonal conditions including hypoxia, coma, pyrexia, seizure, dehydration, hypoglycemia, multiorgan failure, skull fracture, ingestion of neurotoxic substances or prolonged agonal duration, which is known to affect tissue pH, RNA integrity and gene expression profile in postmortem brain, and showed brain tissue pH of more than 6.5. In order to detect reliable gene expression differences between diagnostic groups, we performed experimentally as well as biologically replicated experiments as follows. Experiment 1: Total RNA was extracted from AnCg, DLPFC and CB of the Cohort A, and purified with silica-based mini-spin columns (Qiagen RNeasy Mini Kit, Valencia, Calif.). The oligonucleotide microarray experiments were carried out following the manufacturer's protocol (Affymetrix, Santa Clara, Calif.). For technical replication, each of RNA samples was run on Affymetrix U95Av2 GeneChips at two laboratories. Experiment 2: For further technical replication, samples from the 22 subjects from cohort A were reanalyzed in AnCg and DLPFC utilizing U133A GeneChips at two laboratories. Experiment 3: Samples from the additional cohort B were analyzed on U133A GeneChips in AnCg and DLPFC at two laboratories. Signal intensity data was extracted with Robust Multi-array Average (RMA) for each probe set and each subject. Gene-wise Pearson's correlation coefficients between experimental duplicates were calculated, and only the genes significantly correlated between experimental duplicates were considered to be reliably detectable genes, and subjected to the downstream analyses. For these reliably detectable genes, mixed-model multivariate ANOVA analyses were employed utilizing Partek Pro 6.0 (Partek, St. Charles, Mo.) to adjust the effect of the diagnostic classification (BPD, MDD, control) for possible confounders, including site for experiment, experimental batch, and gender. Post hoc tests (least-squares difference) were run to generate p value for the differences between case and control means, and false discovery rate multiple comparison corrections at the level of accepting 5% false positives was applied to each ANOVA result. When the p value passed false discovery rate multiple testing correction at the level of accepting 5% false positives and percent fold change exceeds 20%, the genes were consider to be significantly differentially expressed between case and control groups. Also, in order to evaluate more subtle but consistent expression differences between case and control groups, we also selected genes passed p value of 0.05 regardless of FDR correction and % FC>10% on both experimental duplicates utilizing U95Av2 or U133A GeneChips.

Figure 26A:
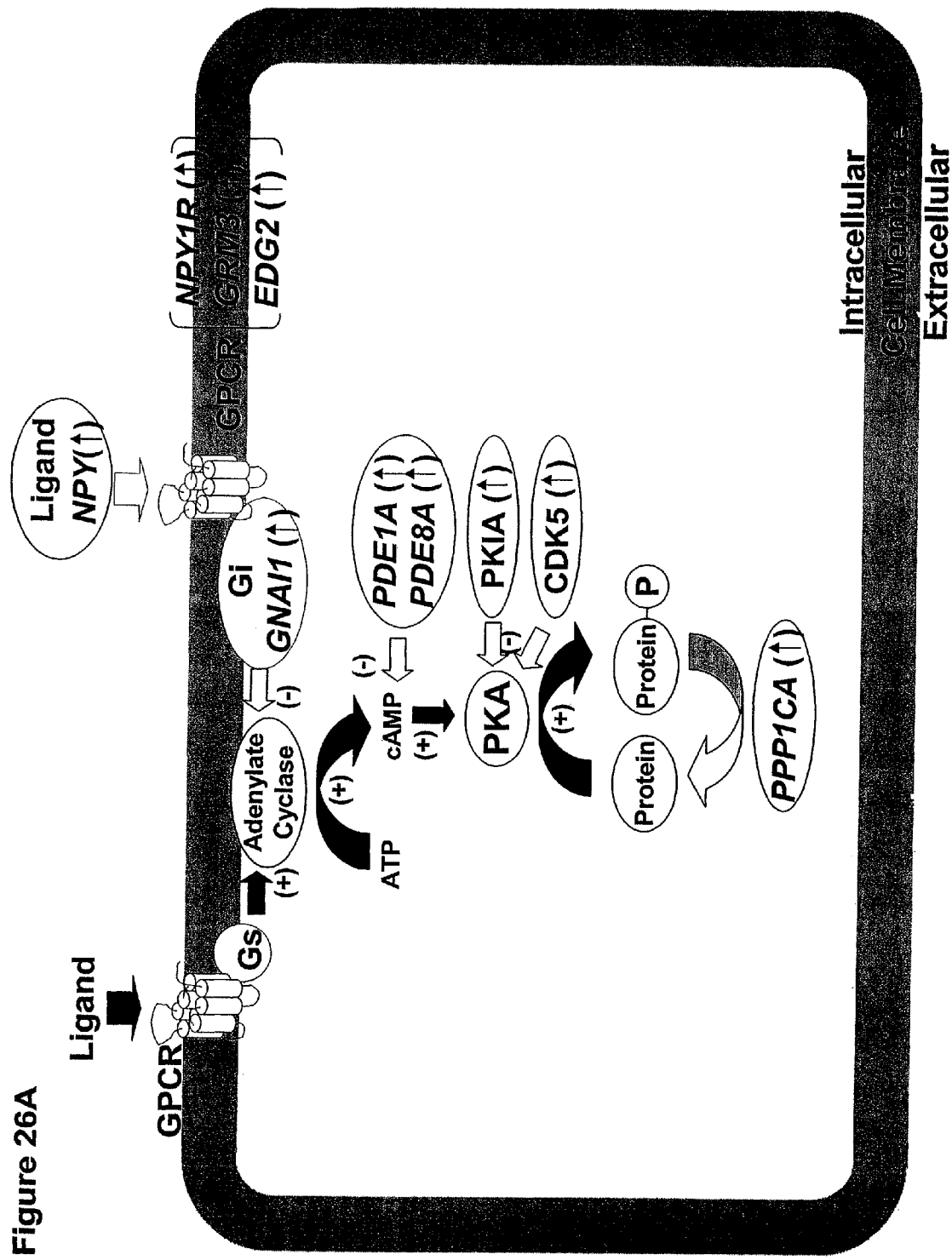
FIGS. 26A-D: summarize differential expressed genes regulating cAMP-(A, B) and phosphatidylinositol-(C, D) signaling pathways in the brain of BPD (A,C) and MDD (B, D). GNAI1: G protein alpha inhibiting activity 1, RGS20: Regulator of G-protein signaling 20, PDE1A: Phosphodiesterase 1A, PDE8A: Phosphodiesterase 8A, PKIA: Protein kinase A inhibitor alpha, CDK5: Cyclin-dependent kinase 5, PPP1CA: Protein phosphatase 1, catalytic alpha, PPP1R3c: Protein phosphatase 1, regulatory 3C, INPP5A: Inositol polyphosphate-5-phosphatase A, INPP5F: Inositol polyphosphate-5-phosphatase F, ITPKB: Inositol 1,4,5-trisphosphate 3-kinase B, INPP1: Inositol polyphosphate-1-phosphatase, CDS1: CDP-diacylglycerol synthase 1, PIK3C2A: Phosphoinositide-3-kinase catalytic 2A, PIK3C2B: Phosphoinositide-3-kinase catalytic 2B, PIK3R1: Phosphoinositide-3-kinase regulatory 1, PRKCI: Protein kinase C iota, ITPR1: Inositol 1,4,5-triphosphate receptor 1, PRKB1: Protein kinase C beta 1, NPY: Neuropeptide Y, SST: Somatostatin, NPY1R: Neuropeptide Y receptor Y1, TACR2: Tachykinin receptor 2, NTSR2: Neurotensin receptor 2, EDNRB: Endothelin receptor type B, GRM3: Metabotropic Glutamate receptor 3, EDG:1Endothelial differentiation GPCR 1, EDG2: Endothelial differentiation GPCR 2.
Figure 26B:
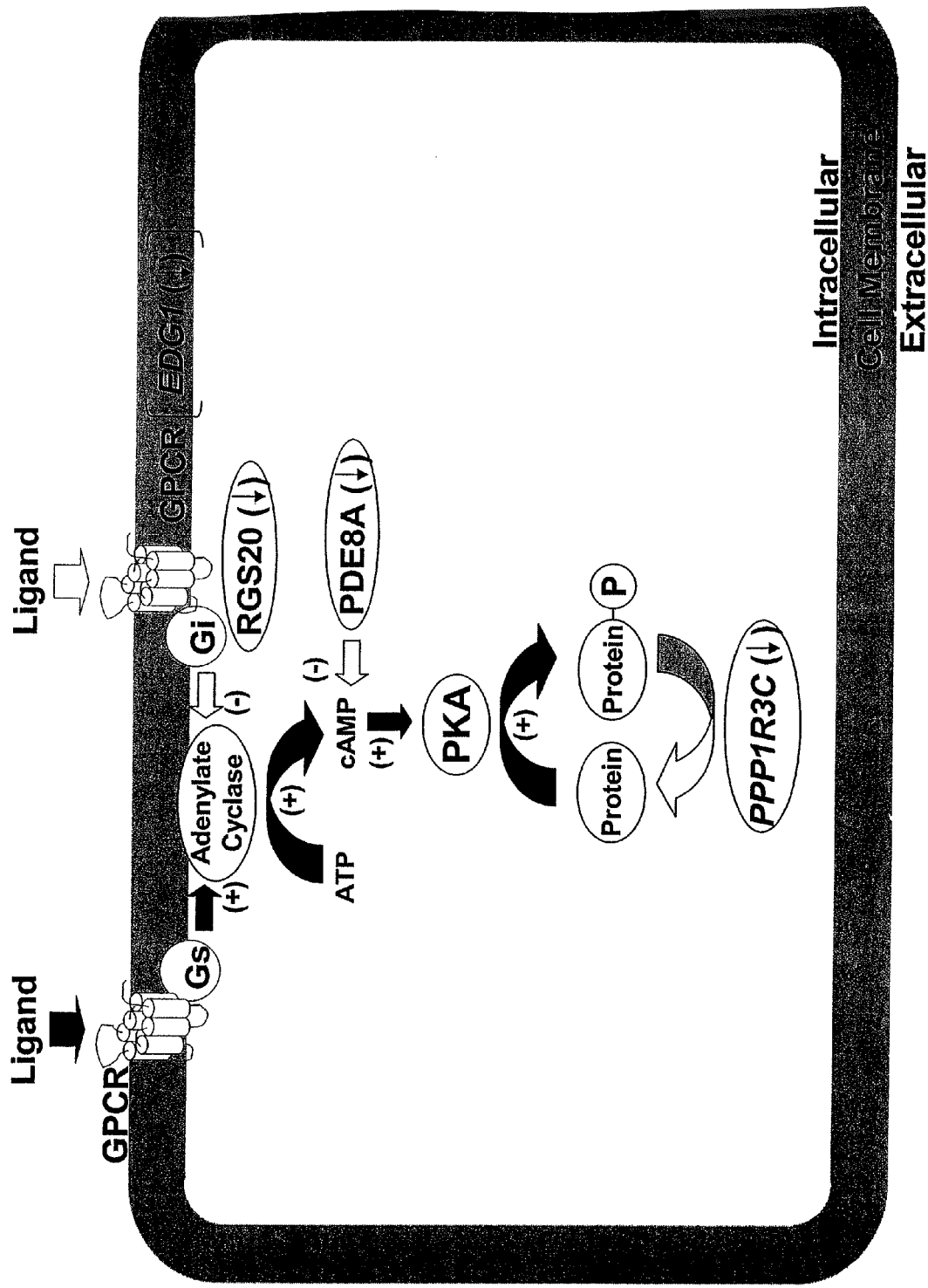

FIG. 26A and Table 14 summarize cAMP signaling pathway related genes which were differentially expressed in anterior cingulate cortex (AnCg) of bipolar disorder (BPD) patients compared with controls. Among GPCRs coupled with G protein inhibitory subunit (Gi), which inhibits adenylate cyclase activity, neuropeptide Y receptor 1 (NPYR1) was significantly increased in AnCg of BPD. The ligand, neuropeptide Y was also significantly increased in AnCg of BPD. Gi-linked metabotropic glutamate receptor 3 (GRM3) was also increased in AnCg as well as dorsolateral prefrontal cortex (DLPFC) of BPD. Somatostatin (SST), a ligand for Gi-coupled GPCR, was significantly increased in AnCg in our microarray data.

Contrasted to the finding in AnCg, SST mRNA expression was decreased in DLPFC of BPD as well as major depressive disorder (MDD). Adrenergic beta-1 receptor (ADRB1) was decreased by 13-18% in DLPFC of BPD, although the change did not reach the significant criteria (Table 17). Proenkephalin (PENK), a ligand for Gi-coupled GPCR, was not altered in AnCg and DLPFC of BPD and MDD, but significantly increased in CB of both BPD and MDD.

Messenger RNA expression level of G protein alpha subunit inhibitory peptide 1 (GNAI1) and phosphodiesterase 1A (PDE1A) were significantly increased in AnCg of BPD patients. Protein kinase A inhibitor alpha (PKIA) and cyclin dependent kinase 5 (CDK5), phosphodiesterase 8A (PDE8A) and protein phosphatase 1, catalytic subunit, alpha (PPP1CA) did not reach significant criteria, but were increased by 10%-20% in AnCg of BPD. Thus, mRNA expression of molecules suppressing cAMP concentration and PKA activity were generally increased in BPD, while molecules activating cAMP signaling (Gs-coupled GPCR, Gs, adenylate cyclase, protein kinase A) did not show significant alteration at the transcript level.

FIG. 26 and Table 14 summarize cAMP signaling pathway related genes which were differentially expressed in AnCg of MDD patients compared with controls. Gi-linked endothelial differentiation GPCR 1 (EDG1) was significantly decreased in AnCg of MDD. Regulator of G protein signaling 20 (RGS20), phosphodiesterase 8A (PDE8A), and protein phosphatase 1 regulatory subunit 3C(PPP1R3C) showed significantly lower expression in AnCg of MDD patients compared with controls. Expression levels of PDE8A and PPP1R3c mRNAs were significantly lower also in DLPFC of MDD (Table 15). Significant decrease in RGS20 expression in MDD was observed also in CB (Table 16). Thus, mRNA expression of molecules suppressing cAMP concentration and PKA activity were generally decreased in MDD, while the molecules activating cAMP signaling did not show significant alteration at the transcript level.

Phosphatidylinositol Signaling Pathway

Figure 26C:
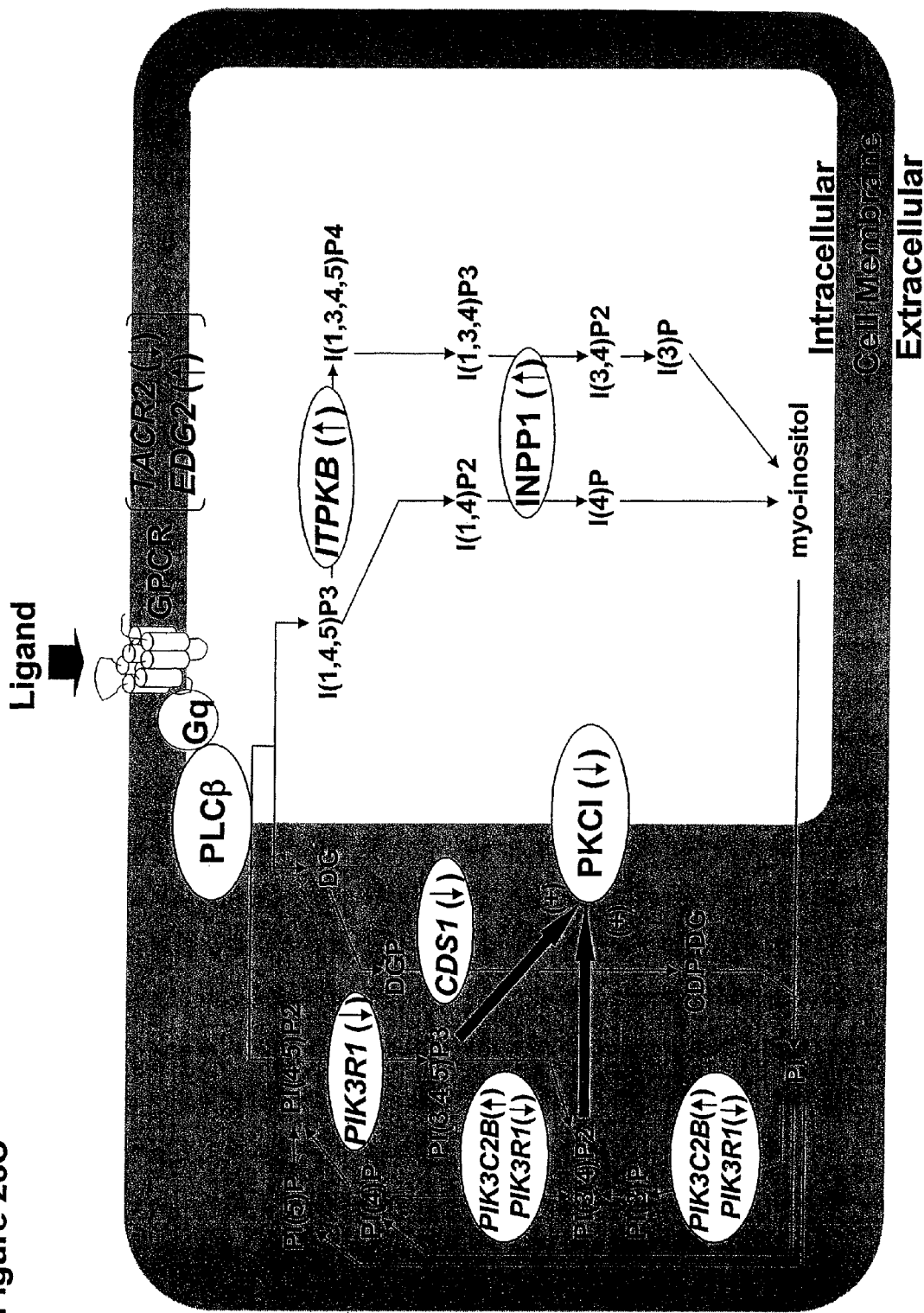

FIG. 26C and Table 14 summarize phosphatidylinositol signaling (PI) pathway related genes which were differentially expressed in AnCg of BPD patients compared with controls. Gq-linked tachykinin (neuropeptide K) receptor 2 (TACR2) was significantly decreased in AnCg of BPD. Messenger RNA expression of inositol polyphosphate-1-phosphatase (INPP1) was significantly higher, while CDP-diacylglycerol synthase 1 (CDS1), a regulatory subunit of class I phosphatidylinositol 3 kinase (PIK3R1) and protein kinase C iota (PKCI) were significantly lower in AnCg of BPD patients compared with control group. Inositol 1,4,5-trisphosphate 3-kinase B (ITPKB) and catalytic beta subunit of class II phosphatidylinositol 3 kinase (PIK3C2B) did not reach significance criteria, but increased by 10%-20% in AnCg of BPD.

Figure 26D:
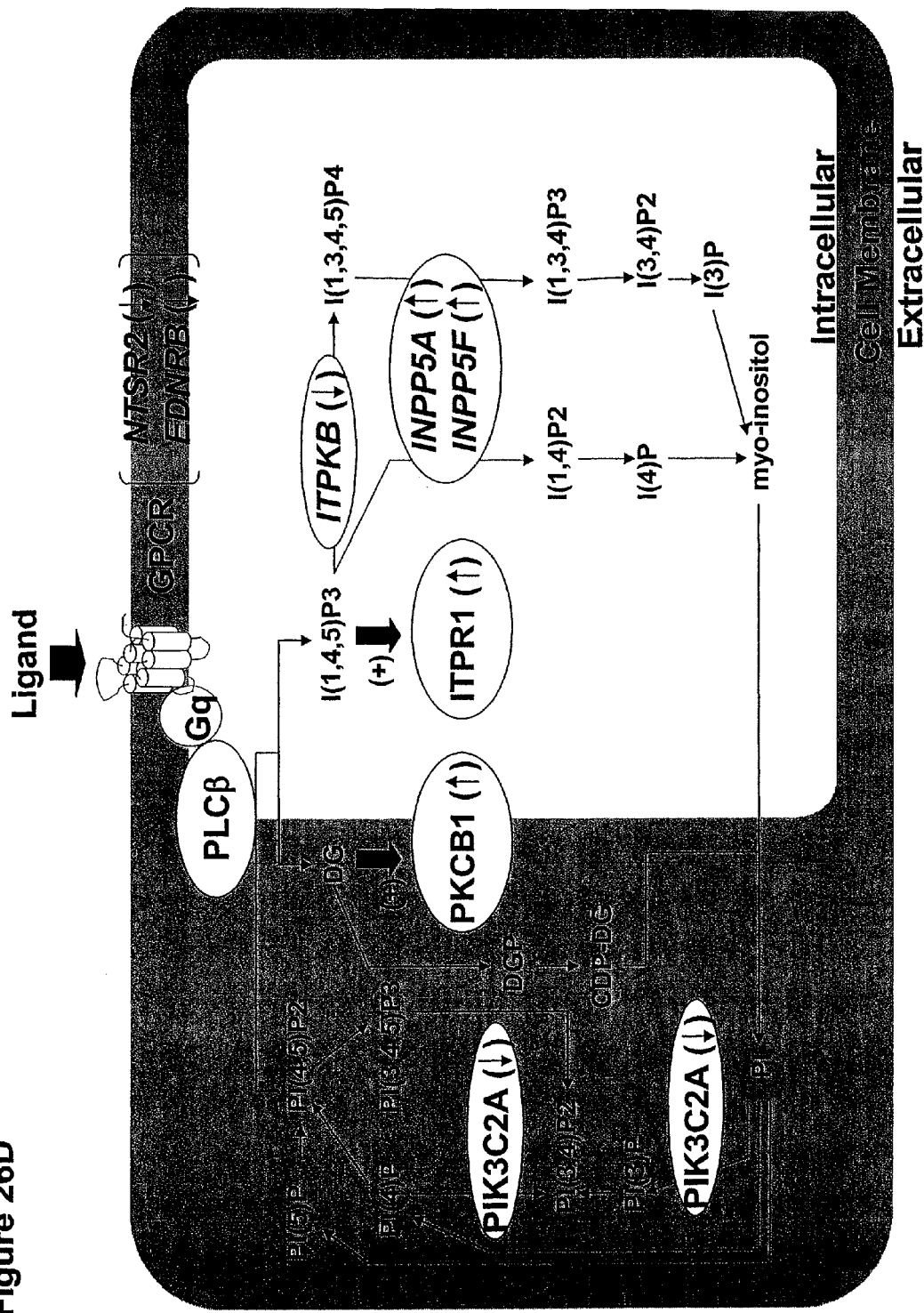

FIG. 26D and Table 14 summarize PI signaling pathway related genes which were differentially expressed in AnCg of MDD patients compared with controls. Gq-linked neurotensin receptor 2 (NTSR2) and endothelin receptor type B (EDNRB) were significantly decreased in AnCg of MDD. Messenger RNA expression of inositol polyphosphate-5-phosphatase F (INPP5F) was significantly higher, while inositol 1,4,5-trisphosphate 3-kinase B (ITPKB) and catalytic alpha subunit of class II phosphatidylinositol 3 kinase (PIK3C2A) were significantly lower in AnCg of MDD compared with control. Inositol polyphosphate-5-phosphatase A (INPP5A), protein kinase C beta 1 (PKCB1) and inositol 1, 4, 5-triphosphate receptor type 1 (ITPR1) did not reach the significance criteria, but increased by 10-20% in AnCg of MDD patients. Significant decrease in ITPKB mRNA expression was observed also in DLPFC of MDD (Table 15). Neither G protein alpha q subunit nor phospholipase C beta mRNAs were altered in any of the brain regions of the disorder groups.

Other G Protein-Coupled Receptors

Among all GPCRs, the most consistent differential expression patterns throughout our experiments were observed in G protein-coupled receptor family C, group 5, member B (GPRC5B) and G protein-coupled receptor 37 (GPR37). GPRC5B was significantly increased in AnCg and DLPFC of BPD. GPRC5B was significantly decreased in AnCg, DLPFC and CB of MDD patients. A significant decrease of GPRC5B in AnCg and DLPFC of MDD patients was replicated by the experiments utilizing another independent cohort B. GPR37 was also significantly increased in AnCg of BPD, and significantly decreased in AnCg, DLPFC and CB of MDD.

Quantitative RT-PCR

For further technical evaluation of the microarray data, we evaluated mRNA expression levels by real-time quantitative reverse transcriptase PCR (qRT-PCR) for the following 7 genes, in anterior cingulate cortex (AnCg): Somatostatin (SST), neuropeptide Y (NPY), G protein-coupled receptor C-5-B (GPRC5B), G protein-coupled receptor 37 (GPR37), regulator of G-protein signaling 20 (RGS20), inositol polyphosphate-1-phosphatase (INPP1) and protein phosphatase 1 regulatory subunit 3C(PPP1R3C).

In consistent with microarray data, qRT-PCR data showed that mRNA expressions of neuropeptide Y (NPY), G protein-coupled receptor C-5-B (GPRC5B), G protein-coupled receptor 37 (GPR37), inositol polyphosphate-1-phosphatase (INPP1) were significantly increased in AnCg of BPD, and expression level of GPRC5B, GPR37, regulator of G-protein signaling 20 (RGS20) and protein phosphatase 1 regulatory subunit 3C (PPP1R3C) were significantly decreased in the AnCg of MDD group. While somatostatin (SST) mRNA expression was increased in AnCg of BPD in both microarray experimental duplicates utilizing U95Av2 and U133A, the finding was not replicated by qRT-PCR (Table 17).

In Situ Hybridization

Figure 27:
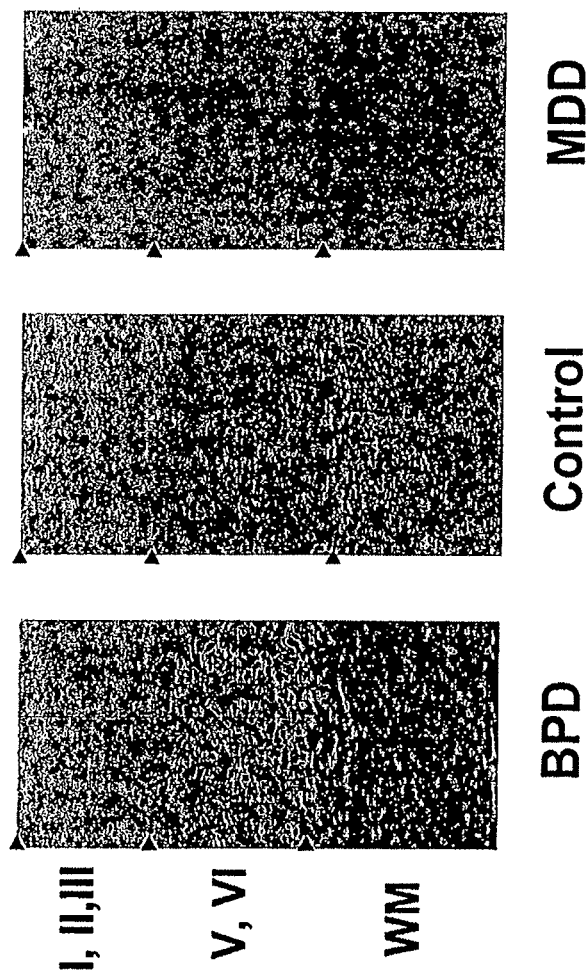
FIG. 27: In situ hybridization images of GPR37 mRNA in representative BPD, MDD and control subjects GPR37 mRNA is preferentially expressed in subcortical white matter. Among 6 layers of cortical gray matter, GPR37 expression in deeper layer (V-VI) is relatively higher than superficial layer (I-III). Expression levels in GPR37 is increased in the BPD subjects, and decreased in MDD subjects in subcortical white matter in anterior cingulate cortex tissue, compared to control subjects. WM: Subcortical white matter, BPD: Bipolar disorder, MDD: Major depressive disorder.
Figure 28:
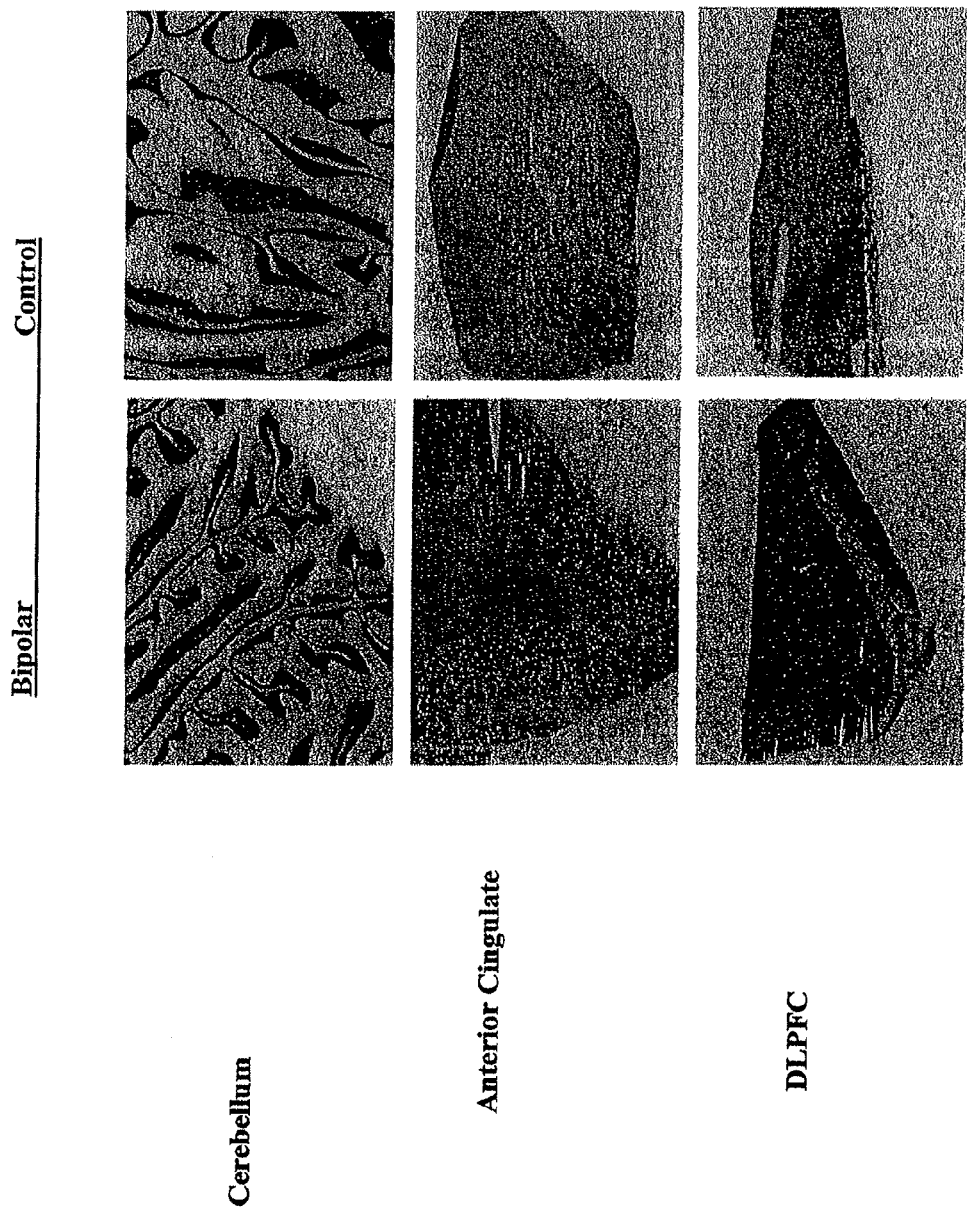
FIGS. 28 and 29: In situ hybridization for LRPPRC (leucine-rich PPR-motif containing) mRNA in three brain regions. (A). LRPPRC expression in BPD and control representative images. (B). Controls with agonal factors showed a 36% reduction in LRPPRC compared to controls with zero agonal factors (p=0.011) in cerebellum and a similar effect was seen across the cortical regions. (C). In DLPFC, the BPD cases without agonal factors show increased LRPPRC compared to controls without agonal factors (p=0.001) and compared to MDD subjects (p=0.02) without agonal factors.
Figure 29:
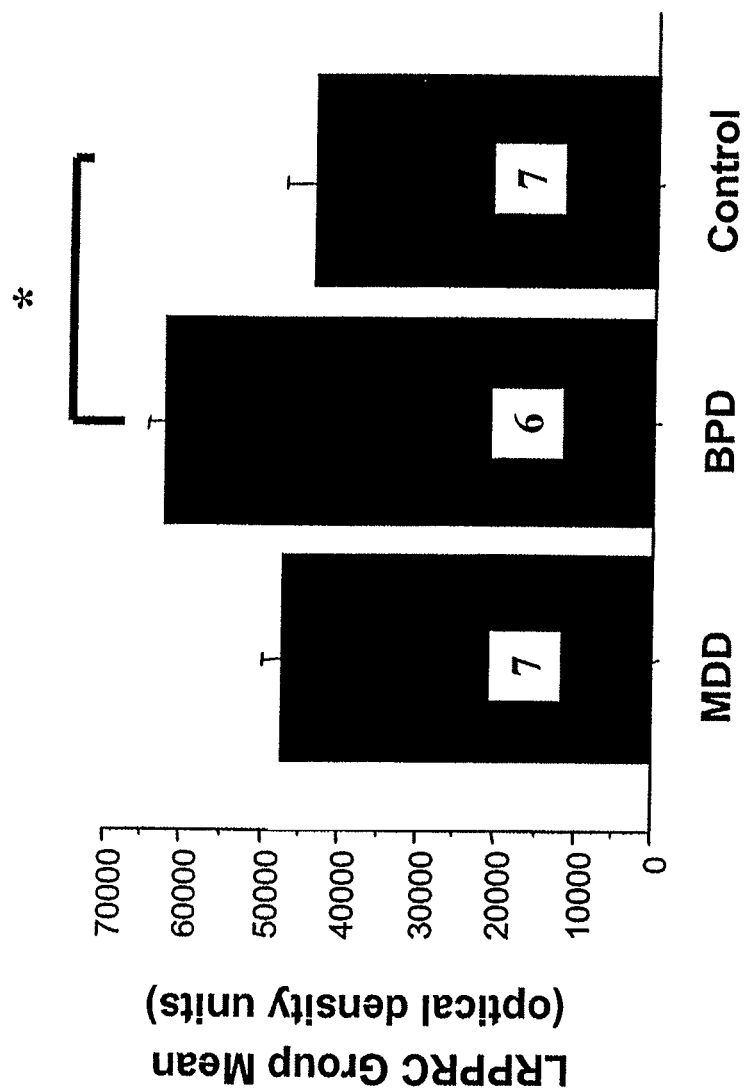

We performed in situ hybridization for GPR37 using. GPR37 mRNA is preferentially expressed in subcortical white matter. GPR37 expression in the deeper layers (V-VI) is relatively higher than the superficial layers (I-III). GPR37 mRNA expression in subcortical white matter was higher in AnCg of the BPD subjects compared to the control subjects. GPR37 mRNA expression was rarely detected in AnCg of the MDD subjects analyzed. FIG. 27 shows the dysregulation of genes involved in cAMP-and phosphatidylinositol signaling pathways in brain tissue from patients with BPD and MDD.

Gene Expression Changes in Amygdala, Hippocampus, Nucleus Accumbens of Bipolar Disorder and Major Depressive Disorder.

We applied the same experimental design on amygdala, hippocampus and nucleus accumbens of BPD and MDD. Table 18 summarizes genes which are differentially expressed in amygdala, hippocampus and nucleus accumbens of BPD patients. Table 19 summarizes genes differentially expressed in the three brain regions of MDD.

Example 6

This Example shows gene dysregulation in pathways related to Mitochondria, Proteasome, Apoptosis, and Chaperone in Mood Disorder. Three brain regions were studied: AnCg, Cerebellum, and DLPFC. The results are compiled in Tables 20-22.

Example 7

NCAM1 Association with Bipolar Disorder and Schizophrenia and Splice Variants of NCAM1

SNP and Sample Selection: Genomic DNA (gDNA) was extracted from human postmortem brain cerebellum tissue. Primers were designed for SNP 9 and then tested via PCR to determine correct band size. Using the SNP 9 primers, gDNA of 40 cases (20 controls, 9 BPDs and 11 MDDs) was sequenced with both the forward and reverse primers. The SNPs were located in exons a, b and c. SNPs b and c are intronic and found just before exon 'b' (7 bps upstream) and 'c' (12 bps upstream) respectively. Exon 'a' did not have a SNP in close proximity.

The genotypes were collected on an additional 26 bipolar genomic DNA samples extracted from lymphocytes from the National Institute of Mental Health (NIMH) for all 4 SNPs: SNP 6, SNP 9, SNP b and SNP c (see FIG. 26). A third cohort was genotyped consisting of the Stanley Foundation 105 dorsalateral prefrontal cortex (DLPFC) microarray samples (n=35 controls, n=35 bipolar disorder, n=35 schizophrenia) (Table 24). The Stanley samples were genotyped for SNP 9 and SNP b. For final analysis, the three groups of bipolar cases were combined and three control groups were merged and used for statistical comparisons of SNP 9 and SNP b. The results show an association of SNP 9 and SNP b haplotype with bipolar disorder and schizophrenia.

Genotype X Diagnosis Interaction for NCAM1 Splice Variants.

Figure 30:
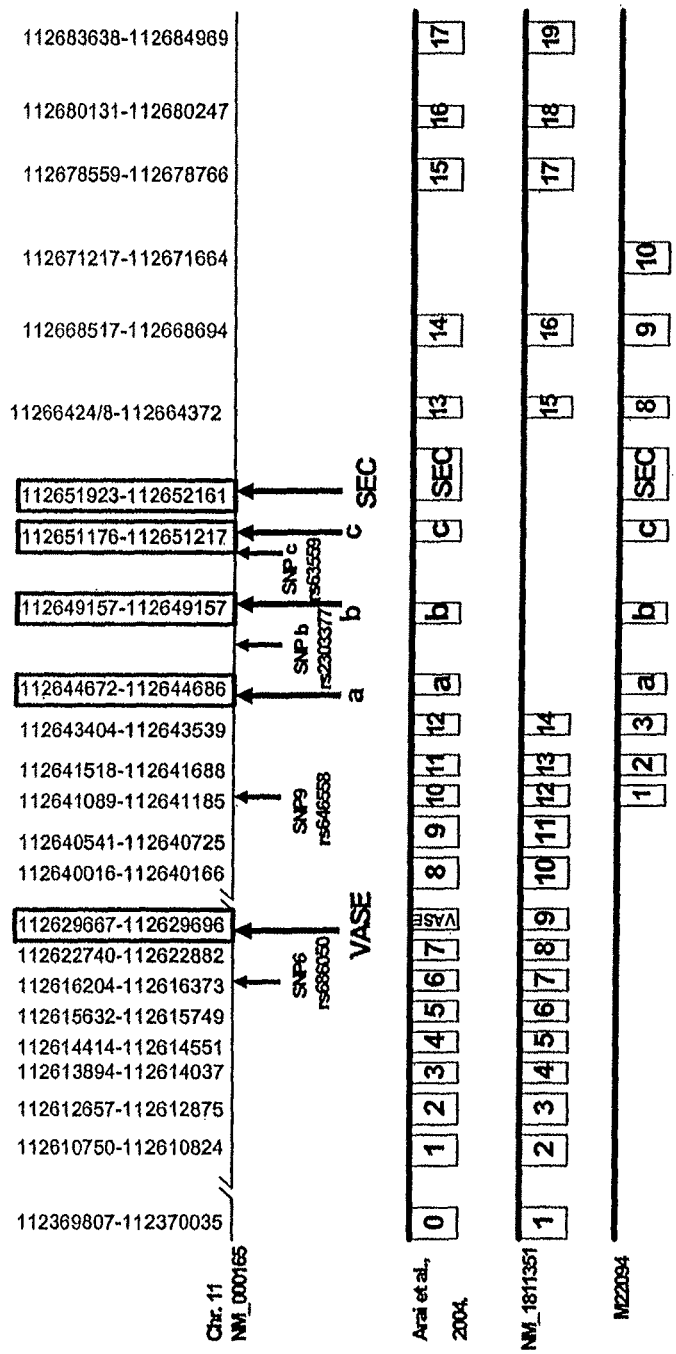
FIG. 30: NCAM1 (i.e., neural cell adhesion molecule 1) genomic organization and location of four polymorphic sites. The gene spans 214 kb, but does not contain any exonic SNPs. The arrows indicate the location of the four polymorphisms and the five exons used in this exploratory analysis.
Figure 31:
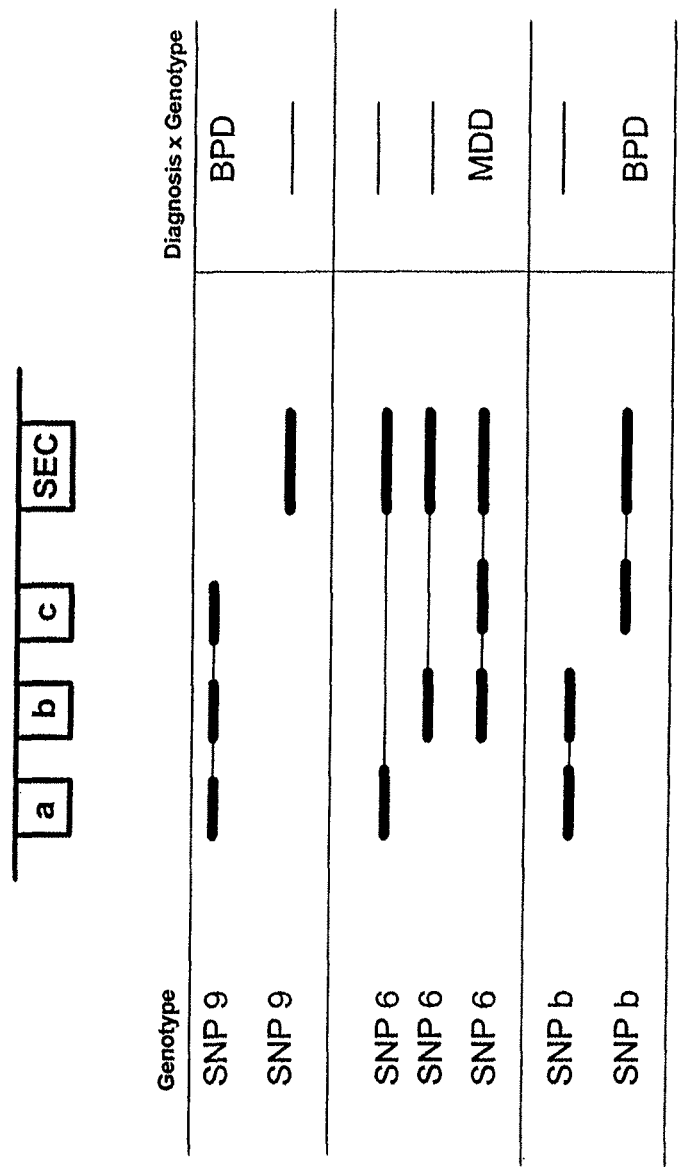
FIG. 31: Significant alterations of NCAM1 exon splice variant levels are shown by genotype and diagnosis by genotype.

The splice variants are alternative splicing combinations of 3 mini-exons (a,b,c) with the fourth SEC exon are shown in FIG. 30. Two mood disorders were tested (Bipolar Disorder, Type I and Major Depressive Disorder, Recurrent) and both showed differences in NCAM1 splice variants in the DLPFC.

The present data relates NCAM1 polymorphic variation to bipolar disorder and splice variations in mRNA occurring near the polymorphisms. A genotypic association between SNP b in NCAM1 and bipolar disorder and a suggestive association of SNP 9 with schizophrenia were found. Three of the two marker haplotypes for SNP 9 and SNP b, CT, C(T/C), and (C/A)(T/C) display varying frequency distribution between bipolar and controls. Schizophrenia and controls show differences in frequency distribution in four of the two marker haplotypes of SNP 9 and SNP b, CT, C(T/C), (C/A)(T/C) and (C/A)C. Bipolar disorder differs from schizophrenia for SNP 9 and SNP b by haplotype frequency differences. SNP b and SNP 9 are not in LD and they are individually related to schizophrenia (SNP 9) and bipolar disorder (SNP b).

The splice variant evidence for SNP 9 and b confirm that each SNP can be associated with differences in SEC exon splicing, thus providing some differential mechanisms for release of NCAM1 in the brain. We observed notable differences between polymorphisms in NCAM1 and the relative isoform variants of the SEC exon which can lead to truncation and secretion of NCAM1 in the brain. This finding concerning the difference in splice variant relative amounts as a function of certain genotypes was shown in three of the four SNPs where at least one genotype showed a difference in the amount of SEC by splice variant. This evidence suggests that the amount of SEC in brain is not regulated by just one genotype. Since the haplotypes composed of SNP 9 and SNP b are significantly different between controls and bipolar and between controls and schizophrenia this may support the observation of differential splicing patterns of the SEC exon found across many samples. Additionally, SNP 9 and SNP b are not in LD and thus the individual associations in schizophrenia and bipolar with these SNPs also may be transmitted through differential splicing patterns. The SEC exon was clearly regulated by certain combinations of mini-exons. We have identified discrete splice variants that can be further studied and are perhaps associated with regulatory intronic SNPs.

Example 8

Lithium has long been the drug of choice for treating manic-depressive illness (manic-depression; bipolar affective disorder, BPD). This Example shows non-human primate genes which exhibit differential expression in response to treatment with lithium. The results have implications for understanding the mood stabilizing effects of lithium in patients with manic depression.

Gene expression profiling was carried out on the anterior cingulate cortex (AnCg) using high-density oligonucleotide microarrays (Affymetrix GeneChips). We determined differential gene expression profiles of postmortem brains from lithium-treated healthy monkeys over those of untreated controls, and validated candidate genes against those known to be lithium-responsive or disease-selective.

Some of the candidate genes that responded to chronic lithium treatment were the same as those found with changed expression levels in postmortem brains of subjects with mood disorders. Our results show that the GSK3B signaling system is altered in BPD and that it is a physiological target of lithium. The observed GSK3B signaling system change thus constitutes an endophenotype that is likely to be common to BPD and schizophrenia, notwithstanding their clinical and phenotypic disparity. The results, by facilitating reconstruction of the genetic networks underlying BPD pathophysiology will facilitate the rational mood stabilizers targeting the signal transduction network via GSK3.

Major depressive disorder (MDD) and bipolar affective disorder (BPD) are two most severe mood disorders. MDD is characterized by clinical depression, while BPD is marked by recurrent and dramatic swings of emotional highs (mania) and lows (depression). For decades, lithium carbonate ($Li_2CO_3$, commonly known as "lithium") has been the benchmark medication for mania (hyperactive, incoherent and delusional behavior). Lithium unlike other anti-manic treatment agents is unique in its ability to abort the manic condition and restore patient's balanced mental status. Although numerous hypotheses have been proposed accounting for the neuro-protective properties of lithium, the precise molecular mechanism(s) by which lithium elicits its "mood stabilizing" effects in manic-depressive patients remains obscure. We addressed the challenge using a microarray strategy because it can permit simultaneous detection of multiple lithium-responsive genes and pathways in drug-treated primates and direct comparison of the observed gene expression changes with those found in postmortem brains from subjects with BPD. Lithium carbonate suspension (Roxane Laboratories, Inc., Columbus, Ohio) diluted in fruit juice was administered orally (18 mg/kg body weight) to a targeted plasma level of 0.6 to 1.2 mgEq/mL. The animals received the drug twice a day for varying periods ranging from 4 months to 1 year and 5 months to circumvent their tendency to spit the drug out.

AnCg showed a total of 220 candidate transcripts (65 upregulated and 155 down-regulated). The candidate genes from AnCg are listed in Table 28. Ontological annotations mapped candidate genes to several different biological processes and pathways, including GSK3B signaling system, as predicted, in the AnCg.

AnCg involvement demonstrated in this study together with published reports of hippocampus involvement in lithium response implicates likely involvement of the limbic system in mood disorders as well as in the differential gene expression elicited by chronic lithium treatment. The present study also illuminates multiple interrelated functional networks of neuronal signaling pathways acting in unity with GSK3B as a pivotal functional switch regulating gene expression in behavioral diseases of apparent disparate phenotypic diversity, BPD and SZ. The results show that manipulating GSK3B could affect one or more of the inositol triphosphate, NF-kB family, mitochondrial apoptosis, and ubiquitin-proteasome pathways.

Example 9

V-ATPase Subunits as Gene Candidates of Interest for Major Depressive Disorder (MDD)

Of the 14 V-ATPase subunits that we have interrogated with Affy microarrays and Illumina microarrays, 7 subunits (50%) are differentially expressed (P<0.05) in hippocampal MDD versus control on either the Affymetrix or Illumina arrays. Three of the 7 subunits are differentially expressed in MDD hippocampus on both the Affymetrix and Illumina arrays (see Table 29). Two of the V-ATPase subunits are also differentially expressed (P<0.05) in our Affy microarray study of monkey hippocampus (i.e., Table 30, showing chronic social stress versus no-stress comparison). These findings demonstrate that drugs now being developed to inhibit V-ATPase in patients with cancer and osteoporosis may also prove useful as novel antidepressants.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

TABLE 1a

Subject Data for Cohort A.

| subject ID | gender | age | diagnosis | brain pH | PMI | AnCg 18S/28S | AnCg 3'/5' ratio | DLPFC 3'/5' ratio |
|---|---|---|---|---|---|---|---|---|
| 1881 | M | 69 | BPD | 6.91 | 11 | 0.68 | 1.36 | 1.21 |
| 2311 | M | 23 | BPD | 7.12 | 9 | 1.80 | 1.47 | 1.13 |
| 2466 | M | 26 | BPD | 6.92 | 19 | 1.35 | 1.75 | 1.64 |
| 2566 | F | 56 | BPD | 6.83 | 29 | 1.05 | 1.48 | 1.34 |
| 3038 | M | 52 | BPD | 7.05 | 28 | 1.04 | 1.37 | 1.20 |
| 3241 | M | 59 | BPD | 6.99 | 16 | 1.38 | 1.33 | 1.17 |
| averages for BPDs | | 47.5 | | 6.97 | 18.6 | 1.22 | 1.46 | 1.28 |
| 2861 | F | 60 | Ct | 6.99 | 24 | 1.25 | 2.07 | 1.80 |
| 3018 | M | 70 | Ct | 7.03 | 27 | 0.91 | 1.57 | 1.20 |
| 2169 | M | 18 | Ct | 6.97 | 22 | 1.61 | 1.62 | 1.18 |
| 2316 | M | 58 | Ct | 7.02 | 26 | 1.27 | 1.47 | 1.27 |
| 2292 | M | 55 | Ct | 6.89 | 15 | 1.45 | 1.29 | 1.18 |
| 2805 | M | 45 | Ct | 6.86 | 21 | 1.84 | 1.61 | 1.06 |
| 3196 | M | 44 | Ct | 6.87 | 23 | 1.26 | 1.67 | 1.22 |
| averages for controls | | 50 | | 6.95 | 22.6 | 1.37 | 1.61 | 1.27 |
| 2208 | F | 72 | MD | 7.13 | 21 | 1.26 | 1.83 | 1.19 |
| 2267 | M | 19 | MD | 7.11 | 18 | 2.05 | 1.75 | 1.44 |
| 2315 | M | 58 | MD | 6.93 | 24 | 1.34 | 1.52 | 1.31 |
| 3071 | M | 49 | MD | 7.00 | 31 | 1.58 | 1.44 | 1.25 |
| 3064 | M | 46 | MD | 6.91 | 27 | 2.18 | 1.28 | 1.19 |
| 3031 | M | 49 | MD | 7.19 | 27 | 1.60 | 1.60 | 1.04 |
| 2944 | M | 52 | MD | 6.82 | 16 | 1.37 | 1.91 | 1.43 |
| 3004 | F | 48 | MD | 6.95 | 37 | 1.31 | 1.81 | 1.20 |
| 3168 | M | 39 | MD | 6.79 | 28 | 1.34 | 1.49 | 1.19 |
| averages for MDDs | | 48.0 | | 6.98 | 25.4 | 1.56 | 1.63 | 1.25 |

TABLE 1b

Subject Data for Cohort B.

| subject ID | gender | age | diagnosis | brain pH | PMI | AnCg 18S/28S | AnCg 3'/5' ratio | DLPFC 3'/5' ratio |
|---|---|---|---|---|---|---|---|---|
| 3145 | M | 77 | Ct | 6.62 | 7 | | | |
| 3281 | F | 70 | Ct | 6.9 | 21 | | | |
| 3516 | M | 41 | Ct | 7.01 | 23 | | | |
| 3519 | M | 65 | Ct | 6.88 | 14 | | | |
| 3523 | M | 40 | Ct | 7.07 | 37 | | | |
| 3572 | M | 49 | Ct | 6.68 | 28 | | | |
| averages for controls | | 57 | | 6.86 | 21.67 | | | |
| 3169 | M | 35 | MD | 7.04 | 25 | | | |
| 3365 | M | 47 | MD | 7.25 | 29 | | | |
| 3398 | F | 80 | MD | 6.68 | 15 | | | |
| 3481 | M | 66 | MD | 7.05 | 32 | | | |
| averages for MDDs | | 57 | | 7.01 | 25.25 | | | |

TABLE 2

Microarray data for all FGF transcripts reliably detected in either DLPFC or AnCg and summary data for confirmation studies.

| UniGene ID | Transcript | DLPFC p-value | DLPFC direction | AnCg p-value | AnCg direction |
|---|---|---|---|---|---|
| Hs.278954 | FGF1 | <0.01[‡,†] | Decreased | 0.01 | Decreased |
| Hs.284244 | FGF2 | NS | | <0.01[*,‡] | Decreased |
| Hs.433252 | FGF7 | NS | | NS | |
| Hs.111 | FGF9 | <0.01 | Increased | <0.01[*] | Increased |
| Hs.343809 | FGF12 | NS | | <0.01[*] | Increased |
| Hs.6540 | FGF13 | NS | | NS | |
| Hs.223851 | FGF14 | 0.05 | Increased | NS | |
| Hs.748 | FGFR1 | NS | Increased | NS | |
| Hs.404081 | FGFR2 | <0.01[*,‡,†] | Decreased | <0.01[*,‡] | Decreased |
| Hs.1420 | FGFR3 | <0.01[*,‡,†] | Decreased | <0.01[*] | Decreased |

[*]Met FDR multiple testing correction at the level of accepting 5% false positives.
[‡]Observation was confirmed in an independent cohort of MDD and control subjects given in Table 1b, meeting p-values of <0.05 in all cases indicated.
[†]Observation was confirmed by real-time PCR analysis with p < 0.05.
NS = not significant.

TABLE 3

| UniGene ID | Gene Symbol | Gene Name | RefSeq ID | Gene Bank Acc. No. | LocusLink |
|---|---|---|---|---|---|
| Hs.407520 | CHN2 | chimerin (chimaerin) 2 | NM_004067 | U07223 | 1124 |
| Hs.13351 | LANCL1 | LanC lantibiotic synthetase component C-like 1 (bacterial) | NM_006055 | Y11395 | 10314 |
| Hs.309090 | SFRS7 | splicing factor, arginine/serinerich 7, 35 kDa | NM_006276 | L41887 | 6432 |
| Hs.7910 | RYBP | RING1 and YY1 binding protein | NM_012234 | AL049940 | 23429 |
| Hs.150101 | LAMP1 | lysosomal-associated membrane protein 1 | NM_005561 | J04182 | 3916 |
| Hs.90458 | SPTLC1 | serine palmitoyl transferase, long chain base subunit 1 | NM_006415 | Y08685 | 10558 |
| Hs.406532 | RPN2 | ribophorin II | NM_002951 | AL031659 | 6185 |
| Hs.408883 | SCN1B | sodium channel, voltage-gated, type I, beta | NM_001037 | L10338 | 6324 |
| Hs.91971 | CGEF2 | cAMP-regulated guanine nucleotide exchange factor II | NM_007023 | U78516 | 11069 |
| Hs.49117 | — | hypothetical protein DKFZp564 N1662 | — | AL080093 | — |
| Hs.84244 | KCNB1 | potassium volta | NM_004 | L02840 | 3745 |

| UniGene ID | Chromosome | AnCg-BP | AnCg-MD | Criteria | DLPFC-BP | DLPFC-MD | Criteria |
|---|---|---|---|---|---|---|---|
| Hs.407520 | Chr: 7p15.3 | UP | NC | 2a, 3 | | | |
| Hs.13351 | Chr: 2q33-q35 | UP | NC | 1, 2a | UP | NC | 2a |
| Hs.309090 | Chr: 2p22.1 | | | | UP | NC | 1, 2a, 3 |
| Hs.7910 | Chr: 3p14.2 | | | | UP | NC | 1, 2a, 3 |
| Hs.150101 | Chr: 13q34 | UP | NC | 2a, 3 | | | |
| Hs.90458 | Chr: 9q22.2 | | | | UP | NC | 1, 2a, 3 |
| Hs.406532 | Chr: 20q12-q13.1 | UP | NC | 2a | UP | NC | 1, 2a |
| Hs.408883 | Chr: 19q13.1 | DOWN | NC | 1, 3 | | | |
| Hs.91971 | Chr: 2q31-q32 | DOWN | NC | 1, 3 | | | |
| Hs.49117 | — | | | | UP | NC | 1, 3 |
| Hs.84244 | Chr: 20q13.2 | DOWN | NC | 1, 3 | | | |

TABLE 4

| UniGene ID | Gene Symbol | Gene Name | RefSeq ID | Gene Bank Acc. No. | Locus Link | Chromosome | MDD AnCg-BP | AnCg-MD | Criteria | DLPFC-BP | DLPFC-MD | Criteria |
|---|---|---|---|---|---|---|---|---|---|---|---|---|
| Hs.5462 | SLC4A4 | solute carrier family 4, sodium bicarbonate cotransporter, member 4 | NM_003759 | AF007216 | 8671 | Chr: 4q21 | NC | DOWN | 2b | NC | DOWN | 3 |
| Hs.44 | PTN | pleiotrophin (heparin binding growth factor 8, neurite growth-promoting factor 1) | NM_002825 | M57399 | 5764 | Chr: 7q33-q34 | | | | NC | DOWN | 1, 2b |
| Hs.144845 | BBOX1 | butyrobetaine (gamma), 2-oxoglutarate dioxygenase (gamma-butyrobetaine hydroxylase) 1 | NM_003986 | AF082868 | 8424 | Chr: 11p14.2 | | | | NC | DOWN | 1, 2b, 3 |
| Hs.170133 | FOXO1A | forkhead box O1A (rhabdomyosarcoma) | NM_002015 | AF032885 | 2308 | Chr: 13q14.1 | NC | DOWN | 1, 2b | NC | DOWN | 1, 3 |
| Hs.62192 | F3 | coagulation factor III (thromboplastin, tissue factor) | NM_001993 | J02931 | 2152 | Chr: 1p22-p21 | | | | NC | DOWN | 1, 2b, 3 |
| Hs.166994 | FAT | FAT tumor suppressor homolog 1 (Drosophila) | NM_005245 | X87241 | 2195 | Chr: 4q34-q35 | | | | NC | DOWN | 1, 2b, 3 |
| Hs.82002 | EDNRB | endothelin receptor type B | NM_000115 | S57283 | 1910 | 13q22 | NC | DOWN | 1, 2b | NC | DOWN | 1, 2b, 3 |
| Hs.403997 | VIL2 | villin 2 (ezrin) | NM_003379 | X51521 | 7430 | Chr: 6q25.2-q26 | NC | | | NC | DOWN | 1, 2b |
| Hs.8022 | TU3A | TU3A protein | NM_007177 | AF035283 | 11170 | Chr: 3p21.1 | NC | DOWN | 1, 2b | | | |
| Hs.356876 | GPR125 | G protein-coupled receptor 125 | XM_291111 | AK027494 | 166647 | 4p15.32-p15.31 | | | | NC | DOWN | 1, 2b, 3 |
| Hs.450919 | GPC5 | glypican 5 | NM_004466 | U66033 | 2262 | Chr: 13q32 | NC | DOWN | 2b | NC | DOWN | 1, 2b |
| Hs.414151 | DAAM2 | dishevelled associated activator of morphogenesis 2 | NM_015345 | AB002379 | 23500 | Chr: 6p21.1 | NC | | | NC | DOWN | 3 |
| Hs.172089 | PORIMIN | pro-oncosis receptor inducing membrane injury gene | NM_052932 | AL050161 | 114908 | Chr: 11q22.1 | NC | DOWN | 1, 3 | | | |
| Hs.77546 | ANKRD15 | ankyrin repeat domain 15 | NM_015158 | D79994 | 23189 | Chr: 9p24.3 | | | | NC | DOWN | 1, 3 |
| Hs.26208 | COL16A1 | collagen, type XVI, alpha 1 | NM_001856 | M92642 | 1307 | Chr: 1p35-p34 | | | | NC | DOWN | 1, 3 |
| Hs.434494 | SYNJ2 | synaptojanin 2 | NM_003898 | AF039945 | 8871 | Chr: 6q25.3 | NC | DOWN | 1, 3 | | | |
| Hs.434418 | MYT1L | myelin transcription factor 1-like | | AB029029 | 23040 | Chr: 2p25.3 | NC | UP | 1, 3 | | | |
| Hs.78748 | RIMS3 | regulating synaptic membrane exocytosis 3 | | D87074 | 9783 | Chr: 1pter-p22.2 | NC | UP | 1, 3 | | | |
| Hs.436987 | ZNF288 | zinc finger protein 288 | NM_015642 | AL050276 | 26137 | Chr: 3q13.2 | NC | DOWN | 1 | NC | DOWN | 1 |
| Hs.391392 | ID4 | inhibitor of DNA binding 4, dominant negative helix-loop-helix protein | NM_001546 | AL022726 | 3400 | Chr: 6p22-p21 | | | | NC | DOWN | 1 |
| Hs.109052 | C14orf2 | chromosome 14 open reading frame 2 | NM_004894 | AF054175 | 9556 | Chr: 14q32.33 | NC | UP | 1 | | | |
| Hs.33455 | PADI2 | peptidyl arginine deiminase, type II | NM_007365 | AB023211 | 11240 | Chr: 1p35.2-p35.1 | NC | DOWN | 1 | | | |
| Hs.438240 | ZFYVE16 | zinc finger, FYVE domain containing 16 | NM_014733 | AB002303 | 9765 | Chr: 5p15.2-q14.3 | NC | DOWN | 1 | | | |
| Hs.75462 | BTG2 | BTG family, member 2 | NM_006763 | U72649 | 7832 | Chr: 1q32 | | | | NC | DOWN | 1 |

TABLE 5

| | | Growth Factor Pathway Genes | | |
|---|---|---|---|---|
| UniGene ID | Gene Symbol | Gene Name | RefSeq Transcript ID | LocusLink |
| Hs.433326 | IGFBP2 | insulin-like growth factor binding protein 2, 36 kDa | NM_000597 | 3485 |
| Hs.16512 | OGFRL1 | opioid growth factor receptor-like 1 | NM_024576 | 79627 |
| Hs.799 | DTR | diphtheria toxin receptor (heparin-binding epidermal growth factor-like growth factor) | NM_001945 | 1839 |
| Hs.105689 | LTBP2 | latent transforming growth factor beta binding protein 2 | NM_000428 | 4053 |
| Hs.289019 | LTBP3 | latent transforming growth factor beta binding protein 3 | NM_021070 | 4054 |
| Hs.376032 | PDGFA | platelet-derived growth factor alpha polypeptide | NM_002607 /// NM_033023 | 5154 |
| Hs.839 | IGFALS | insulin-like growth factor binding protein, acid labile subunit | NM_004970 | 3483 |
| Hs.342874 | TGFBR3 | transforming growth factor, beta receptor III (betaglycan, 300 kDa) | NM_003243 | 7049 |
| Hs.404081 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | NM_000141 /// NM_022969 /// NM_022970 /// NM_022971 /// NM_022972 /// NM_022973 /// NM_022974 /// NM_022975 /// NM_022976 /// NM_023028 /// NM_023029 /// NM_023030 /// NM_023031 | 2263 |
| Hs.433252 | FGF7 | fibroblast growth factor 7 (keratinocyte growth factor) | NM_002009 | 2252 |
| Hs.67896 | OGFR | opioid growth factor receptor | NM_007346 | 11054 |
| Hs.446350 | TGFBRAP1 | transforming growth factor, beta receptor associated protein 1 | NM_004257 | 9392 |
| Hs.194208 | FRS3 | fibroblast growth factor receptor substrate 3 | NM_006653 | 10817 |
| Hs.169300 | TGFB2 | transforming growth factor, beta 2 | NM_003238 | 7042 |
| Hs.411881 | GRB14 | growth factor receptor-bound protein 14 | NM_004490 | 2888 |
| Hs.1420 | FGFR3 | fibroblast growth factor receptor 3 (achondroplasia, thanatophoric dwarfism) | NM_000142 /// NM_022965 | 2261 |
| Hs.450230 | IGFBP3 | insulin-like growth factor binding protein 3 | NM_000598 | 3486 |
| Hs.308053 | IGF1 | insulin-like growth factor 1 (somatomedin C) | NM_000618 | 3479 |
| Hs.419124 | MET | met proto-oncogene (hepatocyte growth factor receptor) | NM_000245 | 4233 |
| Hs.284244 | FGF2 | fibroblast growth factor 2 (basic) | NM_002006 | 2247 |
| Hs.76473 | IGF2R | insulin-like growth factor 2 receptor | NM_000876 | 3482 |
| Hs.410037 | CTGF | connective tissue growth factor | NM_001901 | 1490 |
| Hs.274313 | IGFBP6 | insulin-like growth factor binding protein 6 | NM_002178 | 3489 |
| Hs.111 | FGF9 | fibroblast growth factor 9 (glia-activating factor) | NM_002010 | 2254 |
| Hs.380833 | IGFBP5 | insulin-like growth factor binding protein 5 | NM_000599 | 3488 |
| Hs.79095 | EPS15 | epidermal growth factor receptor pathway substrate 15 | NM_001981 | 2060 |
| Hs.2132 | EPS8 | epidermal growth factor receptor pathway substrate 8 | NM_004447 | 2059 |

TABLE 5-continued

| | | Growth Factor Pathway Genes | | |
|---|---|---|---|---|
| Hs.278954 | FGF1 | fibroblast growth factor 1 (acidic) | NM_000800 /// NM_013394 /// NM_033136 /// NM_033137 | 2246 |
| Hs.343809 | FGF12 | fibroblast growth factor 12 | NM_004113 /// NM_021032 | 2257 |
| Hs.7768 | FIBP | fibroblast growth factor (acidic) intracellular binding protein | NM_004214 /// NM_198897 | 9158 |
| Hs.127842 | HDGFRP3 | hepatoma-derived growth factor, related protein 3 | NM_016073 | 50810 |
| Hs.416959 | HGS | hepatocyte growth factor-regulated tyrosine kinase substrate | NM_004712 | 9146 |
| Hs.239176 | IGF1R | insulin-like growth factor 1 receptor | NM_000875 | 3480 |
| Hs.435795 | IGFBP7 | insulin-like growth factor binding protein 7 | NM_001553 | 3490 |
| Hs.439109 | NTRK2 | neurotrophic tyrosine kinase, receptor, type 2 | NM_006180 | 4915 |
| Hs.26776 | NTRK3 | neurotrophic tyrosine kinase, receptor, type 3 | NM_002530 | 4916 |
| Hs.43080 | PDGFC | platelet derived growth factor C | NM_016205 | 56034 |
| Hs.44 | PTN | pleiotrophin (heparin binding growth factor 8, neurite growth-promoting factor 1) /// pleiotrophin (heparin binding growth factor 8, neurite growth-promoting factor 1) | NM_002825 | 5764 |
| Hs.114360 | TSC22 | transforming growth factor beta-stimulated protein TSC-22 | NM_006022 /// NM_183422 | 8848 |
| Hs.73793 | VEGF | vascular endothelial growth factor | NM_003376 | 7422 |

| UniGene ID | Chromosomal Location | % P | DLPFC MD direction | DLPFC BP direction | AnCg MD direction | AnCg BP direction |
|---|---|---|---|---|---|---|
| Hs.433326 | Chr: 2q33-q34 | 25 | up | none | up | down |
| Hs.16512 | Chr: 6q13 | 28 | down | none | none | down |
| Hs.799 | Chr: 5q23 | 38 | none | up | none | none |
| Hs.105689 | Chr: 14q24 | 42 | none | none | none | down |
| Hs.289019 | Chr: 11q12 | 43 | none | none | none | up |
| Hs.376032 | Chr: 7p22 | 43 | none | none | none | down |
| Hs.839 | Chr: 16p13.3 | 48 | none | none | none | down |
| Hs.342874 | Chr: 1p33-p32 | 54 | none | up | none | none |
| Hs.404081 | Chr: 10q26 | 55 | down | none | down | up |
| Hs.433252 | Chr: 15q15-q21.1 | 59 | none | down | none | none |
| Hs.67896 | Chr: 20q13.3 | 59 | none | down | none | down |
| Hs.446350 | Chr: 2q12.2 | 61 | up | up | none | none |
| Hs.194208 | Chr: 6p21.1 | 64 | none | down | up | down |
| Hs.169300 | Chr: 1q41 | 68 | none | none | down | none |
| Hs.411881 | Chr: 2q22-q24 | 69 | none | up | up | up |
| Hs.1420 | Chr: 4p16.3 | 76 | down | none | down | none |
| Hs.450230 | Chr: 7p13-p12 | 76 | none | down | none | down |
| Hs.308053 | Chr: 12q22-q23 | 81 | down | none | down | down |
| Hs.419124 | Chr: 7q31 | 81 | none | up | up | none |
| Hs.284244 | Chr: 4q26-q27 | 84 | none | up | down | none |
| Hs.76473 | Chr: 6q26 | 92 | none | none | down | down |
| Hs.410037 | Chr: 6q23.1 | 93 | down | none | none | up |
| Hs.274313 | Chr: 12q13 | 94 | none | none | up | down |
| Hs.111 | Chr: 13q11-q12 | 99 | up | up | up | none |
| Hs.380833 | Chr: 2q33-q36 | 99 | down | none | none | down |
| Hs.79095 | Chr: 1p32 | 100 | none | none | none | up |
| Hs.2132 | Chr: 12q23-q24 | 100 | down | up | down | none |
| Hs.278954 | Chr: 5q31 | 100 | down | none | down | none |
| Hs.343809 | Chr: 3q28 | 100 | none | none | none | none |
| Hs.7768 | Chr: 11q13.1 | 100 | none | none | none | up |
| Hs.127842 | Chr: 15q11.2 | 100 | none | none | up | none |

TABLE 5-continued

| Growth Factor Pathway Genes | | | | | | |
|---|---|---|---|---|---|---|
| Hs.416959 | Chr: 17q25 | 100 | none | none | none | up |
| Hs.239176 | Chr: 15q25-q26 | 100 | none | none | none | down |
| Hs.435795 | Chr: 4q12 | 100 | down | down | down | none |
| Hs.439109 | Chr: 9q22.1 | 100 | down | none | down | none |
| Hs.26776 | Chr: 15q25 | 100 | none | none | none | down |
| Hs.43080 | Chr: 4q32 | 100 | none | none | none | up |
| Hs.44 | Chr: 7q33-q34 /// Chr: 7q33-q34 | 100 | down | none | down | none |
| Hs.114360 | Chr: 13q14 | 100 | none | none | up | none |
| Hs.73793 | Chr: 6p12 | 100 | down | none | down | none |

TABLE 6

GPCR Pathway Genes

| U95Av2 probe set | UniGene ID | Gene Symbol | Gene Name | RefSeq ID | Gene Bank Acc. No. | LocusLink | Chromosome | AnCg-BP | AnCg-MD | DLPFC-BP | DLPFC-MD |
|---|---|---|---|---|---|---|---|---|---|---|---|
| CINP 38604_at | Hs.1832 | NPY | neuropeptide Y | NM_000905 | NM_000905 | 4852 | Chr: 7p15.1 | UP | | | |
| CINP 1430_at | Hs.12409 | SST | somatostatin | NM_001048 | NM_001048 | 6750 | Chr: 3q28 | UP | | | |
| CINP 2083_at | Hs.203 | CCKBR | cholecystokinin B receptor | NM_000731 | BC000740 | 887 | Chr: 11p15.4 | UP | | | |
| CINP 39928_at | Hs.512145 | GRM3 | glutamate receptor, metabotropic 3 | NM_000840 | NM_000840 | 2913 | Chr: 7q21.1-q21.2 | UP | | UP | |
| CINP 32623_at | Hs.167017 | GABBR1 | gamma-aminobutyric acid (GABA) B receptor, 1 | NM_001470 | NM_001470 | 2550 | Chr: 6p21.31 | | | UP | |
| CINP 37095_r_at | Hs.99855 | FPRL1 | formyl peptide receptor-like 1 | NM_001462 | M88107 | 2358 | Chr: 19q13.3-q13.4 | DOWN | | | |
| CINP 1198_at | Hs.82002 | EDNRB | endothelin receptor type B | NM_000115 | M74921 | 1910 | Chr: 13q22 | | | | DOWN |
| CINP 34297_at | Hs.406094 | GPR37 | G protein-coupled receptor 37 (endothelin receptor type B-like) | NM_005302 | T16257 | 2861 | Chr: 7q31 | UP | DOWN | UP | DOWN |
| CINP 40240_at | Hs.448805 | GPRC5B | G protein-coupled receptor, family C, group 5, member B | NM_016235 | AF202640 | 51704 | Chr: 16p12 | UP | DOWN | UP | DOWN |
| CINP 38580_at | Hs.469951 | GNAQ | guanine nucleotide binding protein (G protein), q polypeptide | NM_002072 | U40038 | 2776 | Chr: 9q21 | UP | | | UP |
| CINP 38279_at | Hs.437081 | GNAZ | guanine nucleotide binding protein (G protein), alpha z polypeptide | NM_002073 | NM_002073 | 2781 | Chr: 22q11.22 | UP | | | |
| CINP 38176_at | Hs.155090 | GNB5 | guanine nucleotide binding protein (G protein), beta 5 | NM_006578 | NM_016194 | 10681 | Chr: 15q21.1 | | | UP | UP |
| 41086_at | Hs.141492 | RGS20 | regulator of G-protein signalling 20 | NM_003702 | AF074979 | 8601 | Chr: 8q12.1 | | DOWN | | DOWN |
| 34272_at | Hs.386726 | RGS4 | regulator of G-protein signalling 4 | NM_005613 | AL514445 | 5999 | Chr: 1q23.2 | UP | | | UP |
| CINP 36311_at | Hs.416061 | PDE1A | phosphodiesterase 1A, calmodulin-dependent | NM_005019 | NM_005019 | 5136 | Chr: 4 | | | | |
| CINP 32645_at | Hs.502577 | PDE4DIP | phosphodiesterase 4D interacting protein (myomegalin) | XM_380170 | NM_022359 | 9659 | Chr: 1q12 | | UP | | |
| CINP 37676_at | Hs.78746 | PDE8A | phosphodiesterase 8A | NM_002605 | BE568219 | 5151 | Chr: 15q25.2 | | | | DOWN |
| CINP 226_at | Hs.280342 | PRKAR1A | protein kinase, cAMP-dependent, regulatory, type I, alpha (tissue specific extinguisher 1) | NM_002734 | AL050038 | 5573 | Chr: 17q23-q24 | | | UP | |
| CINP 1383_at | Hs.512628 | PPP2R2A | protein phosphatase 2 (formerly 2A), regulatory subunit B (PR 52), alpha isoform | NM_002717 | NM_002717 | 5520 | Chr: 8p21.1 | UP | | | |
| 39364_s_at | Hs.303090 | PPP1R3C | protein phosphatase 1, regulatory (inhibitor) subunit 3C | NM_005398 | N26005 | 5507 | Chr: 10q23-q24 | | DOWN | | DOWN |

TABLE 6-continued

GPCR Pathway Genes

| U95Av2 probe set | UniGene ID | Gene Symbol | Gene Name | RefSeq ID | Gene Bank Acc. No. | LocusLink | Chromosome | AnCg-BP | AnCg-MD | DLPFC-BP | DLPFC-MD |
|---|---|---|---|---|---|---|---|---|---|---|---|
| 39.780_at | Hs.187543 | PPP3CB | protein phosphatase 3 (formerly 2B), catalytic subunit, beta isoform (calcineurin A beta) | NM_021132 | NM_021132 | 5532 | Chr: 10q21-q22 |  | UP |  |  |
| CINP 40704_at | Hs.85701 | PIK3CA | phosphoinositide-3-kinase, catalytic, alpha polypeptide | NM_006218 | NM_006218 | 5290 | Chr: 3q26.3 | DOWN |  |  |  |
| CINP 33628_g_at | Hs.426967 | PIK3CD | phosphoinositide-3-kinase, catalytic, delta polypeptide | NM_005026 | U86453 | 5293 | Chr: 1p36.2 | DOWN |  |  |  |
| CINP 146_at | Hs.154846 | PIK4CB | phosphatidylinositol 4-kinase, catalytic, beta polypeptide | NM_002651 | NM_002651 | 5298 | Chr: 1q21 | UP |  |  |  |
| CINP 40217_s_at | Hs.380684 | CDS1 | CDP-diacylglycerol synthase (phosphatidate cytidylyltransferase) 1 | NM_001263 | NM_001263 | 1040 | Chr: 4q21.23 | DOWN |  |  |  |
| CINP 656_at | Hs.32309 | INPR1 | inositol polyphosphate-1-phosphatase | NM_002194 | NM_002194 | 3628 | Chr: 2q32 | UP |  |  |  |
| CINP 118_at | Hs.2722 | ITPKA | inositol 1,4,5-trisphosphate 3-kinase A | NM_002220 | NM_002220 | 3706 | Chr: 15q14-q21 |  |  |  | UP |
| CINP 33508_at | Hs.334575 | INPP4A | inositol polyphosphate-4-phosphatase, type I, 107 kDa | NM_001566 | AA355179 | 3631 | Chr: 2q11.2 |  |  |  | UP |
| 32779_s_at | Hs.149900 | ITPR1 | inositol 1,4,5-triphosphate receptor, type 1 | NM_002222 | NM_002222 | 3708 | Chr: 3p26-p25 |  | UP |  |  |
| 353_at | Hs.7370 | PITPNB | phosphotidylinositol transfer protein, beta | NM_012399 | AL031591 | 23760 | Chr: 22q12.1 |  |  |  | UP |
| 1217_g_at | Hs.349845 | PRKCB1 | protein kinase C, beta 1 | NM_002738 | NM_002738 | 5579 | Chr: 16p11.2 |  | UP |  |  |
| 362_at | Hs.407181 | PRKCZ | protein kinase C, zeta | NM_002744 | NM_002744 | 5590 | Chr: 1p36.33-p36.2 |  | UP |  |  |
| CINP 976_s_at | Hs.324473 | MAPK1 | mitogen-activated protein kinase 1 | NM_002745 | NM_002745 | 5594 | Chr: 22q11.2 | UP |  |  | UP |
| CINP 1844_s_at | Hs.132311 | MAP2K1 | mitogen-activated protein kinase kinase 1 | NM_002755 | AI571419 | 5604 | Chr: 15q22.1-q22.33 | UP |  |  |  |
| CINP 1712_g_at | Hs.134106 | MAP2K4 | mitogen-activated protein kinase kinase 4 | NM_003010 | NM_003010 | 6416 | Chr: 17p11.2 | UP |  |  | UP |
| CINP 1557_at | Hs.64056 | PAK1 | p21/Cdc42/Rac1-activated kinase 1 (STE 20 homolog, yeast) | NM_002576 | U51120 | 5058 | Chr: 11q13-q14 | UP |  |  | UP |
| CINP 33073_at | Hs.152663 | PAK3 | p21(CDKN1A)-activated kinase 3 | NM_002578 | AW085556 | 5063 | Chr: Xq22.3-q23 | UP | UP | UP |  |
| CINP 39736_at | Hs.355832 | CDC42 | cell division cycle 42 (GTP binding protein, 25 kDa) | NM_001791 | NM_015858 | 998 | Chr: 1p36.1 |  | UP | UP |  |
| CINP 1590_s_at | Hs.37003 | HRAS | v-Ha-ras Harvey rat sarcoma a viral oncogene homolog | NM_005343 | NM_005343 | 3265 | Chr: 11p15.5 | UP | UP |  |  |

TABLE 7

| | | GROWTH FACTOR | | | | | | | | | |
|---|---|---|---|---|---|---|---|---|---|---|---|
| | Gene | MDD | | | | | BPD | | | | |
| UniGene ID | Symbol | Amy | AnCg | DLPFC | HC | nAcc | Amy | AnCg | DLPFC | HC | nAcc |
| | | Epidermal Growth Factor System | | | | | | | | | |
| Hs.419815 | EGF | | | −1.1 | | | | | | | |
| Hs.79095 | EPS15 | | | | | | | | | | 1.3 |
| Hs.147176 | EPS15R | | | | | | | | | | |
| Hs.2132 | EPS8 | | −1.2 | | | | | | | | |
| Hs.799 | DTR | | | | | | | | | −1.1 | |
| | | Fibroblast Growth Factor System | | | | | | | | | |
| Hs.278954 | FGF1 | −1.2 | | −1.4 | | | | | | | |
| Hs.343809 | FGF12 | 1.5 | | 1.5 | | | | | | | |
| Hs.6540 | FGF13 | | | | | 1.5 | | | | 1.5 | |
| Hs.223851 | FGF14 | 1.5 | | | | | 1.3 | | | 1.4 | |
| Hs.284244 | FGF2 | −1.4 | −1.3 | | −1.4 | | | | | | −1.8 |
| Hs.433252 | FGF7 | | | | | | | | −1.1 | | |
| Hs.111 | FGF9 | 1.4 | 1.2 | 1.3 | 1.6 | | | | | | |
| Hs.748 | FGFR1 | | | | | | | | | | |
| Hs.404081 | FGFR2 | −1.1 | −1.3 | −1.2 | −1.3 | | | | | | |
| Hs.1420 | FGFR3 | −1.2 | −1.4 | −1.5 | | | | | | | |
| Hs.7768 | FIBP | | | | 1.3 | | | | | | |
| Hs.194208 | FRS3 | | | | | | | | | | |
| | | Insulin-Like Growth Factor System | | | | | | | | | |
| Hs.308053 | IGF1 | | | | | | | | | | |
| Hs.239176 | IGF1R | | | | −1.2 | | | −1.3 | | | |
| Hs.76473 | IGF2R | | | | | | | | | | |
| Hs.839 | IGFALS | | | | | | | | | | |
| Hs.433326 | IGFBP2 | | 1.4 | | | | | | | | |
| Hs.450230 | IGFBP3 | −1.3 | | | | | | −1.4 | | | |
| Hs.1516 | IGFBP4 | | | | | | | −1.6 | | | |
| Hs.380833 | IGFBP5 | | −1.2 | −1.2 | | | | | | | |
| Hs.274313 | IGFBP6 | | | | | | | | | | |
| Hs.435795 | IGFBP7 | | | | | | | | | | |
| | | Neurotrophins | | | | | | | | | |
| Hs.439027 | BDNF | | | | | | | | | | |
| Hs.439109 | NTRK2 | −1.2 | −1.4 | −1.3 | −1.3 | | | | | | |
| Hs.26776 | NTRK3 | | | | | | | | | | |
| Hs.194774 | CNTFR | | | | | | | | | | |
| | | Opioid Growth Factor System | | | | | | | | | |
| Hs.67896 | OGFR | | | | | | | | | | |
| Hs.16512 | OGFRL1 | | | −1.2 | | | | −1.2 | | | |
| | | Platelet-Derived Growth Factor System | | | | | | | | | |
| Hs.1976 | PDGFB | | | | | | | | | | |
| Hs.43080 | PDGFC | | | | | | | | | | |
| Hs.74615 | PDGFRA | −1.3 | | | −1.3 | | | −1.2 | | −1.3 | |
| Hs.307783 | PDGFRB | | | | | | | | | | |
| | | Transforming Growth Factor System | | | | | | | | | |
| Hs.25195 | EBAF | | | | | | | | | | |
| Hs.435067 | ECGF1 | | | | | | | | | | |
| Hs.170009 | TGFA | | | | | | | | | −1.1 | |
| Hs.169300 | TGFB2 | | | | | | | | | | |
| Hs.421496 | TGFBI | | | | | | −1.9 | | | | |
| Hs.82028 | TGFBR2 | | | | | | | | | | |
| Hs.342874 | TGFBR3 | | | | | | −1.3 | | | | |
| Hs.446350 | TGFBRAP1 | | | | | | | | | | |
| Hs.114360 | TSC22 | | | | | | | | | | |
| Hs.241257 | LTBP1 | | | | | | −1.2 | −1.1 | | | |
| Hs.105689 | LTBP2 | | | | | | −1.2 | | | | |
| Hs.289019 | LTBP3 | | | | | | | | | | |
| | | Vascular Endothelial Growth Factor System | | | | | | | | | |
| Hs.73793 | VEGF | | | −1.4 | | | | | | | |
| Hs.78781 | VEGFB | | | | | | | | | | |
| Hs.79141 | VEGFC | | | | | | | | | | |
| | | Other Growth Factors/Receptors | | | | | | | | | |
| Hs.89525 | HDGF | | | | | | | | | | |
| Hs.127842 | HDGFRP3 | | | | 1.3 | 1.3 | | | | 1.3 | 1.2 |

TABLE 7-continued

GROWTH FACTOR

| UniGene ID | Gene Symbol | MDD Amy | AnCg | DLPFC | HC | nAcc | BPD Amy | AnCg | DLPFC | HC | nAcc |
|---|---|---|---|---|---|---|---|---|---|---|---|
| Hs.44 | PTN | | | −1.2 | | | | | | | |
| Hs.270833 | AREG | | | | | | | | | | |
| Hs.410037 | CTGF | | | | | | | | | | |

Other Growth Factor Receptor Signalling Proteins

| Hs.512118 | GRB10 | | | | | | | | | | |
| Hs.411881 | GRB14 | | | | | | | | | | |
| Hs.411366 | GRB2 | 1.1 | | | | | | | | | |
| Hs.416959 | HGS | | | | | | | | | 1.1 | |
| Hs.419124 | MET | | | | | | | | | | |

TABLE 8

GLU/GABA
GABA/glutamate signaling genes in Mood Disorders - SFN genes For IDF inclusion

| UniGene ID | Gene | Common name | Locus | BPD AnCg | DLPFC | HC | Amy | MDD AnCg | DLPFC | HC | Amy |
|---|---|---|---|---|---|---|---|---|---|---|---|
| | GABAergic: GABA A receptor | | | | | | | | | | |
| Hs.24969 | alpha 5 | GABRA5 | GABA (A) receptor, alpha 5 | GABA-A-Ra5 | 15q11.2 | 1.58 | 1.64 | | | 1.58 | | |
| Hs.302352 | beta 3 | GABARB3 | GABA (A) receptor, beta 3 | GABA-A-Rb3 | 15q11.2 | | | | | 1.54 | | |
| Hs.7195 | gamma 2 | GABARG2 | GABA (A) receptor, gamma 2 | GABA-A-Rg2 | 5q3.1 | | | | | 1.58 | 1.64 | 1.59 |
| | Glutamate receptor | | | | | | | | | | | |
| Hs.7117 | ionotropic, AMPA1 | GRIA1 | | IGluR1 | 5q31.1 | | | | | | 1.18 | |
| Hs.512145 | Glutamate receptor, metabotropic 3 | GRM3 | Glutamate receptor, metabotropic 3 | mGluR3 | 7q21.1 | | 1.22 | 1.32 | | | | |
| | Glutamate transporters | | | | | | | | | | | |
| Hs.349088 | Glutamate transporter, Na+-dependent, EAAT2 | SLC1A2 | Solute carrier family 1 (glial high affinity | GLT-1; EAAT2 | 11p13 | | 0.84 | | 0.71 | | 0.87 | 0.81 |
| Hs.371369 | Glutamate Transporter, Na+-dependent, EAAT1 | SLC1A3 | Solute carrier family 1 (glial high affinity - | GLAST; EAAT1 | 5p13 | | | | | 0.65 | | |
| | Glutamine synthetase | | | | | | | | | | | |
| Hs.442669 | Glutamate-ammonia ligase | GLUL | Glutamate-ammonia ligase (glut synthetase) | Glutamine synthetase | 1q31 | | | | | 0.72 | | 0.86 |

GABA, gamma amino butyric acid;
glut/glutamate, glutamic acid;
MDD, major depressive disorder;
BPD, bipolar disorder
AnCg, anterior cingulate cortex;
DLPFC, dorso-lateral prefrontal cortex;
HC, hippocampus;
Amy, amygdala.
Numbers (Fold Change) in RED denote INCREASES, and BLUE the DECREASES

TABLE 9

G protein and GPCR signaling pathways and mood disorders

Pathway Analysis

| Gene Category | System | Rank | EASE score | Major Depressive Disorder Gene Category | System | Rank | EASE score |
|---|---|---|---|---|---|---|---|
| Dorsolareral Prefrontal Cortex Bipolar Disorder | | | | | | | |
| PKC | | 1st | 0.00495 | Hs_Glutamate Metabolism | GenMAPP | 1st | 0.338 |
| Hs_G Protein Signaling | GenMAPP | 2nd | 0.121 | Hs_G13 Signaling Pathway | GenMAPP | 2nd | 0.387 |
| Hs_Electron Transport Chain | GenMAPP | 3rd | 0.212 | G protein beta, gamma | | 3rd | 0.478 |
| Hs_Ribosomal Proteins | GenMAPP | 4th | 0.29 | Hs_Peptide GPCRs | GenMAPP | 4th | 0.566 |
| Hs_Wnt signaling | GenMAPP | 5th | 0.362 | Hs_G Protein Signaling | GenMAPP | 5th | 0.571 |
| Anterior Cingulate Cortex Bipolar Disorder | | | | | | | |
| Hs_Electron Transport Chain | GenMAPP | 1st | 0.0972 | GPCR-orphan | | 1st | 0.0407 |
| Hs_Ribosomal Proteins | GenMAPP | 2nd | 0.102 | Hs_Orphan GPCRs | GenMAPP | 2nd | 0.0447 |
| GPCR-orphan | | 3rd | 0.289 | Hs_Electron Transport Chain | GenMAPP | 3rd | 0.0677 |
| PKA | | 4th | 0.368 | GPCR | | 4th | 0.189 |
| Hs_Proteasome Degradation | GenMAPP | 5th | 0.427 | PI signaling | | 5th | 0.198 |
| Amygdala Bipolar Disorder | | | | | | | |
| Hs_Nuclear Receptors | GenMAPP | 1st | 0.0826 | Hs_Glycolysis and Gluconeogenesis | GenMAPP | 1st | 0.0022 |
| Hs_Apoptosis | GenMAPP | 2nd | 0.228 | Hs_Krebs-TCA Cycle | GenMAPP | 2nd | 0.00447 |
| GPCR-orphan | | 3rd | 0.46 | Hs_Electron Transport Chain | GenMAPP | 3rd | 0.0563 |
| GPCR | | 4th | 0.555 | PI signaling | | 4th | 0.0846 |
| Hs_Krebs-TCA Cycle | GenMAPP | 5th | 0.61 | Hs_G Protein Signaling | GenMAPP | 5th | 0.154 |
| Hippocampus Bipolar Disorder | | | | | | | |
| Hs_Electron Transport Chain | GenMAPP | 1st | 0.00000276 | Hs_Electron Transport Chain | GenMAPP | 1st | 2.41E−07 |
| Hs_Glycolysis and Gluconeogenesis | GenMAPP | 2nd | 0.00838 | Hs_Glycolysis and Gluconeogenesis | GenMAPP | 2nd | 0.0059 |
| cAMP signaling | | 3rd | 0.134 | Rn_Ribosomal Proteins | GenMAPP | 3rd | 0.16 |
| PKA | | 4th | 0.14 | Hs_Krebs-TCA Cycle | GenMAPP | 4th | 0.179 |
| GPCR | | 5th | 0.187 | MAPK signaling | | 5th | 0.22 |

Arrray Data

| UniGene Cluster | NAME | SYMBOL | Large Category | Subcategory | p-value (BP - Control) | FC (BP - Control) |
|---|---|---|---|---|---|---|
| Dorsolateral Prefrontal Cortex Bipolar Disorder vs Control | | | | | | |
| Hs.458426 | cholecystokinin | CCK | Ligand | Ligand-neuropeptide | 0.021 | 1.164 |
| Hs.155090 | guanine nucleotide binding protein (G protein), beta 5 | GNB5 | G protein beta, gamma | GNB | 0.025 | 1.210 |
| Hs.434387 | protein kinase C, nu | PRKCN | PI signaling | PKC | 0.023 | 1.081 |
| Hs.496511 | protein kinase C, iota | PRKCI | PI signaling | PKC | 0.048 | 1.184 |
| Hs.408049 | protein kinase C, theta | PRKCQ | PI signaling | PKC | 0.046 | 1.104 |
| Hs.2890 | protein kinase C, gamma | PRKCG | PI signaling | PKC | 0.032 | 0.757 |
| Major Depressive Disorder vs Control | | | | | | |
| Hs.458426 | cholecystokinin | CCK | Ligand | Ligand-neuropeptide | 0.015 | 1.152 |
| Hs.82002 | endothelin receptor type B | EDNRB | GPCR | GPCR-neuropeptide | 0.000 | 0.550 |
| Hs.184841 | somatostatin receptor 2 | SSTR2 | GPCR | GPCR-neuropeptide | 0.007 | 1.142 |
| Hs.448805 | G protein-coupled receptor, family C, group 5, member B | GPRC5B | GPCR | GPCR-orphan | 0.009 | 0.694 |
| Hs.6527 | G protein-coupled receptor 56 | GPR56 | GPCR | GPCR-orphan | 0.010 | 0.790 |
| Hs.155090 | guanine nucleotide binding protein (G protein), beta 5 | GNB5 | G protein beta, gamma | GNB | 0.024 | 1.184 |
| Hs.8107 | guanine nucleotide binding protein (G protein), gamma 12 | GNG12 | G protein beta, gamma | GNG | 0.004 | 0.743 |
| Hs.141492 | regulator of G-protein signalling 20 | RGS20 | G protein regulator | RGS | 0.007 | 0.582 |
| Anterior Cingulate Cortex Bipolar Disorder vs Control | | | | | | |
| Hs.203 | cholecystokinin B receptor | CCKBR | GPCR | GPCR-neuropeptide | 0.019 | 1.215 |
| Hs.188 | phosphodiesterase 4B, cAMP-specific (phosphodiesterase E4 dunce homolog, *Drosophila*) | PDE4B | cAMP signaling | phosphodiesterase | 0.026 | 0.880 |

TABLE 9-continued

G protein and GPCR signaling pathways and mood disorders

| | | | | | | |
|---|---|---|---|---|---|---|
| Hs.350631 | A kinase (PRKA) anchor protein 13 | AKAP13 | cAMP signaling | PKA | 0.019 | 0.887 |
| Hs.440404 | protein kinase, cAMP-dependent, regulatory, type II, alpha | PRKAR2A | cAMP signaling | PKA | 0.007 | 0.954 |
| Hs.183994 | protein phosphatase 1, catalytic subunit, alpha isoform | PPP1CA | cAMP signaling | PP related | 0.004 | 1.152 |
| Hs.435238 | protein phosphatase 1, regulatory (inhibitor) subunit 1A | PPP1R1A | cAMP signaling | PP related | 0.017 | 1.233 |
| Major Depressive Disorder vs Control | | | | | | |
| Hs.82002 | endothelin receptor type B | EDNRB | GPCR | GPCR-neuropeptide | 0.001 | 0.565 |
| Hs.203 | cholecystokinin B receptor | CCKBR | GPCR | GPCR-neuropeptide | 0.011 | 1.205 |
| Hs.406094 | G protein-coupled receptor 37 | GPR37 | GPCR | GPCR-orphan | 0.003 | 0.595 |
| Hs.448805 | G protein-coupled receptor, family C, group 5, member B | GPRC5B | GPCR | GPCR-orphan | 0.000 | 0.662 |
| Hs.6527 | G protein-coupled receptor 56 | GPR56 | GPCR | GPCR-orphan | 0.002 | 0.787 |
| Hs.46332 | G protein-coupled receptor 6 | GPR6 | GPCR | GPCR-orphan | 0.042 | 1.249 |
| Hs.160271 | G protein-coupled receptor 48 | GPR48 | GPCR | GPCR-orphan | 0.000 | 0.713 |
| Hs.166705 | G protein-coupled receptor 49 | GPR49 | GPCR | GPCR-orphan | 0.011 | 0.839 |
| Hs.198612 | G protein-coupled receptor 51 | GPR51 | GPCR | GPCR-orphan | 0.003 | 1.173 |
| Hs.155090 | guanine nucleotide binding protein (G protein), beta 5 | GNB5 | G protein beta, gamma | GNB | 0.010 | 1.199 |
| Hs.149900 | inositol 1,4,5-triphosphate receptor, type 1 | ITPR1 | PI signaling | IP3 receptor | 0.003 | 1.227 |
| Hs.153687 | inositol polyphosphate-4-phosphatase, type II, 105 kDa | INPP4B | PI signaling | Phosphatidylinositol metabolism | 0.001 | 1.246 |
| Hs.151408 | phospholipase C, beta 4 | PLCB4 | PI signaling | Phosphatidylinositol metabolism | 0.005 | 1.215 |
| Hs.52463 | inositol polyphosphate-5-phosphatase F | INPP5F | PI signaling | Phosphatidylinositol metabolism | 0.003 | 1.181 |
| Hs.158318 | diacylglycerol kinase, beta 90 kDa | DGKB | PI signaling | Phosphatidylinositol metabolism | 0.024 | 1.192 |
| Hs.249235 | phosphoinositide-3-kinase, class 2, alpha polypeptide | PIK3C2A | PI signaling | Phosphatidylinositol metabolism | 0.027 | 0.770 |
| Hs.408063 | inositol polyphosphate-5-phosphatase, 40 kDa | INPP5A | PI signaling | Phosphatidylinositol metabolism | 0.011 | 1.126 |
| Hs.239818 | phosphoinositide-3-kinase, catalytic, beta polypeptide | PIK3CB | PI signaling | Phosphatidylinositol metabolism | 0.021 | 1.084 |
| Hs.349845 | protein kinase C, beta 1 | PRKCB1 | PI signaling | PKC | 0.014 | 1.125 |
| Hs.79000 | growth associated protein 43 | GAP43 | PI signaling | PKC related | 0.006 | 1.133 |
| Amygdala Bipolar Disorder vs Control Column ID | | | | | | |
| Hs.12409 | somatostatin | SST | Ligand | Ligand-neuropeptide | 0.011 | 1.672 |
| Hs.46453 | G protein-coupled receptor 17 | GPR17 | GPCR | GPCR-orphan | 0.034 | 1.457 |
| Hs.118552 | likely ortholog of rat GRP78-binding protein | GBP | GPCR | GPCR-orphan | 0.009 | 1.170 |
| Major Depressive Disorder vs Control | | | | | | |
| Hs.22584 | prodynorphin | PDYN | Ligand | Ligand-neuropeptide | 0.003 | 2.184 |
| Hs.131138 | neurotensin receptor 2 | NTSR2 | GPCR | GPCR-neuropeptide | 0.001 | 0.684 |
| Hs.82002 | endothelin receptor type B | EDNRB | GPCR | GPCR-neuropeptide | 0.005 | 0.706 |
| Hs.46453 | G protein-coupled receptor 17 | GPR17 | GPCR | GPCR-orphan | 0.003 | 0.661 |
| Hs.6527 | G protein-coupled receptor 56 | GPR56 | GPCR | GPCR-orphan | 0.000 | 0.781 |
| Hs.448805 | G protein-coupled receptor, family C, group 5, member B | GPRC5B | GPCR | GPCR-orphan | 0.039 | 0.870 |
| Hs.155090 | guanine nucleotide binding protein (G protein), beta 5 | GNB5 | G protein beta, gamma | GNB | 0.000 | 1.295 |
| Hs.8107 | guanine nucleotide binding protein (G protein), gamma 12 | GNG12 | G protein beta, gamma | GNG | 0.001 | 0.732 |
| Hs.50612 | guanine nucleotide binding protein (G protein), alpha 14 | GNA14 | PI signaling | GNA | 0.007 | 0.691 |
| Hs.149900 | inositol 1,4,5-triphosphate receptor, type 1 | ITPR1 | PI signaling | IP3 receptor | 0.003 | 1.454 |
| Hs.158318 | diacylglycerol kinase, beta 90 kDa | DGKB | PI signaling | Phosphatidylinositol metabolism | 0.001 | 1.444 |
| Hs.78877 | inositol 1,4,5-trisphosphate 3-kinase B | ITPKB | PI signaling | Phosphatidylinositol metabolism | 0.001 | 0.727 |
| Hs.2722 | inositol 1,4,5-trisphosphate 3-kinase A | ITPKA | PI signaling | Phosphatidylinositol metabolism | 0.011 | 1.461 |
| Hs.408063 | inositol polyphosphate-5-phosphatase, 40 kDa | INPP5A | PI signaling | Phosphatidylinositol metabolism | 0.003 | 1.358 |
| Hs.429643 | phospholipase C, beta 1 (phosphoinositide-specific) | PLCB1 | PI signaling | Phosphatidylinositol metabolism | 0.004 | 1.203 |
| Hs.249235 | phosphoinositide-3-kinase, class 2, alpha polypeptide | PIK3C2A | PI signaling | Phosphatidylinositol metabolism | 0.013 | 0.782 |

TABLE 9-continued

G protein and GPCR signaling pathways and mood disorders

| Hs.52463 | inositol polyphosphate-5-phosphatase F | INPP5F | PI signaling | Phosphatidylinositol metabolism | 0.004 | 1.282 |
|---|---|---|---|---|---|---|
| Hs.334575 | inositol polyphosphate-4-phosphatase, type I, 107 kDa | INPP4A | PI signaling | Phosphatidylinositol metabolism | 0.013 | 1.138 |
| Hs.25156 | inositol polyphosphate-5-phosphatase, 72 kDa | INPP5E | PI signaling | Phosphatidylinositol metabolism | 0.014 | 0.914 |
| Hs.349845 | protein kinase C, beta 1 | PRKCB1 | PI signaling | PKC | 0.002 | 1.600 |
| Hs.512640 | protein kinase C substrate 80K-H | PRKCSH | PI signaling | PKC | 0.004 | 0.916 |
| Hs.349611 | protein kinase C, alpha | PRKCA | PI signaling | PKC | 0.005 | 0.923 |

Hippocampus
Bipolar Disorder vs Control

| Hs.296341 | CAP, adenylate cyclase-associated protein, 2 (yeast) | CAP2 | cAMP signaling | adenylate cyclase related | 0.035 | 1.396 |
|---|---|---|---|---|---|---|
| Hs.13313 | cAMP responsive element binding protein-like 2 | CREBL2 | cAMP signaling | CRE | 0.033 | 1.341 |
| Hs.203862 | guanine nucleotide binding protein (G protein), alpha inhibiting activity polypeptide 1 | GNAI1 | cAMP signaling | GNA | 0.000 | 2.075 |
| Hs.157307 | GNAS complex locus | GNAS | cAMP signaling | GNA | 0.038 | 1.127 |
| Hs.416467 | phosphodiesterase 10A | PDE10A | cAMP signaling | phosphodiesterase | 0.001 | 0.921 |
| Hs.386791 | phosphodiesterase 3A, cGMP-inhibited | PDE3A | cAMP signaling | phosphodiesterase | 0.005 | 0.790 |
| Hs.337616 | phosphodiesterase 3B, cGMP-inhibited | PDE3B | cAMP signaling | phosphodiesterase | 0.009 | 0.835 |
| Hs.43322 | protein kinase, AMP-activated, alpha 1 catalytic subunit | PRKAA1 | cAMP signaling | PKA | 0.001 | 0.880 |
| Hs.350631 | A kinase (PRKA) anchor protein 13 | AKAP13 | cAMP signaling | PKA | 0.001 | 0.806 |
| Hs.280342 | protein kinase, cAMP-dependent, regulatory, type I, alpha (tissue specific extinguisher 1) | PRKAR1A | cAMP signaling | PKA | 0.003 | 1.569 |
| Hs.156324 | protein kinase, cAMP-dependent, catalytic, beta | PRKACB | cAMP signaling | PKA | 0.012 | 1.418 |
| Hs.3136 | protein kinase, AMP-activated, gamma 1 non-catalytic subunit | PRKAG1 | cAMP signaling | PKA | 0.014 | 1.225 |
| Hs.433700 | protein kinase (cAMP-dependent, catalytic) inhibitor alpha | PKIA | cAMP signaling | PKA related | 0.014 | 1.385 |
| Hs.79081 | protein phosphatase 1, catalytic subunit, gamma isoform | PPP1CC | cAMP signaling | PP related | 0.001 | 1.426 |
| Hs.267819 | protein phosphatase 1, regulatory (inhibitor) subunit 2 | PPP1R2 | cAMP signaling | PP related | 0.002 | 1.933 |
| Hs.187543 | protein phosphatase 3 (formerly 2B), catalytic subunit, beta isoform (calcineurin A beta) | PPP3CB | cAMP signaling | PP related | 0.007 | 1.476 |
| Hs.166071 | cyclin-dependent kinase 5 | CDK5 | cAMP signaling | PP related | 0.017 | 1.296 |
| Hs.21537 | protein phosphatase 1, catalytic subunit, beta isoform | PPP1CB | cAMP signaling | PP related | 0.005 | 1.334 |
| Hs.272458 | protein phosphatase 3 (formerly 2B), catalytic subunit, alpha isoform (calcineurin A alpha) | PPP3CA | cAMP signaling | PP related | 0.017 | 1.357 |
| Hs.431156 | protein phosphatase 2 (formerly 2A), regulatory subunit A (PR 65), beta isoform | PPP2R1B | cAMP signaling | PP related | 0.017 | 0.927 |
| Hs.380764 | protein phosphatase 2 (formerly 2A), regulatory subunit B (PR 52), beta isoform | PPP2R2B | cAMP signaling | PP related | 0.009 | 1.215 |
| Hs.118244 | protein phosphatase 2, regulatory subunit B (B56), delta isoform | PPP2R5D | cAMP signaling | PP related | 0.008 | 1.118 |
| Hs.356590 | protein phosphatase 1, regulatory (inhibitor) subunit 8 | PPP1R8 | cAMP signaling | PP related | 0.011 | 1.210 |
| Hs.76556 | protein phosphatase 1, regulatory (inhibitor) subunit 15A | PPP1R15A | cAMP signaling | PP related | 0.045 | 0.828 |

Major Depressive Disorder vs Control

| Hs.234521 | mitogen-activated protein kinase-activated protein kinase 3 | MAPKAPK3 | | MAPK | 0.007 | 0.845 |
|---|---|---|---|---|---|---|
| Hs.324473 | mitogen-activated protein kinase 1 | MAPK1 | MAPK signaling | MAPK | 0.007 | 1.612 |
| Hs.348446 | mitogen-activated protein kinase 9 | MAPK9 | | MAPK | 0.002 | 1.630 |
| Hs.75074 | mitogen-activated protein kinase-activated protein kinase 2 | MAPKAPK2 | | MAPK | 0.006 | 0.872 |
| Hs.271980 | mitogen-activated protein kinase 6 | MAPK6 | | MAPK | 0.004 | 1.471 |
| Hs.25209 | mitogen-activated protein kinase 10 | MAPK10 | MAPK signaling | MAPK | 0.012 | 1.374 |
| Hs.134106 | mitogen-activated protein kinase kinase 4 | MAP2K4 | MAPK signaling | MAPKK | 0.004 | 1.657 |
| Hs.432453 | mitogen-activated protein kinase kinase kinase 8 | MAP3K8 | | MAPKKK | 0.004 | 0.807 |

TABLE 9-continued

G protein and GPCR signaling pathways and mood disorders

| | | | | | | | |
|---|---|---|---|---|---|---|---|
| Hs.437214 | mitogen-activated protein kinase kinase kinase 9 | MAP3K9 | | MAPKKK | | 0.008 | 1.162 |
| Hs.28827 | mitogen-activated protein kinase kinase kinase 2 | MAP3K2 | | MAPKKK | | 0.004 | 0.873 |
| Hs.403927 | mitogen-activated protein kinase kinase kinase 7 interacting protein 1 | MAP3K7IP1 | | MAPKKK | | 0.041 | 0.847 |
| Hs.206097 | related RAS viral (r-ras) oncogene homolog 2 | RRAS2 | MAPK signaling | RAS-MAPK | | 0.002 | 0.863 |
| Hs.37003 | v-Ha-ras Harvey rat sarcoma viral oncogene homolog | HRAS | MAPK signaling | RAS-MAPK | | 0.008 | 1.196 |
| Hs.412107 | v-Ki-ras2 Kirsten rat sarcoma 2 viral oncogene homolog | KRAS2 | MAPK signaling | RAS-MAPK | | 0.013 | 1.451 | qRT-PCR

| Symbol | UniGene | Gene Name | Fold Change AnCg U133A | qRT-PCR | DLPFC U133A | qRT-PCR |
|---|---|---|---|---|---|---|
| Bipolar Disorder vs Control | | | | | | |
| CCKBR | Hs.203 | Cholecystokinin B receptor | 1.21^ | 1.44** | | |
| Major Depressive Disorder vs Control | | | | | | |
| EDNRB | Hs.82002 | Endothelin receptor type B | 0.57 | 0.63* | 0.55^ | 0.76 |
| CCKBR | Hs.203 | cholecystokinin B receptor | 1.21 | 1.09 | | |
| GPR37 | Hs.406094 | G protein-coupled receptor 37 | 0.59^ | 0.74 | | |
| GPRC5B | Hs.448805 | G protein-coupled receptor C-5-B | 0.66^ | 0.65** | 0.69^ | 0.85 |
| GNB5 | Hs.155090 | G protein, beta 5 | 1.20 | 1.09 | 1.18^ | 1.61** |
| RGS20 | Hs.141492 | Regulator of G-protein signalling 20 | | | 0.58^ | 0.70* |

^Microarray U133A, ANOVA p < 0.05
*qRT-PCR, one tailed Student's t-test, p < 0.1
**qRT-PCR, one tailed Student's t-test, p < 0.05

TABLE 10

| Mood And Region | Probe_ID | Hs. Unigene | Differential Expression Value | Rank | Accession | UniGene_ID | LocusLink_ID | Symbol | Description |
|---|---|---|---|---|---|---|---|---|---|
| Probe_ID (BPDv C) AnCg | Hs.20021_at | Hs.20021 | -7.727057737 | 9 | R17168 | Hs.20021 | 6843 | VAMP1 | VESICLE-ASSOCIATED MEMBRANE PROTEIN 1 (SYNAPTOBREVIN 1) |
| Probe_ID (BPDv C) AnCg | Hs.119316_at | Hs.119316 | 7.019916677 | 17 | AI075114 | Hs.119316 | 5188 | PET112L | PET112-LIKE (YEAST) |
| Probe_ID (BPDv C) AnCg | Hs.194673_at | Hs.194673 | 6.739939746 | 24 | AA954646 | Hs.194673 | 8682 | PEA15 | PHOSPHOPROTEIN ENRICHED IN ASTROCYTES 15 |
| Probe_ID (BPDv C) AnCg | Hs.356231_at | Hs.356231 | -6.670345597 | 28 | AI038963 | Hs.356231 | 79085 | SLC25A23 | SOLUTE CARRIER FAMILY 25 (MITOCHONDRIAL CARRIER; PHOSPHATE CARRIER), MEMBER 23 |
| Probe_ID (BPDv C) AnCg | Hs.438303_at | Hs.438303 | 5.313202083 | 72 | AA969386 | Hs.438303 | 23395 | LARS2 | LEUCYL-TRNA SYNTHETASE 2, MITOCHONDRIAL |
| Probe_ID (BPDv C) AnCg | Hs.109052_at | Hs.109052 | 5.019252834 | 103 | AA865834 | Hs.109052 | 9556 | C14orf2 | CHROMOSOME 14 OPEN READING FRAME 2 |
| Probe_ID (BPDv C) AnCg | Hs.76366_at | Hs.76366 | 4.693419228 | 127 | AA999694 | Hs.76366 | 572 | BAD | BCL2-ANTAGONIST OF CELL DEATH |
| Probe_ID (BPDv C) AnCg | Hs.279939_at | Hs.279939 | 4.582420323 | 138 | AA977776 | Hs.279939 | 23787 | MTCH1 | MITOCHONDRIAL CARRIER HOMOLOG 1 (C. ELEGANS) |
| Probe_ID (BPDv C) AnCg | Hs.74047_at | Hs.74047 | 4.496465885 | 150 | | Hs.74047 | | | |
| Probe_ID (BPDv C) AnCg | Hs.3100_at | Hs.3100 | 4.309487236 | 169 | AA954213 | Hs.3100 | 3735 | KARS | LYSYL-TRNA SYNTHETASE |
| Probe_ID (BPDv C) AnCg | Hs.243491_at | Hs.243491 | -4.224934266 | 183 | | Hs.243491 | | | |
| Probe_ID (BPDv C) AnCg | Hs.3254_at | Hs.3254 | 4.193592918 | 195 | AA971301 | Hs.3254 | 6150 | MRPL23 | MITOCHONDRIAL RIBOSOMAL PROTEIN L23 |
| Probe_ID (BPDv C) AnCg | Hs.177584_at | Hs.177584 | 4.165654802 | 200 | AA961910 | Hs.177584 | 5019 | OXCT1 | 3-OXOACID COA TRANSFERASE 1 |
| Probe_ID (BPDv C) AnCg | Hs.14945_at | Hs.14945 | -4.158983584 | 201 | R17684 | Hs.14945 | 23305 | ACSL6 | ACYL-COA SYNTHETASE LONG-CHAIN FAMILY MEMBER 6 |
| Probe_ID (BPDv C) AnCg | Hs.511880_at | Hs.511880 | -4.005278821 | 239 | NM_000498 | Hs.511880 | 1585 | CYP11B2 | CYTOCHROME P450, FAMILY 11, SUBFAMILY B, POLYPEPTIDE 2 |
| Probe_ID (BPDv C) AnCg | Hs.149156_at | Hs.149156 | 3.978596138 | 243 | AI148899 | Hs.149156 | 2731 | GLDC | GLYCINE DEHYDROGENASE (DECARBOXYLATING; GLYCINE DECARBOXYLASE, GLYCINE CLEAVAGE SYSTEM PROTEIN P) |
| Probe_ID (BPDv C) AnCg | Hs.433419_at | Hs.433419 | 3.863300127 | 269 | AA968887 | Hs.433419 | 1327 | COX4I1 | CYTOCHROME C OXIDASE SUBUNIT IV ISOFORM 1 |
| Probe_ID (BPDv C) AnCg | Hs.107476_at | Hs.107476 | 3.852124446 | 271 | AA961439 | Hs.107476 | 10632 | ATP5L | ATP SYNTHASE, H+ TRANSPORTING, MITOCHONDRIAL F0 COMPLEX, SUBUNIT G |
| Probe_ID (BPDv C) AnCg | Hs.198269_at | Hs.198269 | 3.842264322 | 274 | AA970515 | Hs.198269 | 4696 | NDUFA3 | NADH DEHYDROGENASE (UBIQUINONE) 1 ALPHA SUBCOMPLEX, 3, 9 KDA |
| Probe_ID (BPDv C) AnCg | Hs.75859_at | Hs.75859 | 3.825790421 | 277 | AA975309 | Hs.75859 | 740 | MRPL49 | MITOCHONDRIAL RIBOSOMAL PROTEIN L49 |

TABLE 10-continued

| | | | | | | |
|---|---|---|---|---|---|---|
| Probe_ID (BPDv C) AnCg | Hs.144130_at | -3.81230531 | 284 | AA865892 | Hs.144130 | 55186 | FLJ10618 | HYPOTHETICAL PROTEIN FLJ10618 |
| Probe_ID (BPDv C) AnCg | Hs.3548_at | 3.79318498 | 290 | AA972489 | Hs.3548 | 4515 | MTCP1 | MATURE T-CELL PROLIFERATION 1 |
| Probe_ID (BPDv C) AnCg | Hs.7527_at | 3.709781697 | 312 | AA911794 | Hs.7527 | 25996 | DKFZP566E144 | SMALL FRAGMENT NUCLEASE |
| Probe_ID (BPDv C) AnCg | Hs.154672_at | -3.613944429 | 338 | AA962299 | Hs.154672 | 10797 | MTHFD2 | METHYLENE TETRAHYDROFOLATE DEHYDROGENASE (NAD+ DEPENDENT), METHENYLTETRAHYDROFOLATE CYCLOHYDROLASE |
| Probe_ID (BPDv C) AnCg | Hs.151573_at | 3.581789697 | 347 | AA905519 | Hs.151573 | 1407 | CRY1 | CRYPTOCHROME 1 (PHOTOLYASE-LIKE) |
| Probe_ID (BPDv C) AnCg | Hs.384944_at | -3.45700168 | 390 | R15701 | Hs.384944 | 6648 | SOD2 | SUPEROXIDE DISMUTASE 2, MITOCHONDRIAL |
| Probe_ID (BPDv C) AnCg | Hs.8364_at | 3.403571903 | 412 | AI051630 | Hs.8364 | 5166 | PDK4 | PYRUVATE DEHYDROGENASE KINASE, ISOENZYME 4 |
| Probe_ID (BPDv C) AnCg | Hs.139410_at | -3.380539628 | 424 | AI004719 | Hs.139410 | 1629 | DBT | DIHYDROLIPOAMIDE BRANCHED CHAIN TRANSACYLASE (E2 COMPONENT OF BRANCHED CHAIN KETO ACID DEHYDROGENASE COMPLEX; MAPLE SYRUP URINE DISEASE) |
| Probe_ID (BPDv C) AnCg | Hs.409430_at | 3.374251626 | 427 | AA954940 | Hs.409430 | 1716 | DGUOK | DEOXYGUANOSINE KINASE |
| Probe_ID (BPDv C) AnCg | Hs.300463_at | 3.35163141 | 436 | | Hs.300463 | | | |
| Probe_ID (BPDv C) AnCg | Hs.211914_at | 3.322183756 | 446 | R15290 | Hs.211914 | 374291 | NDUFS7 | NADH DEHYDROGENASE (UBIQUINONE) FE-S PROTEIN 7, 20 KDA (NADH-COENZYME Q REDUCTASE) |
| Probe_ID (MDD v C) AnCg | Hs.3260_at | -8.020507698 | 35 | AA972181 | Hs.3260 | 5663 | PSEN1 | PRESENILIN 1 (ALZHEIMER DISEASE 3) |
| Probe_ID (MDD v C) AnCg | Hs.109052_at | 6.385329749 | 97 | AA865834 | Hs.109052 | 9556 | C14orf2 | CHROMOSOME 14 OPEN READING FRAME 2 |
| Probe_ID (MDD v C) AnCg | Hs.75335_at | -5.88132842 | 127 | AA888620 | Hs.75335 | 145663 | GATM | GLYCINE AMIDINOTRANSFERASE (L-ARGININE:GLYCINE AMIDINOTRANSFERASE) |
| Probe_ID (MDD v C) AnCg | Hs.247309_at | -5.878102056 | 128 | | Hs.247309 | | | |
| Probe_ID (MDD v C) AnCg | Hs.433419_at | 5.758749759 | 136 | AA968887 | Hs.433419 | 1327 | COX4I1 | CYTOCHROME C OXIDASE SUBUNIT IV ISOFORM 1 |
| Probe_ID (MDD v C) AnCg | Hs.1342_at | 5.348334665 | 175 | AA902930 | Hs.1342 | 1329 | COX5B | CYTOCHROME C OXIDASE SUBUNIT VB |
| Probe_ID (MDD v C) AnCg | Hs.49598_at | 5.345843386 | 176 | AA969459 | Hs.49598 | 23600 | AMACR | ALPHA-METHYLACYL-COA RACEMASE |
| Probe_ID (MDD v C) AnCg | Hs.353282_at | 5.301845199 | 185 | | Hs.353282 | | | |
| Probe_ID (MDD v C) AnCg | Hs.14945_at | -5.275227195 | 190 | R17684 | Hs.14945 | 23305 | ACSL6 | ACYL-COA SYNTHETASE LONG-CHAIN FAMILY MEMBER 6 |

TABLE 10-continued

| Probe_ID (MDD v C) | | | | | | Gene | Description |
|---|---|---|---|---|---|---|---|
| Probe_ID (MDD v C) AnCg | Hs.436405_at | 5.186191647 | 200 | AA976445 | Hs.436405 | 3420 | IDH3B | ISOCITRATE DEHYDROGENASE 3 (NAD+) BETA |
| Probe_ID (MDD v C) AnCg | Hs.20021_at | 4.974117426 | 234 | R17168 | Hs.20021 | 6843 | VAMP1 | VESICLE-ASSOCIATED MEMBRANE PROTEIN 1 (SYNAPTOBREVIN 1) |
| Probe_ID (MDD v C) AnCg | Hs.182490_at | 4.921605558 | 239 | AA962471 | Hs.182490 | 10128 | LRPPRC | LEUCINE-RICH PPR-MOTIF CONTAINING |
| Probe_ID (MDD v C) AnCg | Hs.153792_at | −4.902140124 | 243 | AA905280 | Hs.153792 | 4552 | MTRR | 5-METHYLTETRAHYDROFOLATE-HOMOCYSTEINE METHYLTRANSFERASE REDUCTASE |
| Probe_ID (MDD v C) AnCg | Hs.3100_at | 4.804444009 | 257 | AA954213 | Hs.3100 | 3735 | KARS | LYSYL-TRNA SYNTHETASE |
| Probe_ID (MDD v C) AnCg | Hs.423404_at | 4.802805566 | 259 | AA975616 | Hs.423404 | 9167 | COX7A2L | CYTOCHROME C OXIDASE SUBUNIT VIIA POLYPEPTIDE 2 LIKE |
| Probe_ID (MDD v C) AnCg | Hs.279939_at | 4.722208682 | 269 | AA977776 | Hs.279939 | 23787 | MTCH1 | MITOCHONDRIAL CARRIER HOMOLOG 1 (C. ELEGANS) |
| Probe_ID (MDD v C) AnCg | Hs.128410_at | 4.581815327 | 287 | AA886323 | Hs.128410 | 2744 | GLS | GLUTAMINASE |
| Probe_ID (MDD v C) AnCg | Hs.293970_at | −4.511696936 | 306 | AA975064 | Hs.293970 | 4329 | ALDH6A1 | ALDEHYDE DEHYDROGENASE 6 FAMILY, MEMBER A1 |
| Probe_ID (MDD v C) AnCg | Hs.528295_at | −4.499310703 | 310 | AI022321 | Hs.528295 | 10157 | AASS | AMINOADIPATE-SEMIALDEHYDE SYNTHASE |
| Probe_ID (MDD v C) AnCg | Hs.75760_at | −4.363940471 | 336 | R19294 | Hs.75760 | 6342 | SCP2 | STEROL CARRIER PROTEIN 2 |
| Probe_ID (MDD v C) AnCg | Hs.9599_at | −4.285016072 | 355 | AI032701 | Hs.9599 | 10165 | SLC25A13 | SOLUTE CARRIER FAMILY 25, MEMBER 13 (CITRIN) |
| Probe_ID (MDD v C) AnCg | Hs.7744_at | 4.058060577 | 409 | AA954362 | Hs.7744 | 4723 | NDUFV1 | NADH DEHYDROGENASE (UBIQUINONE) FLAVOPROTEIN 1, 51 KDA |
| Probe_ID (MDD v C) AnCg | Hs.350702_at | 4.051168637 | 410 | AA968881 | Hs.350702 | 23479 | ISCU | IRON-SULFUR CLUSTER ASSEMBLY ENZYME |
| Probe_ID (MDD v C) AnCg | Hs.77690_at | −4.044194861 | 414 | R14803 | Hs.77690 | 5869 | RAB5B | RAB5B, MEMBER RAS ONCOGENE FAMILY |
| Probe_ID (MDD v C) AnCg | Hs.287518_at | −3.967121349 | 437 | AA970122 | Hs.287518 | 5414 | PNUTL2 | PEANUT-LIKE 2 (DROSOPHILA) |
| Probe_ID (MDD v C) DLPFC | Hs.1342_at | 8.751574623 | 7 | AA902930 | Hs.1342 | 1329 | COX5B | CYTOCHROME C OXIDASE SUBUNIT VB |
| Probe_ID (MDD v C) DLPFC | Hs.182490_at | 8.000187313 | 18 | AA962471 | Hs.182490 | 10128 | LRPPRC | LEUCINE-RICH PPR-MOTIF CONTAINING |
| Probe_ID (MDD v C) DLPFC | Hs.128410_at | 7.058759677 | 48 | AA886323 | Hs.128410 | 2744 | GLS | GLUTAMINASE |
| Probe_ID (MDD v C) DLPFC | Hs.353282_at | 6.886768262 | 54 | | Hs.353282 | | | |
| Probe_ID (MDD v C) DLPFC | Hs.173554_at | 6.797907829 | 64 | AA961851 | Hs.173554 | 7385 | UQCRC2 | UBIQUINOL-CYTOCHROME C REDUCTASE CORE PROTEIN II |
| Probe_ID (MDD v C) DLPFC | Hs.405860_at | 6.789034734 | 66 | AA961135 | Hs.405860 | 4191 | MDH2 | MALATE DEHYDROGENASE 2, NAD (MITOCHONDRIAL) |
| Probe_ID (MDD v C) DLPFC | Hs.3100_at | 6.757315126 | 70 | AA954213 | Hs.3100 | 3735 | KARS | LYSYL-TRNA SYNTHETASE |
| Probe_ID (MDD v C) DLPFC | Hs.505824_at | 6.576861944 | 81 | AI023273 | Hs.505824 | 25813 | CGI-51 | CGI-51 PROTEIN |

TABLE 10-continued

| Probe_ID (MDD v C) DLPFC | | | | | |
|---|---|---|---|---|---|
| Probe_ID (MDD v C) DLPFC | Hs.81886_at | 6.233700436 | 98 | AA905726 | Hs.81886 | 549 | AUH | AU RNA BINDING PROTEIN/ENOYL-COENZYME A HYDRATASE |
| Probe_ID (MDD v C) DLPFC | Hs.279939_at | 6.126403025 | 103 | AA977776 | Hs.279939 | 23787 | MTCH1 | MITOCHONDRIAL CARRIER HOMOLOG 1 (C. ELEGANS) |
| Probe_ID (MDD v C) DLPFC | Hs.290404_at | 5.971266153 | 119 | AA954185 | Hs.290404 | 5250 | SLC25A3 | SOLUTE CARRIER FAMILY 25 (MITOCHONDRIAL CARRIER; PHOSPHATE CARRIER), MEMBER 3 |
| Probe_ID (MDD v C) DLPFC | Hs.196270_at | 5.880975299 | 124 | AI126840 | Hs.196270 | 81034 | MFTC | MITOCHONDRIAL FOLATE TRANSPORTER/CARRIER |
| Probe_ID (MDD v C) DLPFC | Hs.350702_at | 5.844647665 | 128 | AA968881 | Hs.350702 | 23479 | ISCU | IRON-SULFUR CLUSTER ASSEMBLY ENZYME |
| Probe_ID (MDD v C) DLPFC | Hs.62185_at | 5.820175161 | 130 | AA954490 | Hs.62185 | 10479 | SLC9A6 | SOLUTE CARRIER FAMILY 9 (SODIUM/HYDROGEN EXCHANGER), ISOFORM 6 |
| Probe_ID (MDD v C) DLPFC | Hs.194673_at | 5.818156637 | 131 | AA954646 | Hs.194673 | 8682 | PEA15 | PHOSPHOPROTEIN ENRICHED IN ASTROCYTES 15 |
| Probe_ID (MDD v C) DLPFC | Hs.439510_at | 5.725481617 | 147 | AA989107 | Hs.439510 | 10730 | YME1L1 | YME1-LIKE 1 (S. CEREVISIAE) |
| Probe_ID (MDD v C) DLPFC | Hs.109052_at | 5.710330465 | 150 | AA865834 | Hs.109052 | 9556 | C14orf2 | CHROMOSOME 14 OPEN READING FRAME 2 |
| Probe_ID (MDD v C) DLPFC | Hs.409140_at | 5.639633997 | 156 | AA864297 | Hs.409140 | 539 | ATP5O | ATP SYNTHASE, H+ TRANSPORTING, MITOCHONDRIAL F1 COMPLEX, O SUBUNIT (OLIGOMYCIN SENSITIVITY CONFERRING PROTEIN) |
| Probe_ID (MDD v C) DLPFC | Hs.250616_at | 5.60246391 | 159 | | Hs.250616 | | | |
| Probe_ID (MDD v C) DLPFC | Hs.182217_at | 5.57828738 | 164 | AA984684 | Hs.182217 | 8803 | SUCLA2 | SUCCINATE-COA LIGASE, ADP-FORMING, BETA SUBUNIT |
| Probe_ID (MDD v C) DLPFC | Hs.7744_at | 5.54184827 | 169 | AA954362 | Hs.7744 | 4723 | NDUFV1 | NADH DEHYDROGENASE (UBIQUINONE) FLAVOPROTEIN 1, 51 KDA |
| Probe_ID (MDD v C) DLPFC | Hs.436405_at | 5.39739172 | 196 | AA976445 | Hs.436405 | 3420 | IDH3B | ISOCITRATE DEHYDROGENASE 3 (NAD+) BETA |
| Probe_ID (MDD v C) DLPFC | Hs.126608_at | 5.3276937 | 207 | AA962235 | Hs.126608 | 2908 | NR3C1 | NUCLEAR RECEPTOR SUBFAMILY 3, GROUP C, MEMBER 1 (GLUCOCORTICOID RECEPTOR) |
| Probe_ID (MDD v C) DLPFC | Hs.2043_at | 5.280565636 | 214 | AA977341 | Hs.2043 | 291 | SLC25A4 | SOLUTE CARRIER FAMILY 25 (MITOCHONDRIAL CARRIER; ADENINE NUCLEOTIDE TRANSLOCATOR), MEMBER 4 |
| Probe_ID (MDD v C) DLPFC | Hs.144130_at | 5.2188642 | 224 | AA865892 | Hs.144130 | 55186 | FLJ10618 | HYPOTHETICAL PROTEIN FLJ10618 |
| Probe_ID (MDD v C) DLPFC | Hs.78614_at | 5.189788976 | 230 | | Hs.78614 | | | |
| Probe_ID (MDD v C) DLPFC | Hs.20716_at | 5.188149858 | 231 | AI021900 | Hs.20716 | 10440 | TIMM17A | TRANSLOCASE OF INNER MITOCHONDRIAL MEMBRANE 17 HOMOLOG A (YEAST) |

TABLE 10-continued

| | | | | | | |
|---|---|---|---|---|---|---|
| Probe_ID (MDD v C) DLPFC | Hs.407860_at | 5.099673885 | 245 | AA973726 | Hs.407860 | 4718 | NDUFC2 | NADH DEHYDROGENASE (UBIQUINONE) 1, SUBCOMPLEX UNKNOWN, 2, 14.5 KDA |
| Probe_ID (MDD v C) DLPFC | Hs.20021_at | 5.093990486 | 246 | R17168 | Hs.20021 | 6843 | VAMP1 | VESICLE-ASSOCIATED MEMBRANE PROTEIN 1 (SYNAPTOBREVIN 1) |
| Probe_ID (MDD v C) DLPFC | Hs.268016_at | 5.077587148 | 250 | AA987838 | Hs.268016 | 64968 | MRPS6 | MITOCHONDRIAL RIBOSOMAL PROTEIN S6 |
| Probe_ID (MDD v C) DLPFC | Hs.44298_at | 5.017621789 | 266 | AI141870 | Hs.44298 | 51373 | MRPS17 | MITOCHONDRIAL RIBOSOMAL PROTEIN S17 |
| Probe_ID (MDD v C) DLPFC | Hs.19236_at | 4.976913834 | 281 | AA888160 | Hs.19236 | 4711 | NDUFB5 | NADH DEHYDROGENASE (UBIQUINONE) 1 BETA SUBCOMPLEX, 5, 16 KDA |
| Probe_ID (MDD v C) DLPFC | Hs.429_at | 4.87511346 | 311 | BI761550 | Hs.429 | 518 | ATP5G3 | ATP SYNTHASE, H+ TRANSPORTING, MITOCHONDRIAL F0 COMPLEX, SUBUNIT C (SUBUNIT 9) ISOFORM 3 |
| Probe_ID (MDD v C) DLPFC | Hs.131273_at | 4.855540013 | 318 | AA978176 | Hs.131273 | 4976 | OPA1 | OPTIC ATROPHY 1 (AUTOSOMAL DOMINANT) |
| Probe_ID (MDD v C) DLPFC | Hs.433419_at | 4.837055096 | 325 | AA968887 | Hs.433419 | 1327 | COX4I1 | CYTOCHROME C OXIDASE SUBUNIT IV ISOFORM 1 |
| Probe_ID (MDD v C) DLPFC | Hs.436988_at | 4.817176809 | 332 | AI025620 | Hs.436988 | 1353 | COX11 | COX11 HOMOLOG, CYTOCHROME C OXIDASE ASSEMBLY PROTEIN (YEAST) |
| Probe_ID (MDD v C) DLPFC | Hs.119251_at | 4.800384591 | 337 | AA954171 | Hs.119251 | 7384 | UQCRC1 | UBIQUINOL-CYTOCHROME C REDUCTASE CORE PROTEIN I |
| Probe_ID (MDD v C) DLPFC | Hs.37_at | 4.766384912 | 340 | AI139512 | Hs.37 | 38 | ACAT1 | ACETYL-COENZYME A ACETYLTRANSFERASE 1 (ACETOACETYL COENZYME A THIOLASE) |
| Probe_ID (MDD v C) DLPFC | Hs.11866_at | 4.718266874 | 353 | AA974086 | Hs.11866 | 10431 | TIMM23 | TRANSLOCASE OF INNER MITOCHONDRIAL MEMBRANE 23 HOMOLOG (YEAST) |
| Probe_ID (MDD v C) DLPFC | Hs.444757_at | 4.716048741 | 354 | AA968467 | Hs.444757 | 23095 | KIF1B | KINESIN FAMILY MEMBER 1B |
| Probe_ID (MDD v C) DLPFC | Hs.5556_at | 4.68842541 | 358 | AA961682 | Hs.5556 | 4706 | NDUFAB1 | NADH DEHYDROGENASE (UBIQUINONE) 1, ALPHA/BETA SUBCOMPLEX, 1, 8 KDA |
| Probe_ID (MDD v C) DLPFC | Hs.211571_at | 4.682127722 | 362 | AA923565 | Hs.211571 | 3052 | HCCS | HOLOCYTOCHROME C SYNTHASE (CYTOCHROME C HEME-LYASE) |
| Probe_ID (MDD v C) DLPFC | Hs.289271_at | 4.679567034 | 365 | AA863409 | Hs.289271 | 1537 | CYC1 | CYTOCHROME C-1 |
| Probe_ID (MDD v C) DLPFC | Hs.184860_at | 4.647024454 | 373 | AA973406 | Hs.184860 | 57128 | C6orf149 | CHROMOSOME 6 OPEN READING FRAME 149 |
| Probe_ID (MDD v C) DLPFC | Hs.247309_at | -4.631146258 | 374 | | Hs.247309 | | | |
| Probe_ID (MDD v C) DLPFC | Hs.76366_at | 4.541868883 | 388 | AA999694 | Hs.76366 | 572 | BAD | BCL2-ANTAGONIST OF CELL DEATH |

TABLE 10-continued

| | Mood And Region | Hs. Unigene | Differential Expression Value | Rank | Accession | UniGene_ID | LocusLink_ID | Symbol | Description |
|---|---|---|---|---|---|---|---|---|---|
| | Probe_ID (MDD v C) DLPFC | Hs.184233_at | 4.524597014 | 395 | AA961767 | Hs.184233 | 3313 | HSPA9B | HEAT SHOCK 70 KDA PROTEIN 9B (MORTALIN-2) |
| | Probe_ID (MDD v C) DLPFC | Hs.300463_at | 4.491205579 | 403 | | Hs.300463 | | | |
| | Probe_ID (MDD v C) DLPFC | Hs.107476_at | 4.487968916 | 405 | AA961439 | Hs.107476 | 10632 | ATP5L | ATP SYNTHASE, H+ TRANSPORTING, MITOCHONDRIAL F0 COMPLEX, SUBUNIT G |
| | Probe_ID (MDD v C) DLPFC | Hs.43549_at | 4.482655426 | 407 | AA975374 | Hs.43549 | 55847 | C10orf70 | CHROMOSOME 10 OPEN READING FRAME 70 |
| | Probe_ID (MDD v C) DLPFC | Hs.161357_at | 4.415481565 | 415 | R14727 | Hs.161357 | 5162 | PDHB | PYRUVATE DEHYDROGENASE (LIPOAMIDE) BETA |
| | Probe_ID (MDD v C) DLPFC | Hs.198269_at | 4.313217236 | 434 | AA970515 | Hs.198269 | 4696 | NDUFA3 | NADH DEHYDROGENASE (UBIQUINONE) 1 ALPHA SUBCOMPLEX, 3, 9 KDA |

Summary MDD with Drecti Change

| Duplicate 1 = No | | Mood And Region | Hs. Unigene | Differential Expression Value | Rank | Accession | UniGene_ID | LocusLink_ID | Symbol | Description |
|---|---|---|---|---|---|---|---|---|---|---|
| 0 | 2 | Probe_ID (BPDv C) AnCg | Hs.107476_at | 3.852124446 | 271 | AA961439 | Hs.107476 | 10632 | ATP5L | ATP SYNTHASE, H+ TRANSPORTING, MITOCHONDRIAL F0 COMPLEX, SUBUNIT G |
| 1 | 3 | Probe_ID (MDD v C) DLPFC | Hs.107476_at | 4.487968916 | 405 | AA961439 | Hs.107476 | 10632 | ATP5L | ATP SYNTHASE, H+ TRANSPORTING, MITOCHONDRIAL F0 COMPLEX, SUBUNIT G |
| 0 | 4 | Probe_ID (BPDv C) AnCg | Hs.109052_at | 5.019252834 | 103 | AA865834 | Hs.109052 | 9556 | C14orf2 | CHROMOSOME 14 OPEN READING FRAME 2 |
| 0 | 5 | Probe_ID (MDD v C) AnCg | Hs.109052_at | 6.385329749 | 97 | AA865834 | Hs.109052 | 9556 | C14orf2 | CHROMOSOME 14 OPEN READING FRAME 2 |
| 1 | 6 | Probe_ID (MDD v C) DLPFC | Hs.109052_at | 5.710330465 | 150 | AA865834 | Hs.109052 | 9556 | C14orf2 | CHROMOSOME 14 OPEN READING FRAME 2 |
| 1 | 7 | Probe_ID (MDD v C) DLPFC | Hs.11866_at | 4.718266874 | 353 | AA974086 | Hs.11866 | 10431 | TIMM23 | TRANSLOCASE OF INNER MITOCHONDRIAL MEMBRANE 23 HOMOLOG (YEAST) |
| 1 | 8 | Probe_ID (MDD v C) DLPFC | Hs.119251_at | 4.800384591 | 337 | AA954171 | Hs.119251 | 7384 | UQCRC1 | UBIQUINOL-CYTOCHROME C REDUCTASE CORE PROTEIN I |
| 1 | 9 | Probe_ID (BPDv C) AnCg | Hs.119316_at | 7.019916677 | 17 | AI075114 | Hs.119316 | 5188 | PET112L | PET112-LIKE (YEAST) |

TABLE 10-continued

| | | | | | | | | | | |
|---|---|---|---|---|---|---|---|---|---|---|
| 1 | 10 | Probe_ID (MDD v C) DLPFC | Hs.126608_at | 5.3276937 | 207 | AA962235 | Hs.126608 | 2908 | NR3C1 | NUCLEAR RECEPTOR SUBFAMILY 3, GROUP C, MEMBER 1 (GLUCOCORTICOID RECEPTOR) |
| 0 | 11 | Probe_ID (MDD v C) AnCg | Hs.128410_at | 4.581815327 | 287 | AA886323 | Hs.128410 | 2744 | GLS | GLUTAMINASE |
| 1 | 12 | Probe_ID (MDD v C) DLPFC | Hs.128410_at | 7.058759677 | 48 | AA886323 | Hs.128410 | 2744 | GLS | GLUTAMINASE |
| 1 | 13 | Probe_ID (MDD v C) DLPFC | Hs.131273_at | 4.855540013 | 318 | AA978176 | Hs.131273 | 4976 | OPA1 | OPTIC ATROPHY 1 (AUTOSOMAL DOMINANT) |
| 0 | 14 | Probe_ID (MDD v C) AnCg | Hs.1342_at | 5.348334665 | 175 | AA902930 | Hs.1342 | 1329 | COX5B | CYTOCHROME C OXIDASE SUBUNIT VB |
| 1 | 15 | Probe_ID (MDD v C) DLPFC | Hs.1342_at | 8.751574623 | 7 | AA902930 | Hs.1342 | 1329 | COX5B | CYTOCHROME C OXIDASE SUBUNIT VB |
| 1 | 16 | Probe_ID (BPDv C) AnCg | Hs.139410_at | −3.380539628 | 424 | AI004719 | Hs.139410 | 1629 | DBT | DIHYDROLIPOAMIDE BRANCHED CHAIN TRANSACYLASE (E2 COMPONENT OF BRANCHED CHAIN KETO ACID DEHYDROGENASE COMPLEX; MAPLE SYRUP URINE DISEASE) |
| 0 | 17 | Probe_ID (MDD v C) AnCg | Hs.144130_at | −3.81230531 | 284 | AA865892 | Hs.144130 | 55186 | FLJ10618 | HYPOTHETICAL PROTEIN FLJ10618 |
| 1 | 18 | Probe_ID (MDD v C) DLPFC | Hs.144130_at | 5.2188642 | 224 | AA865892 | Hs.144130 | 55186 | FLJ10618 | HYPOTHETICAL PROTEIN FLJ10618 |
| 1 | 19 | Probe_ID (MDD v C) AnCg | Hs.149156_at | 3.978596138 | 243 | AI148899 | Hs.149156 | 2731 | GLDC | GLYCINE DEHYDROGENASE (DECARBOXYLATING; GLYCINE DECARBOXYLASE, GLYCINE CLEAVAGE SYSTEM PROTEIN P) |
| 0 | 20 | Probe_ID (MDD v C) AnCg | Hs.14945_at | −4.158983584 | 201 | R17684 | Hs.14945 | 23305 | ACSL6 | ACYL-COA SYNTHETASE LONG-CHAIN FAMILY MEMBER 6 |
| 1 | 21 | Probe_ID (MDD v C) AnCg | Hs.14945_at | −5.275227195 | 190 | R17684 | Hs.14945 | 23305 | ACSL6 | ACYL-COA SYNTHETASE LONG-CHAIN FAMILY MEMBER 6 |
| 1 | 22 | Probe_ID (BPDv C) AnCg | Hs.151573_at | 3.581789697 | 347 | AA905519 | Hs.151573 | 1407 | CRY1 | CRYPTOCHROME 1 (PHOTOLYASE-LIKE) |
| 1 | 23 | Probe_ID (MDD v C) AnCg | Hs.153792_at | −4.902140124 | 243 | AA905280 | Hs.153792 | 4552 | MTRR | 5-METHYLTETRAHYDROFOLATE-HOMOCYSTEINE METHYLTRANSFERASE REDUCTASE |

TABLE 10-continued

| | # | Probe | Probe_ID | Value | # | Accession | Hs. | Symbol | ID | Description |
|---|---|---|---|---|---|---|---|---|---|---|
| 1 | 24 | Probe_ID (BPDv C) AnCg | Hs.154672_at | −3.613394429 | 338 | AA962299 | Hs.154672 | MTHFD2 | 10797 | METHYLENE TETRAHYDROFOLATE DEHYDROGENASE (NAD+ DEPENDENT), METHENYLTETRAHYDROFOLATE CYCLOHYDROLASE |
| 1 | 25 | Probe_ID (MDD v C) DLPFC | Hs.161357_at | 4.415481565 | 415 | R14727 | Hs.161357 | PDHB | 5162 | PYRUVATE DEHYDROGENASE (LIPOAMIDE) BETA |
| 1 | 26 | Probe_ID (BPDv C) AnCg | Hs.173554_at | 6.797907829 | 64 | AA961851 | Hs.173554 | UQCRC2 | 7385 | UBIQUINOL-CYTOCHROME C REDUCTASE CORE PROTEIN II |
| 1 | 27 | Probe_ID (MDD v C) DLPFC | Hs.177584_at | 4.165654802 | 200 | AA961910 | Hs.177584 | OXCT1 | 5019 | 3-OXOACID COA TRANSFERASE 1 |
| 1 | 28 | Probe_ID (MDD v C) DLPFC | Hs.182217_at | 5.57828738 | 164 | AA984684 | Hs.182217 | SUCLA2 | 8803 | SUCCINATE-COA LIGASE, ADP-FORMING, BETA SUBUNIT |
| 0 | 29 | Probe_ID (MDD v C) DLPFC | Hs.182490_at | 4.921605558 | 239 | AA962471 | Hs.182490 | LRPPRC | 10128 | LEUCINE-RICH PPR-MOTIF CONTAINING |
| 1 | 30 | Probe_ID (MDD v C) AnCg | Hs.182490_at | 8.000187313 | 18 | AA962471 | Hs.182490 | LRPPRC | 10128 | LEUCINE-RICH PPR-MOTIF CONTAINING |
| 1 | 31 | Probe_ID (MDD v C) DLPFC | Hs.184233_at | 4.524597014 | 395 | AA961767 | Hs.184233 | HSPA9B | 3313 | HEAT SHOCK 70 KDA PROTEIN 9B (MORTALIN-2) |
| 1 | 32 | Probe_ID (MDD v C) DLPFC | Hs.184860_at | 4.647024454 | 373 | AA973406 | Hs.184860 | C6orf149 | 57128 | CHROMOSOME 6 OPEN READING FRAME 149 |
| 1 | 33 | Probe_ID (MDD v C) DLPFC | Hs.19236_at | 4.976913834 | 281 | AA888160 | Hs.19236 | NDUFB5 | 4711 | NADH DEHYDROGENASE (UBIQUINONE) 1 BETA SUBCOMPLEX, 5, 16 KDA |
| 0 | 34 | Probe_ID (BPDv C) AnCg | Hs.194673_at | 6.739939746 | 24 | AA954646 | Hs.194673 | PEA15 | 8682 | PHOSPHOPROTEIN ENRICHED IN ASTROCYTES 15 |
| 1 | 35 | Probe_ID (MDD v C) DLPFC | Hs.194673_at | 5.818156637 | 131 | AA954646 | Hs.194673 | PEA15 | 8682 | PHOSPHOPROTEIN ENRICHED IN ASTROCYTES 15 |
| 1 | 36 | Probe_ID (MDD v C) DLPFC | Hs.196270_at | 5.880975299 | 124 | AI126840 | Hs.196270 | MFTC | 81034 | MITOCHONDRIAL FOLATE TRANSPORTER/CARRIER |

TABLE 10-continued

| | | | | | | | | | | |
|---|---|---|---|---|---|---|---|---|---|---|
| 0 | 37 | Probe_ID (BPDv C) AnCg | Hs.198269_at | 3.834264322 | 274 | AA970515 | Hs.198269 | 4696 | NDUFA3 | NADH DEHYDROGENASE (UBIQUINONE) 1 ALPHA SUBCOMPLEX, 3, 9 KDA |
| 1 | 38 | Probe_ID (MDD v C) AnCg | Hs.198269_at | 4.313217236 | 434 | AA970515 | Hs.198269 | 4696 | NDUFA3 | NADH DEHYDROGENASE (UBIQUINONE) 1 ALPHA SUBCOMPLEX, 3, 9 KDA |
| 0 | 39 | Probe_ID (BPDv C) DLPFC | Hs.20021_at | −7.727057737 | 9 | R17168 | Hs.20021 | 6843 | VAMP1 | VESICLE-ASSOCIATED MEMBRANE PROTEIN 1 (SYNAPTOBREVIN 1) |
| 0 | 40 | Probe_ID (MDD v C) AnCg | Hs.20021_at | 4.974117426 | 234 | R17168 | Hs.20021 | 6843 | VAMP1 | VESICLE-ASSOCIATED MEMBRANE PROTEIN 1 (SYNAPTOBREVIN 1) |
| 1 | 41 | Probe_ID (MDD v C) DLPFC | Hs.20021_at | 5.093990486 | 246 | R17168 | Hs.20021 | 6843 | VAMP1 | VESICLE-ASSOCIATED MEMBRANE PROTEIN 1 (SYNAPTOBREVIN 1) |
| 1 | 42 | Probe_ID (MDD v C) DLPFC | Hs.2043_at | 5.280565636 | 214 | AA977341 | Hs.2043 | 291 | SLC25A4 | SOLUTE CARRIER FAMILY 25 (MITOCHONDRIAL CARRIER; ADENINE NUCLEOTIDE TRANSLOCATOR), MEMBER 4 |
| 1 | 43 | Probe_ID (MDD v C) DLPFC | Hs.20716_at | 5.188149858 | 231 | AI021900 | Hs.20716 | 10440 | TIMM17A | TRANSLOCASE OF INNER MITOCHONDRIAL MEMBRANE 17 HOMOLOG A (YEAST) |
| 1 | 44 | Probe_ID (MDD v C) DLPFC | Hs.211571_at | 4.682127722 | 362 | AA923565 | Hs.211571 | 3052 | HCCS | HOLOCYTOCHROME C SYNTHASE (CYTOCHROME C HEME-LYASE) |
| 1 | 45 | Probe_ID (BPDv C) AnCg | Hs.211914_at | 3.322183756 | 446 | R15290 | Hs.211914 | 374291 | NDUFS7 | NADH DEHYDROGENASE (UBIQUINONE) FE-S PROTEIN 7, 20 KDA (NADH-COENZYME Q REDUCTASE) |
| 1 | 46 | Probe_ID (MDD v C) DLPFC | Hs.243491_at | −4.224934266 | 183 | | Hs.243491 | | | |
| 0 | 47 | Probe_ID (MDD v C) AnCg | Hs.247309_at | −5.878102056 | 128 | | Hs.247309 | | | |
| 1 | 48 | Probe_ID (MDD v C) DLPFC | Hs.247309_at | −4.631146258 | 374 | | Hs.247309 | | | |
| 1 | 49 | Probe_ID (MDD v C) DLPFC | Hs.250616_at | 5.60246391 | 159 | | Hs.250616 | | | |
| 1 | 50 | Probe_ID (MDD v C) DLPFC | Hs.268016_at | 5.077587148 | 250 | AA987838 | Hs.268016 | 64968 | MRPS6 | MITOCHONDRIAL RIBOSOMAL PROTEIN S6 |

TABLE 10-continued

| | | | | | | | | | | |
|---|---|---|---|---|---|---|---|---|---|---|
| 0 | 51 | Probe_ID (BPDv C) AnCg | Hs.279939_at | 4.582420323 | 138 | AA977776 | Hs.279939 | MTCH1 | 23787 | MITOCHONDRIAL CARRIER HOMOLOG 1 (C. ELEGANS) |
| 0 | 52 | Probe_ID (MDDv C) AnCg | Hs.279939_at | 4.722208682 | 269 | AA977776 | Hs.279939 | MTCH1 | 23787 | MITOCHONDRIAL CARRIER HOMOLOG 1 (C. ELEGANS) |
| 1 | 53 | Probe_ID (MDDv C) DLPFC | Hs.279939_at | 6.126403025 | 103 | AA977776 | Hs.279939 | MTCH1 | 23787 | MITOCHONDRIAL CARRIER HOMOLOG 1 (C. ELEGANS) |
| 1 | 54 | Probe_ID (MDDv C) AnCg | Hs.287518_at | -3.967121349 | 437 | AA970122 | Hs.287518 | PNUTL2 | 5414 | PEANUT-LIKE 2 (DROSOPHILA) |
| 1 | 55 | Probe_ID (MDDv C) DLPFC | Hs.289271_at | 4.679567034 | 365 | AA863409 | Hs.289271 | CYC1 | 1537 | CYTOCHROME C-1 |
| 1 | 56 | Probe_ID (MDDv C) DLPFC | Hs.290404_at | 5.971266153 | 119 | AA954185 | Hs.290404 | SLC25A3 | 5250 | SOLUTE CARRIER FAMILY 25 (MITOCHONDRIAL CARRIER; PHOSPHATE CARRIER), MEMBER 3 |
| 1 | 57 | Probe_ID (MDDv C) AnCg | Hs.293970_at | -4.511696936 | 306 | AA975064 | Hs.293970 | ALDH6A1 | 4329 | ALDEHYDE DEHYDROGENASE 6 FAMILY, MEMBER A1 |
| 0 | 58 | Probe_ID (BPDv C) AnCg | Hs.300463_at | 3.35163141 | 436 | | Hs.300463 | | | |
| 1 | 59 | Probe_ID (MDDv C) DLPFC | Hs.300463_at | 4.491205579 | 403 | | Hs.300463 | | | |
| 0 | 60 | Probe_ID (BPDv C) AnCg | Hs.3100_at | 4.309487236 | 169 | AA954213 | Hs.3100 | KARS | 3735 | LYSYL-TRNA SYNTHETASE |
| 0 | 61 | Probe_ID (MDDv C) AnCg | Hs.3100_at | 4.804444009 | 257 | AA954213 | Hs.3100 | KARS | 3735 | LYSYL-TRNA SYNTHETASE |
| 1 | 62 | Probe_ID (MDDv C) DLPFC | Hs.3100_at | 6.757315126 | 70 | AA954213 | Hs.3100 | KARS | 3735 | LYSYL-TRNA SYNTHETASE |
| 1 | 63 | Probe_ID (BPDv C) AnCg | Hs.3254_at | 4.193592918 | 195 | AA971301 | Hs.3254 | MRPL23 | 6150 | MITOCHONDRIAL RIBOSOMAL PROTEIN L23 |
| 1 | 64 | Probe_ID (MDDv C) AnCg | Hs.3260_at | -8.020507698 | 35 | AA972181 | Hs.3260 | PSEN1 | 5663 | PRESENILIN 1 (ALZHEIMER DISEASE 3) |
| 0 | 65 | Probe_ID (MDDv C) AnCg | Hs.350702_at | 4.051168637 | 410 | AA968881 | Hs.350702 | ISCU | 23479 | IRON-SULFUR CLUSTER ASSEMBLY ENZYME |

TABLE 10-continued

| | | | | | | | | |
|---|---|---|---|---|---|---|---|---|
| 1 | 66 | Probe_ID (MDD v C) DLPFC | Hs.350702_at | 5.844647665 | 128 | AA968881 | Hs.350702 | 23479 | ISCU | IRON-SULFUR CLUSTER ASSEMBLY ENZYME |
| 0 | 67 | Probe_ID (MDD v C) AnCg | Hs.353282_at | 5.301845199 | 185 | | Hs.353282 | | | |
| 1 | 68 | Probe_ID (MDD v C) DLPFC | Hs.353282_at | 6.886768262 | 54 | | Hs.353282 | | | |
| 1 | 69 | Probe_ID (BPDv C) AnCg | Hs.3548_at | 3.79318498 | 290 | AA972489 | Hs.3548 | 4515 | MTCP1 | MATURE T-CELL PROLIFERATION 1 |
| 1 | 70 | Probe_ID (BPDv C) AnCg | Hs.356231_at | -6.670345597 | 28 | AI038963 | Hs.356231 | 79085 | SLC25A23 | SOLUTE CARRIER FAMILY 25 (MITOCHONDRIAL CARRIER; PHOSPHATE CARRIER), MEMBER 23 |
| 1 | 71 | Probe_ID (MDD v C) DLPFC | Hs.37_at | 4.766384912 | 340 | AI139512 | Hs.37 | 38 | ACAT1 | ACETYL-COENZYME A ACETYLTRANSFERASE 1 (ACETOACETYL COENZYME A THIOLASE) |
| 1 | 72 | Probe_ID (BPDv C) AnCg | Hs.384944_at | -3.45700168 | 390 | R15701 | Hs.384944 | 6648 | SOD2 | SUPEROXIDE DISMUTASE 2, MITOCHONDRIAL |
| 1 | 73 | Probe_ID (MDD v C) DLPFC | Hs.405860_at | 6.789034734 | 66 | AA961135 | Hs.405860 | 4191 | MDH2 | MALATE DEHYDROGENASE 2, NAD (MITOCHONDRIAL) |
| 1 | 74 | Probe_ID (MDD v C) DLPFC | Hs.407860_at | 5.099673885 | 245 | AA973726 | Hs.407860 | 4718 | NDUFC2 | NADH DEHYDROGENASE (UBIQUINONE) 1, SUBCOMPLEX UNKNOWN, 2, 14.5 KDA |
| 1 | 75 | Probe_ID (MDD v C) DLPFC | Hs.409140_at | 5.639633997 | 156 | AA864297 | Hs.409140 | 539 | ATP5O | ATP SYNTHASE, H+ TRANSPORTING, MITOCHONDRIAL F1 COMPLEX, O SUBUNIT (OLIGOMYCIN SENSITIVITY CONFERRING PROTEIN) |
| 1 | 76 | Probe_ID (BPDv C) AnCg | Hs.409430_at | 3.374251626 | 427 | AA954940 | Hs.409430 | 1716 | DGUOK | DEOXYGUANOSINE KINASE |
| 1 | 77 | Probe_ID (MDD v C) AnCg | Hs.423404_at | 4.802805566 | 259 | AA975616 | Hs.423404 | 9167 | COX7A2L | CYTOCHROME C OXIDASE SUBUNIT VIIa POLYPEPTIDE 2 LIKE |
| 1 | 78 | Probe_ID (MDD v C) DLPFC | Hs.429_at | 4.87511346 | 311 | BI761550 | Hs.429 | 518 | ATP5G3 | ATP SYNTHASE, H+ TRANSPORTING, MITOCHONDRIAL F0 COMPLEX, SUBUNIT C (SUBUNIT 9) ISOFORM 3 |
| 0 | 79 | Probe_ID (BPDv C) AnCg | Hs.433419_at | 3.863300127 | 269 | AA968887 | Hs.433419 | 1327 | COX4I1 | CYTOCHROME C OXIDASE SUBUNIT IV ISOFORM 1 |

TABLE 10-continued

| | | | | | | | | | | |
|---|---|---|---|---|---|---|---|---|---|---|
| 0 | 80 | Probe_ID (MDD v C) AnCg | Hs.433419_at | 5.758749759 | 136 | AA968887 | Hs.433419 | 1327 | COX4I1 | CYTOCHROME C OXIDASE SUBUNIT IV ISOFORM 1 |
| 1 | 81 | Probe_ID (MDD v C) AnCg | Hs.433419_at | 4.837055096 | 325 | AA968887 | Hs.433419 | 1327 | COX4I1 | CYTOCHROME C OXIDASE SUBUNIT IV ISOFORM 1 |
| 1 | 82 | Probe_ID (MDD v C) DLPFC | Hs.43549_at | 4.482655426 | 407 | AA975374 | Hs.43549 | 55847 | C10orf70 | CHROMOSOME 10 OPEN READING FRAME 70 |
| 0 | 83 | Probe_ID (MDD v C) AnCg | Hs.436405_at | 5.186131647 | 200 | AA976445 | Hs.436405 | 3420 | IDH3B | ISOCITRATE DEHYDROGENASE 3 (NAD+) BETA |
| 1 | 84 | Probe_ID (MDD v C) DLPFC | Hs.436405_at | 5.39739172 | 196 | AA976445 | Hs.436405 | 3420 | IDH3B | ISOCITRATE DEHYDROGENASE 3 (NAD+) BETA |
| 1 | 85 | Probe_ID (MDD v C) DLPFC | Hs.436988_at | 4.817176809 | 332 | AI025620 | Hs.436988 | 1353 | COX11 | COX11 HOMOLOG, CYTOCHROME C OXIDASE ASSEMBLY PROTEIN (YEAST) |
| 1 | 86 | Probe_ID (BPDv C) AnCg | Hs.438303_at | 5.313202083 | 72 | AA969386 | Hs.438303 | 23395 | LARS2 | LEUCYL-TRNA SYNTHETASE 2, MITOCHONDRIAL |
| 1 | 87 | Probe_ID (MDD v C) DLPFC | Hs.439510_at | 5.725481617 | 147 | AA989107 | Hs.439510 | 10730 | YME1L1 | YME1-LIKE 1 (S. CEREVISIAE) |
| 1 | 88 | Probe_ID (MDD v C) DLPFC | Hs.44298_at | 5.017621789 | 266 | AI141870 | Hs.44298 | 51373 | MRPS17 | MITOCHONDRIAL RIBOSOMAL PROTEIN S17 |
| 1 | 89 | Probe_ID (MDD v C) DLPFC | Hs.444757_at | 4.716048741 | 354 | AA968467 | Hs.444757 | 23095 | KIF1B | KINESIN FAMILY MEMBER 1B |
| 1 | 90 | Probe_ID (MDD v C) AnCg | Hs.49598_at | 5.345843386 | 176 | AA969459 | Hs.49598 | 23600 | AMACR | ALPHA-METHYLACYL-COA RACEMASE |
| 1 | 91 | Probe_ID (MDD v C) DLPFC | Hs.505824_at | 6.576861944 | 81 | AI023273 | Hs.505824 | 25813 | CGI-51 | CGI-51 PROTEIN |
| 1 | 92 | Probe_ID (BPDv C) AnCg | Hs.511880_at | -4.005278821 | 239 | NM_000498 | Hs.511880 | 1585 | CYP11B2 | CYTOCHROME P450, FAMILY 11, SUBFAMILY B, POLYPEPTIDE 2 |
| 1 | 93 | Probe_ID (MDD v C) AnCg | Hs.528295_at | -4.499310703 | 310 | AI022321 | Hs.528295 | 10157 | AASS | AMINOADIPATE-SEMIALDEHYDE SYNTHASE |

TABLE 10-continued

| | | | | | | | | |
|---|---|---|---|---|---|---|---|---|
| 1 | 94 | Probe_ID (MDD v C) DLPFC | Hs.5556_at | 4.68842541 | 358 AA961682 | Hs.5556 | 4706 | NDUFAB1 | NADH DEHYDROGENASE (UBIQUINONE) 1, ALPHA/BETA SUBCOMPLEX, 1, 8 KDA |
| 1 | 95 | Probe_ID (MDD v C) DLPFC | Hs.62185_at | 5.820175161 | 130 AA954490 | Hs.62185 | 10479 | SLC9A6 | SOLUTE CARRIER FAMILY 9 (SODIUM/HYDROGEN EXCHANGER), ISOFORM 6 |
| 1 | 96 | Probe_ID (BPDv C) AnCg | Hs.74047_at | 4.496465885 | 150 | Hs.74047 | | | |
| 1 | 97 | Probe_ID (BPDv C) AnCg | Hs.7527_at | 3.709781697 | 312 AA911794 | Hs.7527 | 25996 | DKFZP566E144 | SMALL FRAGMENT NUCLEASE |
| 1 | 98 | Probe_ID (MDD v C) AnCg | Hs.75335_at | -5.88132842 | 127 AA888620 | Hs.75335 | 145663 | GATM | GLYCINE AMIDINOTRANSFERASE (L-ARGININE: GLYCINE AMIDINOTRANSFERASE) |
| 1 | 99 | Probe_ID (MDD v C) AnCg | Hs.75760_at | -4.363940471 | 336 R19294 | Hs.75760 | 6342 | SCP2 | STEROL CARRIER PROTEIN 2 |
| 1 | 100 | Probe_ID (BPDv C) AnCg | Hs.75859_at | 3.825790421 | 277 AA975309 | Hs.75859 | 740 | MRPL49 | MITOCHONDRIAL RIBOSOMAL PROTEIN L49 |
| 0 | 101 | Probe_ID (BPDv C) AnCg | Hs.76366_at | 4.693419228 | 127 AA999694 | Hs.76366 | 572 | BAD | BCL2-ANTAGONIST OF CELL DEATH |
| 1 | 102 | Probe_ID (MDD v C) DLPFC | Hs.76366_at | 4.541868883 | 388 AA999694 | Hs.76366 | 572 | BAD | BCL2-ANTAGONIST OF CELL DEATH |
| 0 | 103 | Probe_ID (MDD v C) AnCg | Hs.7744_at | 4.058060577 | 409 AA954362 | Hs.7744 | 4723 | NDUFV1 | NADH DEHYDROGENASE (UBIQUINONE) FLAVOPROTEIN 1, 51 KDA |
| 1 | 104 | Probe_ID (MDD v C) DLPFC | Hs.7744_at | 5.54184827 | 169 AA954362 | Hs.7744 | 4723 | NDUFV1 | NADH DEHYDROGENASE (UBIQUINONE) FLAVOPROTEIN 1, 51 KDA |
| 1 | 105 | Probe_ID (MDD v C) AnCg | Hs.77690_at | -4.044194861 | 414 R14803 | Hs.77690 | 5869 | RAB5B | RAB5B, MEMBER RAS ONCOGENE FAMILY |

TABLE 10-continued

| | | Probe_ID | | | | | | |
|---|---|---|---|---|---|---|---|---|
| 1 | 106 | Probe_ID (MDD v C) DLPFC | Hs.78614_at | 5.189788976 | | Hs.78614 | | | |
| 1 | 107 | Probe_ID (MDD v C) DLPFC | Hs.81886_at | 6.233700436 | 98 AA905726 | Hs.81886 | 549 | AUH | AU RNA BINDING PROTEIN/ENOYL-COENZYME A HYDRATASE |
| 1 | 108 | Probe_ID (BPDv C) AnCg | Hs.8364_at | 3.403571903 | 412 AI051630 | Hs.8364 | 5166 | PDK4 | PYRUVATE DEHYDROGENASE KINASE, ISOENZYME 4 |
| 1 | 109 | Probe_ID (MDD v C) AnCg | Hs.9599_at | −4.285016072 | 355 AI032701 | Hs.9599 | 10165 | SLC25A13 | SOLUTE CARRIER FAMILY 25, MEMBER 13 (CITRIN) |

TABLE 11

Genes dysregulated in MD, BP, and schizophrenia

| | UniGene ID | probe set | Acc | Name | Symbol | Direction of Change |
|---|---|---|---|---|---|---|
| 2 | Hs.282878 | Hs.282878_at | NM_021633 | Kelch-like 12 (*Drosophila*) | KLHL12 | DLPFC-BPD&MDD&SCZ-U |
| 3 | Hs.435039 | Hs.435039_at | NM_014914 | Trinucleotide repeat containing 17 | CENTG2 | DLPFC-BPD&MDD&SCZ-U |
| 4 | Hs.530712 | Hs.530712_at | NM_017917 | Chromosome 14 open reading frame 10 | C14orf10 | DLPFC-BPD&MDD&SCZ-U |
| 5 | Hs.56294 | Hs.56294_at | NM_004794 | RAB33A, member RAS oncogene family | RAB33A | DLPFC-BPD&MDD&SCZ-U |
| 6 | Hs.21577 | Hs.21577_at | NM_005701 | RNA, U transporter 1 | RNUT1 | DLPFC-BPD&SCZ-U |
| 7 | Hs.274479 | Hs.274479-_at | NM_197972 | Non-metastatic cells 7, protein expressed in (nucleoside-diphosphate kinase) | NME7 | DLPFC-BPD&SCZ-U |
| 8 | Hs.368486 | Hs.368486_at | NM_001649 | Apical protein-like (*Xenopus laevis*) | APXL | DLPFC-BPD&SCZ-U |
| 9 | Hs.468415 | Hs.468415_at | NM_002643 | Phosphatidylinositol glycan, class F | PIGF | DLPFC-BPD&SCZ-U |
| 10 | Hs.471401 | Hs.471401_at | NM_004328 | BCS1-like (yeast) | BCS1L | DLPFC-BPD&SCZ-U |
| 11 | Hs.502145 | Hs.502145_at | NM_006157 | NEL-like 1 (chicken) | NELL1 | DLPFC-BPD&SCZ-U |
| 12 | Hs.514036 | Hs.514036_at | NM_006923 | Stromal cell-derived factor 2 | SDF2 | DLPFC-BPD&SCZ-U |
| 13 | Hs.532853 | Hs.532853+_at | NM_004146 | NADH dehydrogenase (ubiquinone) 1 beta subcomplex, 7, 18 kDa | NDUFB7 | DLPFC-BPD&SCZ-U |
| 14 | Hs.111779 | Hs.111779_at | NM_003118 | Secreted protein, acidic, cysteine-rich (osteonectin) | SPARC | DLPFC-BPD&MDD&SCZ-D |
| 15 | Hs.171695 | Hs.171695_at | NM_004417 | Dual specificity phosphatase 1 | DUSP1 | DLPFC-BPD&MDD&SCZ-D |
| 16 | Hs.212838 | Hs.212838-_at | NM_000014 | Alpha-2-macroglobulin | A2M | DLPFC-BPD&MDD&SCZ-D |
| 17 | Hs.34560 | Hs.34560-_at | NM_005574 | LIM domain only 2 (rhombotin-like 1) | LMO2 | DLPFC-BPD&MDD&SCZ-D |
| 18 | Hs.347270 | Hs.347270-_at | NM_033554 | Major histocompatibility complex, class II, DP alpha 1 | HLA-DPA1 | DLPFC-BPD&MDD&SCZ-D |
| 19 | Hs.436568 | Hs.436568_at | BC024272 | CD74 antigen (invariant polypeptide of major histocompatibility complex, class II antigen-associated) | CD74 | DLPFC-BPD&MDD&SCZ-D |
| 20 | Hs.491582 | Hs.491582_at | NM_000931 | Plasminogen activator, tissue | PLAT | DLPFC-BPD&MDD&SCZ-D |
| 21 | Hs.534115 | Hs.534115_at | NM_006988 | A disintegrin-like and metalloprotease (reprolysin type) with thrombospondin type 1 motif, 1 | ADAMTS1 | DLPFC-BPD&MDD&SCZ-D |
| 22 | Hs.17109 | Hs.17109_at | NM_004867 | Integral membrane protein 2A | ITM2A | DLPFC-BPD&SCZ-D |
| 23 | Hs.485130 | Hs.485130_at | K01615 | Major histocompatibility complex, class II, DP beta 1 | HLA-DPB1 | DLPFC-BPD&SCZ-D |
| 24 | Hs.504877 | Hs.504877_at | X69549 | Rho GDP dissociation inhibitor (GDI) beta | ARHGDIB | DLPFC-BPD&SCZ-D |
| 25 | Hs.520048 | Hs.520048_at | NM_019111 | Major histocompatibility complex, class II, DR alpha | HLA-DRA | DLPFC-BPD&SCZ-D |

TABLE 12

Genes dysregulated in MD, BP, and schizophrenia

| Symbol | Name | UniGene ID | AnCg | DLPFC | CB | nAcc |
|---|---|---|---|---|---|---|
| PTGDS | Prostaglandin | Hs.446429 | | | CB-D | nAcc-D |
| PLAT | Plasminogen activator, tissue | Hs. 491582 | AnCg-D | DLPFC-D | | |
| ADAMTS1 | Disintegrin-like and metalloprotease | Hs. 534115 | | DLPFC-D | | nAcc-D |

TABLE 13

| UniGene ID | GDB | Accession # | Name | Symbol | Cytoband | Bipolar Disorder | | | | Major Depressive Disorder | | | |
|---|---|---|---|---|---|---|---|---|---|---|---|---|---|
| | | | | | | U95Av2 Cohort A | | U133A Cohort A | | U95Av2 Cohort A | | U133A Cohort A | U133A Cohort B |
| | | | | | | P Value | % Fold Change | P Value | % Fold Change | P Value | % Fold Change | P Value | % Fold Change | P Value | % Fold Change |

*Note: The table has the following column structure with data:*

| UniGene ID | GDB | Accession # | Name | Symbol | Cytoband | U95Av2 A P | U95Av2 A %FC | U133A A P | U133A A %FC | U95Av2 A P | U95Av2 A %FC | U133A A P | U133A A %FC | U133A B P | U133A B %FC |
|---|---|---|---|---|---|---|---|---|---|---|---|---|---|---|---|
| | | | | | | Monoamine Metabolism | | | | | | | | | |
| Hs.370408 | | AL390148 | Catechol-O-methyltransferase | COMT | 22q11.21-q11.23 | <0.01 | 15.8 | <0.01 | 11.5 | | | | | | |
| Hs.46732 | | NM_000898 | Monoamine oxidase B | MAOB | Xp11.23 | <0.01 | 15.9 | <0.01 | 18.9 | | | | | | |
| | | | | | | Neuropeptide Ligand | | | | | | | | | |
| Hs.1832 | | BF680552 | Neuropeptide Y | NPY | 7p15.1 | <0.01* | 22.1 | <0.01* | 33.0 | | | | | | |
| Hs.12409 | | BI918626 | Somatostatin | SST | 3q28 | <0.01* | 29.0 | <0.01* | 22.1 | | | | | | |
| Hs.1408 | | BC053866 | Endothelin 3 | EDN3 | 20q13.2-q13.3 | <0.01 | -12.3 | <0.01 | -10.0 | | | | | | |
| | | | | | | GPCRs | | | | | | | | | |
| Hs.519057 | | L07615 | Neuropeptide Y receptor Y1 | NPY1R | 4q31.3-q32 | | | <0.01* | 24.4 | | | <0.01* | 21.9 | <0.05 | -17.7 |
| Hs.131138 | | NM_012344 | Neurotensin receptor 2 | NTSR2 | 2p25.1 | | | | | <0.01 | -13.9 | <0.01 | -18.6 | <0.01* | -24.7 |
| Hs.112621 | | BC041407 | Metabotropic Glutamate receptor 3 | GRM3 | 7q21.1-q21.2 | <0.01* | 33.4 | <0.01* | 34.4 | | | | | | |
| Hs.88372 | | BC033742 | Tachykinin receptor 2 | TACR2 | 10q11-q21 | | | <0.01* | -22.9 | | | | | | |
| Hs.154210 | | BC018650 | Endothelial differentiation G-protein-coupled receptor 1 | EDG1 | 1p21 | | | | | <0.01 | -19.7 | <0.01* | -21.2 | <0.01 | -10.4 |
| Hs.126667 | | BC036034 | Endothelial differentiation G-protein-coupled receptor 2 | EDG2 | 9q31.3 | <0.05 | 24.1 | <0.01 | 18.2 | | | | | | |
| Hs.82002 | | NM_000115 | Endothelin receptor type B | EDNRB | 13q22 | | | | | | | <0.01* | -31.2 | <0.01 | -15.9 |
| Hs.406094 | | BX649006 | G protein-coupled receptor 37 | GPR37 | 7q31 | <0.01* | 53.1 | <0.01* | 38.3 | <0.01* | -53.5 | <0.01* | -40.5 | <0.01* | -27.0 |
| Hs.513633 | | NM_201524 | G protein-coupled receptor 56 | GPR56 | 16q13 | | | <0.01 | | <0.01 | -12.0 | <0.01 | -15.9 | <0.01 | -14.9 |

TABLE 13-continued

| UniGene ID | GDB Accession # | Name | Symbol | Cytoband | Bipolar Disorder | | | | Major Depressive Disorder | | | | | |
|---|---|---|---|---|---|---|---|---|---|---|---|---|---|---|
| | | | | | U95Av2 Cohort A | | U133A Cohort A | | U95Av2 Cohort A | | U133A Cohort A | | U133A Cohort B | |
| | | | | | P Value | % Fold Change | P Value | % Fold Change | P Value | % Fold Change | P Value | % Fold Change | P Value | % Fold Change |
| | | | | | | | | | G protein and Regulators | | | | | |
| Hs.148685 | NM_016235 | G protein-coupled receptor C-5-B | GPRC5B | 16p12 | <0.01* | 38.4 | <0.01* | 24.6 | <0.01* | −36.5 | <0.01* | −38.3 | <0.01* | −30.3 |
| Hs.99195 | XM_291111 | G protein-coupled receptor 125 | GPR125 | 4p15.31 | | | | | <0.05 | −14.1 | <0.05 | −11.5 | | |
| Hs.134587 | BC026326 | G protein alpha inhibiting activity polypeptide 1 | GNAI1 | 7q21 | | | <0.01* | 40.4 | | | | | | |
| Hs.24950 | NM_003617 | Regulator of G-protein signalling 5 | RGS5 | 1q23.1 | <0.01 | −19.0 | <0.01* | −27.2 | | | | | | |
| Hs.368733 | AK094559 | Regulator of G-protein signalling 20 | RGS20 | 8q12.1 | | | <0.01 | 15.6 | <0.01* | −28.2 | <0.01* | −29.2 | <0.01 | −13.9 |
| | | | | | | | | | Cyclic AMP Signaling Pathway | | | | | |
| Hs.416061 | NM_005019 | Phosphodiesterase 1A, calmodulin-dependent | PDE1A | 2q32.1 | <0.01* | 20.1 | <0.01* | 24.1 | | | | | | |
| Hs.9333 | NM_173457 | Phosphodiesterase 8A | PDE8A | 15q25.3 | <0.01 | 16.3 | <0.01 | 12.5 | <0.01* | −24.3 | <0.01* | −23.1 | <0.01 | −17.8 |
| Hs.433700 | NM_006823 | cAMP-dependent Protein kinase inhibitor alpha | PKIA | 8q21.11 | <0.05 | 14.2 | <0.01 | 16.6 | | | | | | |
| Hs.183994 | AK098311 | Protein phosphatase 1, catalytic subunit, alpha | PPP1CA | 11q13 | <0.01 | 13.1 | <0.01 | 16.8 | | | | | | |
| Hs.303090 | BX537399 | Protein phosphatase 1, regulatory subunit 3C | PPP1R3C | 10q23-q24 | | | <0.01 | −15.4 | <0.01* | −35.4 | <0.01* | −63.2 | <0.01* | −21.4 |
| Hs.166071 | AK026533 | Cyclin-dependent kinase 5 | CDK5 | 7q36 | <0.01 | 10.5 | <0.01 | 12.0 | | | | | | |
| | | | | | | | | | Phosphatidylinositol Signaling Pathway | | | | | |
| Hs.374613 | D26070 | Inositol 1,4,5-triphosphate receptor, type 1 | ITPR1 | 3p26-p25 | | | | | <0.05 | 13.0 | <0.01 | 17.4 | | |

TABLE 13-continued

| UniGene ID | Accession # | GDB | Name | Symbol | Cytoband | Bipolar Disorder U95Av2 Cohort A P Value | % Fold Change | U133A Cohort A P Value | % Fold Change | Major Depressive Disorder U95Av2 Cohort A P Value | % Fold Change | U133A Cohort A P Value | % Fold Change | U133A Cohort B P Value | % Fold Change |
|---|---|---|---|---|---|---|---|---|---|---|---|---|---|---|---|
| Hs.460355 | AL833252 | | Protein kinase C, beta 1 | PRKCB1 | 16p11.2 | <0.01 | | | | <0.01 | 14.8 | <0.01 | 11.5 | | |
| Hs.478199 | NM_002740 | | Protein kinase C, iota | PRKCI | 0 | <0.01* | -29.5 | | | | | | | | |
| Hs.444924 | NM_001263 | | CDP-diacylglycerol synthase 1 | CDS1 | 4q21.23 | <0.01* | -29.5 | | | | | | | | |
| Hs.32309 | AK093560 | | Inositol polyphosphate-1-phosphatase | INPP1 | 2q32 | <0.01* | 21.5 | <0.01* | 24.9 | | | | | | |
| Hs.369755 | NM_014937 | | Inositol polyphosphate-5-phosphatase F | INPP5F | 10q26.11-q26.12 | | | | | | | <0.01* | 21.8 | | |
| Hs.528087 | NM_002221 | | Inositol 1,4,5-trisphosphate 3-kinase B | ITPKB | 0 | <0.01 | 14.8 | <0.05 | 11.5 | <0.01 | -12.7 | <0.05 | -12.3 | | |
| Hs.175343 | BX648778 | | Phosphoinositide-3-kinase, class 2, alpha polypeptide | PIK3C2A | 11p15.5-p14 | | | <0.05 | 22.3 | <0.05 | -14.1 | <0.01* | -35.9 | | |
| Hs.497487 | Y11312 | | Phosphoinositide-3-kinase, class 2, beta polypeptide | PIK3C2B | 1q32 | <0.01 | 16.6 | <0.01 | 14.8 | | | | | | |
| Hs.132225 | NM_181523 | | Phosphoinositide-3-kinase, regulatory subunit 1 | PIK3R1 | 5q13.1 | <0.01* | -32.0 | | | | | | | | |
| Hs.467192 | AK090488 | | Protein phosphatase 2, regulatory subunit A, alpha isoform | PPP2R1A | 19q13.41 | <0.01 | 12.1 | <0.01 | 10.1 | | | | | | |
| Hs.146339 | NM_002717 | | Protein phosphatase 2, regulatory subunit B, alpha isoform | PPP2R2A | 8p21.2 | <0.01* | 32.3 | | | | | <0.01* | | | -34.0 |

TABLE 14

| Name | Symbol | UniGene ID | GDB Acc # | G protein | Cytoband | Bipolar Disorder | | | | Major Depressive Disorder | | | |
|------|--------|-----------|-----------|-----------|----------|---|---|---|---|---|---|---|---|
| | | | | | | U95Av2 Cohort A | | U133A Cohort A | | U95Av2 Cohort A | | U133A Cohort B | |
| | | | | | | P Value | % FC | P Value | % FC | P Value | % FC | P Value | % FC |
| | | | | | Monoamine Metabolism | | | | | | | | |
| Catechol-O-methyltransferase | COMT | Hs.370408 | AL390148 | | 22q11.21-q11.23 | <0.01 | 15.8 | <0.01 | 11.5 | | | | |
| Monoamine oxidase B | MAOB | Hs.46732 | NM_000898 | | Xp11.23 | <0.01 | 15.9 | <0.01 | 18.9 | | | | |
| | | | | | Ligand peptide | | | | | | | | |
| Neuropeptide Y | NPY | Hs.1832 | BF680552 | Gi, Gq | 7p15 | <0.01* | 22.1 | <0.01* | 33.0 | | | | |
| Somatostatin | SST | Hs.12409 | BI918626 | Gi | 3q28 | <0.01* | 29.0 | <0.01* | 22.1 | | | | |
| Endothelin 3 | EDN3 | Hs.1408 | BC053866 | Gq | 20q13.2-q13.3 | <0.01 | -12.3 | <0.01 | -10.0 | | | | |
| | | | | | GPCRs | | | | | | | | |
| Neuropeptide Y receptor Y1 | NPY1R | Hs.519057 | L07615 | Gi | 4q31-q32 | | | <0.01* | 24.4 | | | | |
| Tachykinin receptor 2 | TACR2 | Hs.88372 | BC033742 | Gq | 10q11-q21 | | | <0.01* | -22.9 | | | | |
| Neurotensin receptor 2 | NTSR2 | Hs.131138 | NM_012344 | Gq | 2p25.1 | | | | | <0.01 | -13.9 | <0.01 | -24.7 |
| Endothelin receptor type B | EDNRB | Hs.82002 | NM_000115 | Gq | 13q22 | | | | | <0.01* | -31.2 | <0.01 | -15.9 |
| Glutamate receptor 3 Metabotropic | GRM3 | Hs.112621 | BC041407 | Gi | 7q21 | <0.01* | 33.4 | <0.01* | 34.4 | | | | |
| Endothelial differentiation GPCR 1 | EDG1 | Hs.154210 | BC018650 | Gi, G12 | 1p21 | <0.01 | | | | <0.01 | -19.7 | <0.01* | -21.2 |
| Endothelial differentiation GPCR 2 | EDG2 | Hs.126667 | BC036034 | Gi, Gq, G12 | 9q31.3 | <0.05 | 24.1 | <0.01 | 18.2 | | | | -10.4 |
| G protein-coupled receptor 37 | GPR37 | Hs.406094 | BX649006 | Unknown | 7q31 | <0.01* | 53.1 | <0.01* | 38.3 | <0.01* | -53.5 | <0.01* | -27.0 |
| G protein-coupled receptor C-5-B | GPRC5B | Hs.148685 | NM_016235 | Unknown | 16p12 | <0.01* | 38.4 | <0.01* | 24.6 | <0.01* | -36.5 | <0.01* | -30.3 |
| G protein-coupled receptor 56 | GPR56 | Hs.513633 | NM_201524 | Unknown | 16q13 | | | | | <0.01 | -12.0 | <0.01 | -14.9 |
| G protein-coupled receptor 125 | GPR125 | Hs.99195 | XM_291111 | Unknown | 4p15 | | | | | <0.05 | -14.1 | | -11.5 |
| | | | | | Cyclic AMP Signaling Pathway | | | | | | | | |
| G protein alpha inhibiting activity 1 | GNAI1 | Hs.134587 | BC026326 | | 7q21 | | | <0.01* | 40.4 | | | | |
| Regulator of G-protein signalling 20 | RGS20 | Hs.368733 | AK094559 | | 8q12 | | | | | <0.01* | -28.2 | <0.01* | -13.9 |
| Phosphodiesterase 1A | PDE1A | Hs.416061 | NM_005019 | | 2q32 | <0.01* | 20.1 | <0.01* | 24.1 | | | | |
| Phosphodiesterase 8A | PDE8A | Hs.9333 | NM_173457 | | 15q25 | <0.01 | 16.3 | <0.01 | 12.5 | | | | |
| Protein kinase A inhibitor alpha | PKIA | Hs.433700 | NM_006823 | | 8q21 | <0.05 | 14.2 | <0.01 | 16.6 | <0.01* | -24.3 | <0.01 | -17.8 |
| Cyclin-dependent kinase 5 | CDK5 | Hs.166071 | AK026533 | | 7q36 | <0.01 | 10.5 | <0.01 | 12.0 | | | | |
| Protein phosphatase 1, catalytic alpha | PPP1CA | Hs.183994 | AK098311 | | 11q13 | <0.01 | 13.1 | <0.01 | 16.8 | | | | |
| Protein phosphatase 1, | PPP1R3C | Hs.303090 | BX537399 | | 10q23-q24 | | | | | <0.01* | -35.4 | <0.01* | -21.4 |

TABLE 14-continued

| | | | | | | Bipolar Disorder | | | | Major Depressive Disorder | | | | | |
| | | | | | | U95Av2 Cohort A | | U133A Cohort A | | U95Av2 Cohort A | | U133A Cohort A | | U133A Cohort B | |
| Name | Symbol | UniGene ID | GDB Acc # | G protein | Cytoband | P Value | % FC | P Value | % FC | P Value | % FC | P Value | % FC | P Value | % FC |
|---|---|---|---|---|---|---|---|---|---|---|---|---|---|---|---|
| regulatory 3C | | | | | | | | | | | | | | | |
| | | | | | Phosphatidylinositol Signaling Pathway | | | | | | | | | | |
| Inositol polyphosphate-5-phosphatase A | INPP5A | Hs.523360 | NM_005539 | | 10q26 | | | | | | | <0.01 | 13.2 | <0.05 | 12.2 |
| Inositol polyphosphate-5-phosphatase F | INPP5F | Hs.369755 | NM_014937 | | 10q26 | | | | | | | <0.01* | 21.8 | | |
| Inositol 1,4,5-trisphosphate 3-kinase B | ITPKB | Hs.528087 | NM_002221 | | 1q41-q43 | <0.01 | 14.8 | <0.05 | 11.5 | <0.01 | -12.7 | <0.05 | -12.3 | <0.01* | -34.0 |
| Inositol polyphosphate-1-phosphatase | INPP1 | Hs.32309 | AK093560 | | 2q32 | <0.01* | 21.5 | <0.01* | 24.9 | | | | | | |
| CDP-diacylglycerol synthase 1 | CDS1 | Hs.444924 | NM_001263 | | 4q21.23 | <0.01* | -29.5 | | | | | | | | |
| Phosphoinositide-3-kinase catalytic 2A | PIK3C2A | Hs.175343 | BX648778 | | 11p15-p14 | | | | | <0.05 | -14.1 | <0.01* | -35.9 | | |
| Phosphoinositide-3-kinase catalytic 2B | PIK3C2B | Hs.497487 | Y11312 | | 1q32 | <0.01 | 16.6 | <0.01 | 14.8 | | | | | | |
| Phosphoinositide-3-kinase regulatory 1 | PIK3R1 | Hs.132225 | NM_181523 | | 5q13 | <0.01* | -32.0 | | | | | | | | |
| Protein kinase C iota | PRKCI | Hs.478199 | NM_002740 | | 3p25-q27 | <0.01* | -29.5 | | | | | | | | |
| Inositol 1,4,5-triphosphate receptor 1 | ITPR1 | Hs.374613 | D26070 | | 3p26-p25 | | | | | <0.05 | 13.0 | <0.01 | 17.4 | | |
| Protein kinase C beta 1 | PRKCB1 | Hs.460355 | AL833252 | | 16p11 | | | | | <0.01 | 14.8 | <0.01 | 11.5 | | |

TABLE 15

| Name | Symbol | UniGene ID | GDB Accession # | G protein | Cytoband | Bipolar Disorder U95Av2 Cohort A | |
|---|---|---|---|---|---|---|---|
| | | | | | | P Value | % FC |
| Protein phosphatase 1 regulatory 3C | PPP1R3C | Hs.303090 | BX537399 | | 10q23-q24 | | |
| Phosphodiesterase 8A | PDE8A | Hs.9333 | NM_173457 | | 15q25 | | |
| Inositol 1,4,5-trisphosphate 3-kinase B | ITPKB | Hs.528087 | AJ242780 | | 1q42 | | |
| G protein beta 5 | GNB5 | Hs.155090 | AK092059 | | 15q21 | | |
| Somatostatin | SST | Hs.12409 | BI918626 | Gi | 3q28 | <0.01 | −16.8 |
| Adrenergic, beta-1-, receptor | ADRB1 | Hs.99913 | BC045633 | Gs | 10q24-q26 | <0.01 | −18.4 |
| Glutamate receptor, metabotropic 3 | GRM3 | Hs.112621 | BC041407 | Gi | 7q21 | <0.01* | 28.4 |
| G protein-coupled receptor C-5-B | GPRC5B | Hs.148685 | NM_016235 | Unknown | 16p12 | <0.01* | 31.8 |
| G protein-coupled receptor 37 | GPR37 | Hs.406094 | BX649006 | Unknown | 7q31 | | |
| G protein-coupled receptor 56 | GPR56 | Hs.513633 | NM_201524 | Unknown | 16q13 | | |

| Name | Bipolar Disorder U133A Cohort A | | Major Depresive Disorder | | | | | |
|---|---|---|---|---|---|---|---|---|
| | | | U95Av2 Cohort A | | U133A Cohort A | | U133A Cohort B | |
| | P Value | % FC | P Value | % FC | P Value | % FC | P Value | % FC |
| Protein phosphatase 1 regulatory 3C | | | <0.01* | −26.4 | <0.01* | −62.5 | <0.01* | −29.6 |
| Phosphodiesterase 8A | | | <0.01* | −32.0 | | | | |
| Inositol 1,4,5-trisphosphate 3-kinase B | | | <0.01 | −12.5 | | | <0.01* | −46.1 |
| G protein beta 5 | | | | | <0.05 | 12.8 | <0.01 | 18.7 |
| Somatostatin | <0.01* | −25.7 | <0.01* | −26.6 | <0.01* | −34.2 | | |
| Adrenergic, beta-1-, receptor | <0.05 | −13.4 | | | | | | |
| Glutamate receptor, metabotropic 3 | | | | | | | | |
| G protein-coupled receptor C-5-B | | | <0.01* | −35.6 | <0.01* | −34.3 | <0.01* | −24.0 |
| G protein-coupled receptor 37 | | | <0.01* | −62.5 | | | | |
| G protein-coupled receptor 56 | | | <0.01 | −14.2 | <0.01* | −20.0 | <0.01* | −23.2 |

TABLE 16

| Name | Symbol | UniGene ID | GDB Accession # | G protein | Cytoband | BPD U95Av2 | | MDD U95Av2 | |
|---|---|---|---|---|---|---|---|---|---|
| | | | | | | P Value | % FC | P Value | % FC |
| Phosphodiesterase 4B | PDE4B | Hs.198072 | CR749667 | | 1p31 | | | <0.01* | −45.3 |
| Inositol polyphosphate-5-phosphatase A | INPP5A | Hs.523360 | NM_005539 | | 10q26 | <0.01* | 26.1 | | |
| Regulator of G-protein signalling 20 | RGS20 | Hs.368733 | AK094559 | | 8q12 | | | <0.01* | −23.8 |
| Proenkephalin | PENK | Hs.339831 | AK091563 | Gi | 8q23-q24 | <0.01* | 83.4 | <0.01* | 34.5 |
| G protein-coupled receptor C-5-B | GPRC5B | Hs.148685 | NM_016235 | Unknown | 16p12 | | | <0.01* | −31.7 |
| G protein-coupled receptor 37 | GPR37 | Hs.406094 | BX649006 | Unknown | 7q31 | | | <0.01* | −42.4 |

TABLE 17

| UniGene | Gene Name | Symbol | BPD vs Control | | | | | | MDD vs Control | | | | | |
|---|---|---|---|---|---|---|---|---|---|---|---|---|---|---|
| | | | U95Av2 | % FC | U133A | % FC | qRT-PCR | % FC | U95Av2 | % FC | U133A | % FC | qRT-PCR | % FC |
| Hs.1832 | Neuropeptide Y | NPY | 22.1 | ** | 33.0 | ** | 37.6 | * | | | | | | |
| Hs.12409 | Somatostatin | SST | 29.0 | ** | 22.1 | ** | N.S. | | | | | | | |
| Hs.148685 | G protein-coupled receptor C-5-B | GPRC5B | 38.4 | ** | 24.6 | ** | 46.8 | * | −36.5 | ** | −38.3 | ** | −54.0 | ** |
| Hs.406094 | G protein-coupled receptor 37 | GPR37 | 53.1 | ** | 38.3 | ** | 54.1 | * | −53.5 | ** | −40.5 | ** | −62.7 | * |
| Hs.368733 | Regulator of G-protein signalling 20 | RGS20 | | | | | | | −28.2 | ** | −29.2 | ** | −36.9 | ** |
| Hs.303090 | Protein phosphatase 1 regulatory subunit 3C | PPP1R3C | | | | | | | −35.4 | ** | −63.2 | ** | −46.1 | ** |
| Hs.32309 | Inositol polyphosphate-1-phosphatase | INPP1 | 21.5 | ** | 24.9 | ** | 21.7 | * | | | | | | |

TABLE 18

| | | | | | BP - Control | | | | | |
|---|---|---|---|---|---|---|---|---|---|---|
| | | | | | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Ligands | | | | | | | | | | |
| Adrenomedullin | ADM | Hs.441047 | CR603703 | 11p15 | <0.01* | 31.53 | | | | |
| Brain-specific angiogenesis inhibitor 3 | BAI3 | Hs.13261 | AB011122 | 6q12 | <0.01* | 22.18 | <0.01* | 36.44 | | |
| Cholecystokinin | CCK | Hs.458426 | BC028133 | 3p22-p21 | | | <0.01* | 58.95 | <0.01* | 75.64 |
| Somatostatin | SST | Hs.12409 | BI918626 | 3q28 | <0.01* | 43.64 | | | | |
| Chemokine (C-C motif) ligand 25 | CCL25 | Hs.310511 | CR603063 | 19p13 | | | <0.01* | −23.50 | | |
| Chemokine (C—X—C motif) ligand 14 | CXCL14 | Hs.483444 | NM_004887 | 5q31 | <0.01* | −21.63 | <0.01* | −37.40 | <0.01* | −26.52 |
| Frizzled homolog 7 (Drosophila) | FZD7 | Hs.173859 | AB017365 | 2q33 | | | <0.01* | 26.17 | | |
| Monoamine oxidase B | MAOB | Hs.46732 | NM_000898 | Xp113 | <0.01* | 21.95 | | | | |
| Neuropeptide Y | NPY | Hs.1832 | BF680552 | 7p15 | <0.01* | 27.35 | | | | |
| Neurotensin | NTS | Hs.80962 | BF698911 | 12q21 | | | <0.01* | 31.10 | | |
| Prodynorphin | PDYN | Hs.22584 | BC026334 | 20pter-p12 | <0.01* | 73.04 | <0.01* | 20.40 | | |
| Proenkephalin | PENK | Hs.339831 | AK091563 | 8q23-q24 | <0.01* | 121.58 | | | <0.01 | 19.08 |
| GPCR | | | | | | | | | | |
| Neuropeptide Y receptor Y1 | NPY1R | Hs.519057 | L07615 | 4q31-q32 | <0.01* | 42.45 | | | | |
| Gamma-aminobutyric acid (GABA) A receptor, delta | GABRD | Hs.113882 | NM_000815 | 1p | | | | | <0.01* | 27.99 |
| Neurotensin receptor 2 | NTSR2 | Hs.131138 | NM_012344 | 2p25 | | | | | <0.01* | −26.66 |
| Oxytocin receptor | OXTR | Hs.2820 | NM_000916 | 3p25 | | | | | <0.01* | −27.98 |
| Adenosine A2a receptor | ADORA2A | Hs.197029 | BC013780 | 22q11 | <0.01* | 42.45 | | | | |
| Cadherin, EGF LAG seven-pass G-type receptor 2 | CELSR2 | Hs.57652 | AF234887 | 1p21 | | | <0.01* | 20.09 | | |
| G protein-coupled receptor 116 | GPR116 | Hs.362806 | BC066121 | 6p12 | <0.01* | −33.15 | | | | |
| G protein-coupled receptor 125 | GPR125 | Hs.99195 | XM_291111 | 4p15 | <0.05 | −11.08 | | | | |
| G protein-coupled receptor 17 | GPR17 | Hs.46453 | AK126849 | 2q21 | <0.05 | 8.77 | | | | |
| G protein-coupled receptor 22 | GPR22 | Hs.432557 | AK122621 | 7q22-q31 | <0.05 | 12.47 | | | | |
| G protein-coupled receptor 37 | GPR37 | Hs.406094 | BX649006 | 7q31 | <0.01 | −16.70 | | | | |
| G protein-coupled receptor 51 | GPR51 | Hs.198612 | AF056085 | 9q22-q22 | <0.01 | −19.60 | <0.01 | 15.51 | <0.01* | 23.38 |
| G protein-coupled receptor 6 | GPR6 | Hs.46332 | NM_005284 | 6q21 | <0.01* | 78.20 | | | <0.01* | 24.14 |
| G protein-coupled receptor, C-5-B | GPRC5B | Hs.148685 | NM_016235 | 16p12 | <0.01 | 11.08 | | | | |
| Glutamate receptor, metabotropic 3 | GRM3 | Hs.112621 | BC041407 | 7q21 | <0.01* | 28.68 | | | | |
| Histamine receptor H3 | HRH3 | Hs.251399 | NM_007232 | 20q13 | | | | | <0.01 | 18.90 |
| Dopamine receptor D1 | DRD1 | Hs.2624 | NM_000794 | 5q35 | <0.01* | 53.37 | | | <0.05 | 17.68 |
| Endothelin receptor type B | EDNRB | Hs.82002 | NM_000115 | 13q22 | | | <0.01* | 24.03 | <0.01* | −37.40 |
| 5-hydroxytryptamine (serotonin) receptor 2C | HTR2C | Hs.149037 | NM_000868 | Xq24 | <0.01* | 97.85 | <0.01* | 24.17 | <0.01* | 33.87 |

TABLE 18-continued

|  |  |  |  |  | BP - Control | | | | | |
|  |  |  |  |  | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| --- | --- | --- | --- | --- | --- | --- | --- | --- | --- | --- |
| G protein | | | | | | | | | | |
| G protein, alpha inhibiting activity polypeptide 1 | GNAI1 | Hs.134587 | BC026326 | 7q21 | <0.01* | 22.98 | <0.01* | 32.60 | | |
| Guanine nucleotide binding protein, beta polypeptide 1 | GNB1 | Hs.430425 | AK123609 | 1p36 | | | <0.01 | 19.19 | | |
| Guanine nucleotide binding protein (G protein), beta 5 | GNB5 | Hs.155090 | AK092059 | 15q21 | <0.01 | 19.68 | <0.01* | 21.92 | | |
| Guanine nucleotide binding protein (G protein), gamma 3 | GNG3 | Hs.179915 | BM668891 | 11p11 | <0.05 | 9.70 | <0.01* | 28.84 | <0.01* | 31.30 |
| Guanine nucleotide binding protein (G protein), gamma 7 | GNG7 | Hs.515544 | AK024465 | 19p13 | <0.01* | 25.24 | | | | |
| Regulator of G protein signaling | | | | | | | | | | |
| Regulator of G-protein signalling 1 | RGS1 | Hs.75256 | AK093544 | 1q31 | | | <0.05 | −9.16 | | |
| Regulator of G-protein signalling 2 | RGS2 | Hs.78944 | BC042755 | 1q31 | <0.01* | 23.56 | <0.01* | 20.60 | | |
| Regulator of G-protein signalling 20 | RGS20 | Hs.368733 | AK094559 | 8q12 | | | <0.01* | 25.58 | | |
| Regulator of G-protein signalling 4 | RGS4 | Hs.386726 | NM_005613 | 1q23 | | | <0.05 | −8.25 | <0.01* | 21.82 |
| Regulator of G-protein signalling 5 | RGS5 | Hs.24950 | NM_003617 | 1q23 | <0.01* | −26.85 | <0.01* | −32.51 | <0.01* | −20.65 |
| Regulator of G-protein signalling 7 | RGS7 | Hs.130171 | CR627366 | 1q43 | <0.01 | 18.39 | | | | |
| Regulator of G-protein signalling 9 | RGS9 | Hs.132327 | BC022504 | 17q23-q24 | <0.01* | 25.58 | | | | |
| Cyclic AMP signaling | | | | | | | | | | |
| Protein kinase, cAMP-dependent, catalytic, beta | PRKACB | Hs.487325 | BX537705 | 1p36 | <0.01* | 26.80 | <0.01* | 20.88 | <0.01* | 22.95 |
| Protein kinase, cAMP-dependent, regulatory, type I, alpha | PRKAR1A | Hs.280342 | CR749311 | 17q23-q24 | <0.01* | 21.71 | <0.01* | 23.64 | <0.01* | 26.15 |
| Protein kinase, cAMP-dependent, regulatory, type II, beta | PRKAR2B | Hs.433068 | BC075800 | 7q22 | <0.01* | 23.30 | <0.01* | 54.89 | | |
| Protein kinase (cAMP-dependent, catalytic) inhibitor alpha | PKIA | Hs.433700 | NM_006823 | 8q21 | | | <0.01* | 30.00 | | |
| Phosphodiesterase 8A | PDE8A | Hs.9333 | NM_173457 | 15q25 | | | <0.01* | −25.56 | | |
| Cyclic AMP phosphoprotein, 19 kD | ARPP-19 | Hs.512908 | AL833077 | 15q21 | <0.01* | 27.29 | | | <0.01 | 19.35 |
| Adenylate cyclase-associated protein, 2 | CAP2 | Hs.132902 | NM_006366 | 6p22 | <0.05 | 10.52 | <0.01* | 35.43 | | |
| Cyclin-dependent kinase 5 | CDK5 | Hs.166071 | AK026533 | 7q36 | | | <0.01* | 20.85 | | |
| Phosphatidylinositol signaling | | | | | | | | | | |
| Diacylglycerol kinase, beta 90 kDa | DGKB | Hs.487619 | NM_004080 | 7p21 | <0.01 | 18.61 | | | <0.01* | 26.46 |
| Inositol polyphosphate-5-phosphatase | INPP5A | Hs.523360 | NM_005539 | 10q26 | <0.01* | 34.39 | <0.01* | 27.86 | | |
| Inositol polyphosphate-5-phosphatase F | INPP5F | Hs.369755 | NM_014937 | 10q26 | <0.01* | 31.06 | <0.01* | 29.81 | | |
| Inositol 1,4,5-triphosphate receptor, type 1 | ITPR1 | Hs.374613 | D26070 | 3p26-p25 | <0.01* | 23.50 | <0.01* | 29.24 | | |
| Phosphatidylinositol-4-phosphate 5-kinase, type I, beta | PIP5K1B | Hs.534371 | BC030587 | 9q13 | <0.01* | 20.75 | | | | |
| Phosphatidylinositol-4-phosphate 5-kinase, type II, gamma | PIP5K2C | Hs.144502 | AK125526 | 12q13 | | | <0.01* | 23.03 | | |
| Phospholipase C, beta 1 (phosphoinositide-specific) | PLCB1 | Hs.310537 | NM_182734 | 20p12 | | | <0.01 | 19.28 | | |
| Protein kinase C, beta 1 | PRKCB1 | Hs.460355 | AL833252 | 16p11 | <0.01* | 23.66 | <0.01 | 18.25 | | |
| Myristoylated alanine-rich protein kinase C substrate | MARCKS | Hs.519909 | NM_002356 | 6q22 | | | <0.01* | 23.12 | | |
| Growth associated protein 43 | GAP43 | Hs.134974 | AK091466 | 3q13 | | | <0.01* | 27.99 | <0.01* | 46.79 |
| YWHA | | | | | | | | | | |
| Tyrosine 3-monooxygenase/tryptophan 5-monooxygenase activation protein, beta polypeptide | YWHAB | Hs.279920 | NM_003404 | 20q13 | | | <0.01* | 37.20 | <0.01* | 22.45 |

TABLE 18-continued

|  |  |  |  |  | BP - Control | | | | | |
|---|---|---|---|---|---|---|---|---|---|---|
|  |  |  |  |  | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Chromosome 22 open reading frame 24 | YWHAH | Hs.226755 | CR622695 | 22q12 |  |  | <0.01* | 73.39 | <0.01* | 66.65 |
| Tyrosine 3-monooxygenase/ tryptophan 5-monooxygenase activation protein, theta polypeptide | YWHAQ | Hs.74405 | NM_006826 | 2p25 |  |  | <0.01* | 32.96 |  |  |
| Tyrosine 3-monooxygenase/ tryptophan 5-monooxygenase activation protein, zeta polypeptide | YWHAZ | Hs.492407 | BC051814 | 8q23 | <0.01 | 13.55 | <0.01* | 42.25 | <0.01* | 31.83 |
| Calcium signaling | | | | | | | | | | |
| Calmodulin 1 (phosphorylase kinase, delta) | CALM1 | Hs.282410 | BC047523 | 14q24-q31 |  |  | <0.01* | 21.80 |  |  |
| Calmodulin 3 (phosphorylase kinase, delta) | CALM3 | Hs.515487 | AK094964 | 19q13 |  |  |  |  | <0.01* | 30.65 |
| Calcium/calmodulin-dependent protein kinase I | CAMK1 | Hs.434875 | AK094026 | 3p25 |  |  | <0.05 | 18.27 |  |  |
| Calcium/calmodulin-dependent protein kinase II alpha | CAMK2A | Hs.143535 | NM_015981 | 5q32 |  |  | <0.01* | 20.41 |  |  |
| Calcium/calmodulin-dependent protein kinase II beta | CAMK2B | Hs.351887 | NM_001220 | 22q12 |  |  | <0.01* | 21.93 |  |  |
| Calmodulin binding transcription activator 1 | CAMTA1 | Hs.397705 | NM_015215 | 1p36 | <0.01 | 16.05 | <0.05 | 14.94 |  |  |
| Doublecortin and CaM kinase-like 1 | DCAMKL1 | Hs.507755 | NM_004734 | 13q13 |  |  |  |  | <0.01* | 29.98 |
| MAPK signaling | | | | | | | | | | |
| P21/Cdc42/Rac1-activated kinase 1 (STE20 homolog, yeast) | PAK1 | Hs.435714 | NM_002576 | 11q13-q14 | <0.05 | 13.71 | <0.01 | 16.23 |  |  |
| Mitogen-activated protein kinase kinase 1 | MAP2K1 | Hs.145442 | NM_002755 | 15q22 | <0.01* | 33.40 | <0.01* | 57.55 | <0.01* | 46.39 |
| Mitogen-activated protein kinase kinase 1 interacting protein 1 | MAP2K1IP1 | Hs.433332 | AK022313 | 4q23 |  |  | <0.01* | 20.94 |  |  |
| Mitogen-activated protein kinase kinase 4 | MAP2K4 | Hs.514681 | AK131544 | 17p11 | <0.01 | 17.47 | <0.01* | 29.05 | <0.01* | 22.97 |
| Mitogen-activated protein kinase kinase kinase 4 | MAP4K4 | Hs.431550 | NM_145686 | 2q11-q12 | <0.01* | -23.32 |  |  |  |  |
| Mitogen-activated protein kinase 1 | MAPK1 | Hs.431850 | NM_002745 | 22q11 | <0.01* | 31.80 | <0.01* | 52.27 | <0.01* | 41.35 |
| Mitogen-activated protein kinase 10 | MAPK10 | Hs.25209 | AK124791 | 4q22-q23 |  |  | <0.01* | 25.47 |  |  |
| Mitogen-activated protein kinase 9 | MAPK9 | Hs.484371 | BC032539 | 5q35 |  |  | <0.01 | 13.93 | <0.01* | 22.88 |
| Protein Phosphatase | | | | | | | | | | |
| Protein phosphatase 1, catalytic subunit, gamma isoform | PPP1CC | Hs.79081 | NM_002710 | 12q24 |  |  | <0.01* | 25.65 |  |  |
| Protein phosphatase 1, regulatory (inhibitor) subunit 2 | PPP1R2 | Hs.184840 | NM_006241 | 3q29 |  |  | <0.01* | 21.53 |  |  |
| Protein phosphatase 1, regulatory subunit 3C | PPP1R3C | Hs.303090 | BX537399 | 10q23-q24 | <0.01 | -16.80 |  |  | <0.01* | -47.55 |
| Protein phosphatase 2C, magnesium-dependent, catalytic subunit | PPM2C | Hs.22265 | NM_018444 | 8q22 | <0.05 | 23.33 |  |  |  |  |
| Protein phosphatase 2 (formerly 2A), catalytic subunit, alpha isoform | PPP2CA | Hs.483408 | BX640662 | 5q23-q31 |  |  | <0.01* | 24.59 |  |  |
| Protein phosphatase 2 (formerly 2A), regulatory subunit A (PR 65), alpha isoform | PPP2R1A | Hs.467192 | AK090488 | 19q13 |  |  | <0.01* | 27.34 | <0.01* | 24.11 |
| Protein phosphatase 2 (formerly 2A), regulatory subunit B (PR 52), beta isofrom | PPP2R2B | Hs.193825 | M64930 | 5q31-5q32 |  |  | <0.01* | 38.94 |  |  |
| Protein phosphatase 2, regulatory subunit B (B56), gamma isoform | PPP2R5C | Hs.368264 | NM_002719 | 14q32 |  |  | <0.01* | 23.54 |  |  |
| Protein phosphatase 3 (formerly 2B), catalytic subunit, alpha isoform (calcineurin A alpha) | PPP3CA | Hs.435512 | NM_000944 | 4q21-q24 | <0.01* | 29.94 | <0.01* | 23.23 |  |  |
| Protein phosphatase 3 (formerly | PPP3CB | Hs.500067 | BC028049 | 10q21-q22 | <0.01* | 20.95 | <0.01* | 45.82 | <0.01* | 31.17 |

TABLE 18-continued

|  |  |  |  |  | BP - Control | | | | | |
|---|---|---|---|---|---|---|---|---|---|---|
|  |  |  |  |  | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| 2B), catalytic subunit, beta isoform (calcineurin A beta) | | | | | | | | | | |
| Protein phosphatase 3 (formerly 2B), regulatory subunit B, 19 kDa, alpha isoform (calcineurin B, type I) | PPP3R1 | Hs.280604 | BC027913 | 2p15 | | | <0.01* | 25.69 | | |
| AP1 | | | | | | | | | | |
| V-fos FBJ murine osteosarcoma viral oncogene homolog | FOS | Hs.25647 | BX647104 | 14q24 | | | <0.01* | −40.86 | <0.01* | −80.23 |
| V-jun sarcoma virus 17 oncogene homolog (avian) | JUN | Hs.525704 | NM_002228 | 1p32-p31 | <0.01* | −25.24 | | | | |
| Small G protein | | | | | | | | | | |
| Rho guanine nucleotide exchange factor (GEF) 3 | ARHGEF3 | Hs.476402 | AL833224 | 3p21-p13 | | | <0.01* | 31.85 | | |
| Ras homolog gene family, member I | ARHI | Hs.194695 | AK096393 | 1p31 | <0.01* | 132.94 | | | <0.01* | 33.15 |
| DIRAS family, GTP-binding RAS-like 2 | DIRAS2 | Hs.165636 | NM_017594 | 9q22 | | | | | | |
| RAB31, member RAS oncogene family | RAB31 | Hs.99528 | NM_006868 | 18p11 | <0.05 | −9.44 | | | | |
| RAB33A, member RAS oncogene family | RAB33A | Hs.56294 | AK094927 | Xq25 | | | | | <0.01* | 21.72 |
| Rab acceptor 1 (prenylated) | RABAC1 | Hs.11417 | BE779053 | 19q13 | | | | | <0.01* | 21.97 |
| RAN binding protein 6 | RANBP6 | Hs.167496 | BX537405 | 9p24 | | | <0.01* | 25.82 | | |
| RAP1, GTPase activating protein 1 | RAP1GA1 | Hs.148178 | BC035030 | 1p36-p35 | <0.01* | 52.74 | | | | |
| Hypothetical protein LOC145899 | RASGRF1 | Hs.459035 | NM_002891 | 15q24 | | | <0.01* | 28.36 | | |
| RAS guanyl releasing protein 1 (calcium and DAG-regulated) | RASGRP1 | Hs.511010 | AF081195 | 15q15 | <0.01* | 24.37 | | | | |
| RAS guanyl releasing protein 3 (calcium and DAG-regulated) | RASGRP3 | Hs.143674 | BC027849 | 2p25-p24 | | | <0.01 | −14.27 | | |
| Ras-like without CAAX 2 | RIT2 | Hs.464985 | AL713637 | 18q12 | | | | | <0.01* | 32.56 |
| RAS-related on chromosome 22 | RRP22 | Hs.73088 | NM_001007279 | 22q12 | | | | | <0.01* | 20.87 |
| V-Ki-ras2 Kirsten rat sarcoma 2 viral oncogene homolog | KRAS2 | Hs.505033 | NM_033360 | 12p12 | | | <0.01* | 22.38 | | |
| Ras-GTPase activating protein SH3 domain-binding protein 2 | G3BP2 | Hs.303676 | NM_203505 | 4q21 | | | <0.01* | 23.35 | <0.01* | 36.80 |
| Potassium channel | | | | | | | | | | |
| Potassium channel modulatory factor 1 | KCMF1 | Hs.345694 | NM_020122 | 2p11 | | | <0.01* | 22.07 | | |
| Potassium voltage-gated channel, shaker-related beta 2 | KCNAB2 | Hs.440497 | AK124696 | 1p36 | | | <0.01* | 24.09 | | |
| Potassium voltage-gated channel, Shal-related 2 | KCND2 | Hs.21703 | AB028967 | 7q31 | | | <0.01* | 20.05 | | |
| Potassium inwardly-rectifying channel, subfamily J 2 | KCNJ2 | Hs.1547 | NM_000891 | 17q23-q24 | | | <0.01* | −28.13 | | |
| Potassium inwardly-rectifying channel, subfamily J 6 | KCNJ6 | Hs.50927 | AK058042 | 21q22 | | | <0.01* | 26.12 | | |
| Potassium inwardly-rectifying channel, subfamily J 13 | KCNJ13 | Hs.467338 | NM_002242 | 2q37 | | | <0.01* | 31.87 | | |
| Potassium channel, subfamily K, member 1 | KCNK1 | Hs.208544 | AL833343 | 1q42-q43 | | | | | <0.01* | 23.33 |
| Potassium intermediate/small conductance calcium-activated channel, subfamily N, member 2 | KCNN2 | Hs.98280 | NM_021614 | 5q22 | | | <0.01* | 28.96 | | |
| Potassium intermediate/small conductance calcium-activated channel, subfamily N, member 3 | KCNN3 | Hs.490765 | BX649146 | 1q21 | <0.01 | −13.90 | | | | |
| Potassium channel, subfamily V, member 1 | KCNV1 | Hs.13285 | NM_014379 | 8q22-q24 | | | <0.01 | 11.16 | | |
| Sodium channel | | | | | | | | | | |
| Sodium channel, voltage-gated, type III, beta | SCN3B | Hs.4865 | AB032984 | 11q24 | | | <0.01* | 41.71 | <0.01* | 37.41 |
| Solute carrier family 12, (potassium-chloride transporter) member 5 | SLC12A5 | Hs.21413 | NM_020708 | 20q132 | <0.01 | 11.53 | <0.01* | 21.22 | | |

TABLE 18-continued

| | | | | | BP - Control | | | | | |
|---|---|---|---|---|---|---|---|---|---|---|
| | | | | | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Solute carrier family 24 (sodium/potassium/calcium exchanger), member 3 | SLC24A3 | Hs.211252 | AL833544 | 20p13 | | | <0.01* | 60.32 | | |
| Voltage-dependent anion channel 1 | VDAC1 | Hs.519320 | AK122953 | 5q31 | | | <0.01* | 27.48 | | |
| Calcium Channel | | | | | | | | | | |
| Calcium channel, voltage-dependent, alpha 2/delta 3 | CACNA2D3 | Hs.369421 | NM_018398 | 3p21 | | | <0.01* | 36.34 | | |
| Calcium channel, voltage-dependent, beta 2 subunit | CACNB2 | Hs.59093 | NM_000724 | 10p12 | | | <0.01* | 21.04 | <0.01* | 23.85 |
| Calcium channel, voltage-dependent, beta 3 subunit | CACNB3 | Hs.250712 | AK122911 | 12q13 | | | <0.01* | 22.11 | | |
| Calcium channel, voltage-dependent, gamma subunit 3 | CACNG3 | Hs.7235 | AK095553 | 16p12-p13 | | | <0.01* | 32.54 | | |
| Chloride channel | | | | | | | | | | |
| Chloride intracellular channel 4 | CLIC4 | Hs.440544 | AL117424 | 1p36 | | | <0.05 | -17.97 | | |

TABLE 19

| | | | | | MD - Control | | | | | |
|---|---|---|---|---|---|---|---|---|---|---|
| | | | | | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Ligands | | | | | | | | | | |
| Adrenomedullin | ADM | Hs.441047 | CR603703 | 11p15 | <0.05 | -7.16 | <0.01* | -34.24 | | |
| Brain-specific angiogenesis inhibitor 3 | BAI3 | Hs.13261 | AB011122 | 6q12 | <0.01* | 20.13 | <0.01* | 20.61 | | |
| Cholecystokinin | CCK | Hs.458426 | BC028133 | 3p22-p21 | <0.01* | 29.74 | <0.01* | 81.09 | | |
| Somatostatin | SST | Hs.12409 | BI918626 | 3q28 | <0.01* | 20.70 | | | | |
| Frizzled homolog 7 (Drosophila) | FZD7 | Hs.173859 | AB017365 | 2q33 | | | <0.05 | 8.11 | | |
| Latrophilin 2 | LPHN2 | Hs.24212 | AF104266 | 1p31 | <0.01* | 29.33 | | | | |
| Prodynorphin | PDYN | Hs.22584 | BC026334 | 20pter-p12 | <0.01* | 34.43 | | | <0.01* | 31.55 |
| Proenkephalin | PENK | Hs.339831 | AK091563 | 8q23-q24 | <0.01* | 57.92 | <0.01* | 21.80 | <0.01* | 22.13 |
| Prostaglandin D2 synthase 21 kDa (brain) | PTGDS | Hs.446429 | BM805807 | 9q34-q34 | | | <0.01* | -23.24 | | |
| GPCR | | | | | | | | | | |
| Neuropeptide Y receptor Y1 | NPY1R | Hs.519057 | L07615 | 4q31-q32 | <0.01* | 44.09 | | | | |
| Gamma-aminobutyric acid (GABA) A receptor, delta | GABRD | Hs.113882 | NM_000815 | 1p | | | <0.01* | 22.04 | <0.01* | 22.85 |
| Neurotensin receptor 2 | NTSR2 | Hs.131138 | NM_012344 | 2p25 | <0.01* | -37.48 | | | <0.01 | -17.42 |
| Oxytocin receptor | OXTR | Hs.2820 | NM_000916 | 3p25 | | | | | <0.01 | -15.90 |
| Cholecystokinin B receptor | CCKBR | Hs.203 | AF239668 | 11p15 | | | <0.01* | 27.01 | | |
| Adenosine A2a receptor | ADORA2A | Hs.197029 | BC013780 | 22q11 | <0.01 | 18.30 | | | <0.01* | 23.23 |
| Angiotensin II receptor-like 1 | AGTRL1 | Hs.438311 | AK075252 | 11q12 | | | <0.01* | -22.99 | | |
| G protein-coupled receptor 125 | GPR125 | Hs.99195 | XM_291111 | 4p15 | <0.01* | -22.88 | | | | |
| G protein-coupled receptor 17 | GPR17 | Hs.46453 | AK126849 | 2q21 | <0.01* | -27.08 | | | | |
| G protein-coupled receptor 22 | GPR22 | Hs.432557 | AK122621 | 7q22-q31 | | | <0.01* | 24.51 | | |
| G protein-coupled receptor 37 | GPR37 | Hs.406094 | BX649006 | 7q31 | | | <0.01* | -43.90 | | |
| G-protein coupled receptor 37 like 1 | GPR37L1 | Hs.132049 | BC050334 | 1q32 | <0.01* | -27.67 | | | | |
| G protein-coupled receptor 51 | GPR51 | Hs.198612 | AF056085 | 9q22-q22 | <0.01* | 31.80 | <0.01* | 29.07 | | |
| G protein-coupled receptor 56 | GPR56 | Hs.513633 | NM_201524 | 16q13 | <0.01* | -24.98 | | | | |
| G protein-coupled receptor 6 | GPR6 | Hs.46332 | NM_005284 | 6q21 | <0.01* | 27.88 | | | <0.01* | 41.21 |
| Chemokine (C—X—C motif) receptor 4 | CXCR4 | Hs.421986 | CR614663 | 2q21 | | | <0.01* | -20.68 | | |
| G protein-coupled receptor, C-5-B | GPRC5B | Hs.148685 | NM_016235 | 16p12 | <0.01* | -27.94 | <0.01* | -36.01 | | |
| Histamine receptor H3 | HRH3 | Hs.251399 | NM_007232 | 20q13 | | | | | <0.01* | 30.42 |
| Dopamine receptor D1 | DRD1 | Hs.2624 | NM_000794 | 5q35 | <0.01* | 27.79 | | | <0.01* | 25.88 |
| Endothelial differentiation, sphingolipid GPCR 1 | EDG1 | Hs.154210 | BC018650 | 1p21 | <0.01* | -20.04 | | | | |

TABLE 19-continued

|  |  |  |  |  | MD - Control | | | | | |
|---|---|---|---|---|---|---|---|---|---|---|
|  |  |  |  |  | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Endothelin receptor type B | EDNRB | Hs.82002 | NM_000115 | 13q22 | <0.01* | −64.83 | <0.01 | −14.45 | <0.01* | −37.17 |
| 5-hydroxytryptamine (serotonin) receptor 2A | HTR2A | Hs.424980 | NM_000621 | 13q14-q21 | <0.01* | 45.03 | <0.01* | 42.32 |  |  |
| 5-hydroxytryptamine (serotonin) receptor 2C | HTR2C | Hs.149037 | NM_000868 | Xq24 | <0.01 | 14.27 | <0.01 | −18.49 | <0.01* | 31.98 |
| G protein |  |  |  |  |  |  |  |  |  |  |
| Guanine nucleotide binding protein (G protein), alpha 13 | GNA13 | Hs.515018 | NM_006572 | 17q24 | <0.01* | −20.84 |  |  |  |  |
| G protein, alpha inhibiting activity polypeptide 1 | GNAI1 | Hs.134587 | BC026326 | 7q21 | <0.05 | 17.13 |  |  |  |  |
| Guanine nucleotide binding protein, beta polypeptide 1 | GNB1 | Hs.430425 | AK123609 | 1p36 |  |  | <0.01* | 22.06 |  |  |
| Guanine nucleotide binding protein (G protein), beta 5 | GNB5 | Hs.155090 | AK092059 | 15q21 | <0.01* | 24.99 | <0.01* | 32.65 |  |  |
| Guanine nucleotide binding protein (G protein), gamma 12 | GNG12 | Hs.431101 | NM_018841 | 1p31 | <0.01* | −21.46 |  |  |  |  |
| Guanine nucleotide binding protein (G protein), gamma 3 | GNG3 | Hs.179915 | BM668891 | 11p11 | <0.01* | 26.57 | <0.01* | 41.14 | <0.05 | 14.55 |
| Regulator of G protein signaling |  |  |  |  |  |  |  |  |  |  |
| Regulator of G-protein signalling 1 | RGS1 | Hs.75256 | AK093544 | 1q31 |  |  | <0.01* | −34.56 |  |  |
| Regulator of G-protein signalling 2 | RGS2 | Hs.78944 | BC042755 | 1q31 | <0.01* | 36.07 | <0.01 | 17.15 |  |  |
| Regulator of G-protein signalling 20 | RGS20 | Hs.368733 | AK094559 | 8q12 | <0.01* | −32.34 |  |  |  |  |
| Regulator of G-protein signalling 4 | RGS4 | Hs.386726 | NM_005613 | 1q23 | <0.01* | 72.22 | <0.01* | 40.31 | <0.05 | 10.50 |
| Regulator of G-protein signalling 5 | RGS5 | Hs.24950 | NM_003617 | 1q23 | <0.01 | 8.03 |  |  |  |  |
| Regulator of G-protein signalling 7 | RGS7 | Hs.130171 | CR627366 | 1q43 | <0.01* | 36.06 | <0.01* | 36.42 |  |  |
| Regulator of G-protein signalling 9 | RGS9 | Hs.132327 | BC022504 | 17q23-q24 | <0.01 | 11.68 |  |  |  |  |
| Cyclic AMP signaling |  |  |  |  |  |  |  |  |  |  |
| Protein kinase, cAMP-dependent, catalytic, beta | PRKACB | Hs.487325 | BX537705 | 1p36 | <0.01 | 17.60 | <0.01 | 16.51 |  |  |
| Protein kinase, cAMP-dependent, regulatory, type I, alpha (tissue specific extinguisher 1) | PRKAR1A | Hs.280342 | CR749311 | 17q23-q24 | <0.01 | 11.92 | <0.05 | 10.27 |  |  |
| Protein kinase, cAMP-dependent, regulatory, type II, beta | PRKAR2B | Hs.433068 | BC075800 | 7q22 | <0.01* | 26.41 | <0.01* | 52.17 |  |  |
| Protein kinase (cAMP-dependent, catalytic) inhibitor alpha | PKIA | Hs.433700 | NM_006823 | 8q21 |  |  | <0.05 | 14.78 |  |  |
| Phosphodiesterase 4D interacting protein (myomegalin) | PDE4DIP | Hs.487925 | NM_014644 | 1q12 | <0.01* | −21.98 |  |  |  |  |
| Phosphodiesterase 8A | PDE8A | Hs.9333 | NM_173457 | 15q25 | <0.01* | −20.78 | <0.01* | −39.39 |  |  |
| Phosphodiesterase 8B | PDE8B | Hs.78106 | AF079529 | 5q13 | <0.01* | 20.36 |  |  |  |  |
| Cyclic AMP phosphoprotein, 19 kD | ARPP-19 | Hs.512908 | AL833077 | 15q21 | <0.01* | 24.18 | <0.01* | 25.33 | <0.01* | 27.45 |
| Adenylate cyclase-associated protein, 2 | CAP2 | Hs.132902 | NM_006366 | 6p22 | <0.01* | 32.38 |  | 27.21 |  |  |
| Cyclin-dependent kinase 5 | CDK5 | Hs.166071 | AK026533 | 7q36 |  |  | <0.01 | 18.67 |  |  |
| Phosphatidylinositol signaling |  |  |  |  |  |  |  |  |  |  |
| Diacylglycerol kinase, beta 90 kDa | DGKB | Hs.487619 | NM_004080 | 7p21 | <0.01* | 32.70 |  |  | <0.01* | 26.36 |
| Inositol polyphosphate-5-phosphatase, 40 kDa | INPP5A | Hs.523360 | NM_005539 | 10q26 | <0.01* | 22.52 | <0.01* | 40.16 | <0.01* | 22.98 |
| Inositol polyphosphate-5-phosphatase F | INPP5F | Hs.369755 | NM_014937 | 10q26 | <0.01* | 40.58 | <0.01* | 45.18 | <0.01* | 32.42 |
| Inositol 1,4,5-trisphosphate 3-kinase A | ITPKA | Hs.2722 | BC026331 | 15q14-q21 | <0.01* | 29.49 | <0.01* | 32.18 |  |  |
| Inositol 1,4,5-trisphosphate 3-kinase B | ITPKB | Hs.528087 | AJ242780 | 1q423 | <0.01* | −34.51 | <0.01* | −34.14 |  |  |
| Inositol 1,4,5-triphosphate receptor, type 1 | ITPR1 | Hs.374613 | D26070 | 3p26-p25 | <0.01* | 45.62 | <0.01* | 51.25 |  |  |
| Phosphoinositide-3-kinase, class 2, alpha polypeptide | PIK3C2A | Hs.175343 | BX648778 | 11p15-p14 | <0.01* | −63.06 |  |  |  |  |
| Phosphoinositide-3-kinase, class 2, alpha polypeptide | PIK3C2A | Hs.175343 | BX648778 | 11p15-p14 | <0.01* | −63.06 |  |  |  |  |
| Phosphatidylinositol-4-phosphate 5-kinase, type I, beta | PIP5K1B | Hs.534371 | BC030587 | 9q13 | <0.01* | 24.44 |  |  |  |  |

TABLE 19-continued

| | | | | | MD - Control | | | | | |
| --- | --- | --- | --- | --- | --- | --- | --- | --- | --- | --- |
| | | | | | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| Phosphatidylinositol-4-phosphate 5-kinase, type II, gamma | PIP5K2C | Hs.144502 | AK125526 | 12q13 | | | <0.05 | 17.13 | | |
| Phospholipase C, beta 1 (phosphoinositide-specific) | PLCB1 | Hs.310537 | NM_182734 | 20p12 | | | <0.01* | 26.19 | | |
| Protein kinase C, beta 1 | PRKCB1 | Hs.460355 | AL833252 | 16p11 | <0.01* | 51.20 | <0.01* | 43.94 | | |
| Growth associated protein 43 | GAP43 | Hs.134974 | AK091466 | 3q13 | | | <0.01* | 49.55 | <0.01* | 30.12 |
| YWHA | | | | | | | | | | |
| Tyrosine 3-monooxygenase/tryptophan 5-monooxygenase activation protein, beta polypeptide | YWHAB | Hs.279920 | NM_003404 | 20q13 | <0.01* | 20.42 | <0.01* | 30.24 | <0.05 | 13.58 |
| Chromosome 22 open reading frame 24 | YWHAH | Hs.226755 | CR622695 | 22q12 | <0.01* | 31.18 | <0.01* | 56.74 | <0.01* | 26.27 |
| Tyrosine 3-monooxygenase/tryptophan 5-monooxygenase activation protein, zeta polypeptide | YWHAZ | Hs.492407 | BC051814 | 8q23 | <0.01* | 20.06 | <0.01* | 30.03 | <0.01* | 20.91 |
| Calcium signaling | | | | | | | | | | |
| Calmodulin 1 (phosphorylase kinase, delta) | CALM1 | Hs.282410 | BC047523 | 14q24-q31 | | | <0.01 | 16.48 | | |
| Calmodulin 3 (phosphorylase kinase, delta) | CALM3 | Hs.515487 | AK094964 | 19q13 | | | | | <0.01 | 14.08 |
| Calcium/calmodulin-dependent protein kinase I | CAMK1 | Hs.434875 | AK094026 | 3p25 | | | <0.01* | 20.75 | | |
| Calcium/calmodulin-dependent protein kinase II alpha | CAMK2A | Hs.143535 | NM_015981 | 5q32 | | | <0.01* | 30.59 | | |
| Calcium/calmodulin-dependent protein kinase II beta | CAMK2B | Hs.351887 | NM_001220 | 22q12 | | | <0.05 | 13.91 | | |
| Calcium/calmodulin-dependent protein kinase II | CaMKIInalpha | Hs.197922 | CR604926 | 1p36 | | | <0.01* | 21.16 | | |
| Calcium/calmodulin-dependent protein kinase kinase 2, beta | CAMKK2 | Hs.297343 | NM_006549 | 12q24 | | | <0.01* | 22.16 | | |
| Calmodulin binding transcription activator 1 | CAMTA1 | Hs.397705 | NM_015215 | 1p36 | <0.01* | 31.29 | <0.01* | 41.27 | | |
| Doublecortin and CaM kinase-like 1 | DCAMKL1 | Hs.507755 | NM_004734 | 13q13 | | | | | <0.05 | 16.77 |
| MAPK signaling | | | | | | | | | | |
| P21/Cdc42/Rac1-activated kinase 1 (STE20 homolog, yeast) | PAK1 | Hs.435714 | NM_002576 | 11q13-q14 | <0.01* | 32.71 | <0.01* | 36.58 | | |
| Mitogen-activated protein kinase kinase 1 | MAP2K1 | Hs.145442 | NM_002755 | 15q22 | <0.01* | 23.61 | <0.01* | 35.94 | <0.01* | 26.19 |
| Mitogen-activated protein kinase kinase 1 interacting protein 1 | MAP2K1IP1 | Hs.433332 | AK022313 | 4q23 | | | <0.05 | 13.15 | | |
| Mitogen-activated protein kinase kinase 4 | MAP2K4 | Hs.514681 | AK131544 | 17p11 | <0.01* | 23.15 | <0.01 | 19.77 | <0.05 | 8.77 |
| Mitogen-activated protein kinase kinase kinase kinase 4 | MAP4K4 | Hs.431550 | NM_145686 | 2q11-q12 | <0.01* | −24.08 | | | | |
| Mitogen-activated protein kinase kinase kinase kinase 5 | MAP4K5 | Hs.130491 | NM_198794 | 14q11-q21 | | | <0.01* | −24.23 | | |
| Mitogen-activated protein kinase 1 | MAPK1 | Hs.431850 | NM_002745 | 22q11 | <0.05 | 9.57 | <0.01* | 22.13 | | |
| Mitogen-activated protein kinase 10 | MAPK10 | Hs.25209 | AK124791 | 4q22-q23 | | | <0.01* | 21.09 | | |
| Mitogen-activated protein kinase 6 | MAPK6 | Hs.411847 | NM_002748 | 15q21 | | | <0.01* | 23.03 | | |
| Mitogen-activated protein kinase 9 | MAPK9 | Hs.484371 | BC032539 | 5q35 | | | <0.01* | 21.30 | <0.05 | 12.07 |
| Protein Phosphatase | | | | | | | | | | |
| Protein phosphatase 1, regulatory (inhibitor) subunit 2 | PPP1R2 | Hs.184840 | NM_006241 | 3q29 | | | <0.01* | 20.02 | | |
| Protein phosphatase 1, regulatory subunit 3C | PPP1R3C | Hs.303090 | BX537399 | 10q23-q24 | <0.01* | −54.15 | <0.01* | −47.47 | <0.01* | −43.72 |
| Protein phosphatase 2C, magnesium-dependent, catalytic subunit | PPM2C | Hs.22265 | NM_018444 | 8q22 | <0.01* | 35.09 | <0.01* | 47.45 | | |
| Protein phosphatase 2 (formerly | PPP2CA | Hs.483408 | BX640662 | 5q23-q31 | | | <0.01 | 17.92 | | |

TABLE 19-continued

| | | | | | MD - Control | | | | | |
|---|---|---|---|---|---|---|---|---|---|---|
| | | | | | Amy 133A-22 | | HC 133A-22 | | nAcc 133A-22 | |
| Name | Symbol | UniGene ID | UGRepAcc | Cytoband | p-value | % FC | p-value | % FC | p-value | % FC |
| 2A), catalytic subunit, alpha isoform | | | | | | | | | | |
| Protein phosphatase 2 (formerly 2A), regulatory subunit A (PR 65), alpha isoform | PPP2R1A | Hs.467192 | AK090488 | 19q13 | | | <0.05 | 16.04 | <0.05 | 12.64 |
| Protein phosphatase 2 (formerly 2A), regulatory subunit B (PR 52), beta isoform | PPP2R2B | Hs.193825 | M64930 | 5q31-5q32 | | | <0.01* | 29.87 | | |
| Protein phosphatase 2, regulatory subunit B (B56), gamma isoform | PPP2R5C | Hs.368264 | NM_002719 | 14q32 | | | <0.01 | 18.07 | | |
| Protein phosphatase 3 (formerly 2B), catalytic subunit, alpha isoform (calcineurin A alpha) | PPP3CA | Hs.435512 | NM_000944 | 4q21-q24 | <0.01* | 43.20 | <0.01* | 26.06 | | |
| Protein phosphatase 3 (formerly 2B), catalytic subunit, beta isoform (calcineurin A beta) | PPP3CB | Hs.500067 | BC028049 | 10q21-q22 | <0.01* | 37.18 | <0.01* | 47.07 | <0.01 | 17.08 |
| Protein phosphatase 3 (formerly 2B), regulatory subunit B, 19 kDa, alpha isoform (calcineurin B, type I) | PPP3R1 | Hs.280604 | BC027913 | 2p15 | <0.01* | 33.47 | <0.01* | 31.25 | | |
| AP1 | | | | | | | | | | |
| V-fos FBJ murine osteosarcoma viral oncogene homolog | FOS | Hs.25647 | BX647104 | 14q24 | | | <0.01* | -55.69 | <0.01* | -46.49 |
| Small G protein | | | | | | | | | | |
| Rho guanine nucleotide exchange factor (GEF) 3 | ARHGEF3 | Hs.476402 | AL833224 | 3p21-p13 | | | <0.01* | 28.51 | | |
| Ras homolog gene family, member I | ARHI | Hs.194695 | AK096393 | 1p31 | <0.05 | 20.60 | | | <0.01* | 28.06 |
| DIRAS family, GTP-binding RAS-like 2 | DIRAS2 | Hs.165636 | NM_017594 | 9q22 | <0.01* | 63.78 | | | | |
| RAB31, member RAS oncogene family | RAB31 | Hs.99528 | NM_006868 | 18p11 | <0.01* | -27.47 | | | | |
| Rab acceptor 1 (prenylated) | RABAC1 | Hs.11417 | BE779053 | 19q13 | | | | | <0.01 | 16.11 |
| RAN binding protein 6 | RANBP6 | Hs.167496 | BX537405 | 9p24 | | | <0.05 | 17.28 | | |
| RAP1, GTPase activating protein 1 | RAP1GA1 | Hs.148178 | BC035030 | 1p36-p35 | <0.01* | 22.75 | | | | |
| Hypothetical protein LOC145899 | RASGRF1 | Hs.459035 | NM_002891 | 15q24 | | | <0.01* | 26.84 | | |
| RAS guanyl releasing protein 1 (calcium and DAG-regulated) | RASGRP1 | Hs.511010 | AF081195 | 15q15 | <0.05 | 18.52 | | | | |
| RAS guanyl releasing protein 3 (calcium and DAG-regulated) | RASGRP3 | Hs.143674 | BC027849 | 2p25-p24 | | | <0.01* | -20.95 | | |
| Rho-related BTB domain containing 3 | RHOBTB3 | Hs.445030 | NM_014899 | 5q15 | <0.01* | -24.67 | | | | |
| Ras and Rab interactor 2 | RIN2 | Hs.472270 | NM_018993 | | | | <0.01* | -37.60 | | |
| Ras-like without CAAX 2 | RIT2 | Hs.464985 | AL713637 | 18q12 | | | | | <0.01* | 29.34 |
| Rho family GTPase 1 | RND1 | Hs.124940 | AK124288 | 12q12-q13 | | | <0.01* | 28.02 | | |
| V-Ki-ras2 Kirsten rat sarcoma 2 viral oncogene homolog | KRAS2 | Hs.505033 | NM_033360 | 12p12 | | | <0.01* | 20.01 | | |
| Ras-GTPase activating protein SH3 domain-binding protein 2 | G3BP2 | Hs.303676 | NM_203505 | 4q21 | | | <0.01* | 25.13 | <0.05 | 17.74 |
| Potassium channel | | | | | | | | | | |
| Potassium channel modulatory factor 1 | KCMF1 | Hs.345694 | NM_020122 | 2p11 | | | <0.01* | 23.55 | | |
| Potassium voltage-gated channel, shaker-related beta 2 | KCNAB2 | Hs.440497 | AK124696 | 1p36 | | | <0.05 | 19.97 | | |
| Potassium inwardly-rectifying channel, subfamily J 2 | KCNJ2 | Hs.1547 | NM_000891 | 17q23-q24 | | | <0.01* | -41.14 | | |
| Potassium inwardly-rectifying channel, subfamily J 10 | KCNJ10 | Hs.408960 | NM_002241 | 1q22-q23 | | | | | <0.01* | -25.25 |
| Potassium channel, subfamily K, member 1 | KCNK1 | Hs.208544 | AL833343 | 1q42-q43 | | | | | <0.05 | 11.05 |
| Potassium intermediate/small conductance calcium-activated channel, subfamily N, member 3 | KCNN3 | Hs.490765 | BX649146 | 1q21 | <0.01* | -30.93 | <0.01* | -23.10 | | |
| Potassium channel, subfamily V, member 1 | KCNV1 | Hs.13285 | NM_014379 | 8q22-q24 | | | <0.01* | 21.10 | | |
| Sodium channel | | | | | | | | | | |
| Sodium channel, voltage-gated, type II, alpha 2 | SCN2A2 | Hs.470470 | NM_021007 | 2q23-q24 | | | <0.01* | 26.22 | | |
| Sodium channel, voltage-gated, type III, beta | SCN3B | Hs.4865 | AB032984 | 11q24 | | | <0.01* | 22.62 | <0.01 | 17.61 |

TABLE 19-continued

| Name | Symbol | UniGene ID | UGRepAcc | Cytoband | MD - Control | | | | | |
| | | | | | Amy 133A-22 | | HC 133A-22 | | nAcc 133A-22 | |
| | | | | | p-value | % FC | p-value | % FC | p-value | % FC |
|---|---|---|---|---|---|---|---|---|---|---|
| Solute carrier family 12, (potassium-chloride transporter) member 5 | SLC12A5 | Hs.21413 | NM_020708 | 20q132 | <0.01* | 26.35 | <0.01* | 23.76 | | |
| Voltage-dependent anion channel 1 | VDAC1 | Hs.519320 | AK122953 | 5q31 | | | <0.01 | 18.44 | | |
| Calcium Channel | | | | | | | | | | |
| Calcium channel, voltage-dependent, alpha 2/delta 3 | CACNA2D3 | Hs.369421 | NM_018398 | 3p21 | | | <0.01* | 31.61 | | |
| Calcium channel, voltage-dependent, beta 2 subunit | CACNB2 | Hs.59093 | NM_000724 | 10p12 | | | <0.01* | 32.21 | | |
| Calcium channel, voltage-dependent, beta 3 subunit | CACNB3 | Hs.250712 | AK122911 | 12q13 | | | <0.01* | 43.88 | | |
| Calcium channel, voltage-dependent, gamma subunit 3 | CACNG3 | Hs.7235 | AK095553 | 16p12-p13 | | | <0.01* | 32.10 | | |
| Chloride channel | | | | | | | | | | |
| Chloride intracellular channel 4 | CLIC4 | Hs.440544 | AL117424 | 1p36 | | | <0.01* | −34.30 | | |

TABLE 20

| Gene Symbol | Accession | Gene Name | Chromosomal Location | Unigene clusters | Pathway | Anterior Cingulate Cortex ||||| Dorsolateral Prefrontal Cortex |||||
|---|---|---|---|---|---|---|---|---|---|---|---|---|---|---|---|
| | | | | | | FC BPD | FC MDD | FC Control | T BPD | T MDD | T Control | FC BPD | FC MDD | FC Control | T BPD | T MDD | T Control |
| HSPA2 | NM_021979 | heat shock 70 kDa protein 2 | 14q24.1 | Hs.432648 | Chaperone | 1.36 | 0.68 | 0.69 | 9.00 | -11.58 | -12.22 | 1.21 | 0.69 | 1.01 | 5.95 | -12.25 | 0.36 |
| SPP1 | NM_000582 | secreted phosphoprotein 1 (osteopontin, bone sialoprotein I, early T-lymphocyte activation 1) | 4q21-q25 | Hs.313 | Apoptosis | 1.28 | 0.84 | 0.36 | 7.67 | -5.88 | -35.42 | 1.32 | 0.86 | 0.70 | 8.49 | -5.10 | -12.35 |
| TM4SF10 | NM_031442 | transmembrane 4 superfamily member 10 | Xp11.4 | Hs.8769 | Apoptosis | 1.27 | 0.86 | 0.75 | 7.34 | -4.73 | -10.03 | 1.48 | 0.92 | 0.69 | 10.52 | -2.30 | -10.96 |
| CAT | NM_001752 | catalase | 11p13 | Hs.395771 | Oxidative Stress | 1.22 | 0.89 | 0.68 | 6.28 | -3.94 | -13.28 | 1.22 | 0.85 | 0.78 | 6.14 | -4.94 | -8.30 |
| S100B | NM_006272 | S100 calcium binding protein, beta (neural) | 21q22.3 | Hs.422181 | Apoptosis | 1.21 | 0.94 | 0.68 | 6.39 | -2.25 | -14.39 | 1.19 | 0.89 | 0.75 | 5.16 | -3.57 | -9.70 |
| NR4A1 | NM_173157 | nuclear receptor subfamily 4, group A, member 1 | 12q13 | Hs.1119 | Mitochondria | 0.83 | 0.86 | 1.17 | -9.63 | -8.30 | 9.19 | 0.83 | 0.90 | 1.15 | 8.36 | -5.21 | 7.06 |
| BZRAP1 | NM_004758 | benzodiazepine receptor (peripheral) associated protein 1 | 17q22-q23 | Hs.112499 | Mitochondria | 0.82 | 1.02 | 1.16 | -7.05 | 0.68 | 6.01 | 1.00 | 0.96 | 1.21 | 0.10 | -1.13 | 5.47 |
| GSK3B | NM_002093 | glycogen synthase kinase 3 beta | 3q13.3 | Hs.282359 | Apoptosis | 0.76 | 1.03 | 1.20 | -9.16 | 0.94 | 7.11 | 0.93 | 1.00 | 1.05 | -2.43 | 0.02 | 1.76 |
| COX7A1 | NM_001864 | cytochrome c oxidase subunit VIIa polypeptide 1 (muscle) | 19q13.1 | Hs.421621 | Mitochondria | 0.73 | 1.15 | 1.36 | -7.65 | 3.54 | 8.57 | 0.94 | 1.08 | 1.16 | -1.73 | 2.08 | 4.48 |
| UQCRB | NM_006294 | ubiquinol-cytochrome c reductase binding protein | 8q22 | Hs.131255 | Mitochondria | 1.06 | 1.20 | 0.98 | 1.64 | 5.37 | -0.58 | 1.15 | 1.09 | 1.14 | 3.48 | 2.16 | 3.62 |
| DUSP1 | NM_004417 | dual specificity phosphatase 1 | 5q34 | Hs.171695 | Oxidative Stress | 0.87 | 0.74 | 1.10 | -4.00 | -8.85 | 2.92 | 0.84 | 0.83 | 1.13 | -4.06 | -4.54 | 3.31 |
| DUSP6 | NM_001946 | dual specificity phosphatase 6 | 12q22-q23 | Hs.298654 | Apoptosis | 0.84 | 0.70 | 1.59 | -4.15 | -8.89 | 12.26 | 0.96 | 0.77 | 1.77 | -0.93 | -5.46 | 13.19 |
| TM4SF10 | NM_031442 | transmembrane 4 superfamily member 10 | Xp11.4 | Hs.8769 | Apoptosis | 1.27 | 0.86 | 0.75 | 7.34 | -4.73 | -10.03 | 1.48 | 0.92 | 0.69 | 10.52 | -2.30 | -10.96 |
| ATP6V0E | NM_003945 | ATPase, H+ transporting, lysosomal 9 kDa, V0 subunit e | 5q35.2 | Hs.440165 | Lysosyme | 1.15 | 0.88 | 0.59 | 2.89 | -2.87 | -12.33 | 1.36 | 0.90 | 0.63 | 6.10 | -2.23 | -10.14 |

TABLE 20-continued

| Gene Symbol | Accession | Gene Name | Chromosomal Location | Unigene clusters | Pathway | Anterior Cingulate Cortex | | | | | | Dorsalateral Prefrontal Cortex | | | |
|---|---|---|---|---|---|---|---|---|---|---|---|---|---|---|---|
| | | | | | | FC BPD | FC MDD | FC Control | T BPD | T MDD | T Control | FC BPD | FC MDD | FC Control | T BPD | T MDD | T Control |
| GLUL | S70290 | glutamate-ammonia ligase (glutamine synthase) | 1q31 | Hs.442669 | Mitochondria | 1.00 | 0.67 | 0.78 | -0.07 | -7.65 | -5.22 | 1.33 | 0.78 | 0.70 | 4.96 | -4.42 | -7.06 |
| SPP1 | NM_000582 | secreted phosphoprotein 1 (osteopontin, bone sialoprotein I, early T-lymphocyte activation 1) | 4q21-q25 | Hs.313 | Apoptosis | 1.28 | 0.84 | 0.36 | 7.67 | -5.88 | -35.42 | 1.32 | 0.86 | 0.70 | 8.49 | -5.10 | -12.35 |
| APG-1 | NM_014278 | heat shock protein (hsp110 family) | 4q28 | Hs.135554 | Chaperone | 0.98 | 1.05 | 1.06 | -0.22 | 0.64 | 0.92 | 1.26 | 1.19 | 0.95 | 2.81 | 2.20 | -0.77 |
| HSPA5 | NM_005347 | heat shock 70 kDa protein 5 (glucose-regulated protein, 78 kDa) | 9q33-q34.1 | Hs.310769 | Chaperone | 1.07 | 0.98 | 0.94 | 1.78 | -0.42 | -1.76 | 1.25 | 1.19 | 1.00 | 5.09 | 4.08 | 0.09 |
| GATM | NM_001482 | glycine amidinotransferase (L-arginine:glycine amidinotransferase) | 15q15.1 | Hs.75335 | Mitochondria | 1.08 | 0.80 | 0.61 | 2.62 | -7.64 | -18.24 | 1.23 | 0.78 | 0.79 | 7.34 | -8.90 | -9.41 |
| CAT | NM_001752 | catalase | 11p13 | Hs.395771 | Oxidative Stress | 1.22 | 0.89 | 0.68 | 6.28 | -3.94 | -13.28 | 1.22 | 0.85 | 0.78 | 6.14 | -4.94 | -8.30 |
| HADHB | NM_000183 | hydroxyacyl-Coenzyme A dehydrogenase/3-ketoacyl-Coenzyme A thiolase/enoyl-Coenzyme A hydratase (trifunctional protein), beta subunit | 2p23 | Hs.269878 | Mitochondria | 1.11 | 0.88 | 0.71 | 3.71 | -5.10 | -14.11 | 1.22 | 0.87 | 0.74 | 6.30 | -4.74 | -10.47 |
| CCT3 | NM_005998 | chaperonin containing TCP1, subunit 3 (gamma) | 1q23 | Hs.1708 | Chaperone | 1.15 | 1.07 | 0.96 | 4.98 | 2.43 | -1.67 | 1.22 | 1.04 | 1.03 | 5.97 | 1.34 | 0.96 |
| DAD1 | NM_001344 | defender against cell death 1 | 14q11-q12 | Hs.82890 | Apoptosis | 1.13 | 1.00 | 0.88 | 4.36 | 0.15 | -5.31 | 1.21 | 1.00 | 0.93 | 6.31 | 0.05 | -2.86 |
| HSPA2 | NM_021979 | heat shock 70 kDa protein 2 | 14q24.1 | Hs.432648 | Chaperone | 1.36 | 0.68 | 0.69 | 9.00 | -11.58 | -12.22 | 1.21 | 0.69 | 1.01 | 5.95 | -12.25 | 0.36 |
| NR4A1 | NM_173157 | nuclear receptor subfamily 4, group A, member 1 | 12q13 | Hs.1119 | Mitochondria | 0.83 | 0.86 | 1.17 | -9.63 | -8.30 | 9.19 | 0.83 | 0.90 | 1.15 | -8.36 | -5.21 | 7.06 |
| NAPG | NM_003826 | N-ethylmaleimide-sensitive factor attachment protein, gamma | 18p11.21 | Hs.370431 | Mitochondria | 0.94 | 1.07 | 1.69 | -1.32 | 1.53 | 12.83 | 0.83 | 1.04 | 1.83 | -3.06 | 0.60 | 10.97 |
| MAPK1 | NM_002745 | mitogen-activated protein kinase 1 | 22q11.21 | Hs.324473 | Mitochondria | 0.85 | 0.99 | 1.12 | -4.35 | -0.35 | 3.34 | 0.82 | 0.96 | 1.07 | -4.77 | -1.10 | 1.82 |

TABLE 20-continued

| Gene Symbol | Accession | Gene Name | Chromosomal Location | Unigene clusters | Pathway | Anterior Cingulate Cortex ||||| Dorsalateral Prefrontal Cortex |||||
|---|---|---|---|---|---|---|---|---|---|---|---|---|---|---|---|
| | | | | | | FC BPD | FC MDD | FC Control | T BPD | T MDD | T Control | FC BPD | FC MDD | FC Control | T BPD | T MDD | T Control |
| DAD1 | NM_001344 | defender against cell death 1 | 14q11-q12 | Hs.82890 | Apoptosis | 1.04 | 1.04 | 1.39 | 0.94 | 0.91 | 8.60 | 0.79 | 1.07 | 1.46 | -3.99 | 1.14 | 7.17 |
| STIP1 | NM_006819 | stress-induced-phosphoprotein 1 (Hsp70/Hsp90-organizing protein) | 11q13 | Hs.257827 | Chaperone | 1.17 | 1.16 | 0.97 | 4.50 | 4.51 | -0.86 | 1.06 | 1.23 | 1.00 | 1.49 | 5.06 | 0.06 |
| DUSP1 | NM_004417 | dual specificity phosphatase 1 | 5q34 | Hs.171695 | Oxidative Stress | 0.87 | 0.74 | 1.10 | -4.00 | -8.85 | 2.92 | 0.84 | 0.83 | 1.13 | -4.06 | -4.54 | 3.31 |
| SLC25A13 | NM_014251 | solute carrier family 25, member 13 (citrin) | 7q21.3 | Hs.9599 | Mitochondria | 1.06 | 0.91 | 0.97 | 2.33 | -3.94 | -1.55 | 1.03 | 0.83 | 1.03 | 1.11 | -6.61 | 1.10 |
| PER2 | NM_022817 | period homolog 2 (*Drosophila*) | 2q37.3 | Hs.410692 | Cycling | 0.90 | 0.83 | 1.31 | -3.22 | -5.79 | 8.81 | 0.97 | 0.80 | 1.35 | -0.76 | -5.58 | 8.02 |
| SST | NM_001048 | somatostatin | 3q28 | Hs.12409 | Apoptosis | 1.16 | 0.88 | 3.34 | 3.92 | -3.70 | 36.03 | 0.85 | 0.78 | 3.71 | 4.96 | -7.89 | 45.04 |
| DUSP6 | NM_001946 | dual specificity phosphatase 6 | 12q22-q23 | Hs.298654 | Apoptosis | 0.84 | 0.70 | 1.59 | -4.15 | -8.89 | 12.26 | 0.96 | 0.77 | 1.77 | -0.93 | -5.46 | 13.19 |
| USP9Y | NM_004654 | ubiquitin specific protease 9, Y-linked (fat facets-like, *Drosophila*) | Yq11.2 | Hs.371255 | 26S proteasome | 1.05 | 0.85 | 1.91 | 0.89 | -3.32 | 13.69 | 1.17 | 0.75 | 2.20 | 2.39 | -4.51 | 13.38 |
| HSPA2 | NM_021979 | heat shock 70 kDa protein 2 | 14q24.1 | Hs.432648 | Chaperone | 1.36 | 0.68 | 0.69 | 9.00 | -11.58 | -12.22 | 1.21 | 0.69 | 1.01 | 5.95 | -12.25 | 0.36 |
| SEMA6A | NM_020796 | sema domain, transmembrane domain (TM), and cytoplasmic domain, (semaphorin) 6A | 5q23.1 | Hs.443012 | Apoptosis | 0.84 | 0.74 | 0.68 | -4.41 | -8.25 | -11.00 | 0.92 | 0.62 | 1.10 | -1.70 | -10.66 | 2.29 |

TABLE 21

| Accession | Symbol | Name | Cytoband | Brain Region | Microarray fold change (BPD v Control) | QPCR fold change (BPD v Control) | Microarray fold change (MDD v Control) | QPCR fold change (MDD v Control) |
|---|---|---|---|---|---|---|---|---|
| NM_001001935 | ATP5A1 | ATP synthase, H+ transporting, mitochondrial F1 complex, alpha subunit, isoform 1, cardiac muscle | 18q12-q21 | DLPFC | 1.203 | 1.587* | 1.149 | 1.135 |
| NM_004047 | ATP6V0B | ATPase, H+ transporting, lysosomal 21 kDa, V0 subunit c" | 1p32.3 | DLPFC | 1.183 | 1.014 | 1.074 | 1.483* |
| NM_001696 | ATP6V1E1 | ATPase, H+ transporting, lysosomal 31 kDa, V1 subunit E isoform 1 | 22pter-q11.2 | DLPFC | 1.138 | 1.694* | 1.081 | 0.939 |
| NM_004458 | ACSL4 | Acyl-CoA synthetase long-chain family member 4 | Xq22.3-q23 | DLPFC | 1.165 | 1.266* | 1.105 | 1.095 |
| NM_174855 | IDH3B | Isocitrate dehydrogenase 3 (NAD+) beta | 20p13 | DLPFC | 1.148 | 1.007 | 1.084 | 1.189* |
| NM_133259 | LRPPRC | Leucine-rich PPR-motif containing | 2p21 | DLPFC | 1.218 | 1.62* | 1.164 | 1.802* |
| NM_021107 | MRPS12 | Mitochondrial ribosomal protein S12 | 19q13.1-q13.2 | DLPFC | 1.091 | 1.140 | 1.110 | 1.276* |
| NM_007103 | NDUFV1 | NADH dehydrogenase (ubiquinone) flavoprotein 1, 51 kDa | 11q13 | DLPFC | 1.115 | 0.989 | 1.104 | 1.430* |
| NM_173157 | NR4A1 | Nuclear receptor subfamily 4, group A, member 1 | 12q13 | DLPFC | 0.832 | 0.584* | 0.895 | 0.516* |
| NM_000021 | PSEN1 | Presenilin 1 (Alzheimer disease 3) | 14q24.3 | DLPFC | 1.081 | 1.306* | 0.882 | 0.825 |
| NM_001183 | ATP6AP1 | ATPase, H+ transporting, lysosomal accessory protein 1 | Xq28 | AnCg | 1.134 | 1.448 | 1.112 | 1.385 |
| NM_021979 | HSPA2 | Heat shock 70 kDa protein 2 | 14q24.1 | AnCg | 1.360 | 2.552* | 0.684 | 0.703 |
| NM_174855 | IDH3B | Isocitrate dehydrogenase 3 (NAD+) beta | 20p13 | AnCg | 1.136 | 0.998 | 1.099 | 0.985 |
| NM_133259 | LRPPRC | Leucine-rich PPR-motif containing | 2p21 | AnCg | 1.198 | 1.079 | 1.08 | 1.023 |
| NM_007103 | NDUFV1 | NADH dehydrogenase (ubiquinone) flavoprotein 1, 51 kDa | 11q13 | AnCg | 1.169 | 1.480 | 1.148 | 1.107 |
| NM_173157 | NR4A1 | Nuclear receptor subfamily 4, group A, member 1 | 12q13 | AnCg | 0.833 | 0.599* | 0.859 | 0.484* |
| NM_000021 | PSEN1 | Presenilin 1 (Alzheimer disease 3) | 14q24.3 | AnCg | 1.109 | 1.460* | 0.845 | 1.089 |
| AK125435 | PSMB1 | Proteasome (prosome, macropain) subunit, beta type, 1 | 6q27 | AnCg | 1.271 | 1.615* | 1.020 | 1.162 |
| NM_002812 | PSMD8 | Proteasome (prosome, macropain) 26S subunit, non-ATPase, 8 | 19q13.2 | AnCg | 1.155 | 1.358* | 1.104 | 1.231* |

TABLE 22

| Accession | MtDNA Encoded Gene | Symbol | Brain Region | | QPCR fold change BPD | QPCR fold change MDD | Description |
|---|---|---|---|---|---|---|---|
| AY882398 | MtATP6 | ATP6 | DLPFC | ATP synthase F0 subunit 6 | 0.853 | 0.876 | *Homo sapiens* isolate 20_U5a1(Tor13) mitochondrion, complete genome. |
| AY882398 | MtATP6 | ATP6 | AnCg | ATP synthase F0 subunit 6 | 0.588* | 0.721* | *Homo sapiens* isolate 20_U5a1(Tor13) mitochondrion, complete genome. |
| AY882398 | MtCO1 | COX1 | DLPFC | cytochrome c oxidase, subunit I | 0.687 | 0.875 | *Homo sapiens* isolate 20_U5a1(Tor13) mitochondrion, complete genome. |
| AY882398 | MtCO1 | COX1 | AnCg | cytochrome c oxidase, subunit I | 0.527* | 0.808 | *Homo sapiens* isolate 20_U5a1(Tor13) mitochondrion, complete genome. |
| AY882398 | MtCO2 | COX2 | DLPFC | cytochrome c oxidase, subunit II | 0.836 | 1.078 | *Homo sapiens* isolate 20_U5a1(Tor13) mitochondrion, complete genome. |
| AY882398 | MtCO2 | COX2 | AnCg | cytochrome c oxidase, subunit II | 0.758# | 0.895 | *Homo sapiens* isolate 20_U5a1(Tor13) mitochondrion, complete genome. |

TABLE 22-continued

| Accession | MtDNA Encoded Gene | Symbol | Brain Region | | | | |
|---|---|---|---|---|---|---|---|
| AY882398 | MtND1 | ND1 | DLPFC | NADH dehydrogenase, subunit I | 0.563# | 1.007 | Homo sapiens isolate 20_U5a1(Tor13) mitochondrion, complete genome. |
| AY882398 | MtND1 | ND1 | AnCg | NADH dehydrogenase, subunit I | 0.855 | 0.957 | Homo sapiens isolate 20_U5a1(Tor13) mitochondrion, complete genome. |
| AY882398 | MtND2 | ND2 | DLPFC | NADH dehydrogenase, subunit II | 0.539 | 0.921 | Homo sapiens isolate 20_U5a1(Tor13) mitochondrion, complete genome. |
| AY882398 | MtND3 | ND3 | DLPFC | NADH dehydrogenase, subunit III | 1.074 | 0.856 | Homo sapiens isolate 20_U5a1(Tor13) mitochondrion, complete genome. |
| AY882398 | MtND3 | ND3 | AnCg | NADH dehydrogenase, subunit III | 0.752# | 0.918 | Homo sapiens isolate 20_U5a1(Tor13) mitochondrion, complete genome. |
| AY882398 | MtATP6 | ATP6 | DLPFC | ATP synthase F0 subunit 6 | 0.853 | 0.876 | Homo sapiens isolate 20_U5a1(Tor13) mitochondrion, complete genome. |

| Accession | MtDNA Encoded Gene | Symbol | Brain Region | start and end bp | Table 1 | Complex | Hs.Unigene |
|---|---|---|---|---|---|---|---|
| AY882398 | MtATP6 | ATP6 | DLPFC | 8528 . . . 9208 | Mito paper Table 11 (mt) | V | Hs.4509 |
| AY882398 | MtATP6 | ATP6 | AnCg | 8528 . . . 9208 | Mito paper Table 11 (mt) | V | Hs.4509 |
| AY882398 | MtCO1 | COX1 | DLPFC | 5905 . . . 7446 | Mito paper Table 11 (mt) | IV | Hs.4512 |
| AY882398 | MtCO1 | COX1 | AnCg | 5905 . . . 7446 | Mito paper Table 11 (mt) | IV | Hs.4512 |
| AY882398 | MtCO2 | COX2 | DLPFC | 7587 . . . 8270 | Mito paper Table 11 (mt) | IV | Hs.4513 |
| AY882398 | MtCO2 | COX2 | AnCg | 7587 . . . 8270 | Mito paper Table 11 (mt) | IV | Hs.4513 |
| AY882398 | MtND1 | ND1 | DLPFC | 3308 . . . 4264 | Mito paper Table 11 (mt) | I | Hs.4535 |
| AY882398 | MtND1 | ND1 | AnCg | 3308 . . . 4264 | Mito paper Table 11 (mt) | I | Hs.4535 |
| AY882398 | MtND2 | ND2 | DLPFC | 4471 . . . 5514 | Mito paper Table 11 (mt) | I | Hs.4536 |
| AY882398 | MtND3 | ND3 | DLPFC | 10060 . . . 10405 | Mito paper Table 11 (mt) | I | Hs.4537 |
| AY882398 | MtND3 | ND3 | AnCg | 10060 . . . 10405 | Mito paper Table 11 (mt) | I | Hs.4537 |
| AY882398 | MtATP6 | ATP6 | DLPFC | 8528 . . . 9208 | Mito paper Table 11 (mt) | V | Hs.4509 |

*significant at $p < 0.05$ two-tailed
trend $p < 0.1$ two-tailed

TABLE 23

| Primer | Forward | Reverse |
|---|---|---|
| VASE | 5'-GACCCCATTCCCTCCATCAC-3' | 5'-GGCTACGCACCACCATGTG-3' |
| Exon a | 5"-GACGCAGCCAGTCCATAGC-3" | *1 |
| Exon b | 5'-CGTCTACCCCTGTTCCATTGTC-3' | 5'-TCTGGTGGAGACAATGGAACAG-3' |
| Exon c | 5'-TCCTGCCCTTGCAACCA-3' | 5'-GGTTGCAAGGGCAGGAAGA-3' |
| SEC exon | 5'-CCAAGCTGGTCTTCATAATGCTCTA-3' | 5'-TTTGATGCTTGAACACTATGAACATG-3' |
| Exon 3 | 5'-GGCGGCGCTCAATGG-3' | *2 |
| Exon 8 | *3 | 5'-GATCAGGTTCACTTTAATAGAGTTTCCA-3' |
| SNP9 for sequencing | 5'-CGCAGCCAGTCCGTAAGTAAAG-3' | 5'-AAGCTGGACCGGCTACTAGGA-3' |

TABLE 24

| | Tests For Genotypic Association (Risk Allele 1) | | | | | |
|---|---|---|---|---|---|---|
| | Heterozygous A/A<->C/A | | Homozygous C/C<->A/A | | Allele Positivity [C/C + C/A]<->A/A | |
| SNP 9 | Odds Ratio [C.I.] | $\chi^2$ (p-value) | Odds Ratio [C.I.] | $\chi^2$ (p-value) | Odds Ratio [C.I.] | $\chi^2$ (p-value) |
| SZ | 0.054 [0.003-1.16] | 6.6 (0.01) | 9.57 [0.47-193.92] | 3.86 (0.049) | 0.084 [0.004-1.67] | 4.88 (0.027) |
| SNP b | C/C<->T/C | | T/T<->C/C | | [T/T + T/C]<->C/C | |
| BPD | 4.05 [1.16-14.12] | 5.33 (0.02) | 2.97 [0.78-11.30] | 2.65 (0.103) | 3.66 [1.08-11.30] | 4.81 (0.028) |

TABLE 25

| Haplotype | Frequency (Odds Ratio) | | | p (value) |
|---|---|---|---|---|
| SNP 9-SNP b | Control | BPD* | SZ# | |
| C - T | 0.2 | 0.19 (0.95) | 0.31 (1.54) | *BPD vs Control <0.0001 |
| C - (T/C) | 0.31 | 0.46 (1.48) | 0.37 (1.19) | # SZ vs Control <0.0001 |
| (C/A) - (T/C) | 0.22 | 0.21 (0.95) | 0.11 (0.50) | SZ vs BPD 0.0003 |

TABLE 26

| Polymorphism | n | Genotype Counts (Frequency) | | | Allele Counts (Frequency) | | p (Fisher's exact test) |
|---|---|---|---|---|---|---|---|
| SNP 9 | | C/C | C/A | A/A | C | A | |
| Control | 55 | 33 (0.60) | 22 (0.40) | 0 (0) | 88 (0.80) | 22 (0.20) | |
| BPD | 70 | 47 (0.67) | 23 (0.33) | 0 (0) | 117 (0.84) | 23 (.16) | 0.466 |
| SZ | 35 | 24 (0.69) | 8 (0.23) | 3 (0.09) | 56 (0.80) | 14 (0.20) | 1 |
| BPD + SZ | 105 | 71 (0.68) | 31 (0.30) | 3 (0.02) | 173 (0.82) | 37 (0.18) | 0.602 |
| SNP b | | T/T | T/C | C/C | T | C | |
| Control | 55 | 16 (0.29) | 29 (0.53) | 10 (0.18) | 61 (0.55) | 49 (0.45) | |
| BPD | 70 | 19 (0.27) | 47 (0.67) | 4 (0.06) | 85 (0.61) | 55 (.39) | 0.402 |
| SZ | 35 | 13 (0.37) | 19 (0.54) | 3 (0.09) | 45 (0.64) | 25 (0.36) | 0.24 |
| BPD + SZ | 105 | 32 (0.30) | 66 (0.63) | 7 (0.07) | 130 (0.62) | 80 (0.38) | 0.264 |

TABLE 27

| SNP | Genotype | Splice Variant | BPD vs C | MDD vs C |
|---|---|---|---|---|
| SNP 9 | C/C | a-b-c | 0.052 ↑ | |
| SNP 6 | G/C | b-c-SEC | | 0.05 ↑ |
| SNP b | T/T | VASE (—) | | 0.056 ↑ |

TABLE 27-continued

| SNP | Genotype | Splice Variant | BPD vs C | MDD vs C |
|---|---|---|---|---|
| SNP b | T/C | c-SEC | 0.013 ↓ | |
| SNP b | T/C | NCAM1 Ct Q-PCR | | 0.053 ↑ |

TABLE 28.1

| UG Cluster | Symbol | Gene Name | Cytoband | fc_AnCg |
|---|---|---|---|---|
| Hs.549038 | | | | 1.919839205 |
| Hs.547062 | | Transcribed locus | | 1.773637669 |
| Hs.483454 | CNN3 | Calponin 3, acidic | 1p22-p21 | 1.71410127 |
| Hs.534365 | ZNF43 | Zinc finger protein 43 (HTF6) | 19p13.1-p12 | 1.653473114 |
| Hs.534314 | EIF5A | Eukaryotic translation initiation factor 5A | 17p13-p12 | 1.616760481 |
| Hs.427236 | | Transcribed locus | | 1.57275662 |
| Hs.336957 | ZNF479 | Zinc finger protein 479 | 7p11.2 | 1.561114027 |
| Hs.534385 | THOC4 | THO complex 4 | 17q25.3 | 1.545094715 |
| Hs.114084 | ENPP7 | Ectonucleotide pyrophosphatase/phosphodiesterase 7 | 17q25.3 | 1.490770143 |
| Hs.315369 | AQP4 | Aquaporin 4 | 18q11.2-q12.1 | 1.478027231 |
| Hs.370410 | KIAA1145 | KIAA1145 protein | 12q22 | 1.435347843 |
| Hs.75914 | RNP24 | Coated vesicle membrane protein | 12q24.31 | 1.419831899 |
| Hs.406708 | ILT7 | Leukocyte immunoglobulin-like receptor, subfamily A (without TM domain), member 4 | 19q13.4 | 1.410439598 |
| Hs.234249 | MAPK8IP1 | Mitogen-activated protein kinase 8 interacting protein 1 | 11p12-p11.2 | 1.371562585 |
| Hs.534525 | LOC114984 | Hypothetical protein BC014089 | 16p13.3 | 1.368785293 |
| Hs.212838 | A2M | Alpha-2-macroglobulin | 12p13.3-p12.3 | 1.365561844 |
| Hs.402752 | TAF15 | TAF15 RNA polymerase II, TATA box binding protein (TBP)-associated factor, 68 kDa | 17q11.1-q11.2 | 1.362205401 |
| Hs.535415 | | Ig rearranged gamma-chain mRNA, subgroup VH2, V-D-J region | | 1.355666889 |
| Hs.467138 | | Transcribed locus, moderately similar to XP_507997.1 similar to Kv channel interacting protein 2 isoform 4; A-type potassium channel modulatory protein 2; cardiac voltage gated potassium channel modulatory subunit; Kv channel-interacting protein 2 [Pan tr | | 1.351924341 |
| Hs.513600 | | Transcribed locus | | 1.347512479 |
| Hs.380218 | | Transcribed locus | | 1.327051286 |
| Hs.458607 | NOPE | Likely ortholog of mouse neighbor of Punc E11 | 15q22.31 | 1.324220424 |
| Hs.42034 | TCP10L | T-complex 10 (mouse)-like | 21q22.11 | 1.322514626 |
| Hs.521286 | RARRES2 | Retinoic acid receptor responder (tazarotene induced) 2 | 7q36.1 | 1.31025151 |
| Hs.25422 | | CDNA FLJ42519 fis, clone BRACE3000787 | | 1.309835897 |
| Hs.293379 | | Transcribed locus | | 1.307793259 |
| Hs.356766 | | Similar to RPE-spondin | 20q13.13 | 1.290259345 |
| Hs.379010 | PSCA | Prostate stem cell antigen | 8q24.2 | 1.287232595 |
| Hs.511757 | GJB6 | Gap junction protein, beta 6 (connexin 30) | 13q11-q12.1 | 1.287226239 |
| Hs.59106 | CGRRF1 | Cell growth regulator with ring finger domain 1 | 14q22.2 | 1.284552431 |
| Hs.83916 | NDUFA5 | NADH dehydrogenase (ubiquinone) 1 alpha subcomplex, 5, 13 kDa | 7q32 | 1.283862892 |
| Hs.119878 | FLJ34389 | Hypothetical protein FLJ34389 | 16q22.3 | 1.28271805 |
| Hs.494261 | PSAT1 | Phosphoserine aminotransferase 1 | 9q21.2 | 1.276727208 |
| Hs.75969 | PNRC1 | Proline-rich nuclear receptor coactivator 1 | 6q15 | 1.273555895 |
| Hs.467273 | CACNG8 | Calcium channel, voltage-dependent, gamma subunit 8 | 19q13.4 | 1.270119391 |
| Hs.280805 | MGC20579 | Hypothetical protein MGC20579 | 13q34 | 1.269164507 |
| Hs.145480 | | Transcribed locus | | 1.266189386 |
| Hs.511454 | PLXNA4 | Plexin A4 | 7q32.3 | 1.263673467 |
| Hs.80132 | SNX15 | Sorting nexin 15 | 11q12 | 1.26259913 |
| Hs.514819 | AP2B1 | Adaptor-related protein complex 2, beta 1 subunit | 17q11.2-q12 | 1.250901951 |
| Hs.385772 | LOC283914 | Hypothetical protein LOC283914 | 16p11.1 | 1.247941693 |
| Hs.151536 | RAB13 | RAB13, member RAS oncogene family | 1q21.2 | 1.247404054 |
| Hs.548424 | | Transcribed locus | | 1.245303451 |
| Hs.519930 | C6orf62 | Chromosome 6 open reading frame 62 | 6p22.2 | 1.233111115 |
| Hs.45140 | TMEM35 | Transmembrane protein 35 | Xq2.1 | 1.232645678 |
| Hs.505295 | MADP-1 | MADP-1 protein | 12q12 | 1.226870897 |
| Hs.513883 | PELP1 | Proline-, glutamic acid-, leucine-rich protein 1 | 17p13.2 | 1.224880728 |
| Hs.474836 | LOC387593 | TPTE/TPIP pseudogene | 22q13 | 1.223415544 |
| Hs.115284 | ZNF213 | Zinc finger protein 213 | 16p13.3 | 1.223309419 |
| Hs.369624 | 15E1.2 | Hypothetical protein 15E1.2 | 12q24.31 | 1.223144605 |
| Hs.467960 | RAB10 | RAB10, member RAS oncogene family | 2p23.3 | 1.222273799 |
| Hs.533282 | NONO | Non-POU domain containing, octamer-binding | Xq13.1 | 1.219220007 |
| Hs.181272 | PKD2 | Polycystic kidney disease 2 (autosomal dominant) | 4q21-q23 | 1.212879872 |
| Hs.80720 | GAB1 | GRB2-associated binding protein 1 | 4q31.21 | 1.211569918 |
| Hs.123464 | P2RY5 | Purinergic receptor P2Y, G-protein coupled, 5 | 13q14 | 1.210914564 |
| Hs.507185 | ZFPM1 | Zinc finger protein, multitype 1 | 16q24.2 | 1.210160133 |
| Hs.5324 | C2orf25 | Chromosome 2 open reading frame 25 | 2q23.3 | 1.209212561 |
| Hs.374847 | LOC400794 | Hypothetical gene supported by BC030596 | 1q23.2 | 1.208951568 |
| Hs.517792 | C3orf10 | Chromosome 3 open reading frame 10 | 3p25.3 | 1.208760837 |
| Hs.517352 | PRODH | Proline dehydrogenase (oxidase) 1 | 22q11.21 | 1.206253745 |
| Hs.483561 | ORF1-FL49 | Putative nuclear protein ORF1-FL49 | 5q31.2 | 1.205748855 |
| Hs.75640 | NPPA | Natriuretic peptide precursor A | 1p36.21 | 1.20542617 |
| Hs.491695 | UBE2V2 | Ubiquitin-conjugating enzyme E2 variant 2 | 8q11.21 | 1.204850064 |

TABLE 28.1-continued

| UG Cluster | Symbol | Gene Name | Cytoband | fc_AnCg |
|---|---|---|---|---|
| Hs.335057 | NEDD5 | Neural precursor cell expressed, developmentally down-regulated 5 | 2q37 | 1.202774491 |
| Hs.28280 | SLC35F4 | Solute carrier family 35, member F4 | 14q22.2 | 1.201026204 |

TABLE 28.2

| UG Cluster | Symbol | Gene Name | Cytoband | fc_AnCg |
|---|---|---|---|---|
| Hs.134974 | GAP43 | Growth associated protein 43 | 3q13.1-q13.2 | 0.833001805 |
| Hs.444637 | LRP8 | Low density lipoprotein receptor-related protein 8, apolipoprotein e receptor | 1p34 | 0.832591468 |
| Hs.268849 | GLO1 | Glyoxalase I | 6p21.3-p21.1 | 0.832479968 |
| Hs.435952 | CDK5RAP1 | CDK5 regulatory subunit associated protein 1 | 20pter-q11.23 | 0.831820461 |
| Hs.360940 | dJ222E13.1 | Kraken-like | 22q13 | 0.828943053 |
| Hs.500721 | MMS19L | MMS19-like (MET18 homolog, S. cerevisiae) | 10q24-q25 | 0.827060597 |
| Hs.200285 | TCF4 | Transcription factor 4 | 18q21.1 | 0.826908526 |
| Hs.2890 | PRKCG | Protein kinase C, gamma | 19q13.4 | 0.82630472 |
| Hs.153661 | | Transcribed locus | | 0.825857073 |
| Hs.483924 | MRPL22 | Mitochondrial ribosomal protein L22 | 5q33.1-q33.3 | 0.825300862 |
| Hs.210385 | HERC1 | Hect (homologous to the E6-AP (UBE3A) carboxyl terminus) domain and RCC1 (CHC1)-like domain (RLD) 1 | 15q22 | 0.82523312 |
| Hs.353454 | FLJ10276 | Hypothetical protein FLJ10276 | 1p35.1 | 0.825093453 |
| Hs.157234 | | MRNA; cDNA DKFZp547A0515 (from clone DKFZp547A0515) | | 0.824586185 |
| Hs.75667 | SYP | Synaptophysin | Xp11.23-p11.22 | 0.824282156 |
| Hs.451353 | | Homo sapiens, clone IMAGE: 5288537, mRNA | | 0.823552515 |
| Hs.514373 | MTMR4 | Myotubularin related protein 4 | 17q22-q23 | 0.823152304 |
| Hs.102696 | MCTS1 | Malignant T cell amplified sequence 1 | Xq22-q24 | 0.822759185 |
| Hs.445503 | SYN2 | Synapsin II | 3p25 | 0.822588683 |
| Hs.524094 | PS1D | Putative S1 RNA binding domain protein | 1p35.2 | 0.822570466 |
| Hs.522668 | UBQLN2 | Ubiquilin 2 | Xp11.23-p11.1 | 0.821156426 |
| Hs.517148 | TH1L | TH1-like (Drosophila) | 20q13 | 0.821107397 |
| Hs.380334 | ZNF148 | Zinc finger protein 148 (pHZ-52) | 3q21 | 0.821027253 |
| Hs.534575 | MGC2198 | Hypothetical protein MGC2198 | 5q35.2 | 0.819426558 |
| Hs.47546 | C6orf70 | Chromosome 6 open reading frame 70 | 6q27 | 0.819049461 |
| Hs.25601 | CHD3 | Chromodomain helicase DNA binding protein 3 | 17p13.1 | 0.818740301 |
| Hs.460978 | APPBP1 | Amyloid beta precursor protein binding protein 1, 59 kDa | 16q22 | 0.818504577 |
| Hs.448851 | USP6 | Ubiquitin specific protease 6 (Tre-2 oncogene) | 17q11 | 0.818420142 |
| Hs.532755 | GTL3 | Likely ortholog of mouse gene trap locus 3 | 16q21 | 0.816593983 |
| Hs.98510 | WDR44 | WD repeat domain 44 | Xq24 | 0.815070227 |
| Hs.189119 | CXXC5 | CXXC finger 5 | 5q31.2 | 0.814065874 |
| Hs.134060 | FNBP1L | Formin binding protein 1-like | 1p22.1 | 0.813237448 |
| Hs.549821 | | Data not found | | 0.812556603 |
| Hs.78944 | RGS2 | Regulator of G-protein signalling 2, 24 kDa | 1q31 | 0.811942329 |
| Hs.535060 | | LOC441385 | 9p24.1 | 0.811837917 |
| Hs.549166 | | Data not found | | 0.811572937 |
| Hs.224418 | | Transcribed locus | | 0.811556308 |
| Hs.5258 | MAGED1 | Melanoma antigen, family D, 1 | Xp11.23 | 0.811035568 |
| Hs.537449 | | Transcribed locus | | 0.810141577 |
| Hs.515545 | TBC1D17 | TBC1 domain family, member 17 | 19q13.33 | 0.809453648 |
| Hs.268122 | LOC51321 | Hypothetical protein LOC51321 | 17q24.2 | 0.808975121 |
| Hs.502910 | NKIRAS2 | NFKB inhibitor interacting Ras-like 2 | 17q21.2 | 0.808919755 |
| Hs.471876 | ING5 | Inhibitor of growth family, member 5 | 2q37.3 | 0.806159689 |
| Hs.198612 | GPR51 | G protein-coupled receptor 51 | 9q22.1-q22.3 | 0.806097527 |
| Hs.401509 | RBM10 | RNA binding motif protein 10 | Xp11.23 | 0.806076882 |
| Hs.380857 | TD-60 | RCC1-like | 1p36.13 | 0.805526827 |
| Hs.49582 | PPP1R12A | Protein phosphatase 1, regulatory (inhibitor) subunit 12A | 12q15-q21 | 0.805427552 |
| Hs.515162 | CALR | Calreticulin | 19p13.3-p13.2 | 0.804252658 |
| Hs.444558 | KHDRBS3 | KH domain containing, RNA binding, signal transduction associated 3 | 8q24.2 | 0.803823019 |
| Hs.317632 | CDH18 | Cadherin 18, type 2 | 5p15.2-p15.1 | 0.803613164 |
| Hs.471104 | NOP5/NOP58 | Nucleolar protein NOP5/NOP58 | 2q33.1 | 0.802352232 |
| Hs.348526 | LOC474358 | Hypothetical BC042079 locus | 10q23-q25 | 0.802291667 |
| Hs.475018 | TCF20 | Transcription factor 20 (AR1) | 22q13.3 | 0.801897074 |
| Hs.463074 | ATP6V0A1 | ATPase, H+ transporting, lysosomal V0 subunit a isoform 1 | 17q21 | 0.801766875 |
| Hs.28144 | FSD1 | Fibronectin type 3 and SPRY domain containing 1 | 19p13.3 | 0.800329999 |
| Hs.32309 | INPP1 | Inositol polyphosphate-1-phosphatase | 2q32 | 0.796446965 |
| Hs.512973 | HSPC121 | Butyrate-induced transcript 1 | 15q22.2 | 0.796376497 |
| Hs.13245 | LPPR4 | Plasticity related gene 1 | 1p21.3 | 0.794472742 |
| Hs.199743 | ME3 | Malic enzyme 3, NADP(+)-dependent, mitochondrial | 11cen-q22.3 | 0.794075417 |
| Hs.523755 | FLRT1 | Fibronectin leucine rich transmembrane protein 1 | 11q12-q13 | 0.792664481 |
| Hs.515785 | BLVRB | Biliverdin reductase B (flavin reductase (NADPH)) | 19q13.1-q13.2 | 0.792511112 |
| Hs.437277 | MGAT4B | Mannosyl (alpha-1,3-)-glycoprotein beta-1,4-N-acetylglucosaminyltransferase, isoenzyme B | 5q35 | 0.790721678 |
| Hs.387982 | | CDNA clone IMAGE; 5261489, partial cds | | 0.789879979 |
| Hs.136164 | TSPYL2 | TSPY-like 2 | Xp11.2 | 0.788609957 |
| Hs.332847 | CRIM1 | Cysteine-rich motor neuron 1 | 2p21 | 0.786568887 |

TABLE 28.2-continued

| UG Cluster | Symbol | Gene Name | Cytoband | fc_AnCg |
|---|---|---|---|---|
| Hs.348493 | GPRASP2 | G protein-coupled receptor associated sorting protein 2 | Xq22.1 | 0.786263129 |
| Hs.7736 | MRPL27 | Mitochondrial ribosomal protein L27 | 17q21.3-q22 | 0.785613917 |
| Hs.177275 | ANKRD6 | Ankyrin repeat domain 6 | 6q14.2-q16.1 | 0.783389812 |
| Hs.124015 | HAGHL | Hydroxyacylglutathione hydrolase-like | 16p13.3 | 0.782617204 |
| Hs.79322 | QARS | Glutaminyl-tRNA synthetase | 3p21.3-p21.1 | 0.781931967 |
| Hs.158748 | SLC35F3 | Solute carrier family 35, member F3 | 1q42.2 | 0.780681609 |
| Hs.158460 | CDK5R2 | Cyclin-dependent kinase 5, regulatory subunit 2 (p39) | 2q35 | 0.779713574 |
| Hs.337730 | LCMT1 | Leucine carboxyl methyltransferase 1 | 16p12.3-16p12.1 | 0.777655555 |
| Hs.282998 | RBM9 | RNA binding motif protein 9 | 22q13.1 | 0.775799713 |
| Hs.60300 | ZNF622 | Zinc finger protein 622 | 5p15.1 | 0.775473024 |
| Hs.405590 | EIF3S6 | Eukaryotic translation initiation factor 3, subunit 6 48 kDa | 8q22-q23 | 0.775166314 |
| Hs.373952 | CAMTA2 | Calmodulin binding transcription activator 2 | 17p13.2 | 0.775135303 |
| Hs.528187 | | Hypothetical gene supported by AK096649 | 2q33.1 | 0.774877993 |
| Hs.536326 | | Transcribed locus | | 0.774173869 |
| Hs.532231 | COPG2 | Coatomer protein complex, subunit gamma 2 | 7q32 | 0.773663441 |
| Hs.114169 | LRRTM2 | Leucine rich repeat transmembrane neuronal 2 | 5q31.3 | 0.773056562 |
| Hs.496267 | IGBP1 | Immunoglobulin (CD79A) binding protein 1 | Xq13.1-q13.3 | 0.771399953 |
| Hs.190722 | HSPC142 | HSPC142 protein | 19p13.11 | 0.770969106 |
| Hs.130197 | KIAA1889 | KIAA1889 protein | 8q12.1 | 0.770498302 |
| Hs.436446 | ARMET | Arginine-rich, mutated in early stage tumors | 3p21.1 | 0.769942554 |
| Hs.381300 | MGC57858 | Hypothetical protein MGC57858 | 6p21.31 | 0.769698647 |
| Hs.33191 | UNC5A | Unc-5 homolog A (C. elegans) | 5q35.2 | 0.769489374 |
| Hs.350065 | PLXNA2 | Plexin A2 | 1q32.2 | 0.767903428 |
| Hs.48372 | | Full length insert cDNA clone YZ87G11 | | 0.766810973 |
| Hs.3797 | RAB26 | RAB26, member RAS oncogene family | 16p13.3 | 0.765394204 |
| Hs.21925 | | Transcribed locus | | 0.764561674 |
| Hs.336588 | LOC147670 | Hypothetical protein LOC147670 | 19q13.43 | 0.763351376 |
| Hs.78466 | PSMD8 | Proteasome (prosome, macropain) 26S subunit, non-ATPase, 8 | 19q13.2 | 0.76234581 |
| Hs.121520 | AMIGO2 | Amphoterin induced gene 2 | 12q13.11 | 0.760653807 |
| Hs.443731 | USP8 | Ubiquitin specific protease 8 | 15q21.2 | 0.75760815 |
| Hs.171501 | USP11 | Ubiquitin specific protease 11 | Xp11.23 | 0.755609225 |
| Hs.187861 | THRB | Thyroid hormone receptor, beta (erythroblastic leukemia viral (v-erb-a) oncogene homolog 2, avian) | 3p24.3 | 0.755503889 |
| Hs.272284 | SLITRK4 | SLIT and NTRK-like family, member 4 | Xq27.3 | 0.755411535 |
| Hs.509736 | HSPCB | Heat shock 90 kDa protein 1, beta | 6p12 | 0.755057388 |
| Hs.188594 | | Transcribed locus | | 0.755026908 |
| Hs.497806 | MARK1 | MAP/microtubule affinity-regulating kinase 1 | 1q41 | 0.751792399 |
| Hs.549761 | | Data not found | | 0.749944 |
| Hs.479867 | CENPC1 | Centromere protein C 1 | 4q12-q13.3 | 0.749713558 |
| Hs.135736 | NGL-1 | Netrin-G1 ligand | 11p12 | 0.747993997 |
| Hs.463466 | CA10 | Carbonic anhydrase X | 17q21 | 0.746516358 |
| Hs.143587 | | Transcribed locus | | 0.745018326 |
| Hs.549196 | | Data not found | | 0.744120055 |
| Hs.534913 | | Hypothetical gene supported by BC019717 | 16p11.2 | 0.743499122 |
| Hs.523550 | ZNF364 | Zinc finger protein 364 | 1q21.1 | 0.742420643 |
| Hs.90242 | | Homo sapiens, clone IMAGE: 4796172, mRNA | | 0.741848633 |
| Hs.475150 | KIAA0767 | KIAA0767 protein | 22q13.31 | 0.741559246 |
| Hs.530698 | CHD8 | Chromodomain helicase DNA binding protein 8 | 14q11.2 | 0.738476834 |
| Hs.55879 | ABCC10 | ATP-binding cassette, sub-family C (CFTR/MRP), member 10 | 6p21.1 | 0.738455293 |
| Hs.323537 | FLJ12953 | Hypothetical protein FLJ12953 similar to Mus musculus D3Mm3e | 2p13.1 | 0.737391028 |
| Hs.301296 | | CDNA: FLJ23131 fis, clone LNG08502 | | 0.737354551 |
| Hs.502460 | DGKZ | Diacylglycerol kinase, zeta 104 kDa | 11p11.2 | 0.734852399 |
| Hs.471096 | ALS2 | Amyotrophic lateral sclerosis 2 (juvenile) | 2q33.1 | 0.73175125 |
| Hs.92732 | PDZK4 | PDZ domain containing 4 | Xq28 | 0.727016153 |
| Hs.537841 | | Transcribed locus | | 0.726748437 |
| Hs.7744 | NDUFV1 | NADH dehydrogenase (ubiquinone) flavoprotein 1, 51 kDa | 11q13 | 0.726496223 |
| Hs.100890 | RPRM | Reprimo, TP53 dependant G2 arrest mediator candidate | 2q23.3 | 0.719810824 |
| Hs.6132 | CPNE6 | Copine VI (neuronal) | 14q11.2 | 0.718586854 |
| Hs.412019 | C6orf80 | Chromosome 6 open reading frame 80 | 6q23.1-q24.1 | 0.715749314 |
| Hs.119594 | CIT | Citron (rho-interacting, serine/threonine kinase 21) | 12q24 | 0.712998565 |
| Hs.518460 | AP2M1 | Adaptor-related protein complex 2, mu 1 subunit | 3q28 | 0.709632072 |
| Hs.65425 | CALB1 | Calbindin 1, 28 kDa | 8q21.3-q22.1 | 0.70924145 |
| Hs.479116 | SH3TC1 | SH3 domain and tetratricopeptide repeats 1 | 4p16.1 | 0.704347818 |
| Hs.173859 | FZD7 | Frizzled homolog 7 (Drosophila) | 2q33 | 0.697933574 |
| Hs.363137 | ACAT2 | Acetyl-Coenzyme A acetyltransferase 2 (acetoacetyl Coenzyme A thiolase) | 6q25.3-q26 | 0.695447549 |
| Hs.153648 | PPFIA4 | Protein tyrosine phosphatase, receptor type, f polypeptide (PTPRF), interacting protein (liprin), alpha 4 | 1q32.1 | 0.694615615 |
| Hs.524071 | | Transcribed locus, strongly similar to XP_084672.3 similar to CDNA sequence BC021608 [Homo sapiens] | | 0.691986755 |
| Hs.506784 | LNK | Lymphocyte adaptor protein | 12q24 | 0.688023619 |
| Hs.516617 | SATB2 | SATB family member 2 | 2q33 | 0.681642635 |
| Hs.23406 | KCTD4 | Potassium channel tetramerisation domain containing 4 | 13q14.12 | 0.676435668 |
| Hs.220950 | FOXO3A | Forkhead box O3A | 6q21 | 0.669990152 |
| Hs.370549 | BCL11A | B-cell CLL/lymphoma 11A (zinc finger protein) | 2p16.1 | 0.654002694 |
| Hs.483239 | ALDH7A1 | Aldehyde dehydrogenase 7 family, member A1 | 5q31 | 0.651849727 |
| Hs.445733 | GSK3B | Glycogen synthase kinase 3 beta | 3q13.3 | 0.647879909 |
| Hs.268515 | MN1 | Meningioma (disrupted in balanced translocation) 1 | 22q11 | 0.64462122 |

TABLE 28.2-continued

| UG Cluster | Symbol | Gene Name | Cytoband | fc_AnCg |
|---|---|---|---|---|
| Hs.319503 | PTCHD1 | Patched domain containing 1 | Xp22.11 | 0.644497163 |
| Hs.106511 | PCDH17 | Hypothetical protein LOC144997 | 13q21.1 | 0.644270897 |
| Hs.91448 | DUSP14 | Dual specificity phosphatase 14 | 17q12 | 0.639891125 |
| Hs.448041 | FLJ32363 | FLJ32363 protein | 5p12 | 0.633100428 |
| Hs.22584 | PDYN | Prodynorphin | 20pter-p12 | 0.630525299 |
| Hs.215839 | DLG2 | Discs, large homolog 2, chapsyn-110 (*Drosophila*) | 11q21 | 0.620144715 |
| Hs.11899 | HMGCR | 3-hydroxy-3-methylglutaryl-Coenzyme A reductase | 5q13.3-q14 | 0.619486994 |
| Hs.23539 | | CDNA FLJ42249 fis, clone TKIDN2007667 | | 0.614085673 |
| Hs.314436 | NEDL2 | NEDD4-related E3 ubiquitin ligase NEDL2 | 2q32.3 | 0.605505392 |
| Hs.490294 | KIAA1549 | KIAA1549 protein | 7q34 | 0.548338996 |
| Hs.518469 | FLJ10560 | Hypothetical protein FLJ10560 | 3q27.3 | 0.498445319 |
| Hs.546322 | NOL4 | Nucleolar protein 4 | 18q12 | 0.491050809 |
| Hs.282177 | PIP5K1C | Phosphatidylinositol-4-phosphate 5-kinase, type I, gamma | 19p13.3 | 0.490622069 |
| Hs.2785 | KRT17 | Keratin 17 | 17q12-q21 | 0.474185311 |
| Hs.536506 | | Transcribed locus | | 0.467413109 |
| Hs.435001 | KLF10 | Kruppel-like factor 10 | 8q22.2 | 0.463636382 |
| Hs.537539 | | Transcribed locus | | 0.358666831 |

TABLE 29 v-ATPase Human MDD vs Monkey stressed Array Results

| UGRepAcc | Name | Symbol | Human T-test Affy HIP t2hcmdd.affy | Human T-test illu HIP tHCMdd.illu | Monkey Midlife Stress change |
|---|---|---|---|---|---|
| BQ230447 | ATPase, H+ transporting, lysosomal 9 kDa, V0 subunit e | ATP6V0E | −2.8565 | −2.2254 | −1.07 |
| AF245517 | ATPase, H+ transporting, lysosomal V0 subunit a isoform 4 | ATP6V0A4 | −1.6935 | −1.5208 | 1.01 |
| NM_012463 | ATPase, H+ transporting, lysosomal V0 subunit a isoform 2 | ATP6V0A2 | −0.8322 | −1.6802 | −1.05 |
| CR607789 | ATPase, H+ transporting, lysosomal 13 kDa, V1 subunit G isoform 1 | ATP6V1G1 | −0.0535 | −0.0440 | −1.08 |
| AK127853 | ATPase, H+ transporting, lysosomal 56/58 kDa, V1 subunit B, isoform 1 (Renal tubular acidosis with deafness) | ATP6V1B1 | 0.3202 | −0.8313 | 1.02 |
| BF214530 | ATPase, H+ transporting, lysosomal 31 kDa, V1 subunit E isoform 1 | ATP6V1E1 | 1.3703 | 1.9643 | −1.01 |
| AK024101 | ATPase, H+ transporting, lysosomal 34 kDa, V1 subunit D | ATP6V1D | 1.6380 | 2.6589 | 1.09 |
| NM_001690 | ATPase, H+ transporting, lysosomal 70 kDa, V1 subunit A | ATP6V1A | 1.7837 | 2.4222 | 1.15 |
| NM_001695 | ATPase, H+ transporting, lysosomal 42 kDa, V1 subunit C, isoform 1 | ATP6V1C1 | 1.7882 | 1.0692 | −1.01 |
| AK128641 | ATPase, H+ transporting, lysosomal 38 kDa, V0 subunit d isoform 1 | ATP6V0D1 | 1.8249 | 2.4330 | 1.03 |
| BC053601 | ATPase, H+ transporting, lysosomal 21 kDa, V0 subunit c" | ATP6V0B | 1.8268 | −0.2217 | 1.10 |
| AK127505 | ATPase, H+ transporting, lysosomal 16 kDa, V0 subunit c | ATP6V0C | 2.5856 | 2.2705 | −1.04 |
| NM_001693 | ATPase, H+ transporting, lysosomal 56/58 kDa, V1 subunit B, isoform 2 | ATP6V1B2 | 2.6827 | 2.6120 | 1.04 |
| AK125927 | ATPase, H+ transporting, lysosomal V0 subunit a isoform 1 | ATP6V0A1 | 3.3021 | 1.2269 | 1.04 |

TABLE 30

| Probe Set Name | Identifier | LocusLink | Name | AII AD H2O Ave | AII AD CUS Ave | CUS T | CUS FC | AII CUS + AD T | AII CUS + AD FC |
|---|---|---|---|---|---|---|---|---|---|
| 1370043_at | NM_031753 | 79559 | activated leukocyte cell adhesion molecule | 8.554991091 | 8.737278 | 0.305517 | 1.134681103 | −0.337997115 | 0.87551622 |
| 1375424_at | BE107525 | 64040 | aldehyde dehydrogenase family 9, subfamily A1 | 7.7269596 | 7.985884 | 0.253566 | 1.196585931 | −0.275888751 | 0.815851533 |
| 1370176_at | BG378620 | 171086 | amyotrophic lateral sclerosis 2 (juvenile) chromosome region, candidate 3 | 8.289171999 | 8.644384 | 0.549287 | 1.279173789 | −0.422598222 | 0.816014485 |
| 1370050_at | NM_053311 | 29598 | ATPase, Ca++ transporting, plasma membrane 1 | 10.02156406 | 10.47301 | 0.407594 | 1.367412006 | −0.303601287 | 0.776657575 |
| 1367585_a_at | M28647 | 24211 | ATPase, Na+K+ transporting, alpha 1 | 10.86677482 | 10.70967 | −0.27986 | 0.896825718 | 0.365553735 | 1.117986929 |
| 1398781_at | NM_053884 | 116664 | ATPase, vacuolar, 14 kD | 9.794708887 | 9.635878 | −0.40588 | 0.895750971 | 0.501130634 | 1.131514226 |
| 1367595_s_at | NM_012512 | 24223 | Beta-2-microglobulin | 10.16168978 | 9.88582 | −0.59779 | 0.825952265 | 0.384629381 | 1.135862492 |

TABLE 30-continued

| Probe Set Name | Identifier | LocusLink | Name | AII AD H2O Ave | AII AD CUS Ave | CUS T | CUS FC | AII CUS + AD T | AII CUS + AD FC |
|---|---|---|---|---|---|---|---|---|---|
| 1370074_at | NM_057196 | 117542 | brain-specific angiogenesis inhibitor 1-associated protein 2 | 8.394268852 | 8.230674 | −0.55098 | 0.892797502 | 0.467062082 | 1.118839281 |
| 1369993_at | NM_133605 | 171140 | calcium/calmodulin-dependent protein kinase (CaM kinase) II gamma | 8.242780231 | 8.480603 | 0.338888 | 1.179211766 | −0.292444973 | 0.860882267 |
| 1389824_at | BF404381 | 25400 | calcium/calmodulin-dependent protein kinase II alpha subunit | 7.810218827 | 7.950381 | 0.416069 | 1.102029271 | −0.470849794 | 0.896960966 |
| 1398251_a_at | NM_021739 | 24245 | calcium/calmodulin-dependent protein kinase II beta subunit | 8.228441025 | 8.843395 | 0.474736 | 1.531509499 | −0.367083116 | 0.701179029 |
| 1367462_at | U10861 | 29156 | calpain, small subunit 1 | 9.116789268 | 8.937121 | −0.50886 | 0.882905842 | 0.648775676 | 1.158940404 |
| 1389876_at | BE111167 | 287005 | CaM-kinase II inhibitor alpha | 8.411415385 | 8.683458 | 0.388539 | 1.207516219 | −0.331393094 | 0.833810939 |
| 1370853_at | AA858621 | 287005 | CaM-kinase II inhibitor alpha | 9.552520138 | 9.824481 | 0.484035 | 1.207447775 | −0.302368972 | 0.879487359 |
| 1369215_a_at | NM_012836 | 25306 | carboxypeptidase D | 7.60221365 | 7.851067 | 0.409687 | 1.188262417 | −0.318247147 | 0.865883498 |
| 1389974_at | BF555171 | 116549 | casein kinase II, alpha 1 polypeptide | 7.070655253 | 7.33655 | 0.576709 | 1.20238131 | −0.509595002 | 0.849661157 |
| 1387436_at | NM_022616 | 64551 | CDC10 (cell division cycle 10, S. cerevisiae, homolog) | 8.264076026 | 7.838606 | −0.82282 | 0.744596339 | 0.558756443 | 1.170398833 |
| 1370922_at | L15011 | 29145 | cortexin | 10.52034023 | 10.29252 | −0.39042 | 0.853925826 | 0.642216784 | 1.297259097 |
| 1368059_at | NM_053955 | 117024 | crystallin, mu | 9.15043777 | 8.934658 | −0.55932 | 0.861080678 | 0.40726188 | 1.109586413 |
| 1370438_at | AF037071 | 192363 | C-terminal PDZ domain ligand of neuronal nitric oxide synthase | 8.478106643 | 8.941752 | 0.528156 | 1.37902155 | −0.286782718 | 0.819872562 |
| 1370810_at | L09752 | 64033 | cyclin D2 | 7.552338207 | 7.824805 | 0.627432 | 1.207871164 | −0.510232497 | 0.856351578 |
| 1370180_at | AA891213 | 94267 | diphosphoinositol polyphosphate phosphohydolase type II | 9.720407691 | 9.551001 | −0.32062 | 0.889208564 | 0.33907154 | 1.112564538 |
| 1399090_at | AA944459 | 252902 | dynein, cytoplasmic, light intermediate chain 1 | 8.708970325 | 9.160194 | 0.592983 | 1.36719938 | −0.611477208 | 0.713171499 |
| 1370048_at | NM_053936 | 116744 | endothelial differentiation, lysophosphatidic acid G-protein-coupled receptor, 2 | 8.190874036 | 8.434857 | 0.460008 | 1.184257781 | −0.276403406 | 0.88926266 |
| 1370341_at | AF019973 | 24334 | enolase 2, gamma | 10.25966095 | 10.09239 | −0.27444 | 0.890528386 | 0.511287186 | 1.226632739 |
| 1367958_at | NM_024397 | 79249 | eps8 binding protein (e3B1), alternatively spliced | 7.501336434 | 7.734993 | 0.390605 | 1.175811622 | −0.214182288 | 0.899358171 |
| 1373067_at | AI102738 | | ESTs | 9.097780684 | 9.795279 | 0.560829 | 1.621690153 | −0.394405591 | 0.691167336 |
| 1375687_at | BE097926 | | ESTs | 9.102908418 | 9.589148 | 0.67554 | 1.400788553 | −0.668809291 | 0.710828697 |
| 1375343_at | BE116572 | | ESTs | 9.636710979 | 10.05569 | 0.637477 | 1.336979858 | −0.600017235 | 0.721789025 |
| 1390722_at | AW531272 | | ESTs | 8.052433531 | 8.445177 | 0.563541 | 1.312887882 | −0.564580433 | 0.737665796 |
| 1371776_at | AA819268 | | ESTs | 8.792612117 | 9.070286 | 0.439984 | 1.21223885 | −0.60941328 | 0.751754214 |
| 1377029_at | AI235414 | | ESTs | 7.519789299 | 8.066421 | 0.538435 | 1.460671268 | −0.347221628 | 0.758851202 |
| 1374002_at | AI045904 | | ESTs | 7.891491864 | 8.3451 | 0.66405 | 1.369460535 | −0.489475041 | 0.773784892 |
| 1372183_at | AI230596 | | ESTs | 7.499883481 | 7.870917 | 0.59093 | 1.293279024 | −0.538050749 | 0.787917813 |
| 1390100_s_at | BG371810 | | ESTs | 8.847513531 | 9.335307 | 0.623353 | 1.402298615 | −0.383584226 | 0.796768397 |
| 1376463_at | AA955579 | | ESTs | 8.580618929 | 8.884818 | 0.477979 | 1.234732891 | −0.512299476 | 0.797964077 |
| 1380433_at | AI229240 | | ESTs | 8.198656524 | 8.544649 | 0.807649 | 1.271025354 | −0.703481364 | 0.812645109 |
| 1376911_at | BM386385 | | ESTs | 8.998969791 | 9.304256 | 0.378751 | 1.235663347 | −0.292496741 | 0.834798828 |
| 1374276_at | BE104102 | | ESTs | 8.042219162 | 8.352924 | 0.479598 | 1.24031378 | −0.357883889 | 0.843306633 |
| 1393268_at | AI071071 | | ESTs | 7.760844879 | 8.008586 | 0.670383 | 1.187346647 | −0.604731486 | 0.847734973 |
| 1385889_at | AA893212 | | ESTs | 7.456567924 | 7.681123 | 0.541819 | 1.168417012 | −0.524932857 | 0.856389756 |
| 1388985_at | AI012869 | | ESTs | 10.3902729 | 10.71161 | 0.771777 | 1.249486875 | −0.374963851 | 0.861337025 |
| 1375144_at | BM388843 | | ESTs | 9.305640348 | 9.77995 | 0.689094 | 1.389253394 | −0.247358915 | 0.862096412 |
| 1375850_at | BG371810 | | ESTs | 10.32943696 | 10.5907 | 0.646492 | 1.198530654 | −0.463027833 | 0.863301098 |
| 1376685_at | AW532489 | | ESTs | 7.03405558 | 7.31854 | 0.585335 | 1.217975253 | −0.362402037 | 0.873963777 |
| 1375538_at | AI230737 | | ESTs | 7.60108064 | 7.77676 | 0.590257 | 1.129495994 | −0.611495294 | 0.87898368 |
| 1377232_at | BF406608 | | ESTs | 7.50385238 | 7.649913 | 0.456061 | 1.106543988 | −0.555511902 | 0.885897068 |

TABLE 30-continued

| Probe Set Name | Identifier | LocusLink Name | AII AD H2O Ave | AII AD CUS Ave | CUS T | CUS FC | AII CUS + AD T | AII CUS + AD FC |
|---|---|---|---|---|---|---|---|---|
| 1374485_at | AI137762 | ESTs | 7.635036986 | 7.803592 | 0.478724 | 1.123932187 | −0.480827091 | 0.88597741 |
| 1389104_s_at | BF388420 | ESTs | 7.793627056 | 7.97877 | 0.44046 | 1.136929557 | −0.340035773 | 0.897093342 |
| 1372790_at | BG671530 | ESTs | 9.913991148 | 9.6554 | −0.42594 | 0.835903569 | 0.333317197 | 1.121671745 |
| 1388738_at | AI411227 | ESTs | 9.013127784 | 8.836253 | −0.32841 | 0.884617394 | 0.421781411 | 1.134002323 |
| 1389600_at | AW524433 | ESTs | 9.341707252 | 9.136027 | −0.31744 | 0.867129737 | 0.294052169 | 1.146455757 |
| 1388195_at | AW140475 | ESTs | 8.841214015 | 8.623431 | −0.48629 | 0.859885815 | 0.493109601 | 1.177343855 |
| 1389867_at | BI281086 | ESTs | 9.622618423 | 9.295352 | −0.44041 | 0.797045168 | 0.527626149 | 1.325364171 |
| 1371977_at | BG381477 | ESTs, Highly similar to actin related protein 2/3 complex, subunit 3 (21 kDa); Arp2/3 complex subunit p21-Arc [Mus musculus] [M. musculus] | 8.22534466 | 7.988656 | −0.43238 | 0.848690922 | 0.274472639 | 1.102307933 |
| 1388683_at | AI411174 | ESTs, Highly similar to hypothetical protein MGC14151 [Homo sapiens] [H. sapiens] | 8.66963072 | 8.511747 | −0.43469 | 0.896338715 | 0.466659704 | 1.111224693 |
| 1375245_at | AA800669 | ESTs, Highly similar to A36180 61K transforming protein - human [H. sapiens] | 10.09883803 | 9.917245 | −0.40076 | 0.881728933 | 0.482696461 | 1.136988127 |
| 1383054_at | BE111631 | ESTs, Highly similar to I48724 zinc finger protein PZF - mouse [M. musculus] | 7.47092638 | 7.691487 | 0.684678 | 1.165186416 | −0.438439828 | 0.895791948 |
| 1389957_at | BG378149 | ESTs, Highly similar to JW0059 mtprd protein - mouse [M. musculus] | 9.604565474 | 9.852639 | 0.339593 | 1.187620315 | −0.23684341 | 0.879305448 |
| 1374593_at | AA799421 | ESTs, Highly similar to KPCE_RAT PROTEIN KINASE C, EPSILON TYPE (NPKC-EPSILON) [R. norvegicus] | 8.436415302 | 8.757416 | 0.610494 | 1.249196498 | −0.371471138 | 0.855707419 |
| 1375119_at | BI284798 | ESTs, Highly similar to S70642 ubiquitin ligase Nedd4 - rat (fragment) [R. norvegicus] | 9.262421398 | 9.747071 | 0.469691 | 1.399245716 | −0.269750886 | 0.795573103 |
| 1375305_at | BI282028 | ESTs, Highly similar to ST1B_MOUSE Syntaxin 1B (P35B) [R. norvegicus] | 10.64049686 | 10.86651 | 0.543331 | 1.169598117 | −0.407433833 | 0.884962553 |
| 1390423_at | BE104245 | ESTs, Highly similar to T14792 hypothetical protein DKFZp586G0322.-1 - human (fragment) [H. sapiens] | 8.796017809 | 9.069358 | 0.231788 | 1.208602479 | −0.333710591 | 0.783587436 |
| 1398971_at | BI283725 | ESTs, Moderately similar to KIAA0100 gene product [Homo sapiens] [H. sapiens] | 9.374401563 | 9.553263 | 0.485723 | 1.13199048 | −0.397357886 | 0.8957128 |
| 1388850_at | BG671521 | ESTs, Moderately similar to HS9B_RAT Heat shock protein HSP 90-beta (HSP 84) [R. norvegicus] | 9.638454301 | 9.957086 | 0.267318 | 1.247146979 | −0.37021886 | 0.693183088 |

TABLE 30-continued

| Probe Set Name | Identifier | LocusLink | Name | AII AD H2O Ave | AII AD CUS Ave | CUS T | CUS FC | AII CUS + AD T | AII CUS + AD FC |
|---|---|---|---|---|---|---|---|---|---|
| 1390592_at | BM389412 | | ESTs, Moderately similar to T14273 zinc finger protein 106 - mouse [M. musculus] | 7.927245389 | 8.209323 | 0.666237 | 1.215944997 | −0.373953853 | 0.883872321 |
| 1390097_at | BI281738 | | ESTs, Moderately similar to Y193_HUMAN Hypothetical protein KIAA0193 [H. sapiens] | 9.3184521 | 9.600735 | 0.359884 | 1.216117474 | −0.289309137 | 0.840945647 |
| 1371590_s_at | BM386159 | | ESTs, Weakly similar to e-Tropomodulin [Rattus norvegicus] [R. norvegicus] | 8.508270545 | 8.290722 | −0.40327 | 0.860025673 | 0.715808502 | 1.286471079 |
| 1390048_at | BF408990 | | ESTs, Weakly similar to hypothetical protein, MNCb-4760 [Mus musculus] [M. musculus] | 7.825368912 | 8.242474 | 0.608206 | 1.335245393 | −0.241815196 | 0.891226221 |
| 1375231_a_at | BI281838 | | ESTs, Weakly similar to inhibitor of the Dvl and Axin complex [Rattus norvegicus] [R. norvegicus] | 9.410742003 | 9.628854 | 0.530944 | 1.163210616 | −0.387267422 | 0.888752574 |
| 1399079_at | AI101659 | | ESTs, Weakly similar to SC65 synaptonemal complex protein [Rattus norvegicus] [R. norvegicus] | 9.836360668 | 10.16998 | 0.396804 | 1.260170799 | −0.239640185 | 0.859334251 |
| 1388903_at | AI179335 | | ESTs, Weakly similar to t-complex testis expressed 1 [Rattus norvegicus] [R. norvegicus] | 8.332638336 | 8.114142 | −0.5078 | 0.859460826 | 0.35815011 | 1.110966168 |
| 1373063_at | BI277000 | | ESTs, Weakly similar to ubiquitin-conjugating enzyme E2N (homologous to yeast UBC13); bendless protein [Rattus norvegicus] [R. norvegicus] | 8.697615098 | 8.502515 | −0.43031 | 0.87351232 | 0.463990102 | 1.15709537 |
| 1371337_at | BG378939 | | ESTs, Weakly similar to S13099 cytochrome-c oxidase (EC 1.9.3.1) chain VIIa precursor - rat [R. norvegicus] | 9.813332563 | 9.642615 | −0.3672 | 0.888400916 | 0.325054592 | 1.106521553 |
| 1398846_at | BE107346 | 56783 | eukaryotic initiation factor 5 (eIF-5) | 8.361376446 | 9.008593 | 0.495006 | 1.566143804 | −0.414497851 | 0.664667317 |
| 1387383_at | NM_031802 | 83633 | G protein-coupled receptor 51 | 9.961560372 | 9.722226 | −0.41601 | 0.847135806 | 0.740340744 | 1.292462812 |
| 1368401_at | M85035 | 29627 | glutamate receptor, ionotropic, 2 | 9.7450637 | 10.12056 | 0.388163 | 1.297283064 | −0.370340093 | 0.761334957 |
| 1388189_at | AW522430 | 24416 | glutamate receptor, metabotropic 3 | 7.922810149 | 8.369635 | 0.603662 | 1.363036876 | −0.282310414 | 0.857046994 |
| 1387659_at | AF245172 | 83585 | guanine deaminase | 8.579875817 | 8.970425 | 0.419618 | 1.310892245 | −0.310557432 | 0.801387052 |
| 1375705_at | AI103622 | 24400 | Guanine nucleotide-binding protein beta 1 | 11.052428 | 11.43942 | 0.624776 | 1.307666247 | −0.713058008 | 0.698548881 |
| 1370053_at | BE116953 | 65040 | guanylate kinase associated protein | 8.181514198 | 8.416934 | 0.402124 | 1.177248901 | −0.304521974 | 0.873239295 |

TABLE 30-continued

| Probe Set Name | Identifier | LocusLink | Name | AII AD H2O Ave | AII AD CUS Ave | CUS T | CUS FC | AII CUS + AD T | AII CUS + AD FC |
|---|---|---|---|---|---|---|---|---|---|
| 1375532_at | AI008792 | 25587 | Inhibitor of DNA binding 2, dominant negative helix-loop-helix protein | 8.470555381 | 9.278552 | 0.655617 | 1.750778223 | −0.467889277 | 0.6448088 |
| 1371148_s_at | X52017 | 24503 | internexin, alpha | 8.348395102 | 8.742675 | 0.442247 | 1.314286384 | −0.351712988 | 0.790245803 |
| 1370865_at | BI277627 | 25179 | isocitrate dehydrogenase 3, gamma | 9.508280943 | 9.334029 | −0.41328 | 0.886227042 | 0.430076542 | 1.117948633 |
| 1387071_a_at | BE107978 | 29477 | microtubule-associated protein tau | 10.20988985 | 11.06574 | 0.440253 | 1.809820398 | −0.40915131 | 0.566925482 |
| 1370831_at | AY081195 | 29254 | monoglyceride lipase | 7.997950072 | 8.519811 | 0.691492 | 1.435806237 | −0.370997892 | 0.797665306 |
| 1370016_at | NM_031070 | 81734 | nel-like 2 homolog (chicken) | 9.366440831 | 9.130241 | −0.3398 | 0.84897858 | 0.629322922 | 1.313198487 |
| 1369690_at | AI547471 | 60355 | N-ethylmaleimide sensitive factor | 9.871860703 | 9.66198 | −0.40131 | 0.864608826 | 0.356371725 | 1.111739806 |
| 1368993_at | NM_020088 | 56762 | neurestin | 7.578732705 | 8.063511 | 0.624639 | 1.399370323 | −0.459690254 | 0.755545133 |
| 1369404_a_at | NM_021767 | 60391 | neurexin 1 | 7.850829037 | 8.133737 | 0.400729 | 1.216644537 | −0.47177386 | 0.798122143 |
| 1370058_at | NM_031783 | 83613 | neurofilament, light polypeptide | 9.844994746 | 9.631533 | −0.42188 | 0.862465188 | 0.366920816 | 1.10425063 |
| 1370517_at | U18772 | 266777 | neuronal pentraxin 1 | 9.516316885 | 9.313932 | −0.51492 | 0.869112366 | 0.522032631 | 1.16884432 |
| 1368255_at | NM_017354 | 50864 | neurotrimin | 8.456459057 | 8.628735 | 0.372202 | 1.126834366 | −0.377704419 | 0.883893225 |
| 1367851_at | J04488 | 25526 | Prostaglandin D synthase | 11.49214354 | 11.29404 | −0.3933 | 0.871692914 | 0.290393494 | 1.108310809 |
| 1398790_at | NM_017039 | 24672 | Protein phosphatase 2 (formerly 2A), catalytic subunit, alpha isoform | 9.819878116 | 9.61136 | −0.34567 | 0.865425423 | 0.311060317 | 1.132692891 |
| 1398825_at | D01046 | 79434 | RAB11B, member RAS oncogene family | 8.467885101 | 8.303234 | −0.51417 | 0.892144413 | 0.494808325 | 1.119497348 |
| 1370087_at | NM_031718 | 65158 | RAB2, member RAS oncogene family | 8.267117217 | 8.013845 | −0.58443 | 0.838991442 | 0.408100105 | 1.123112511 |
| 1370372_at | AF134409 | 171099 | RASD family, member 2 | 8.98764962 | 8.822419 | −0.40481 | 0.891785751 | 0.417570782 | 1.12716855 |
| 1369816_at | NM_013018 | 25531 | Ras-related small GTP binding protein 3A | 9.593343909 | 9.380739 | −0.35073 | 0.862977618 | 0.546884115 | 1.248974009 |
| 1369958_at | NM_022542 | 64373 | rhoB gene | 8.970515013 | 8.798449 | −0.38451 | 0.887570983 | 0.423174482 | 1.123272591 |
| 1375421_a_at | AI600019 | 192256 | rotein carrying the RING-H2 sequence motif | 9.594165696 | 10.03902 | 0.3913 | 1.361178681 | −0.323072636 | 0.74473796 |
| 1375621_at | AI575254 | 261737 | sideroflexin 1 | 7.407218485 | 7.669141 | 0.495738 | 1.199075642 | −0.417215583 | 0.848997619 |
| 1370224_at | BE113920 | 25125 | signal transducer and activator of transcription 3 | 7.635173326 | 7.857439 | 0.709037 | 1.166564469 | −0.459754483 | 0.890983344 |
| 1388000_at | AF021923 | 84550 | solute carrier family 24 (sodium/potassium/calcium exchanger), member 2 | 7.301200621 | 7.512385 | 0.309079 | 1.157637879 | −0.25114173 | 0.870463115 |
| 1368440_at | NM_017216 | 29484 | solute carrier family 3, member 1 | 9.398846616 | 9.93355 | 0.749691 | 1.448643968 | −0.727328652 | 0.650057604 |
| 1389986_at | AI008409 | 117556 | synaptic vesicle glycoprotein 2 b | 8.015724584 | 8.590117 | 0.656167 | 1.489050598 | −0.357264595 | 0.775227175 |
| 1369627_at | L10362 | 117556 | synaptic vesicle glycoprotein 2 b | 8.663172726 | 8.82176 | 0.204444 | 1.116193334 | −0.243485248 | 0.864656842 |
| 1387662_at | L38247 | 64440 | synaptotagmin 4 | 8.677669502 | 9.157806 | 0.309263 | 1.394875371 | −0.334811005 | 0.692224654 |
| 1369879_a_at | NM_019381 | 24822 | Testis enhanced gene transcript | 8.733602786 | 8.580479 | −0.38722 | 0.899301003 | 0.378082787 | 1.115748654 |
| 1368841_at | NM_053369 | 84382 | transcription factor 4 | 8.639946736 | 8.85393 | 0.486185 | 1.159885847 | −0.374241086 | 0.892103037 |
| 1386999_at | BG380730 | 56011 | tyrosine 3-monooxgenase/tryptophan 5 monooxgenase activation protein, beta polypeptide | 8.669827204 | 8.515457 | −0.44737 | 0.898524607 | 0.533133344 | 1.130282208 |

TABLE 30-continued

| Probe Set Name | Identifier | LocusLink | Name | AII AD H2O Ave | AII AD CUS Ave | CUS T | CUS FC | AII CUS + AD T | AII CUS + AD FC |
|---|---|---|---|---|---|---|---|---|---|
| 1398843_at | AI411103 | 58857 | vesicle-associated membrane protein, associated protein a | 10.04441626 | 9.889542 | −0.34531 | 0.898210852 | 0.35733192 | 1.10078515 |
| 1386909_a_at | AF268467 | 83529 | voltage-dependent anion channel 1 | 8.025008371 | 7.83859 | −0.4422 | 0.87878463 | 0.441711122 | 1.146114211 |

What is claimed is:

1. A method for treating anxiety in a mammalian subject, said method comprising administering a therapeutically effective amount of a fibroblast growth factor 9 (FGF9) polypeptide to said subject, wherein said FGF9 polypeptide is administered intravenously, intraperitoneally, or intrathecally.

2. The method of claim 1, wherein said subject has an anxiety disorder.

3. The method of claim 1, wherein said subject has major depression disorder.

4. The method of claim 1, wherein said FGF9 polypeptide is administered with a pharmaceutically acceptable carrier.

5. The method of claim 1, wherein said FGF9 polypeptide is a recombinant polypeptide.

6. The method of claim 1, wherein said therapeutically effective amount is from 1 nanogram to 10 milligrams per kilogram of said subject's body weight.

7. The method of claim 1, wherein said subject is a human.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: VASE forward primer

<400> SEQUENCE: 1
gaccccattc cctccatcac                                          20

<210> SEQ ID NO 2
<211> LENGTH: 19
<212> TYPE: DNA
<213> ORGANISM: Artificial
<220> FEATURE:
<223> OTHER INFORMATION: VASE reverse primer

<400> SEQUENCE: 2
ggctacgcac caccatgtg                                           19

<210> SEQ ID NO 3
<211> LENGTH: 19
<212> TYPE: DNA
<213> ORGANISM: Artificial
<220> FEATURE:
<223> OTHER INFORMATION: Exon a forward primer

<400> SEQUENCE: 3
gacgcagcca gtccatagc                                           19

<210> SEQ ID NO 4
<211> LENGTH: 22
<212> TYPE: DNA
<213> ORGANISM: Artificial
<220> FEATURE:
<223> OTHER INFORMATION: Exon b forward primer

<400> SEQUENCE: 4
cgtctacccc tgttccattg tc                                       22

<210> SEQ ID NO 5
<211> LENGTH: 22
<212> TYPE: DNA
<213> ORGANISM: Artificial
<220> FEATURE:
<223> OTHER INFORMATION: Exon b reverse primer

<400> SEQUENCE: 5
tctggtggag acaatggaac ag                                       22

-continued

<210> SEQ ID NO 6
<211> LENGTH: 17
<212> TYPE: DNA
<213> ORGANISM: Artificial
<220> FEATURE:
<223> OTHER INFORMATION: Exon c forward primer

<400> SEQUENCE: 6
tcctgccctt gcaacca                                                17

<210> SEQ ID NO 7
<211> LENGTH: 19
<212> TYPE: DNA
<213> ORGANISM: Artificial
<220> FEATURE:
<223> OTHER INFORMATION: Exon c reverse primer

<400> SEQUENCE: 7
ggttgcaagg gcaggaaga                                              19

<210> SEQ ID NO 8
<211> LENGTH: 25
<212> TYPE: DNA
<213> ORGANISM: Artificial
<220> FEATURE:
<223> OTHER INFORMATION: SEC exon forward primer

<400> SEQUENCE: 8
ccaagctggt cttcataatg ctcta                                       25

<210> SEQ ID NO 9
<211> LENGTH: 26
<212> TYPE: DNA
<213> ORGANISM: Artificial
<220> FEATURE:
<223> OTHER INFORMATION: SEC exon reverse primer

<400> SEQUENCE: 9
tttgatgctt gaacactatg aacatg                                      26

<210> SEQ ID NO 10
<211> LENGTH: 15
<212> TYPE: DNA
<213> ORGANISM: Artificial
<220> FEATURE:
<223> OTHER INFORMATION: Exon 3 forward primer

<400> SEQUENCE: 10
ggcggcgctc aatgg                                                  15

<210> SEQ ID NO 11
<211> LENGTH: 28
<212> TYPE: DNA
<213> ORGANISM: Artificial
<220> FEATURE:
<223> OTHER INFORMATION: Exon 8 reverse primer

<400> SEQUENCE: 11
gatcaggttc actttaatag agtttcca                                    28

<210> SEQ ID NO 12
<211> LENGTH: 22
<212> TYPE: DNA

```
<213> ORGANISM: Artificial
<220> FEATURE:
<223> OTHER INFORMATION: SNP9 forward sequencing primer

<400> SEQUENCE: 12
cgcagccagt ccgtaagtaa ag                                              22

<210> SEQ ID NO 13
<211> LENGTH: 21
<212> TYPE: DNA
<213> ORGANISM: Artificial
<220> FEATURE:
<223> OTHER INFORMATION: SNP9 reverse sequencing primer

<400> SEQUENCE: 13
aagctggacc ggctactagg a                                               21

<210> SEQ ID NO 14
<211> LENGTH: 166
<212> TYPE: DNA
<213> ORGANISM: Homo sapiens

<400> SEQUENCE: 14
ccgcaggctt ctgcctggcc gccgccgcct ataagctacc aggaggagct ttacgacttc     60
ccgtcctgcg ggaagtggcg ggcacgatcg caaggtagcg cagaagcttc tcaatggcca    120
gcgccagctg cagccccggc ggcgcactcg cctcacctga gcctgg                   166

<210> SEQ ID NO 15
<211> LENGTH: 113
<212> TYPE: DNA
<213> ORGANISM: Homo sapiens

<400> SEQUENCE: 15
gaggaaaatt cttccaagga tgatctccca ctcagagctg aggaagcttt tctactcagc     60
agatgctgtg tgttttgatg ttgacagcac ggtcatcagt gaagaaggaa tcg           113

<210> SEQ ID NO 16
<211> LENGTH: 122
<212> TYPE: DNA
<213> ORGANISM: Homo sapiens

<400> SEQUENCE: 16
gacggagtct cgctctgtca ccaggctgga gtgcaatggt gcaatctcgg ctcactgcaa     60
cctccgcctc ctgggttcag gcagttctcc tgcctccacc tcctgagtag ctgaaactac    120
ag                                                                   122

<210> SEQ ID NO 17
<211> LENGTH: 440
<212> TYPE: DNA
<213> ORGANISM: Homo sapiens

<400> SEQUENCE: 17
gatgctttca ttggctttgg aggaaatgtg atcaggcaac aagtcaagga taacgccaaa     60
tggtatatca ctgattttgt agagctgctg ggagaaccgg aagaataaca tccattgtca    120
tacagctcca acaacttca gatgaatttt tacaagttac acagattgat actgtttgct    180
tacaattgcc tattacaact tgctatagaa agttggtaca gatgatctgc actgtcaagt    240
aaactacagt taggaatcct caaagattgg tttgttgtt tttaactgta gttccagtat    300
tatatgatca ctattgattt cctggagagt tttgtaatct gaattcttta tgtatattcc    360
```

-continued

| tagctatatt tcatacaaag tgttttaaga gtggagagtc aattaaacac ctttactctt | 420 |
| aggaaaaaaa aaaaaaaaaa | 440 |

<210> SEQ ID NO 18
<211> LENGTH: 214
<212> TYPE: DNA
<213> ORGANISM: Homo sapiens

<400> SEQUENCE: 18

| aagccacagg ctccctggct ggcgtcagct aaagtggctg ttgggtgtcc gcaggcttct | 60 |
| gcctggccgc cgccgcctat aagctaccag gaggagcttt acgacttccc gtcctgcggg | 120 |
| aagtggcggg cacgatcgca aggtagcgca gaagcttctc aatggccagc gccagctgca | 180 |
| gccccggcgg cgcactcgcc tcacctgagc ctgg | 214 |

<210> SEQ ID NO 19
<211> LENGTH: 113
<212> TYPE: DNA
<213> ORGANISM: Homo sapiens

<400> SEQUENCE: 19

| gaggaaaatt cttccaagga tgatctccca ctcagagctg aggaagcttt tctactcagc | 60 |
| agatgctgtg tgttttgatg ttgacagcac ggtcatcagt gaagaaggaa tcg | 113 |

<210> SEQ ID NO 20
<211> LENGTH: 512
<212> TYPE: DNA
<213> ORGANISM: Homo sapiens

<400> SEQUENCE: 20

| gatgctttca ttggatttgg aggaaatgtg atcaggcaac aagtcaagga taacgccaaa | 60 |
| tggtatatca ctgattttgt agagctgctg ggagaaccgg aagaataaca tccattgtca | 120 |
| tacagctcca acaacttca gatgaatttt tacaagttac acagattgat actgtttgct | 180 |
| tacaattgcc tattacaact tgctataaaa agttggtaca gatgatctgc actgtcaagt | 240 |
| aaactacagt taggaatcct caaagattgg tttgtttgtt tttaactgta gttccagtat | 300 |
| tatatgatca ctatcgattt cctggagagt tttgtaatct gaattcttta tgtatattcc | 360 |
| tagctatatt tcatacaaag tgttttaaga gtggagagtc aattaaacac ctttactctt | 420 |
| aggaatatag attcggcagc cttcagtgaa tattggtttt tttccctttg gtatgtcaat | 480 |
| aaaagtttat ccatgtgtca gaaaaaaaaa aa | 512 |

<210> SEQ ID NO 21
<211> LENGTH: 16
<212> TYPE: DNA
<213> ORGANISM: Artificial
<220> FEATURE:
<223> OTHER INFORMATION: PSPHL-F1 primer

<400> SEQUENCE: 21

| aggctccctg gctggc | 16 |

<210> SEQ ID NO 22
<211> LENGTH: 17
<212> TYPE: DNA
<213> ORGANISM: Artificial
<220> FEATURE:
<223> OTHER INFORMATION: PSPHL-R1 primer

```
<400> SEQUENCE: 22
caggctcagg tgaggcg                                                    17

<210> SEQ ID NO 23
<211> LENGTH: 21
<212> TYPE: DNA
<213> ORGANISM: Artificial
<220> FEATURE:
<223> OTHER INFORMATION: PSPHL-G-F2 primer

<400> SEQUENCE: 23
aagccagtgc gtctacaggt g                                               21

<210> SEQ ID NO 24
<211> LENGTH: 22
<212> TYPE: DNA
<213> ORGANISM: Artificial
<220> FEATURE:
<223> OTHER INFORMATION: PSPHL-G-R2 primer

<400> SEQUENCE: 24
gtgccagaag aaccacacag tc                                              22
```